US009416378B2

(12) United States Patent
Liao et al.

(10) Patent No.: US 9,416,378 B2
(45) Date of Patent: Aug. 16, 2016

(54) BIOFUEL PRODUCTION BY RECOMBINANT MICROORGANISMS

(71) Applicant: The Regents of the University of California, Oakland, CA (US)

(72) Inventors: James C. Liao, Los Angeles, CA (US); Shota Atsumi, Davis, CA (US); Kevin M. Smith, West Hollywood, CA (US); Roa Pu Claire Shen, Los Angeles, CA (US); Anthony F. Cann, Los Angeles, CA (US); Michael R. Connor, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/637,336

(22) Filed: Mar. 3, 2015

(65) Prior Publication Data

US 2015/0376656 A1 Dec. 31, 2015

Related U.S. Application Data

(62) Division of application No. 12/028,727, filed on Feb. 8, 2008, now Pat. No. 8,975,049.

(60) Provisional application No. 60/900,477, filed on Feb. 9, 2007, provisional application No. 60/900,546, filed on Feb. 9, 2007, provisional application No. 60/921,927, filed on Apr. 4, 2007, provisional application No. 60/956,634, filed on Aug. 17, 2007.

(51) Int. Cl.
*C12P 7/04* (2006.01)
*C12P 7/16* (2006.01)
(Continued)

(52) U.S. Cl.
CPC .................. *C12P 7/16* (2013.01); *C12N 9/0006* (2013.01); *C12N 9/1022* (2013.01); *C12N 9/1025* (2013.01); *C12N 9/1029* (2013.01);
(Continued)

(58) Field of Classification Search
CPC ..................................... C12P 7/04; C12P 7/16
See application file for complete search history.

(56) References Cited

U.S. PATENT DOCUMENTS

| 4,424,275 A | 1/1984 | Levy |
|---|---|---|
| 4,568,643 A | 2/1986 | Levy |

(Continued)

FOREIGN PATENT DOCUMENTS

| CA | 2039245 | 11/2000 |
|---|---|---|
| CA | 2622026 A1 | 5/2007 |

(Continued)

OTHER PUBLICATIONS

Moyse, Ellen, International Preliminary Report on Patentability and Written Opinion, Date of Issuance of Report: Aug. 11, 2009, International Application No. PCT/US08/53514.

(Continued)

*Primary Examiner* — Rebecca Prouty
(74) *Attorney, Agent, or Firm* — Joseph R. Baker, Jr.; Gavrilovich, Dodd & Lindsey, LLP

(57) ABSTRACT

Provided herein are metabolically-modified microorganisms useful for producing biofuels. More specifically, provided herein are methods of producing high alcohols including isobutanol, 1-butanol, 1-propanol, 2-methyl-1-butanol, 3-methyl-1-butanol and 2-phenylethanol from a suitable substrate.

6 Claims, 57 Drawing Sheets

(51) Int. Cl.
    *C12N 15/52* (2006.01)
    *C12P 7/22* (2006.01)
    *C12N 9/04* (2006.01)
    *C12N 9/10* (2006.01)
    *C12N 9/88* (2006.01)

(52) U.S. Cl.
    CPC .............. *C12N 9/88* (2013.01); *C12N 15/52* (2013.01); *C12P 7/04* (2013.01); *C12P 7/22* (2013.01); *C12Y 101/01001* (2013.01); *C12Y 101/01085* (2013.01); *C12Y 101/01086* (2013.01); *C12Y 202/01006* (2013.01); *C12Y 203/01182* (2013.01); *C12Y 203/03013* (2013.01); *C12Y 401/01* (2013.01); *C12Y 402/01009* (2013.01); *C12Y 402/01019* (2013.01); *C12Y 402/01033* (2013.01); *Y02E 50/10* (2013.01); *Y02E 50/17* (2013.01)

(56) References Cited

U.S. PATENT DOCUMENTS

| | | | |
|---|---|---|---|
| 5,210,032 | A | 5/1993 | Kashket |
| 5,908,924 | A | 6/1999 | Burdette et al. |
| 6,358,717 | B1 | 3/2002 | Blaschek et al. |
| 2002/0028492 | A1 | 3/2002 | Lenke et al. |
| 2004/0096946 | A1 | 5/2004 | Kealey et al. |
| 2004/0146996 | A1 | 7/2004 | Yocum et al. |
| 2004/0152159 | A1 | 8/2004 | Causey et al. |
| 2005/0287655 | A1 | 12/2005 | Tabata et al. |
| 2006/0172399 | A1 | 8/2006 | Nomoto |
| 2007/0072279 | A1 | 3/2007 | Meynial-Salles et al. |
| 2007/0087425 | A1 | 4/2007 | Ohto |
| 2007/0092957 | A1 | 4/2007 | Donaldson et al. |
| 2008/0182308 | A1 | 7/2008 | Donaldson et al. |
| 2008/0261230 | A1 | 10/2008 | Liao et al. |
| 2009/0305369 | A1 | 12/2009 | Donaldson et al. |
| 2010/0242345 | A1* | 9/2010 | Keasling ............... C10L 1/026 44/388 |

FOREIGN PATENT DOCUMENTS

| | | |
|---|---|---|
| EP | 0112459 A1 | 4/1984 |
| EP | 0282474 A1 | 9/1988 |
| EP | 0315949 A2 | 5/1989 |
| EP | 1149918 A1 | 4/2001 |
| JP | 6317695 B2 | 4/1988 |
| JP | 63102587 A1 | 5/1988 |
| JP | 63254986 A1 | 10/1988 |
| WO | WO90/02193 A1 | 8/1990 |
| WO | WO98/51813 A1 | 11/1998 |
| WO | WO00/50624 A1 | 8/2000 |
| WO | WO01/21772 A2 | 3/2001 |
| WO | WO2007/050671 A1 | 5/2007 |
| WO | WO2008/072921 A1 | 6/2008 |
| WO | 2011041402 A1 | 4/2011 |

OTHER PUBLICATIONS

Gerischer et al. "mRNA Analysis of the adc Gene Region of Clostridium acetobutylicum during the Shift to Solventogenesis," Journal of Bacteriology, 1992, vol. 174, pp. 426-433.
Inui, Masayuki et al., "Expression of Clostridium acetobutylicum butanol synthetic genes in *Escherichi coli*," Appl. Microbiol. Biotechnol, 2008, vol. 77, pp. 1305-1316.
Louis, et al., "Organization of butyrate synthetic genes in human colonic bacteria: phylogenetic conservation and horizontal gene transfer," FEMS Microbiology Letters, 2007, vol. 269, pp. 240-247.
Minton, N. et al., "Clostridia," New York: Plenum Press, 1989, ISBN 0306432617, pp. 118-123.
Young, Lee W., Transmittal of International Search Report and Written Opinion, International Search Report, and Written Opinion, PCT/US08/79667, Mar. 18, 2009.
Atsumi et al., "Engineering the isobutanl biosynthetic pathway in *Escherichia coli* by comparison of three aldehyde reductase/alcohol dehydrogenase genes," Appl. Microbiol. Biotechnol., Jul. 16, 2009, pp. 651-657, vol. 85, No. 3.
Baez et al, "High-flux isobutanol production using engineered *Escherichi coli*: a bioreactor study with in situ product removal," Appl. Microbiol. Biotechnol., 2011, pp. 1681-1690, vol. 90.
Hansen, et al., "5 Brewer's yeast: genetic structure and targets for improvement," Topics in Curr. Genetics, 2003, pp. 143-170, vol. 2.
Smit, Bart A., "Formation of Amino Acid Derived Cheese Flavour Compounds," Thesis, van Wageningen Universiteit, Apr. 23, 2004.
Smith et al., "Engineering Corynebacterium glutamicum for isobutanol production," Appl. Microbiol. Biotechnol, 2010, pp. 1045-1055, vol. 87.
Sulzenbacher et al., "Crystal Structure of *E. coli* Alcohol Dehydrogenase YqhD: Evidence of a Covalently Modified NADP Coenzyme," J. Mol. Biol., 2004, pp. 489-502, vol. 342.
Yang et al., "The Effects of Feed and Intracellular Pyruvate Levels on the Redistribution of Metabolic Fluxes in *Escherichi coli*," Metabolic Engineering, 2001, pp. 115-123, vol. 3.
Office Action for Harris, Nicole, Patent Application No. 2,678,261, Canadian Intellectual Property Office, Apr. 13, 2015.
Bermejo, Lourdes L., et al., "Expression of Clostridium acetobuylicum ATCC 824 Genes in *Escherichia coli* for Acetone Production and Acetate Detoxification," Applied and Environmental Microbiology, Mar. 1998, pp. 1079-1085, vol. 64, No. 3.
Causey, T.B. et al., "Engineering *Escherichia coli* for efficient conversion of glucose to pyruvate," PNAS, Feb. 24, 2004, vol. 101, No. 8 pp. 2235-2240.
Dickinson, J. Richard et al., "An Investigation of the Metabolism of Valine to Isobutyl Alcohol in *Saccharomyces cerevisiae*," Journal of Biological Chemistry, Oct. 2, 1998, vol. 273, No. 40, pp. 25751-25756.
Dickinson, J. Richard, "A 13C Nuclear Magnetic Resonance Investigation of the Metabolism of Leucine to Isoamyl Alcohol in *Saccharomyces cerevisiae*," The Journal of Biological Chemistry, 1997, vol. 272, pp. 26871-26878.
Durre P., "New insights and novel developments in clostridial acetone/butanol/isopropanol fermentation," Appl. Microbiol. Biotechnol., 1998, vol. 49, pp. 639-648.
Garcia, Ana I., "Fusel Alcohols Production in Beer Fermentation Processes," 1994, Process Biochemistry, vol. 29, pp. 303-309.
Harris, Latonia M., et al., "Characterization of Recombinant Strains of the Clostridium acetobutylicum Butyrate Kinase Inactivation Mutant: Need for New Phenomenological Models for Solventogenesis and Butanol Inhibition?" Biotechnology and Bioengineering, Jan. 5, 2000, vol. 67, No. 1, pp. 1-11.
Larroy, Carol et al., "Characterization of the*Saccharomyces cerevisiae* YMR318C (ADH6) gene product as a broad specificity NADPH-dependent alcohol dehydrogenase: relevance in aldehyde reduction," Biochem. J., 2002, vol. 361, pp. 163-172.
Oliveira, Evelyn Souza, The production of volatile compounds by yeasts isolated from small Brazilian cachaca distilleries, World Journal of Microbiology & Biotechnology, 2005, vol. 21, pp. 1569-1576.
Vogel, Nancy, Transmittal of International Search Report and Written Opinion, International Search Report, and Written Opinion, PCT/US08/53514, Sep. 12, 2008.
Yoshimoto, H. et al., "Genetic and physiological analysis of branched-chain alcohols and isoamyl acetate production in *Saccharomyces cerevisiae*," Appl. Microbiol. Biotechnol., 2002, vol. 59, pp. 501-508.
Vogel, Nancy, Transmittal of International Search Report and Written Opinion, International Search Report, and Written Opinion, PCT/US08/59291, Aug. 15, 2008.
Woods, David R., "The genetic engineering of microbial solvent production," Tibtech, Jul. 1995, vol. 13, pp. 259-264.
Girbal, Lawrence et al., "Regulation of Solvent Production in Clostridium acetobutylicum," Tibtech, Jan. 1998, vol. 16, pp. 11-16.
Ullmann's, Encyclopedia of Industrial Chemistry, 6th Edition, 2003, vol. 5, pp. 716-719.

(56) References Cited

OTHER PUBLICATIONS

T. Hanai, "Engineered Synthetic Pathway for Isopropanol Production in *Escherichia coli*," Applied and Environmental Microbiology, Dec. 2007, vol. 73, No. 24, pp. 7814-7818.

Eden et al., "Involvement of branched-chain amino acid aminotransferases in the production of fusel alcohols during fermentation in yeast," App. Microbiol. Biotechnol, 2001, pp. 296-300, vol. 55.

Girbal et al., "Regualtion of solvent production in Clostridium acetobutylicum," Focus Tibtech, 1998, pp. 11-16, vol. 16.

Gonzalez-Pajuelo et al., "Metabolic engineering of Clostridium acetobutylicum for the industrial production of 1,3-propanediol from glycerol," Metabolic Engineering, 2005, pp. 329-336, vol. 7.

Yu, Rentao, Official Action, CN 200880009662.8, Chinese Patent Office, Aug. 15, 2011.

* cited by examiner

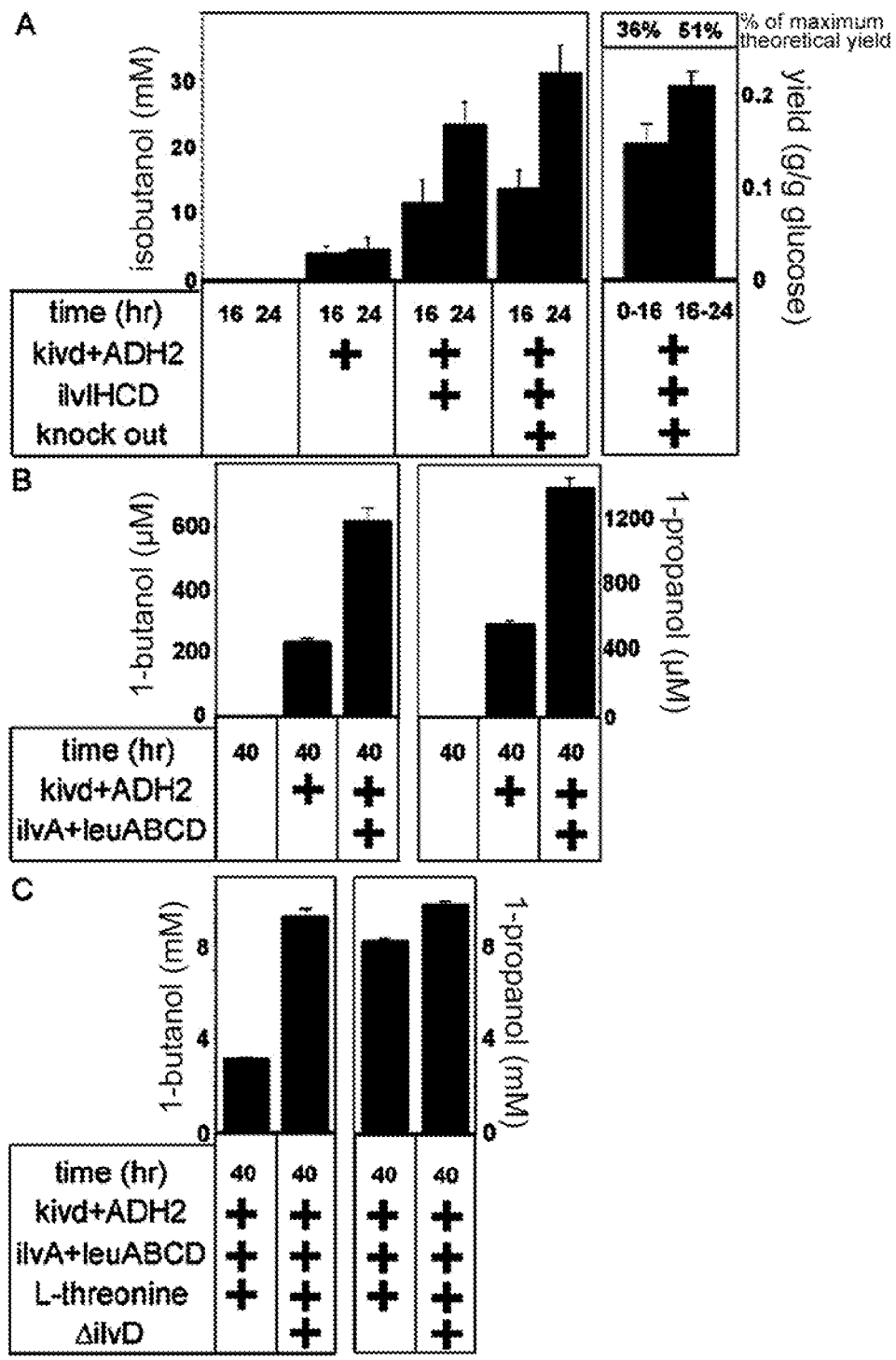
FIGURE 2A-C

*kivd*: pyruvate decarboxylase (*Lactococcus lactis*) (SEQ ID NO:27)
atgtatacagtaggagattacctattagaccgattacacgagttaggaattgaagaaatttt
tggagtccctggagactataacttacaattttttagatcaaattatttcccgcaaggatatga
aatgggtcggaaatgctaatgaattaaatgcttcatatatggctgatggctatgctcgtact
aaaaaagctgccgcatttcttacaacctttggagtaggtgaattgagtgcagttaatggatt
agcaggaagttacgccgaaaattaccagtagtagaaatagtgggatcacctacatcaaaag
ttcaaaatgaaggaaaatttgttcatcatacgctggctgacggtgattttaaacactttatg
aaaatgcacgaacctgttacagcagctcgaactttactgacagcagaaaatgcaaccgttga
aattgaccgagtactttctgcactattaaaagaaagaaaacctgtctatatcaacttaccag
ttgatgttgctgctgcaaaagcagagaaaccctcactccctttgaaaaagaaaactcaact
tcaaatacaagtgaccaagagatcttgaacaaaattcaagaagcttgaaaaatgccaaaaa
accaatcgtgattacaggacatgaaataattagttttggcttagaaaaaacagtctctcaat
ttatttcaaagacaaaactacctattacgacattaaactttggaaaaagttcagttgatgaa
gctctcccttcatttttaggaatctataatggtaaactctcagagcctaatcttaaagaatt
cgtggaatcagccgacttcatcctgatgcttggagttaaactcacagactcttcaacaggag
ccttcactcatcatttaaatgaaaataaaatgatttcactgaatatagatgaaggaaaaata
tttaacgaaagcatccaaaattttgatttgaatccctcatctcctctcttagacctaag
cgaaatagaatacaaaggaaaatatatcgataaaaagcaagaagactttgttccatcaaatg
cgcttttatcacagaccgcctatggcaagcagttgaaaacctaactcaaagcaatgaaaca
atcgttgctgaacaagggacatcattctttggcgcttcatcaattttcttaaaaccaaagag
tcattttattggtcaaccttatggggatcaattggatatacattcccagcagcattaggaa
gccaaattgcagataaagaaagcagacacctttttatttattggtgatggttcacttcaactt
acggtgcaagaattaggattagcaatcagagaaaaattaatccaatttgctttattatcaa
taatgatggttatacagtcgaaagagaaattcatggaccaaatcaaagctacaatgatattc
caatgtggaattactcaaaattaccagaatcatttggagcaacagaagaacgagtagtctcg
aaaatcgttagaactgaaaatgaatttgtgtctgtcatgaaagaagctcaagcagatccaaa
tagaatgtactggattgagttaattttggcaaaagaagatgcaccaaaagtactgaaaaaaa
tgggcaaactatttgctgaacaaaataaatcataa

FIGURE 15

*PDC6* (*Saccharomyces cerevisiae*) (SEQ ID NO:29)
atgtctgaaattactcttggaaaatacttatttgaaagattgaagcaagttaatgttaacac
cattttttgggctaccaggcgacttcaacttgtccctattggacaagatttacgaggtagatg
gattgagatgggctggtaatgcaaatgagctgaacgccgcctatgccgccgatggttacgca
cgcatcaaggggtttatctgtgctggtaactacttttggcgtaggtgaattatccgccttgaa
tggtattgcaggatcgtatgcagaacacgtcggtgtactgcatgttgttggtgtcccctcta
tctccgctcaggctaagcaattgttgttgcatcataccttgggtaacggtgattttaccgtt
tttcacagaatgtccgccaatatctcagaaactacatcaatgattacagacattgctacagc
cccttcagaaatcgataggttgatcaggacaacatttataacacaaaggcctagctacttgg
ggttgccagcgaatttggtagatctaaaggttcctggttctcttttggaaaaaccgattgat
ctatcattaaaacctaacgatcccgaagctgaaaaggaagttattgataccgtactagaatt
gatccagaattcgaaaaaccctgttatactatcggatgcctgtgcttctaggcacaacgtta
aaaagaaacccagaagttaattgatttgacgcaattcccagcttttgtgacacctctaggt
aaagggtcaatagtgaacagcatccagatatggcggtgtttatgtgggaacgctgtccaa
acaagacgtgaaacaggccgttgagtcggctgatttgatcctttcggtcggtgctttgctct
ctgattttaacacaggttcgttttcctactcctacaagactaaaaatgtagtggagtttcat
tccgattacgtaaaggtgaagaacgctacgttcctcggtgtacaaatgaaatttgcactaca
aaacttactgaaggttattcccgatgttgttaagggctacaagagcgttcccgtaccaacca
aaactcccgcaaacaaaggtgtacctgctagcacgccttgaaacaagagtggttgtggaac
gaattgtccaaattcttgcaagaaggtgatgttatcatttccgagaccggcacgtctgcctt
cggtatcaatcaaactatctttcctaaggacgcctacgtatctcgcaggtgttgtggggt
ccatcggttttacaacaggagcaactttaggtgctgcctttgccgctgaggagattgacccc
aacaagagagtcatcttattcataggtgacgggtctttgcagttaaccgtccaagaaatctc
caccatgatcagatgggggttaaagccgtatcttttgtccttaacaacgacggctacacta
tcgaaaagctgattcatgggcctcacgcagagtacaacgaaatccagacctgggatcacctc
gccctgttgcccgcatttggtgcgaaaaagtacgaaatcacaagatcgccactacgggtga
gtgggatgccttaaccactgattcagagttccagaaaaactcggtgatcagactaattgaac
tgaaactgcccgtctttgatgctccggaaagtttgatcaaacaagcgcaattgactgccgct
acaaatgccaaacaataa

FIGURE 16

*ARO10 (Saccharomyces cerevisiae)* (SEQ ID NO:31)
atggcacctgttacaattgaaaagttcgtaaatcaagaagaacgacaccttgtttccaaccg
atcagcaacaattccgtttggtgaatacatatttaaaagattgttgtccatcgatacgaaat
cagttttcggtgttcctggtgacttcaacttatctctattagaatatctctattcacctagt
gttgaatcagctggcctaagatgggtcggcacgtgtaatgaactgaacgccgcttatgcggc
cgacggatattcccgttactctaataagattggctgtttaataaccacgtatggcgttggtg
aattaagcgccttgaacggtatagccggttcgttcgctgaaaatgtcaaagttttgcacatt
gttggtgtggccaagtccatagattcgcgttcaagtaacttagtgatcggaacctacatca
tttggtcccacagctacatgattcaaattttaaagggccaaatcataaagtatatcatgata
tggtaaaagatagagtcgcttgctcggtagcctacttggaggatattgaaactgcatgtgac
caagtcgataatgttatccgcgatatttacaagtattctaaacctggttatatttttgttcc
tgcagattttgcggatatgtctgttacatgtgataatttggttaatgttccacgtatatctc
aacaagattgtatagtatacccttctgaaaaccaattgtctgacataatcaacaagattact
agttggatatattccagtaaaacacctgcgatccttggagacgtactgactgataggtatgg
tgtgagtaacttttgaacaagcttatctgcaaaactgggatttggaattttccactgtta
tgggaaaatctgtaattgatgagtcaaacccaacttatatgggtcaatataatggtaaagaa
ggtttaaaacaagtctatgaacattttgaactgtgcgacttggtcttgcattttggagtcga
catcaatgaattaataatgggcattatacttttacttataaaccaaatgctaaaatcattc
aatttcatccgaattatattcgccttgtggacactaggcagggcaatgagcaaatgttcaaa
ggaatcaattttgcccctatttttaaaagaactatacaagcgcattgacgtttctaaactttc
tttgcaatatgattcaaatgtaactcaatatacgaacgaaacaatgcggttagaagatccta
ccaatggacaatcaagcattattacacaagttcacttacaaaagacgatgcctaaattttg
aaccctggtgatgttgtcgtttgtgaaacaggctcttttcaattctctgttcgtgatttcgc
gtttccttcgcaattaaaatatatatcgcaaggattttttcctttccattggcatggcccttc
ctgccgccctaggtgttggaattgccatgcaagaccactcaaacgctcacatcaatggtggc
aacgtaaaagaggactataagccaagattaattttgtttgaaggtgacggtgcagcacagat
gacaatccaagaactgagcaccattctgaagtgcaatattccactagaagttatcatttgga
acaataacggctacactattgaaagagccatcatgggccctaccaggtcgtataacgacgtt
atgtcttggaaatggaccaaactatttgaagcattcggagacttcgacggaaagtatactaa
tagcactctcattcaatgtccctctaaattagcactgaattggaggagcttaagaattcaa
acaaaagaagcgggatagaacttttagaagtcaaattaggcgaattggatttccccgaacag
ctaaagtgcatggttgaagcagcggcacttaaaagaaataaaaaatag

FIGURE 17

*THI3 (Saccharomyces cerevisiae)* (SEQ ID NO:33)
atgaattctagctatacacagagatatgcactgccgaagtgtatagcaatatcagattatct
tttccatcggctcaaccagctgaacatacataccatatttggactctccggagaatttagca
tgccgttgctggataaactatacaacattccgaacttacgatgggccggtaattctaatgag
ttaaatgctgcctacgcagcagatggatactcacgactaaaaggcttgggatgtctcataac
aacctttggtgtaggcgaattatcggcaatcaatggcgtggccggatcttacgctgaacatg
taggaatacttcacatagtgggtatgccgccaacaagtgcacaaacgaaacaactactactg
catcatactctgggcaatggtgatttcacggtatttcatagaatagccagtgatgtagcatg
ctatacaacattgattattgactctgaattatgtgccgacgaagtcgataagtgcatcaaaa
aggcttggatagaacagaggccagtatacatgggcatgcctgtcaaccaggtaaatctcccg
attgaatcagcaaggcttaatacacctctggatttacaattgcataaaaacgacccagacgt
agagaaagaagttatttctcgaatattgagttttatatacaaaagccagaatccggcaatca
tcgtagatgcatgtactagtcgacagaatttaatcgaggagactaaagagctttgtaatagg
cttaaatttccagttttgttacacctatgggtaagggtacagtaaacgaaacagacccgca
atttgggggcgtattcacgggctcgatatcagccccagaagtaagagaagtagttgattttg
ccgatttatcatcgtcattggttgcatgctctccgaattcagcacgtcaactttccacttc
caatataaaactaagaattgtgcgctactatattctacatctgtgaaattgaaaaatgccac
atatcctgacttgagcattaaattactactacagaaaatattagcaaatcttgatgaatcta
aactgtcttaccaaccaagcgaacaacccagtatgatggttccaagaccttacccagcagga
aatgtcctcttgagacaagaatgggtctggaatgaaatatcccattggttccaaccaggtga
cataatcataacagaaactggtgcttctgcatttggagttaaccagaccagatttccggtaa
atacactaggtatttcgcaagctctttggggatctgtcggatatacaatggggcgtgtctt
ggggcagaatttgctgttcaagagataaacaaggataaattccccgcaactaaacatagagt
tattctgtttatgggtgacggtgctttccaattgacagttcaagaattatccacaattgtta
agtggggattgacacctatattttgtgatgaataaccaaggttactctgtggacaggttt
ttgcatcacaggtcagatgctagttattacgatatccaaccttggaactacttgggattatt
gcgagtatttggttgcacgaactacgaaacgaaaaaaattattactgttggagaattcagat
ccatgatcagtgacccaaactttgcgaccaatgacaaaattcggatgatagagattatgcta
ccaccaagggatgttccacaggctctgcttgacaggtgggtggtagaaaagaacagagcaa
acaagtgcaagaggagaacgaaaattctagcgcagtaaatacgccaactccagaattccaac
cacttctaaaaaaaatcaagttggatactga

FIGURE 18

*pdc* (*Clostridium acetobutylicum*) (SEQ ID NO:35)
ttgaagagtgaatacacaattggaagatatttgttagaccgtttatcagagttgggtattcg
gcatatctttggtgtacctggagattacaatctatcctttttagactatataatggagtaca
aagggatagattgggttggaaattgcaatgaattgaatgctgggtatgctgctgatggatat
gcaagaataaatggaattggagccatacttacaacatttggtgttggagaattaagtgccat
taacgcaattgctggggcatacgctgagcaagttccagttgttaaaattacaggtatcccca
cagcaaaagttagggacaatggattatatgtacaccacacattaggtgacggaaggtttgat
cactttttgaaatgtttagagaagtaacagttgctgaggcattactaagcgaagaaaatgc
agcacaagaaattgatcgtgttcttatttcatgctggagacaaaaacgtcctgttcttataa
atttaccgattgatgtatatgataaaccaattaacaaaccattaaagccattactcgattat
actatttcaagtaacaaagaggctgcatgtgaatttgttacagaaatagtacctataataaa
tagggcaaaaaagcctgttattcttgcagattatggagtatatcgttaccaagttcaacatg
tgcttaaaaacttggccgaaaaaaccggatttcctgtggctacactaagtatgggaaaaggt
gttttcaatgaagcacaccctcaatttattggtgtttataatggtgatgtaagttctcctta
tttaaggcagcgagttgatgaagcagactgcattattagcgttggtgtaaaattgacggatt
caaccacaggggggattttctcatggatttctaaaaggaatgtaattcacattgatcctttt
tcaataaaggcaaaaggtaaaaaatatgcacctattacgatgaaagatgctttaacagaatt
aacaagtaaaattgagcatagaaactttgaggatttagatataaagccttacaaatcagata
atcaaaagtatttttgcaaaagagaagccaattacacaaaaacgttttttttgagcgtattgct
cactttataaaagaaaaagatgtattattagcagaacagggtacatgctttttttggtgcgtc
aaccatacaactacccaaagatgcaacttttattggtcaacctttatggggatctattggat
acacacttcctgctttattaggttcacaattagctgatcaaaaaggcgtaatattcttta
attggggatggtgcatttcaaatgacagcacaagaaatttcaacaatgcttcgtttacaaat
caaacctattattttttttaattaatacgatggttatacaattgaacgtgctattcatggta
gagaacaagtatataacaatattcaaatgtggcgatatcataatgttccaaaggttttaggt
cctaaagaatgcagcttaacctttaaagtacaaagtgaaactgaacttgaaaaggctctttt
agtggcagataaggattgtgaacatttgattttatagaagttgttatggatcgttatgata
aacccgagcctttagaacgtctttcgaacgttttgcaaatcaaataattag

FIGURE 19

*ADH2*: alcohol dehydrogenase (*Saccharomyces cerevisiae*) (SEQ ID NO:37)
atgccttcgcaagtcattcctgaaaaacaaaaggctattgtcttttatgagacagatggaaa
attggaatataaagacgtcacagttccggaacctaagcctaacgaaattttagtccacgtta
aatattctggtgtttgtcatagtgacttgcacgcgtggcacggtgattggccatttcaattg
aaatttccattaatcggtggtcacgaaggtgctggtgttgttgttaagttgggatctaacgt
taagggctggaaagtcggtgattttgcaggtataaaatggttgaatgggacttgcatgtcct
gtgaatattgtgaagtaggtaatgaatctcaatgtccttatttggatggtactggcttcaca
catgatggtacttttcaagaatacgcaactgccgatgccgttcaagctgcccatattccacc
aaacgtcaatcttgctgaagttgccccaatcttgtgtgcaggtatcactgtttataaggcgt
tgaaaagagccaatgtgataccaggccaatggtcactatatccggtgcatgcggtggcttg
ggttctctggcaatccaatacgcccttgctatgggttacagggtcattggtatcgatggtgg
taatgccaagcgaaagttatttgaacaattaggcggagaaatattcatcgatttcacggaag
aaaaagacattgttggtgctataataaaggccactaatggcggttctcatggagttattaat
gtgtctgtttctgaagcagctatcgaggcttctacgaggtattgtaggcccaatggtactgt
cgtcctggttggtatgccagctcatgcttactgcaattccgatgttttcaatcaagttgtaa
aatcaatctccatcgttggatcttgtgttggaaatagagctgatacaagggaggctttagat
ttcttcgccagaggtttgatcaaatctccgatccacttagctggcctatcggatgttcctga
aattttgcaaagatggagaagggtgaaattgttggtagatatgttgttgagacttctaaat
ga

FIGURE 20 ilvI: (E.coli) (SEQ ID NO:39)
atggagatgttgtctggagccgagatggtcgtccgatcgcttatcgatcagggcgttaaaca
agtattcggttatcccggaggcgcagtccttgatatttatgatgcattgcataccgtgggtg
gtattgatcatgtattagttcgtcatgagcaggcggcggtgcatatggccgatggcctggcg
cgcgcgaccggggaagtcggcgtcgtgctggtaacgtcgggtccaggggcgaccaatgcgat
tactggcatcgccaccgcttatatggattccattccattagttgtcctttccgggcaggtag
cgacctcgttgataggttacgatgcctttcaggagtgcgacatggtggggatttcgcgaccg
gtggttaaacacagtttttctggttaagcaaacggaagacattccgcaggtgctgaaaaaggc
tttctggctggcggcaagtggtcgcccaggaccagtagtcgttgatttaccgaaagatattc
ttaatccggcgaacaaattaccctatgtctggccggagtcggtcagtatgcgttcttacaat
cccactactaccggacataaagggcaaattaagcgtgctctgcaaacgctggtagcggcaaa
aaaaccggttgtctacgtaggcggtggggcaatcacggcgggctgccatcagcagttgaaag
aaacggtggaggcgttgaatctgccgttgtttgctcattgatggggctggggcgtttccg
gcaacgcatcgtcaggcactgggcatgctgggaatgcacggtacctacgaagccaatatgac
gatgcataacgcggatgtgattttcgccgtcggggtacgatttgatgaccgaacgacgaaca
atctggcaaagtactgcccaaatgccactgttctgcatatcgatattgatcctacttccatt
tctaaaaccgtgactgcggatatcccgattgtgggggatgctcgccaggtcctcgaacaaat
gcttgaactcttgtcgcaagaatccgcccatcaaccactggatgagatccgcgactggtggc
agcaaattgaacagtggcgcgctcgtcagtgcctgaaatatgacactcacagtgaaaagatt
aaaccgcaggcggtgatcgagactctttggcggttgacgaagggagacgcttacgtgacgtc
cgatgtcgggcagcaccagatgtttgctgcactttattatccattcgacaaaccgcgtcgct
ggatcaattccggtggcctcggcacgatgggttttggtttacctgcggcactgggcgtcaaa
atggcgttgccagaagaaaccgtggtttgcgtcactggcgacggcagtattcagatgaacat
ccaggaactgtctaccgcgttgcaatacgagttgcccgtactggtggtgaatctcaataacc
gctatctggggatggtgaagcagtggcaggacatgatctattccggccgtcattcacaatct
tatatgcaatcgctacccgatttcgtccgtctggcggaagcctatgggcatgtcgggatcca
gatttctcatccgcatgagctggaaagcaaacttagcgaggcgctggaacaggtgcgcaata
atcgcctggtgtttgttgatgttaccgtcgatggcagcgagcacgtctacccgatgcagatt
cgcggggcggaatggatgaaatgtggttaagcaaaacggagagaacctga

FIGURE 21 ilvH: (E.coli) (SEQ ID NO:41)
atgcgccggatattatcagtcttactcgaaaatgaatcaggcgcgttatcccgcgtgattgg
ccttttttcccagcgtggctacaacattgaaagcctgaccgttgcgccaaccgacgatccga
cattatcgcgtatgaccatccagaccgtgggcgatgaaaaagtacttgagcagatcgaaaag
caattacacaaactggtcgatgtcttgcgcgtgagtgagttggggcagggcgcgcatgttga
gcgggaaatcatgctggtgaaaattcaggccagcggttacgggcgtgacgaagtgaaacgta
atacgaaatattccgtgggcaaattatcgatgtcacaccctcgctttataccgttcaatta
gcaggcaccagcggtaagcttgatgcatttttagcatcgattcgcgatgtggcgaaaattgt
ggaggttgctcgctctggtgtggtcggactttcgcgcggcgataaaataatgcgttga

FIGURE 22

*ilvC*: (*E.coli*) (SEQ ID NO:43)

```
atggctaactacttcaatacactgaatctgcgccagcagctggcacagctgggcaaatgtcg
ctttatgggccgcgatgaattcgccgatggcgcgagctaccttcagggtaaaaaagtagtca
tcgtcggctgtggcgcacagggtctgaaccagggcctgaacatgcgtgattctggtctcgat
atctcctacgctctgcgtaaagaagcgattgccgagaagcgcgcgtcctggcgtaaagcgac
cgaaaatggttttaaagtgggtacttacgaagaactgatcccacaggcggatctggtgatta
acctgacgccggacaagcagcactctgatgtagtgcgcaccgtacagccactgatgaaagac
ggcgcggcgctgggctactcgcacggtttcaacatcgtcgaagtgggcgagcagatccgtaa
agatatcaccgtagtgatggttgcgccgaaatgcccaggcaccgaagtgcgtgaagagtaca
aacgtgggttcggcgtaccgacgctgattgccgttcacccggaaaacgatccgaaaggcgaa
ggcatggcgattgccaaagcctgggcggctgcaaccggtggtcaccgtgcgggtgtgctgga
atcgtccttcgttgcggaagtgaaatctgacctgatgggcgagcaaaccatcctgtgcggta
tgttgcaggctggctctctgctgtgcttcgacaagctggtggaagaaggtaccgatccagca
tacgcagaaaaactgattcagttcggttgggaaaccatcaccgaagcactgaaacagggcgg
catcaccctgatgatggaccgtctctctaacccggcgaaactgcgtgcttatgcgctttctg
aacagctgaaagagatcatggcacccctgttccagaaacatatggacgacatcatctccggc
gaattctcttccggtatgatggcggactgggccaacgatgataagaaactgctgacctggcg
tgaagagaccggcaaaaccgcgtttgaaaccgcgccgcagtatgaaggcaaaatcggcgagc
aggagtacttcgataaaggcgtactgatgattgcgatggtgaaagcgggcgttgaactggcg
ttcgaaaccatggtcgattccggcatcattgaagagtctgcatattatgaatcactgcacga
gctgccgctgattgccaacaccatcgcccgtaagcgtctgtacgaaatgaacgtggttatct
ctgataccgctgagtacggtaactatctgttctcttacgcttgtgtgccgttgctgaaaccg
tttatggcagagctgcaaccgggcgacctgggtaaagctattccggaaggcgcggtagataa
cgggcaactgcgtgatgtgaacgaagcgattcgcagccatgcgattgagcaggtaggtaaga
aactgcgcggctatatgacagatatgaaacgtattgctgttgcgggttaa
```

FIGURE 23

*ilvD*: (*E.coli*) (SEQ ID NO:45)
```
atgcctaagtaccgttccgccaccaccactcatggtcgtaatatggcgggtgctcgtgcgct
gtggcgcgccaccggaatgaccgacgccgatttcggtaagccgattatcgcggttgtgaact
cgttcacccaatttgtaccgggtcacgtccatctgcgcgatctcggtaaactggtcgccgaa
caaattgaagcggctggcggcgttgccaaagagttcaacaccattgcggtggatgatggat
tgccatgggccacgggggatgctttattcactgccatctcgcgaactgatcgctgattccg
ttgagtatatggtcaacgccactgcgccgacgccatggtctgcatctctaactgcgacaaa
atcaccccggggatgctgatggcttccctgcgcctgaatattccggtgatctttgtttccgg
cggcccgatggaggccgggaaaaccaaactttccgatcagatcatcaagctcgatctggttg
atgcgatgatccagggcgcagacccgaaagtatctgactcccagagcgatcaggttgaacgt
tccgcgtgtccgacctgcggttcctgctccgggatgtttaccgctaactcaatgaactgcct
gaccgaagcgctgggcctgtcgcagccgggcaacggctcgctgctggcaacccacgccgacc
gtaagcagctgttccttaatgctggtaaacgcattgttgaattgaccaaacgttattacgag
caaaacgacgaaagtgcactgccgcgtaatatcgccagtaaggcggcgtttgaaaacgccat
gacgctggatatcgcgatgggtggatcgactaacaccgtacttcacctgctggcggcggcgc
aggaagcggaaatcgacttcaccatgagtgatatcgataagctttcccgcaaggttccacag
ctgtgtaaagttgcgccgagcacccagaaataccatatggaagatgttcaccgtgctggtgg
tgttatcggtattctcggcgaactggatcgcgcggggttactgaaccgtgatgtgaaaaacg
tacttggcctgacgttgccgcaaacgctggaacaatacgacgttatgctgacccaggatgac
gcggtaaaaaatatgttccgcgcaggtcctgcaggcattcgtaccacacaggcattctcgca
agattgccgttgggatacgctggacgacgatcgcgccaatggctgtatccgctcgctggaac
acgcctacagcaaagacggcggcctggcggtgctctacggtaactttgcggaaaacggctgc
atcgtgaaaacggcaggcgtcgatgacagcatcctcaaattcaccggcccggcgaaagtgta
cgaaagccaggacgatgcggtagaagcgattctcggcggtaaagttgtcgccggagatgtgg
tagtaattcgctatgaaggcccgaaaggcggtccggggatgcaggaaatgctctacccaacc
agcttcctgaaatcaatgggtctcggcaaagcctgtgcgctgatcaccgacggtcgtttctc
tggtggcacctctggtctttccatcggccacgtctcaccggaagcggcaagcggcggcagca
ttggcctgattgaagatggtgacctgatcgctatcgacatcccgaaccgtggcattcagtta
caggtaagcgatgccgaactggcggcgcgtcgtgaagcgcaggacgctcgaggtgacaaagc
ctggacgccgaaaaatcgtgaacgtcaggtctcctttgccctgcgtgcttatgccagcctgg
caaccagcgccgacaaaggcgcggtgcgcgataaatcgaaactggggggttaa
```

FIGURE 24 ilvA: (*E.coli*) (SEQ ID NO:47)
atggctgactcgcaacccctgtccggtgctccggaaggtgccgaatatttaagagcagtgct
gcgcgcgccggtttacgaggcggcgcaggttacgccgctacaaaaaatggaaaaactgtcgt
cgcgtcttgataacgtcattctggtgaagcgcgaagatcgccagccagtgcacagctttaag
ctgcgcggcgcatacgccatgatggcgggcctgacggaagaacagaaagcgcacggcgtgat
cactgcttctgcgggtaaccacgcgcagggcgtcgcgttttcttctgcgcggttaggcgtga
aggccctgatcgttatgccaaccgccaccgccgacatcaaagtcgacgcggtgcgcggcttc
ggcggcgaagtgctgctccacggcgcgaactttgatgaagcgaaagccaaagcgatcgaact
gtcacagcagcaggggttcacctggtgccgccgttcgaccatcgatggtgattgccgggc
aaggcacgctggcgctggaactgctccagcaggacgcccatctcgaccgcgtatttgtgcca
gtcggcggcggcggtctggctgctggcgtggcggtgctgatcaaacaactgatgccgcaaat
caaagtgatcgccgtagaagcggaagactccgcctgcctgaaagcagcgctggatgcgggtc
atccggttgatctgccgcgcgtagggctatttgctgaaggcgtagcggtaaaacgcatcggt
gacgaaaccttccgtttatgccaggagtatctcgacgacatcatcaccgtcgatagcgatgc
gatctgtgcggcgatgaaggatttattcgaagatgtgcgcgcggtggcggaaccctctggcg
cgctggcgctggcgggaatgaaaaaatatatcgccctgcacaacattcgcggcgaacggctg
gcgcatattctttccggtgccaacgtgaacttccacggcctgcgctacgtctcagaacgctg
cgaactgggcgaacagcgtgaagcgttgttggcggtgaccattccggaagaaaaaggcagct
tcctcaaattctgccaactgcttggcggcgttcggtcaccgagttcaactaccgttttgcc
gatgccaaaaacgcctgcatctttgtcggtgtgcgcctgagccgcggcctcgaagagcgcaa
agaaattttgcagatgctcaacgacgcggctacagcgtggttgatctctccgacgacgaaa
tggcgaagctacacgtgcgctatatggtcggcggacgtccatcgcatccgttgcaggaacgc
ctctacagcttcgaattcccggaatcaccgggcgcgctgctgcgcttcctcaacacgctggg
tacgtactggaacatttctttgttccactatcgcagccatggcaccgactacggcgcgtac
tggcggcgttcgaacttggcgaccatgaaccggatttcgaaaccggctgaatgagctgggc
tacgattgccacgacgaaaccaataacccggcgttcaggttcttttggcgggttag

FIGURE 25

*leuA*: (SEQ ID NO:49)
atgagccagcaagtcattattttcgataccacattgcgcgacggtgaacaggcgttacaggc
aagcttgagtgtgaaagaaaaactgcaaattgcgctggcccttgagcgtatgggtgttgacg
tgatggaagtcggtttccccgtctcttcgccgggcgattttgaatcggtgcaaaccatcgcc
cgccaggttaaaaacagccgcgtatgtgcgttagctcgctgcgtggaaaagatatcgacgt
ggcggccgaatccctgaaagtcgccgaagccttccgtattcatacctttattgccacttcgc
caatgcacatcgccaccaagctgcgcagcacgctggacgaggtgatcgaacgcgctatctat
atggtgaaacgcgccgtaattacaccgatgatgttgaattttcttgcgaagatgccggggcg
tacacccattgccgatctggcgcgagtggtcgaagcggcgattaatgccggtgccaccacca
tcaacattccggacaccgtgggctacaccatgccgtttgagttcgccggaatcatcagcggc
ctgtatgaacgcgtgcctaacatcgacaaagccattatctccgtacatacccacgacgattt
gggcctggcggtcggaaactcactggcggcggtacatgccggtgcacgccaggtggaaggcg
caatgaacgggatcggcgagcgtgccggaaactgttcctggaagaagtcatcatggcgatc
aaagttcgtaaggatattctcaacgtccacaccgccattaatcaccaggagatatggcgcac
cagccagttagttagccagatttgtaatatgccgatcccggcaaacaaagccattgttggca
gcggcgcattcgcacactcctccggtatacaccaggatggcgtgctgaaaaaccgcgaaaac
tacgaaatcatgacaccagaatctattggtctgaaccaaatccagctgaatctgacctctcg
ttcggggcgtgcggcggtgaaacatcgcatggatgagatggggtataagaaagtgaatata
atttagacaatttgtacgatgctttcctgaagctggcggacaaaaaaggtcaggtgtttgat
tacgatctggaggcgctggccttcatcggtaagcagcaagaagagccggagcatttccgtct
ggattacttcagcgtgcagtctggctctaacgatatcgccaccgccgccgtcaaactggcct
gtggcgaagaagtcaaagcagaagccgccaacggtaacggtccggtcgatgccgtctatcag
gcaattaaccgcatcactgaatataacgtcgaactggtgaaatacagcctgaccgccaaagg
ccacggtaaagatgcgctgggtcaggtggatatcgtcgctaactacaacggtcgccgcttcc
acggcgtcggcctggctaccgatattgtcgagtcatctgccaaagccatggtgcacgttctg
aacaatatctggcgtgccgcagaagtcgaaaagagttgcaacgcaaagctcaacacaacga
aaacaacaaggaaaccgtgtga

FIGURE 26

*leuB*: (SEQ ID NO:51)
gtgatgtcgaagaattaccatattgccgtattgccgggggacggtattggtccggaagtgat
gacccaggcgctgaaagtgctggatgccgtgcgcaaccgctttgcgatgcgcatcaccacca
gccattacgatgtaggcggcgcagccattgataaccacgggcaaccactgccgcctgcgacg
gttgaaggttgtgagcaagccgatgccgtgctgtttggctcggtaggcggcccgaagtggga
acatttaccaccagaccagcaaccagaacgcggcgcgctgctgcctctgcgtaagcacttca
aattattcagcaacctgcgcccggcaaaactgtatcaggggctggaagcattctgtccgctg
cgtgcagacattgccgcaaacggcttcgacatcctgtgtgtgcgcgaactgaccggcggcat
ctatttcggtcagccaaaaggccgcgaaggtagcggacaatatgaaaagcctttgataccg
aggtgtatcaccgttttgagatcgaacgtatcgcccgcatcgcgtttgaatctgctcgcaag
cgtcgccacaaagtgacgtcgatcgataaagccaacgtgctgcaatcctctattttatggcg
ggagatcgttaacgagatcgccacggaatacccggatgtcgaactggcgcatatgtacatcg
acaacgccaccatgcagctgattaaagatccatcacagtttgacgttctgctgtgctccaac
ctgtttggcgacattctgtctgacgagtgcgcaatgatcactggctcgatggggatgttgcc
ttccgccagcctgaacgagcaaggttttggactgtatgaaccggcgggcggctcggccag
atatcgcaggcaaaaacatcgccaacccgattgcacaaatcctttcgctggcactgctgctg
cgttacagcctggatgccgatgatgcggcttgcgccattgaacgcgccattaaccgcgcatt
agaagaaggcattcgcaccggggattagcccgtggcgctgccgccgttagtaccgatgaaa
tgggcgatatcattgcccgctatgtagcagaaggggtgtaa

FIGURE 27

*leuC*: (SEQ ID NO:53)
atggctaagacgttatacgaaaaattgttcgacgctcacgttgtgtacgaagccgaaaacga
aaccccactgttatatatcgaccgccacctggtgcatgaagtgacctcaccgcaggcgttcg
atggtctgcgcgcccacggtcgcccggtacgtcagccgggcaaaaccttcgctaccatggat
cacaacgtctctacccagaccaaagacattaatgcctgcggtgaaatggcgcgtatccagat
gcaggaactgatcaaaaactgcaagaatttggcgtcgaactgtatgacctgaatcacccgt
atcaggggatcgtccacgtaatggggccggaacagggcgtcaccttgccggggatgaccatt
gtctgcggcgactcgcataccgccacccacggcgcgtttggcgcactggcctttggtatcgg
cacttccgaagttgaacacgtactggcaacgcaaaccctgaaacagggccgcgcaaaaacca
tgaaaattgaagtccagggcaaagccgcgccgggcattaccgcaaaagatatcgtgctggca
attatcggtaaaaccggtagcgcaggcggcaccgggcatgtggtggagttttgcggcgaagc
aatccgtgatttaagcatggaaggtcgtatgaccctgtgcaatatggcaatcgaaatgggcg
caaaagccggtctggttgcaccggacgaaaccaccttaactatgtcaaaggccgtctgcat
gcgccgaaaggcaaagatttcgacgacgccgttgcctactggaaaaccctgcaaaccgacga
aggcgcaactttcgataccgttgtcactctgcaagcagaagaaatttcaccgcaggtcacct
ggggcaccaatcccggccaggtgatttccgtgaacgacaatattcccgatccggcttcgttt
gccgatccggttgaacgcgcgtcggcagaaaagcgctggcctatatggggctgaaaccggg
tattccgctgaccgaagtggctatcgacaaagtgtttatcggttcctgtaccaactcgcgca
ttgaagatttacgcgcggcagcggagatcgccaaggggcgaaaagtcgcgccaggcgtgcag
gcactggtggttcccggctctggcccggtaaaagcccaggcggaagcggaaggtctggataa
aatctttattgaagccggttttgaatggcgcttgcctggctgctcaatgtgtctggcgatga
acaacgaccgtctgaatccgggcgaacgttgtgcctccaccagcaaccgtaactttgaaggc
cgccaggggcgcggcgggcgcacgcatctggtcagcccggcaatggctgccgctgctgctgt
gaccggacatttcgccgacattcgcaacattaaataa

FIGURE 28

*leuD*: (SEQ ID NO:55)
atggcagagaaatttatcaaacacacaggcctggtggttccgctggatgccgccaatgtcga
taccgatgcaatcatcccgaaacagttttgcagaaagtgacccgtacgggttttggcgcgc
atctgtttaacgactggcgttttctggatgaaaaaggccaacagccaaacccggacttcgtg
ctgaacttcccgcagtatcagggcgcttccattttgctggcacgagaaacttcggctgtgg
ctcttcgcgtgagcacgcgcctgggcattgaccgactacggttttaaagtggtgattgcgc
cgagttttgctgacatcttctacggcaatagctttaacaaccagctgctgccggtgaaatta
agcgatgcagaagtggacgaactgtttgcgctggtgaaagctaatccggggatccatttcga
cgtggatctggaagcgcaagaggtgaaagcgggagagaaaacctatcgctttaccatcgatg
ccttccgccgccactgcatgatgaacggtctggacagtattgggcttaccttgcagcacgac
gacgccattgccgcttatgaagcaaaacaacctgcgtttatgaattaa

FIGURE 29

*cimA (Methanocaldococcus jannaschii)*: (SEQ ID NO:57)
atgatggtaaggatatttgatacaacacttagagatggagagcaaacaccaggagtttcttt
aacaccaaatgataagttagagatagcaaaaaaattggatgagcttggagttgatgttatag
aggcaggttcagctataacttcaaaaggagagagagaaggaataaaattaataacaaaagaa
ggtttaaatgcagaaatctgctcatttgttagagctttacctgtagatattgatgctgcctt
agaatgtgatgtagatagtgtccatttagtagtgccaacatctccaatacacatgaaatata
agcttagaaaaacagaagatgaggttttagagacagctttaaaggctgtagagtatgctaaa
gaacatggattgattgttgagttatctgcagaggatgcaacaagaagtgatgtaaatttctt
aataaaactatttaatgaaggggaaaaggttggagcagacagagtttgtgtttgtgacacag
taggagttttaactccacaaaagagtcaggaattatttaaaaaaataactgaaaatgttaat
ttaccggtctcagttcattgccacaacgactttggaatggctactgctaatacttgctcagc
agttttaggtggagctgttcagtgccacgtaacagttaatggtattggagagagagcaggaa
atgcctcattggaagaggttgttgctgctttaaaaatactctatggctatgatactaagata
aagatggaaaagttatatgaggtttcaagaattgtctcaagattgatgaaacttcctgttcc
accaaataaagcaattgttggggacaatgcatttgctcatgaagcaggaatacatgttgatg
gattaataaaaaatactgaaacctatgagccaataaaaccagaaatggttgggaatagaaga
agaattattttgggtaagcattctggtagaaaagctttaaaatacaaacttgatttgatggg
cataaacgttagtgatgagcaattaaataaaatatatgaaagagttaagaatttggggatt
tgggtaaatacatttcagacgctgatttgttggctatagttagagaagttactggaaaattg
gtagaagagaaaatcaaattagatgaattaactgttgtatctggaaataaaataacaccaat
tgcatctgttaaactccattataaggagaagatataactttaatagaaactgcttatggtg
ttggaccggtagatgcagcaataaatgctgtgagaaaggcaataagtggagttgcagatatt
aagttggtagagtatagagttgaagcaattggtggaggaactgatgcgttaatagaggttgt
tgttaaattaagaaaaggaactgaaattgttgaagttagaaaatcagacgctgatataataa
gggcttctgtagatgctgtaatggaaggaatcaatatgttattgaattaa

FIGURE 30

*ilvM*: (SEQ ID NO:59)
atgatgcaacatcaggtcaatgtatcggctcgcttcaatccagaaaccttagaacgtgtttt
acgcgtggtgcgtcatcgtggtttccacgtctgctcaatgaatatggccgccgccagcgatg
cacaaaatataaatatcgaattgaccgttgccagcccacggtcggtcgacttactgtttagt
cagttaaataaactggtggacgtcgcacacgttgccatctgccagagcacaaccacatcaca
acaaatccgcgcctga

FIGURE 31

*ilvG*: (SEQ ID NO:61)
ttgttgttaaaacaactgtcggatcgtaaacctgcggattgcgtcgtgaccacagatgtggg
gcagcaccagatgtgggctgcgcagcacatcgcccacactcgcccggaaaatttcatcacct
ccagcggtttaggtaccatgggttttggtttaccggcggcggttggcgcacaagtcgcgcga
ccgaacgataccgttgtctgtatctccggtgacggctctttcatgatgaatgtgcaagagct
gggcaccgtaaaacgcaagcagttaccgttgaaaatcgtcttactcgataaccaacggttag
ggatggttcgacaatggcagcaactgttttttcaggaacgatacagcgaaaccacccttact
gataacccgatttcctcatgttagccagcgccttcggcatccatggccaacacatcacccg
gaaagaccaggttgaagcggcactcgacaccatgctgaacagtgatgggccatacctgcttc
atgtctcaatcgacgaacttgagaacgtctggccgctggtgccgcctggcgccagtaattca
gaaatgttggagaaattatcatga

FIGURE 32

*ilvN*: (SEQ ID NO:63)
atgcaaaacacaactcatgacaacgtaattctggagctcaccgttcgcaaccatccgggcgt
aatgacccacgtttgtggccttttttgcccgccgcgcttttaacgttgaaggcattctttgtc
tgccgattcaggacagcgacaaaagccatatctggctactggtcaatgacgaccagcgtctg
gagcagatgataagccaaatcgataagctggaagatgtcgtgaaagtgcagcgtaatcagtc
cgatccgacgatgtttaacaagatcgcggtgttttttcagtaa

FIGURE 33 ilvB: (SEQ ID NO:65)
atggcaagttcgggcacaacatcgacgcgtaagcgctttaccggcgcagaatttatcgttca
tttcctggaacagcagggcattaagattgtgacaggcattccgggcggttctatcctgcctg
tttacgatgccttaagccaaagcacgcaaatccgccatattctggcccgtcatgaacagggc
gcgggctttatcgctcagggaatggcgcgcaccgacggtaaaccggcggtctgtatggcctg
tagcggaccgggtgcgactaacctggtgaccgccattgccgatgcgcggctggactccatcc
cgctgatttgcatcactggtcaggttccgcctcgatgatcggcaccgacgccttccaggaa
gtggacacctacggcatctctatccccatcaccaaacacaactatctggtcagacatatcga
agaactcccgcaggtcatgagcgatgccttccgcattgcgcaatcaggccgcccaggcccgg
tgtggatagacattcctaaggatgtgcaaacggcagttttgagattgaaacacagcccgct
atggcagaaaaagccgccgccccgcctttagcgaagaaagcattcgtgacgcagcggcgat
gattaacgctgccaaacgcccggtgctttatctgggcggcggtgtgatcaatgcgcccgcac
gggtgcgtgaactggcggagaaagcgcaactgcctaccaccatgactttaatggcgctgggc
atgttgccaaaagcgcatccgttgtcgctgggtatgctggggatgcacggcgtgcgcagcac
caactatattttgcaggaggcggatttgttgatagtgctcggtgcgcgttttgatgaccggg
cgattggcaaaaccgagcagttctgtccgaatgccaaaatcattcatgtcgatatcgaccgt
gcagagctgggtaaaatcaagcagccgcacgtggcgattcaggcggatgttgatgacgtgct
ggcgcagttgatcccgctggtggaagcgcaaccgcgtgcagagtggcaccagttggtagcgg
atttgcagcgtgagtttccgtgtccaatcccgaaagcgtgcgatccgttaagccattacggc
ctgatcaacgccgttgccgcctgtgtcgatgacaatgcaattataccaccgacgttggtca
gcatcagatgtggaccgcgcaagcttatccgctcaatcgcccacgccagtggctgacctccg
gtgggctgggcacgatgggttttggcctgcctgcggcgattggcgctgcgctggcgaacccg
gatcgcaaagtgttgtgtttctccggcgacggcagcctgatgatgaatattcaggagatggc
gaccgccagtgaaaatcagctggatgtcaaaatcattctgatgaacaacgaagcgctggggc
tggtgcatcagcaacagagtctgttctacgagcaaggcgttttgccgccacctatccgggc
aaaatcaactttatgcagattgccgccggattcggcctcgaaacctgtgatttgaataacga
agccgatccgcaggcttcattgcaggaaatcatcaatcgccctggcccggcgctgatccatg
tgcgcattgatgccgaagaaaaagtttacccgatggtgccgccaggtgcggcgaatactgaa
atggtgggggaataa

*adhE2 (Clostridium acetobutylicum)*: (SEQ ID NO:67)
atgaaagttacaaatcaaaagaactaaaacaaaagctaaatgaattgagagaagcgcaaaa
gaagtttgcaacctatactcaagagcaagttgataaaattttaaacaatgtgccatagccg
cagctaaagaaagaataaacttagctaaattagcagtagaagaaacaggaataggtcttgta
gaagataaaattataaaaatcatttcgcagcagaatatatatacaataaatataaaaatga
aaaaacttgtggcataatagaccatgacgattctttaggcataacaaaggttgctgaaccaa
ttggaattgttgcagccatagttcctactactaatccaacttccacagcaattttcaaatca
ttaatttcttttaaaaacaagaaacgcaatattcttttcaccacatccacgtgcaaaaaatc
tacaattgctgcagcaaaattaattttagatgcagctgttaaagcaggagcacctaaaaata
taataggctggatagatgagccatcaatagaactttctcaagatttgatgagtgaagctgat
ataatattagcaacaggaggtccttcaatggttaaagcggcctattcatctggaaaacctgc
aattggtgttggagcaggaaatacaccagcaataatagatgagagtgcagatatagatatgg
cagtaagctccataatttatcaaagacttatgacaatggagtaatatgcgcttctgaacaa
tcaatattagttatgaattcaatatacgaaaagttaaagaggaatttgtaaaacgaggatc
atatatactcaatcaaaatgaaatagctaaaataaaagaaactatgtttaaaaatggagcta
ttaatgctgacatagttggaaaatctgcttatataattgctaaaatggcaggaattgaagtt
cctcaaactacaaagatacttataggcgaagtacaatctgttgaaaaaagcgagctgttctc
acatgaaaaactatcaccagtacttgcaatgtataaagttaaggattttgatgaagctctaa
aaaaggcacaaaggctaatagaattaggtggaagtggacacacgtcatctttatatatagat
tcacaaaacaataaggataaagttaaagaatttggattagcaatgaaaacttcaaggacatt
tattaacatgccttcttcacagggagcaagcggagatttatacaattttgcgatagccat
catttactcttggatgcggcacttggggaggaaactctgtatcgcaaaatgtagagcctaaa
catttattaaatattaaaagtgttgctgaaagaagggaaaatatgctttggtttaaagtgcc
acaaaaaatatattttaaatatggatgtcttagatttgcattaaaagaattaaagatatga
ataagaaaagagcctttatagtaacagataaagatcttttttaaacttggatatgttaataaa
ataacaaaggtactagatgagatagatattaaatacagtatatttacagatattaaatctga
tccaactattgattcagtaaaaaaaggtgctaaagaaatgcttaactttgaacctgatacta
taatctctattggtggtggatcgccaatggatgcagcaaaggttatgcacttgttatatgaa
tatccagaagcagaaattgaaaatctagctataaacttatggatataagaaagagaatatg
caatttccctaaattaggtacaaaggcgatttcagtagctattcctacaactgctggtaccg
gttcagaggcaacacctttgcagttataactaatgatgaaacaggaatgaaatacccttta
acttcttatgaattgaccccaaacatggcaataatagatactgaattaatgttaaatatgcc
tagaaaattaacagcagcaactggaatagatgcattagttcatgctatagaagcatatgttt
cggttatggctacggattatactgatgaattagccttaagagcaataaaaatgatatttaaa
tatttgcctagagcctataaaaatgggactaacgacattgaagcaagagaaaaaatggcaca
tgcctctaatattgcggggatggcatttgcaaatgctttcttaggtgtatgccattcaatgg
ctcataaacttggggcaatgcatcacgttccacatggaattgcttgtgctgtattaatagaa
gaagttattaaatataacgctacagactgtccaacaaagcaaacagcattccctcaatataa
atctcctaatgctaagagaaaatatgctgaattgcagagtatttgaatttaaagggtacta
gcgataccgaaaggtaacagccttaatagaagctatttcaaagttaaagatagatttgagt
attccacaaaatataagtgccgctggaataaataaaaagatttttataatacgctagataa
aatgtcagagcttgcttttgatgaccaatgtacaacagctaatcctaggtatccacttataa
gtgaacttaaggatatctatataaaatcattttaa

FIGURE 35

Li-*cimA* (*Leptospira interrogans*): (SEQ ID NO:69)
atgacaaaagtagaaactcgattggaaatttagacgtaactttgagagacggggagcagac
cagaggggtcagtttttccacttccgaaaaactaaatatcgcaaaatttctattacaaaaac
taaatgtagatcgggtagagattgcgtctgcaagagtttctaaggggaattggaaacggtc
caaaaaatcatggaatgggctgcaacagaacagcttacggaaagaatcgaaatcttaggttt
tgtagacgggaataaaaccgtagattggatcaaagatagtgggctaaggttttaaatctttt
tgactaagggatcgcttcatcatttagaaaaacaattaggcaaaactccgaaagaattcttt
acagacgtttcttttgtaatagaatacgcgatcaaaagcggacttaaaataaacgtatattt
agaagattggtccaacggtttcagaaacagtccagattacgtcaatcgctcgtagaacatc
taagtaaagaacatatagaagaattttctcttccagacacgttaggcgttctttcgccagaa
gagacgtttcaaggagtggattcactcattcaaaaatacccggatattcattttgaatttca
cggacataacgactacgatctttccgtggcaaatagtcttcaagcgattcgtgccggagtca
aaggtcttcacgcttctataaatggtctcggagaaagagccggaaatactccgttggaagca
ctcgtaaccacgattcatgataagtctaactctaaaacgaacataaacgaaattgcaattac
ggaagcaagccgtcttgtagaagtattcagcggaaaaagaatttctgcaaatagaccgatcg
taggagaagacgtgtttactcagaccgcgggagtacacgcagacggagacaaaaaggaaat
ttatacgcaaatcctattttaccggaaagatttggtaggaaaagaagttacgcgttaggcaa
acttgcaggtaaggcgagtatctccgaaaatgtaaaacaactcggaatggttttaagtgaag
tggttttacaaaaggttttagaaagggtgatcgaattaggagatcagaataaactagtgaca
cctgaagatcttccatttatcattgcggacgtttctggaagaaccggagaaaaggtacttac
aatcaaatcttgtaatattcattccggaattggaattcgtcctcacgcacaaattgaattgg
aatatcagggaaagattcataaggaaatttctgaaggagacggagggtatgatgcgtttatg
aatgcacttactaaaattacgaatcgcctcggtattagtattcctaaattgatagattacga
agtaaggattcctcctggtggaaaaacagatgcacttgtagaaactaggatcacctggaaca
agtccttagatttagaagaggaccagactttcaaaacgatgggagttcatccggatcaaacg
gttgcagcggttcatgcaactgaaaagatgctcaatcaaattctacaaccatggcaaatcta
a

FIGURE 36

Li-*leuC* (*Leptospira interrogans*): (SEQ ID NO:71)
atgaagacaatgttcgaaaaaatttgggaagatcatctagtcggagaactagatgctggatc
ctatctaatctatatagatcgccatctcattcatgaagttacaagtcctcaggcgtttgaag
gacttaaacttgcaggcagaaaggttcgtcgtcctgaagctacttttgccacaatggatcat
aacgtttctactagaacacgtgatttaagtctggccgatcctgtttccgcaattcaaatgca
gactttaaaaaagaactgcgacgaaaacggaatccgcgtttatgattttcaaaccctgacc
aaggaatcattcacgtaatcgctcctgaaatgggactgactcatcctggaatgacaatcgta
tgcggagattctcatacttctacacacggtgcgtttggtgcgcttgctttcgggatcggaac
cagcgaagtagagcacgttcttgcgactcaaaccttagttcaaaaagagcaaaaacaatgg
agattagagtcgatggaaaactttccgataaggtcacagcaaaagacatcattcttgcgatc
attggaaaaattggaaccgcaggtgcgacaggttatgtgatcgaatatagaggttctgcaat
tcaagccctcagtatggaagctagaatgactatttgtaatatgtctatcgaagcgggagcta
gagcaggtttaatcgcaccagatgaaactacttttaattatattcaaggaaaggacttttct
ccaaaaggagtcgaatgggatcttgcggtcaaaaaatggaaacactatgtaacggacgaagg
tgctaaatttgatagaaccgtaattcttcatgcagatgaaatcgctcctatggtaacttggg
gaacttctcccagtcaggttgtttcgataaaggagtcgttccagatccaaaagatgcaaat
gatccggtggaaaaaattggaattgagtctgcgcttaaatatatggatctcaatcgggcca
gaagatagaagacatttcaattaataaagtgtttatcggttcctgtactaattctagaatcg
aagatttaagagcggccgctgctaccgtaaaggaaaaaaagtttcctctaaggttcaggcg
attgtggttcccggttcaggcagagtcaaacgtcaggcggaacaagaaggtctggataaaat
tttaccgcggccggttttgaatggagaaatccaggctgttctatgtgtcttgcgatgaacg
acgacgtattagaaccgggagatcgttgtgcttctacttctaaccgaaactttgaaggtcgt
caaggaaaaggtggaagaacccatctagtaggaccggaaatggccgccgccgcggctatcga
aggccattttgtggatattcgaaactggaaataa

FIGURE 37

Li-*leuD* (*Leptospira interrogans*): (SEQ ID NO:73)
Atgaaaccctttactatattaaatggaattgccgccttactggacagacccaacgtggatac
ggatcagatcattccaaaacaatttttacggaagatagaacgaaccggtttcggagttcatc
tgtttcacgattggagatacttagacgacgcgggtaccaaactcaatcctgatttttccctc
aatcaagaacgatataagggagcttctatccttatcaccagagataactttggttgtggatc
ttccagagaacacgctccttgggctttagaagactacgggtttagggcaatcattgctcctt
cttacgcggatatttttttcaacaactgctttaaaaacggaatgcttccagtcattttaaaa
tcggaagaagtagaagagctgttccatttggtttcgactaacgtaggagcgaaagtcatagt
ggatctggacaaacaaactgtaaccggaccgactggaaaaatatattattttgaagtggatt
cttttcgtaaatactgtctttataacggacttgatgacataggtctaactctaaaacaagaa
agtaaaattggagagtttgaaaaaaagcagaaagaagttgaaccttggttatacgccatata
a

FIGURE 38

Li-*leuB* (*Leptospira interrogans*): (SEQ ID NO:75)
atgaagaatgtagcagtactttcaggagacggaatcggaccggaagtcatggagatagccat
ctccgttttgaaaaaggctctcggtgcaaaagtttccgagtttcaatttaaagaaggatttg
taggtggaatcgcaatcgataaaactggacacccacttccaccggaaactcttaaactatgt
gaagaatcttccgcaattcttttcggaagtgtgggaggtcctaaatgggaaacactccctcc
ggaaaaacaaccggaacgaggggcacttctacctttgagaaaacattttgatctatttgcaa
acttaagacctgcgatcatttatccagagttgaaaaatgcttctccagttcgttctgatatt
attggaaacggattagatattctcatattaagagagttaaccggaggaatttattttggaca
accaaaaggaagagaaggatcaggtcaggaagaatttgcatacgacacgatgaagtattcca
gaagagaaatcgaaaggattgctaaagtcgcattccaggcggccagaaaaagaaataataaa
gtgactagtatcgataaagcaaacgtcttgactacttccgtttttggaaggaagtagtaat
cgaattgcataagaaagaattttcagacgtccaattgaatcatctttatgtggacaatgcgg
cgatgcagttaatcgtaaatccgaaacaattcgacgtggttctttgtgagaatatgtttggt
gatattctttcggacgaggcttccatcattacgggttcaatcggaatgcttccttctgcctc
tctttccgaatctggatttggattgtatgaaccttctggtggttctgcgccggacatagccg
gaaaaggagtggcaaatccgattgctcaagtattgagtgcggcgttgatgttacgttattct
ttttctatggaagaagaagcaaacaagatagaaaccgccgtgcgtaaaacgattgcctccgg
aaaaagaaccagagacatagcggaagtaggatctacgatcgtaggaactaaagaaatcggtc
aattgatcgaatcctttctctaa

FIGURE 39

*pheA*: (SEQ ID NO:77)
atgacatcggaaaacccgttactggcgctgcgagagaaaatcagcgcgctggatgaaaaatt
attagcgttactggcagaacggcgcgaactggccgtcgaggtgggaaaagccaaactgctct
cgcatcgcccggtacgtgatattgatcgtgaacgcgatttgctggaaagattaattacgctc
ggtaaagcgcaccatctggacgcccattacattactcgcctgttccagctcatcattgaaga
ttccgtattaactcagcaggctttgctccaacaacatctcaataaaattaatccgcactcag
cacgcatcgcttttctcggccccaaaggttcttattcccatcttgcggcgcgccagtatgct
gcccgtcactttgagcaattcattgaaagtggctgcgccaaatttgccgatatttttaatca
ggtggaaaccggccaggccgactatgccgtcgtaccgattgaaaataccagctccggtgcca
taaacgacgtttacgatctgctgcaacataccagcttgtcgattgttggcgagatgacgtta
actatcgaccattgtttgttggtctccggcactactgatttatccaccatcaatacggtcta
cagccatccgcagccattccagcaatgcagcaaattccttaatcgttatccgcactggaaga
ttgaatataccgaaagtacgtctgcggcaatggaaaaggttgcacaggcaaaatcaccgcat
gttgctgcgttgggaagcgaagctggcggcactttgtacggtttgcaggtactggagcgtat
tgaagcaaatcagcgacaaaacttcacccgatttgtggtgttggcgcgtaaagccattaacg
tgtctgatcaggttccggcgaaaaccacgttgttaatggcgaccgggcaacaagccggtgcg
ctggttgaagcgttgctggtactgcgcaaccacaatctgattatgacccgtctggaatcacg
cccgattcacggtaatccatgggaagagatgttctatctggatattcaggccaatcttgaat
cagcggaaatgcaaaaagcattgaaagagttaggggaaatcacccgttcaatgaaggtattg
ggctgttacccaagtgagaacgtagtgcctgttgatccaacctga

FIGURE 40

TyrA: (SEQ ID NO:79)
atggttgctgaattgaccgcattacgcgatcaaattgatgaagtcgataaagcgctgctgaa
tttattagcgaagcgtctggaactggttgctgaagtgggcgaggtgaaaagccgctttggac
tgcctatttatgttccggagcgcgaggcatctatgttggcctcgcgtcgtgcagaggcggaa
gctctgggtgtaccgccagatctgattgaggatgttttgcgtcgggtgatgcgtgaatctta
ctccagtgaaaacgacaaaggatttaaaacactttgtccgtcactgcgtccggtggttatcg
tcggcggtggcggtcagatgggacgcctgttcgagaagatgctgaccctctcgggttatcag
gtgcggattctggagcaacatgactgggatcgagcggctgatattgttgccgatgccggaat
ggtgattgttagtgtgccaatccacgttactgagcaagttattggcaaattaccgcctttac
cgaaagattgtattctggtcgatctggcatcagtgaaaaatgggccattacaggccatgctg
gtggcgcatgatggtccggtgctggggctacacccgatgttcggtccggacagcggtagcct
ggcaaagcaagttgtggtctggtgtgatggacgtaaaccggaagcataccaatggtttctgg
agcaaattcaggtctggggcgctcggctgcatcgtattagcgccgtcgagcacgatcagaat
atggcgtttattcaggcactgcgccactttgctacttttgcttacgggctgcacctggcaga
agaaaatgttcagcttgagcaacttctggcgctctcttcgccgatttaccgccttgagctgg
cgatggtcgggcgactgtttgctcaggatccgcagctttatgccgacatcattatgtcgtca
gagcgtaatctggcgttaatcaaacgttactataagcgtttcggcgaggcgattgagttgct
ggagcagggcgataagcaggcgtttattgacagtttccgcaaggtggagcactggttcggcg
attacgcacagcgttttcagagtgaaagccgcgtgttattgcgtcaggcgaatgacaatcgc
cagtaa

FIGURE 41

*alsS*: acetolactate synthase (*Bacillus subtilis subsp. subtilis*) (SEQ ID NO: 81)
atgttgacaaaagcaacaaaagaacaaaaatcccttgtgaaaaacagaggggcggagcttgt
tgttgattgcttagtggagcaaggtgtcacacatgtatttggcattccaggtgcaaaaattg
atgcggtatttgacgctttacaagataaaggacctgaaattatcgttgcccggcacgaacaa
aacgcagcattcatggcccaagcagtcggccgtttaactggaaaaccgggagtcgtgttagt
cacatcaggacccgggtgcctctaacttggcaacaggcctgctgacagcgaacactgaaggag
accctgtcgttgcgcttgctggaaacgtgatccgtgcagatcgtttaaaacggacacatcaa
tctttggataatgcggcgctattccagccgattacaaaatacagtgtagaagttcaagatgt
aaaaaatataccggaagctgttacaaatgcatttaggatagcgtcagcagggcaggctgggg
ccgcttttgtgagctttccgcaagatgttgtgaatgaagtcacaaatacgaaaaacgtgcgt
gctgttgcagcgccaaaactcggtcctgcagcagatgatgcaatcagtgcggccatagcaaa
aatccaaacagcaaaacttcctgtcgttttggtcggcatgaaaggcggaagaccggaagcaa
ttaaagcggttcgcaagcttttgaaaaggttcagcttccatttgttgaaacatatcaagct
gccggtaccctttctagagatttagaggatcaatattttggccgtatcggtttgttccgcaa
ccagcctggcgatttactgctagagcaggcagatgttgttctgacgatcggctatgacccga
ttgaatatgatccgaaattctggaatatcaatggagaccggacaattatccatttagacgag
attatcgctgacattgatcatgcttaccagcctgatcttgaattgatcggtgacattccgtc
cacgatcaatcatatcgaacacgatgctgtgaaagtggaatttgcagagcgtgagcagaaaa
tcctttctgatttaaaacaatatatgcatgaaggtgagcaggtgcctgcagattggaaatca
gacagagcgcaccctcttgaaatcgttaaagagttgcgtaatgcagtcgatgatcatgttac
agtaacttgcgatatcggttcgcacgccatttggatgtcacgttatttccgcagctacgagc
cgttaacattaatgatcagtaacggtatgcaaacactcggcgttgcgcttccttgggcaatc
ggcgcttcattggtgaaaccgggagaaaagtggtttctgtctctggtgacggcggtttctt
attctcagcaatggaattagagacagcagttcgactaaaagcaccaattgtacacattgtat
ggaacgacagcacatatgacatggttgcattccagcaattgaaaaaatataaccgtacatct
gcggtcgatttcggaaatatcgatatcgtgaaatatgcggaaagcttcggagcaactggctt
gcgcgtagaatcaccagaccagctggcagatgttctgcgtcaaggcatgaacgctgaaggtc
ctgtcatcatcgatgtcccggttgactacagtgataacattaatttagcaagtgacaagctt
ccgaaagaattcggggaactcatgaaaacgaaagctctctag

FIGURE 42

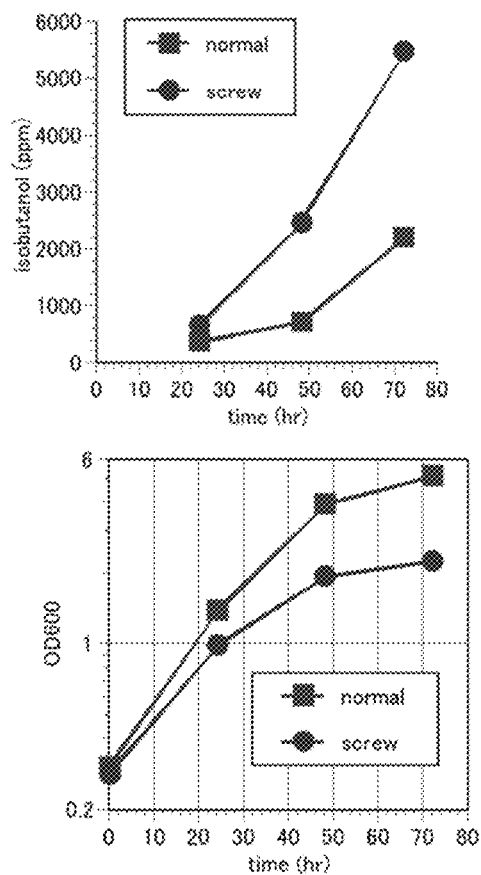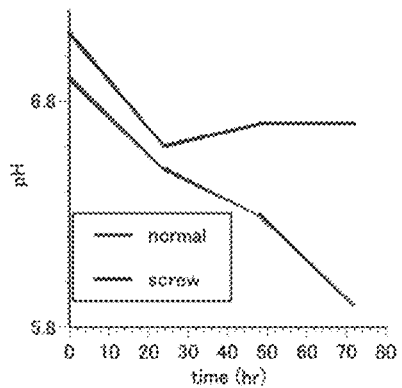
pSA55; $P_L$lacO$_1$::kivd-ADH2 (ColE1)
pSA69:: $P_L$lacO1::alsS (Bacillus)-ilvCD (E.coli) (p15A)
JCL260:: JCL88+$\Delta pflB$
SA237:: JCL260+pSA55&69
30C, 20 ml M9+3.6% glc
normal shake flask
screwcap shake flask
FIGURE 44 at 40 hr add glucose — 0.5 % yeast extracts
at 112 hr add fresh media & glucose — 2 % tryptone
— 0.8 % Casamino Acids Strain
SA237:: JCL260+pSA55&69
pSA55; $P_LlacO_1$::kivd-ADH2 (ColE1)
pSA69:: PLlacO1::alsS (Bacillus)-ilvCD (E.coli) (p15A)
JCL260:: JCL88+ΔpflB
Condition
30C, 20 ml M9+3.6% glc
•0.8% casamino acids,
•2% tryptone
•0.5% yeast extracts
screwcap shake flask

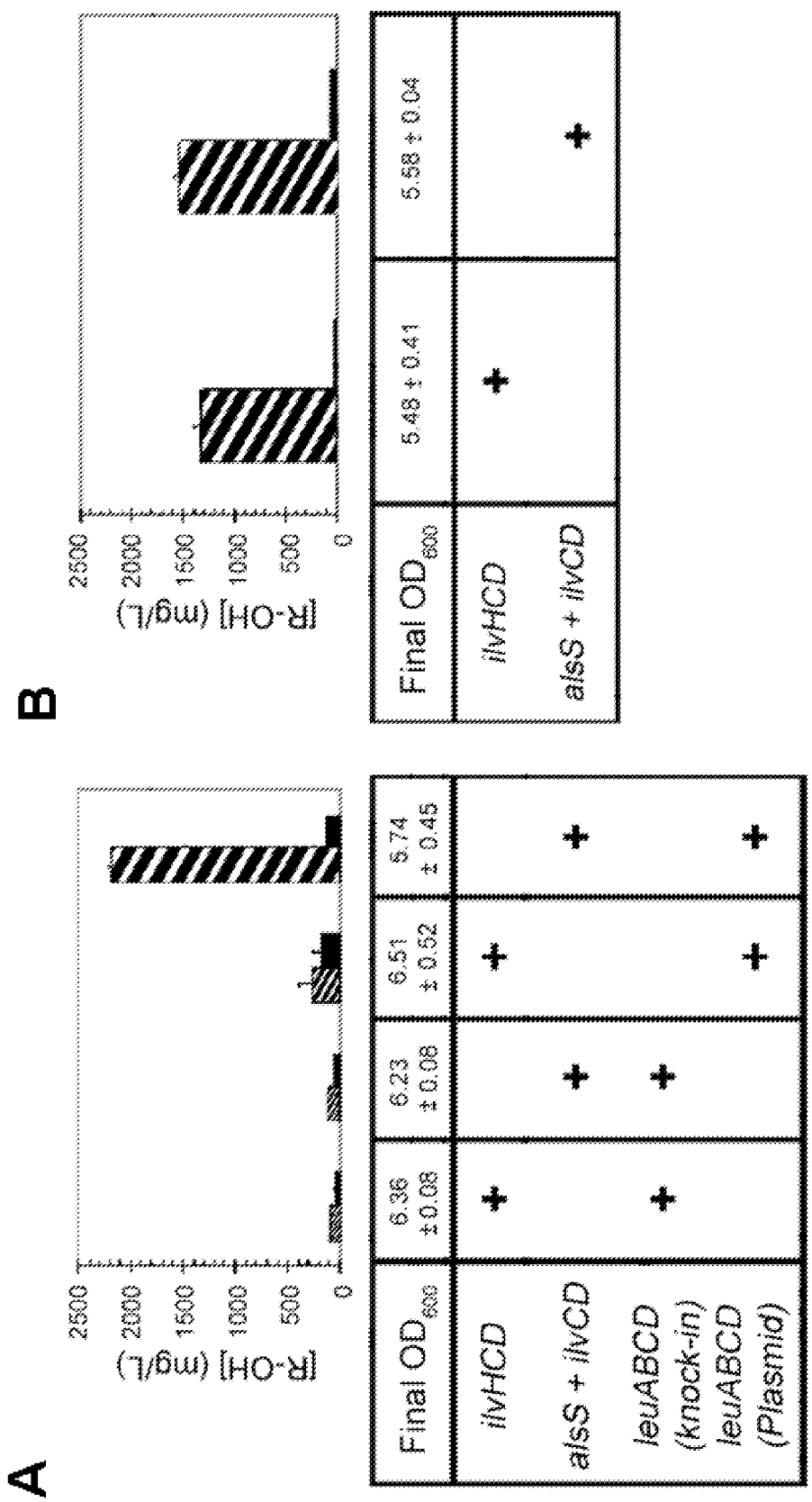
FIGURE 47A-B

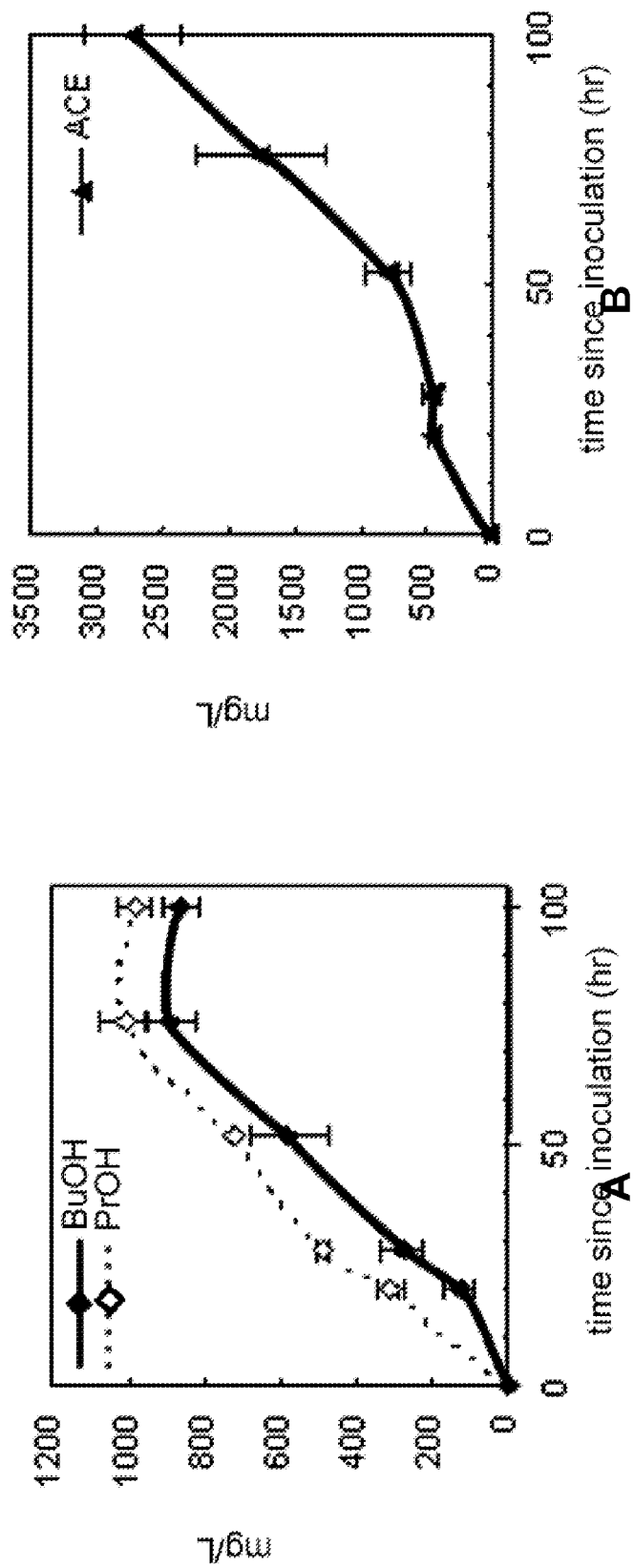
FIGURE 54A-B

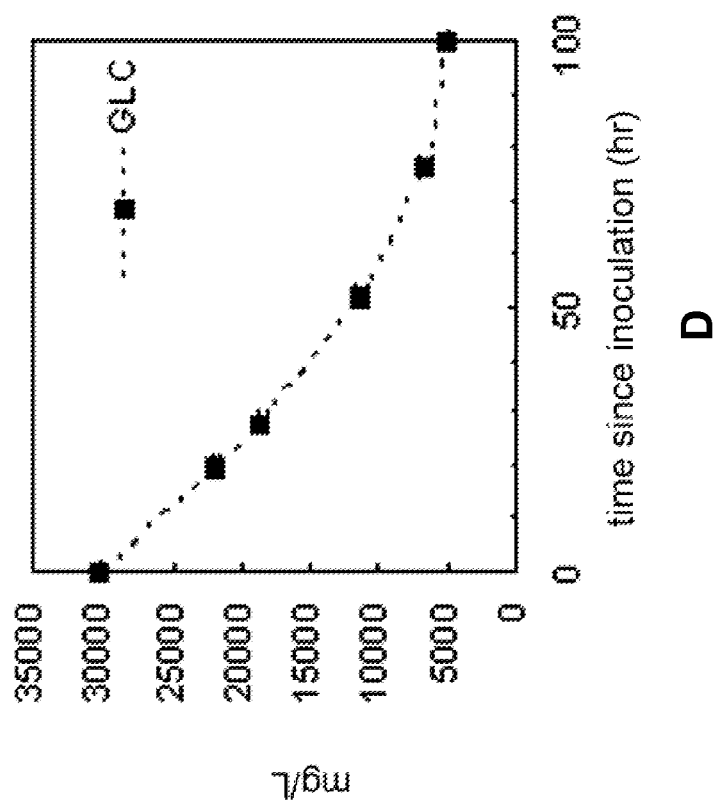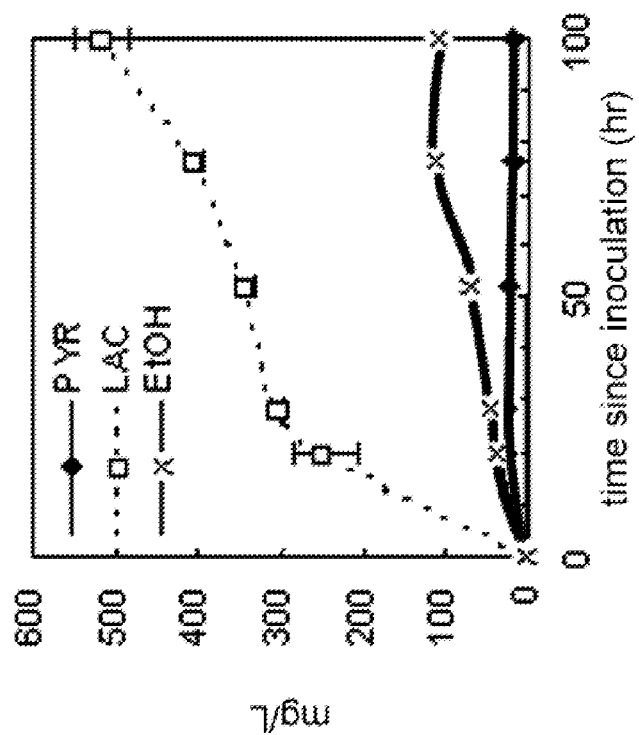
FIGURE 54C-D

SEQUENCE LISTING

<160> NUMBER OF SEQ ID NOS: 88

<210> SEQ ID NO 1
<211> LENGTH: 36
<212> TYPE: DNA

```
<213> ORGANISM: Artificial Sequence
<220> FEATURE:
<223> OTHER INFORMATION: Oligonucleotide Primer Sequence

<400> SEQUENCE: 1
cgagcggtac catgtctgaa attactcttg gaaaat                              36

<210> SEQ ID NO 2
<211> LENGTH: 37
<212> TYPE: DNA
<213> ORGANISM: Artificial Sequence
<220> FEATURE:
<223> OTHER INFORMATION: Oligonucleotide Primer Sequence

<400> SEQUENCE: 2
gcctgcgcat gcttattgtt tggcatttgt agcggca                             37

<210> SEQ ID NO 3
<211> LENGTH: 49
<212> TYPE: DNA
<213> ORGANISM: Artificial Sequence
<220> FEATURE:
<223> OTHER INFORMATION: Oligonucleotide Primer Sequence

<400> SEQUENCE: 3
gcctgcgcat gcaggagata taccatgtct attccagaaa ctcaaaaag               49

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide Primer Sequence

<400> SEQUENCE: 4
gctctagatt atttagaagt gtcaacaacg tat                                 33

<210> SEQ ID NO 5
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 5
acgcagtcga ctcaacgcat tattttatcg ccgcgc                              36

<210> SEQ ID NO 6
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 6
acgcagtcga cgaggaatca ccatggctaa ctactt                              36

<210> SEQ ID NO 7
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 7
aataacccgg gttaacccgc aacagcaata cgtttc                              36
```

<210> SEQ ID NO 8
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 8
cgagcacgcg tttaaccccc cagtttcgat ttatcg                         36

<210> SEQ ID NO 9
<211> LENGTH: 43
<212> TYPE: DNA
<213> ORGANISM: Artificial Sequence
<220> FEATURE:
<223> OTHER INFORMATION: Oligonucleotide Primer Sequence

<400> SEQUENCE: 9
gccaccggtc tccgtaccat ggagatgttg tctggagccg aga                 43

<210> SEQ ID NO 10
<211> LENGTH: 46
<212> TYPE: DNA
<213> ORGANISM: Artificial Sequence
<220> FEATURE:
<223> OTHER INFORMATION: Oligonucleotide Primer Sequence

<400> SEQUENCE: 10
ggctccggaa ggagatatac catgcctaag taccgttccg ccacca              46

<210> SEQ ID NO 11
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 11
cgagcggtac catgtataca gtaggagatt acctat                         36

<210> SEQ ID NO 12
<211> LENGTH: 37
<212> TYPE: DNA
<213> ORGANISM: Artificial Sequence
<220> FEATURE:
<223> OTHER INFORMATION: Oligonucleotide Primer Sequence

<400> SEQUENCE: 12
gcctgcgcat gcttatgatt tattttgttc agcaaat                        37

<210> SEQ ID NO 13
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 13
cgagcggtac catggcacct gttacaattg aaaagt                         36

<210> SEQ ID NO 14
<211> LENGTH: 39
<212> TYPE: DNA
<213> ORGANISM: Artificial Sequence
<220> FEATURE:

-continued

<223> OTHER INFORMATION: Oligonucleotide Primer Sequence

<400> SEQUENCE: 14
gcctgcgcat gcctatttt tatttctttt aagtgccgc                39

<210> SEQ ID NO 15
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 15
cgagcggtac catgaattct agctatacac agagat                36

<210> SEQ ID NO 16
<211> LENGTH: 32
<212> TYPE: DNA
<213> ORGANISM: Artificial Sequence
<220> FEATURE:
<223> OTHER INFORMATION: Oligonucleotide Primer Sequence

<400> SEQUENCE: 16
ggtcagtatc caacttgatt tttttttaga ag                32

<210> SEQ ID NO 17
<211> LENGTH: 37
<212> TYPE: DNA
<213> ORGANISM: Artificial Sequence
<220> FEATURE:
<223> OTHER INFORMATION: Oligonucleotide Primer Sequence

<400> SEQUENCE: 17
cgagcggtac catgaagagt gaatacacaa ttggaag                37

<210> SEQ ID NO 18
<211> LENGTH: 37
<212> TYPE: DNA
<213> ORGANISM: Artificial Sequence
<220> FEATURE:
<223> OTHER INFORMATION: Oligonucleotide Primer Sequence

<400> SEQUENCE: 18
gcctgcgcat gcctaattat tttgatttgc aaaacgt                37

<210> SEQ ID NO 19
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 19
cgagcggtac catggctgac tcgcaacccc tgtccg                36

<210> SEQ ID NO 20
<211> LENGTH: 34
<212> TYPE: DNA
<213> ORGANISM: Artificial Sequence
<220> FEATURE:
<223> OTHER INFORMATION: Oligonucleotide Primer Sequence

<400> SEQUENCE: 20
ccgctcgagc taacccgcca aaagaacct gaac                34

```
<210> SEQ ID NO 21
<211> LENGTH: 40
<212> TYPE: DNA
<213> ORGANISM: Artificial Sequence
<220> FEATURE:
<223> OTHER INFORMATION: Oligonucleotide Primer Sequence

<400> SEQUENCE: 21
acgcagtcga caagagacaa ggacccaaac catgagccag                              40

<210> SEQ ID NO 22
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 22
ggaagatctt taattcataa acgcaggttg ttttgc                                  36

<210> SEQ ID NO 23
<211> LENGTH: 43
<212> TYPE: DNA
<213> ORGANISM: Artificial Sequence
<220> FEATURE:
<223> OTHER INFORMATION: Oligonucleotide Primer Sequence

<400> SEQUENCE: 23
gccacccgtc tccgtaccat gttgacaaaa gcaacaaaag aac                          43

<210> SEQ ID NO 24
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 24
acgcagtcga cctagagagc tttcgttttc atgagt                                  36

<210> SEQ ID NO 25
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 25
cgagctgtac aatgttgaca aaagcaacaa aagaac                                  36

<210> SEQ ID NO 26
<211> LENGTH: 26
<212> TYPE: DNA
<213> ORGANISM: Artificial Sequence
<220> FEATURE:
<223> OTHER INFORMATION: Oligonucleotide Primer Sequence

<400> SEQUENCE: 26
tctctagaaa gggtaccggc agcttg                                             26

<210> SEQ ID NO 27
<211> LENGTH: 1647
<212> TYPE: DNA
<213> ORGANISM: Lactococcus lactis
<220> FEATURE:
<221> NAME/KEY: CDS
<222> LOCATION: (1)..(1647)
```

<400> SEQUENCE: 27

| | | | | | | | | | | | | | | | | |
|---|---|---|---|---|---|---|---|---|---|---|---|---|---|---|---|---|
| atg | tat | aca | gta | gga | gat | tac | cta | tta | gac | cga | tta | cac | gag | tta | gga | 48 |
| Met | Tyr | Thr | Val | Gly | Asp | Tyr | Leu | Leu | Asp | Arg | Leu | His | Glu | Leu | Gly | |
| 1 | | | | 5 | | | | | 10 | | | | | 15 | | |

| att | gaa | gaa | att | ttt | gga | gtc | cct | gga | gac | tat | aac | tta | caa | ttt | tta | 96 |
|---|---|---|---|---|---|---|---|---|---|---|---|---|---|---|---|---|
| Ile | Glu | Glu | Ile | Phe | Gly | Val | Pro | Gly | Asp | Tyr | Asn | Leu | Gln | Phe | Leu | |
| | | 20 | | | | | 25 | | | | | 30 | | | | |

| gat | caa | att | att | tcc | cgc | aag | gat | atg | aaa | tgg | gtc | gga | aat | gct | aat | 144 |
|---|---|---|---|---|---|---|---|---|---|---|---|---|---|---|---|---|
| Asp | Gln | Ile | Ile | Ser | Arg | Lys | Asp | Met | Lys | Trp | Val | Gly | Asn | Ala | Asn | |
| | | | 35 | | | | | 40 | | | | | 45 | | | |

| gaa | tta | aat | gct | tca | tat | atg | gct | gat | ggc | tat | gct | cgt | act | aaa | aaa | 192 |
|---|---|---|---|---|---|---|---|---|---|---|---|---|---|---|---|---|
| Glu | Leu | Asn | Ala | Ser | Tyr | Met | Ala | Asp | Gly | Tyr | Ala | Arg | Thr | Lys | Lys | |
| | 50 | | | | | 55 | | | | | 60 | | | | | |

| gct | gcc | gca | ttt | ctt | aca | acc | ttt | gga | gta | ggt | gaa | ttg | agt | gca | gtt | 240 |
|---|---|---|---|---|---|---|---|---|---|---|---|---|---|---|---|---|
| Ala | Ala | Ala | Phe | Leu | Thr | Thr | Phe | Gly | Val | Gly | Glu | Leu | Ser | Ala | Val | |
| 65 | | | | | 70 | | | | | 75 | | | | | 80 | |

| aat | gga | tta | gca | gga | agt | tac | gcc | gaa | aat | tta | cca | gta | gta | gaa | ata | 288 |
|---|---|---|---|---|---|---|---|---|---|---|---|---|---|---|---|---|
| Asn | Gly | Leu | Ala | Gly | Ser | Tyr | Ala | Glu | Asn | Leu | Pro | Val | Val | Glu | Ile | |
| | | | | 85 | | | | | 90 | | | | | 95 | | |

| gtg | gga | tca | cct | aca | tca | aaa | gtt | caa | aat | gaa | gga | aaa | ttt | gtt | cat | 336 |
|---|---|---|---|---|---|---|---|---|---|---|---|---|---|---|---|---|
| Val | Gly | Ser | Pro | Thr | Ser | Lys | Val | Gln | Asn | Glu | Gly | Lys | Phe | Val | His | |
| | | | 100 | | | | | 105 | | | | | 110 | | | |

| cat | acg | ctg | gct | gac | ggt | gat | ttt | aaa | cac | ttt | atg | aaa | atg | cac | gaa | 384 |
|---|---|---|---|---|---|---|---|---|---|---|---|---|---|---|---|---|
| His | Thr | Leu | Ala | Asp | Gly | Asp | Phe | Lys | His | Phe | Met | Lys | Met | His | Glu | |
| | | 115 | | | | | 120 | | | | | 125 | | | | |

| cct | gtt | aca | gca | gct | cga | act | tta | ctg | aca | gca | gaa | aat | gca | acc | gtt | 432 |
|---|---|---|---|---|---|---|---|---|---|---|---|---|---|---|---|---|
| Pro | Val | Thr | Ala | Ala | Arg | Thr | Leu | Leu | Thr | Ala | Glu | Asn | Ala | Thr | Val | |
| | 130 | | | | | 135 | | | | | 140 | | | | | |

| gaa | att | gac | cga | gta | ctt | tct | gca | cta | tta | aaa | gaa | aga | aaa | cct | gtc | 480 |
|---|---|---|---|---|---|---|---|---|---|---|---|---|---|---|---|---|
| Glu | Ile | Asp | Arg | Val | Leu | Ser | Ala | Leu | Leu | Lys | Glu | Arg | Lys | Pro | Val | |
| 145 | | | | | 150 | | | | | 155 | | | | | 160 | |

| tat | atc | aac | tta | cca | gtt | gat | gtt | gct | gct | gca | aaa | gca | gag | aaa | ccc | 528 |
|---|---|---|---|---|---|---|---|---|---|---|---|---|---|---|---|---|
| Tyr | Ile | Asn | Leu | Pro | Val | Asp | Val | Ala | Ala | Ala | Lys | Ala | Glu | Lys | Pro | |
| | | | | 165 | | | | | 170 | | | | | 175 | | |

| tca | ctc | cct | ttg | aaa | aaa | gaa | aac | tca | act | tca | aat | aca | agt | gac | caa | 576 |
|---|---|---|---|---|---|---|---|---|---|---|---|---|---|---|---|---|
| Ser | Leu | Pro | Leu | Lys | Lys | Glu | Asn | Ser | Thr | Ser | Asn | Thr | Ser | Asp | Gln | |
| | | | 180 | | | | | 185 | | | | | 190 | | | |

| gag | atc | ttg | aac | aaa | att | caa | gaa | agc | ttg | aaa | aat | gcc | aaa | aaa | cca | 624 |
|---|---|---|---|---|---|---|---|---|---|---|---|---|---|---|---|---|
| Glu | Ile | Leu | Asn | Lys | Ile | Gln | Glu | Ser | Leu | Lys | Asn | Ala | Lys | Lys | Pro | |
| | | 195 | | | | | 200 | | | | | 205 | | | | |

| atc | gtg | att | aca | gga | cat | gaa | ata | att | agt | ttt | ggc | tta | gaa | aaa | aca | 672 |
|---|---|---|---|---|---|---|---|---|---|---|---|---|---|---|---|---|
| Ile | Val | Ile | Thr | Gly | His | Glu | Ile | Ile | Ser | Phe | Gly | Leu | Glu | Lys | Thr | |
| | 210 | | | | | 215 | | | | | 220 | | | | | |

| gtc | tct | caa | ttt | att | tca | aag | aca | aaa | cta | cct | att | acg | aca | tta | aac | 720 |
|---|---|---|---|---|---|---|---|---|---|---|---|---|---|---|---|---|
| Val | Ser | Gln | Phe | Ile | Ser | Lys | Thr | Lys | Leu | Pro | Ile | Thr | Thr | Leu | Asn | |
| 225 | | | | | 230 | | | | | 235 | | | | | 240 | |

| ttt | gga | aaa | agt | tca | gtt | gat | gaa | gct | ctc | cct | tca | ttt | tta | gga | atc | 768 |
|---|---|---|---|---|---|---|---|---|---|---|---|---|---|---|---|---|
| Phe | Gly | Lys | Ser | Ser | Val | Asp | Glu | Ala | Leu | Pro | Ser | Phe | Leu | Gly | Ile | |
| | | | | 245 | | | | | 250 | | | | | 255 | | |

| tat | aat | ggt | aaa | ctc | tca | gag | cct | aat | ctt | aaa | gaa | ttc | gtg | gaa | tca | 816 |
|---|---|---|---|---|---|---|---|---|---|---|---|---|---|---|---|---|
| Tyr | Asn | Gly | Lys | Leu | Ser | Glu | Pro | Asn | Leu | Lys | Glu | Phe | Val | Glu | Ser | |
| | | | 260 | | | | | 265 | | | | | 270 | | | |

| gcc | gac | ttc | atc | ctg | atg | ctt | gga | gtt | aaa | ctc | aca | gac | tct | tca | aca | 864 |
|---|---|---|---|---|---|---|---|---|---|---|---|---|---|---|---|---|
| Ala | Asp | Phe | Ile | Leu | Met | Leu | Gly | Val | Lys | Leu | Thr | Asp | Ser | Ser | Thr | |
| | | 275 | | | | | 280 | | | | | 285 | | | | |

| gga | gcc | ttc | act | cat | cat | tta | aat | gaa | aat | aaa | atg | att | tca | ctg | aat | 912 |
|---|---|---|---|---|---|---|---|---|---|---|---|---|---|---|---|---|
| Gly | Ala | Phe | Thr | His | His | Leu | Asn | Glu | Asn | Lys | Met | Ile | Ser | Leu | Asn | |
| | 290 | | | | | 295 | | | | | 300 | | | | | |

```
ata gat gaa gga aaa ata ttt aac gaa agc atc caa aat ttt gat ttt      960
Ile Asp Glu Gly Lys Ile Phe Asn Glu Ser Ile Gln Asn Phe Asp Phe
305                 310                 315                 320 gaa tcc ctc atc tcc tct ctc tta gac cta agc gaa ata gaa tac aaa     1008
Glu Ser Leu Ile Ser Ser Leu Leu Asp Leu Ser Glu Ile Glu Tyr Lys
                325                 330                 335 gga aaa tat atc gat aaa aag caa gaa gac ttt gtt cca tca aat gcg     1056
Gly Lys Tyr Ile Asp Lys Lys Gln Glu Asp Phe Val Pro Ser Asn Ala
            340                 345                 350 ctt tta tca caa gac cgc cta tgg caa gca gtt gaa aac cta act caa     1104
Leu Leu Ser Gln Asp Arg Leu Trp Gln Ala Val Glu Asn Leu Thr Gln
        355                 360                 365 agc aat gaa aca atc gtt gct gaa caa ggg aca tca ttc ttt ggc gct     1152
Ser Asn Glu Thr Ile Val Ala Glu Gln Gly Thr Ser Phe Phe Gly Ala
    370                 375                 380 tca tca att ttc tta aaa cca aag agt cat ttt att ggt caa ccc tta     1200
Ser Ser Ile Phe Leu Lys Pro Lys Ser His Phe Ile Gly Gln Pro Leu
385                 390                 395                 400 tgg gga tca att gga tat aca ttc cca gca gca tta gga agc caa att     1248
Trp Gly Ser Ile Gly Tyr Thr Phe Pro Ala Ala Leu Gly Ser Gln Ile
                405                 410                 415 gca gat aaa gaa agc aga cac ctt tta ttt att ggt gat ggt tca ctt     1296
Ala Asp Lys Glu Ser Arg His Leu Leu Phe Ile Gly Asp Gly Ser Leu
            420                 425                 430 caa ctt acg gtg caa gaa tta gga tta gca atc aga gaa aaa att aat     1344
Gln Leu Thr Val Gln Glu Leu Gly Leu Ala Ile Arg Glu Lys Ile Asn
        435                 440                 445 cca att tgc ttt att atc aat aat gat ggt tat aca gtc gaa aga gaa     1392
Pro Ile Cys Phe Ile Ile Asn Asn Asp Gly Tyr Thr Val Glu Arg Glu
    450                 455                 460 att cat gga cca aat caa agc tac aat gat att cca atg tgg aat tac     1440
Ile His Gly Pro Asn Gln Ser Tyr Asn Asp Ile Pro Met Trp Asn Tyr
465                 470                 475                 480 tca aaa tta cca gaa tca ttt gga gca aca gaa gaa cga gta gtc tcg     1488
Ser Lys Leu Pro Glu Ser Phe Gly Ala Thr Glu Glu Arg Val Val Ser
                485                 490                 495 aaa atc gtt aga act gaa aat gaa ttt gtg tct gtc atg aaa gaa gct     1536
Lys Ile Val Arg Thr Glu Asn Glu Phe Val Ser Val Met Lys Glu Ala
            500                 505                 510 caa gca gat cca aat aga atg tac tgg att gag tta att ttg gca aaa     1584
Gln Ala Asp Pro Asn Arg Met Tyr Trp Ile Glu Leu Ile Leu Ala Lys
        515                 520                 525 gaa gat gca cca aaa gta ctg aaa aaa atg ggc aaa cta ttt gct gaa     1632
Glu Asp Ala Pro Lys Val Leu Lys Lys Met Gly Lys Leu Phe Ala Glu
    530                 535                 540 caa aat aaa tca taa                                                 1647
Gln Asn Lys Ser
545

<210> SEQ ID NO 28
<211> LENGTH: 548
<212> TYPE: PRT
<213> ORGANISM: Lactococcus lactis

<400> SEQUENCE: 28

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
```

```
             35                  40                  45
Glu Leu Asn Ala Ser Tyr Met Ala Asp Gly Tyr Ala Arg Thr Lys Lys
 50                  55                  60

Ala Ala Ala Phe Leu Thr Thr Phe Gly Val Gly Glu Leu Ser Ala Val
 65                  70                  75                  80

Asn Gly Leu Ala Gly Ser Tyr Ala Glu Asn Leu Pro Val Val Glu Ile
                 85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Val
130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
                275                 280                 285

Gly Ala Phe Thr His His Leu Asn Glu Asn Lys Met Ile Ser Leu Asn
290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
                450                 455                 460
```

```
Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
    530                 535                 540

Gln Asn Lys Ser
545

<210> SEQ ID NO 29
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 29
```

| | | | | | | | | | | | | | | | | |
|---|---|---|---|---|---|---|---|---|---|---|---|---|---|---|---|---|
| atg | tct | gaa | att | act | ctt | gga | aaa | tac | tta | ttt | gaa | aga | ttg | aag | caa | 48 |
| Met | Ser | Glu | Ile | Thr | Leu | Gly | Lys | Tyr | Leu | Phe | Glu | Arg | Leu | Lys | Gln | |
| 1 | | | | 5 | | | | | 10 | | | | | 15 | | |
| gtt | aat | gtt | aac | acc | att | ttt | ggg | cta | cca | ggc | gac | ttc | aac | ttg | tcc | 96 |
| Val | Asn | Val | Asn | Thr | Ile | Phe | Gly | Leu | Pro | Gly | Asp | Phe | Asn | Leu | Ser | |
| | | | 20 | | | | | 25 | | | | | 30 | | | |
| cta | ttg | gac | aag | att | tac | gag | gta | gat | gga | ttg | aga | tgg | gct | ggt | aat | 144 |
| Leu | Leu | Asp | Lys | Ile | Tyr | Glu | Val | Asp | Gly | Leu | Arg | Trp | Ala | Gly | Asn | |
| | | 35 | | | | | 40 | | | | | 45 | | | | |
| gca | aat | gag | ctg | aac | gcc | gcc | tat | gcc | gcc | gat | ggt | tac | gca | cgc | atc | 192 |
| Ala | Asn | Glu | Leu | Asn | Ala | Ala | Tyr | Ala | Ala | Asp | Gly | Tyr | Ala | Arg | Ile | |
| 50 | | | | | 55 | | | | | 60 | | | | | | |
| aag | ggt | tta | tct | gtg | ctg | gta | act | act | ttt | ggc | gta | ggt | gaa | tta | tcc | 240 |
| Lys | Gly | Leu | Ser | Val | Leu | Val | Thr | Thr | Phe | Gly | Val | Gly | Glu | Leu | Ser | |
| 65 | | | | | 70 | | | | | 75 | | | | | 80 | |
| gcc | ttg | aat | ggt | att | gca | gga | tcg | tat | gca | gaa | cac | gtc | ggt | gta | ctg | 288 |
| Ala | Leu | Asn | Gly | Ile | Ala | Gly | Ser | Tyr | Ala | Glu | His | Val | Gly | Val | Leu | |
| | | | | 85 | | | | | 90 | | | | | 95 | | |
| cat | gtt | gtt | ggt | gtc | ccc | tct | atc | tcc | gct | cag | gct | aag | caa | ttg | ttg | 336 |
| His | Val | Val | Gly | Val | Pro | Ser | Ile | Ser | Ala | Gln | Ala | Lys | Gln | Leu | Leu | |
| | | | 100 | | | | | 105 | | | | | 110 | | | |
| ttg | cat | cat | acc | ttg | ggt | aac | ggt | gat | ttt | acc | gtt | ttt | cac | aga | atg | 384 |
| Leu | His | His | Thr | Leu | Gly | Asn | Gly | Asp | Phe | Thr | Val | Phe | His | Arg | Met | |
| | | 115 | | | | | 120 | | | | | 125 | | | | |
| tcc | gcc | aat | atc | tca | gaa | act | aca | tca | atg | att | aca | gac | att | gct | aca | 432 |
| Ser | Ala | Asn | Ile | Ser | Glu | Thr | Thr | Ser | Met | Ile | Thr | Asp | Ile | Ala | Thr | |
| 130 | | | | | 135 | | | | | 140 | | | | | | |
| gcc | cct | tca | gaa | atc | gat | agg | ttg | atc | agg | aca | aca | ttt | ata | aca | caa | 480 |
| Ala | Pro | Ser | Glu | Ile | Asp | Arg | Leu | Ile | Arg | Thr | Thr | Phe | Ile | Thr | Gln | |
| 145 | | | | | 150 | | | | | 155 | | | | | 160 | |
| agg | cct | agc | tac | ttg | ggg | ttg | cca | gcg | aat | ttg | gta | gat | cta | aag | gtt | 528 |
| Arg | Pro | Ser | Tyr | Leu | Gly | Leu | Pro | Ala | Asn | Leu | Val | Asp | Leu | Lys | Val | |
| | | | | 165 | | | | | 170 | | | | | 175 | | |
| cct | ggt | tct | ctt | ttg | gaa | aaa | ccg | att | gat | cta | tca | tta | aaa | cct | aac | 576 |
| Pro | Gly | Ser | Leu | Leu | Glu | Lys | Pro | Ile | Asp | Leu | Ser | Leu | Lys | Pro | Asn | |
| | | | 180 | | | | | 185 | | | | | 190 | | | |
| gat | ccc | gaa | gct | gaa | aag | gaa | gtt | att | gat | acc | gta | cta | gaa | ttg | atc | 624 |

```
                Asp Pro Glu Ala Glu Lys Glu Val Ile Asp Thr Val Leu Glu Leu Ile
                                195                 200                 205 cag aat tcg aaa aac cct gtt ata cta tcg gat gcc tgt gct tct agg           672
Gln Asn Ser Lys Asn Pro Val Ile Leu Ser Asp Ala Cys Ala Ser Arg
            210                 215                 220 cac aac gtt aaa aaa gaa acc cag aag tta att gat ttg acg caa ttc           720
His Asn Val Lys Lys Glu Thr Gln Lys Leu Ile Asp Leu Thr Gln Phe
225                 230                 235                 240 cca gct ttt gtg aca cct cta ggt aaa ggg tca ata gat gaa cag cat           768
Pro Ala Phe Val Thr Pro Leu Gly Lys Gly Ser Ile Asp Glu Gln His
                245                 250                 255 ccc aga tat ggc ggt gtt tat gtg gga acg ctg tcc aaa caa gac gtg           816
Pro Arg Tyr Gly Gly Val Tyr Val Gly Thr Leu Ser Lys Gln Asp Val
            260                 265                 270 aaa cag gcc gtt gag tcg gct gat ttg atc ctt tcg gtc ggt gct ttg           864
Lys Gln Ala Val Glu Ser Ala Asp Leu Ile Leu Ser Val Gly Ala Leu
        275                 280                 285 ctc tct gat ttt aac aca ggt tcg ttt tcc tac tcc tac aag act aaa           912
Leu Ser Asp Phe Asn Thr Gly Ser Phe Ser Tyr Ser Tyr Lys Thr Lys
        290                 295                 300 aat gta gtg gag ttt cat tcc gat tac gta aag gtg aag aac gct acg           960
Asn Val Val Glu Phe His Ser Asp Tyr Val Lys Val Lys Asn Ala Thr
305                 310                 315                 320 ttc ctc ggt gta caa atg aaa ttt gca cta caa aac tta ctg aag gtt          1008
Phe Leu Gly Val Gln Met Lys Phe Ala Leu Gln Asn Leu Leu Lys Val
                325                 330                 335 att ccc gat gtt gtt aag ggc tac aag agc gtt ccc gta cca acc aaa          1056
Ile Pro Asp Val Val Lys Gly Tyr Lys Ser Val Pro Val Pro Thr Lys
            340                 345                 350 act ccc gca aac aaa ggt gta cct gct agc acg ccc ttg aaa caa gag          1104
Thr Pro Ala Asn Lys Gly Val Pro Ala Ser Thr Pro Leu Lys Gln Glu
        355                 360                 365 tgg ttg tgg aac gaa ttg tcc aaa ttc ttg caa gaa ggt gat gtt atc          1152
Trp Leu Trp Asn Glu Leu Ser Lys Phe Leu Gln Glu Gly Asp Val Ile
    370                 375                 380 att tcc gag acc ggc acg tct gcc ttc ggt atc aat caa act atc ttt          1200
Ile Ser Glu Thr Gly Thr Ser Ala Phe Gly Ile Asn Gln Thr Ile Phe
385                 390                 395                 400 cct aag gac gcc tac ggt atc tcg cag gtg ttg tgg ggg tcc atc ggt          1248
Pro Lys Asp Ala Tyr Gly Ile Ser Gln Val Leu Trp Gly Ser Ile Gly
                405                 410                 415 ttt aca aca gga gca act tta ggt gct gcc ttt gcc gct gag gag att          1296
Phe Thr Thr Gly Ala Thr Leu Gly Ala Ala Phe Ala Ala Glu Glu Ile
            420                 425                 430 gac ccc aac aag aga gtc atc tta ttc ata ggt gac ggg tct ttg cag          1344
Asp Pro Asn Lys Arg Val Ile Leu Phe Ile Gly Asp Gly Ser Leu Gln
        435                 440                 445 tta acc gtc caa gaa atc tcc acc atg atc aga tgg ggg tta aag ccg          1392
Leu Thr Val Gln Glu Ile Ser Thr Met Ile Arg Trp Gly Leu Lys Pro
    450                 455                 460 tat ctt ttt gtc ctt aac aac gac ggc tac act atc gaa aag ctg att          1440
Tyr Leu Phe Val Leu Asn Asn Asp Gly Tyr Thr Ile Glu Lys Leu Ile
465                 470                 475                 480 cat ggg cct cac gca gag tac aac gaa atc cag acc tgg gat cac ctc          1488
His Gly Pro His Ala Glu Tyr Asn Glu Ile Gln Thr Trp Asp His Leu
                485                 490                 495 gcc ctg ttg ccc gca ttt ggt gcg aaa aag tac gaa aat cac aag atc          1536
Ala Leu Leu Pro Ala Phe Gly Ala Lys Lys Tyr Glu Asn His Lys Ile
            500                 505                 510
```

```
gcc act acg ggt gag tgg gat gcc tta acc act gat tca gag ttc cag    1584
Ala Thr Thr Gly Glu Trp Asp Ala Leu Thr Thr Asp Ser Glu Phe Gln
        515                 520                 525 aaa aac tcg gtg atc aga cta att gaa ctg aaa ctg ccc gtc ttt gat    1632
Lys Asn Ser Val Ile Arg Leu Ile Glu Leu Lys Leu Pro Val Phe Asp
530                 535                 540 gct ccg gaa agt ttg atc aaa caa gcg caa ttg act gcc gct aca aat    1680
Ala Pro Glu Ser Leu Ile Lys Gln Ala Gln Leu Thr Ala Ala Thr Asn
545                 550                 555                 560 gcc aaa caa taa                                                     1692
Ala Lys Gln
```

<210> SEQ ID NO 30
<211> LENGTH: 563
<212> TYPE: PRT
<213> ORGANISM: Saccharomyces cerevisiae

<400> SEQUENCE: 30

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300
```

```
Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
            325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
            355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
            515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 31
<211> LENGTH: 1908
<212> TYPE: DNA
<213> ORGANISM: Saccharomyces cerevisiae
<220> FEATURE:
<221> NAME/KEY: CDS
<222> LOCATION: (1)..(1908)

<400> SEQUENCE: 31 atg gca cct gtt aca att gaa aag ttc gta aat caa gaa gaa cga cac    48
Met Ala Pro Val Thr Ile Glu Lys Phe Val Asn Gln Glu Glu Arg His
1               5                   10                  15 ctt gtt tcc aac cga tca gca aca att ccg ttt ggt gaa tac ata ttt    96
Leu Val Ser Asn Arg Ser Ala Thr Ile Pro Phe Gly Glu Tyr Ile Phe
            20                  25                  30 aaa aga ttg ttg tcc atc gat acg aaa tca gtt ttc ggt gtt cct ggt   144
Lys Arg Leu Leu Ser Ile Asp Thr Lys Ser Val Phe Gly Val Pro Gly
        35                  40                  45 gac ttc aac tta tct cta tta gaa tat ctc tat tca cct agt gtt gaa   192
Asp Phe Asn Leu Ser Leu Leu Glu Tyr Leu Tyr Ser Pro Ser Val Glu
50                  55                  60 tca gct ggc cta aga tgg gtc ggc acg tgt aat gaa ctg aac gcc gct   240
```

```
Ser Ala Gly Leu Arg Trp Val Gly Thr Cys Asn Glu Leu Asn Ala Ala
 65                  70                  75                  80 tat gcg gcc gac gga tat tcc cgt tac tct aat aag att ggc tgt tta      288
Tyr Ala Ala Asp Gly Tyr Ser Arg Tyr Ser Asn Lys Ile Gly Cys Leu
                     85                  90                  95 ata acc acg tat ggc gtt ggt gaa tta agc gcc ttg aac ggt ata gcc      336
Ile Thr Thr Tyr Gly Val Gly Glu Leu Ser Ala Leu Asn Gly Ile Ala
                100                 105                 110 ggt tcg ttc gct gaa aat gtc aaa gtt ttg cac att gtt ggt gtg gcc      384
Gly Ser Phe Ala Glu Asn Val Lys Val Leu His Ile Val Gly Val Ala
            115                 120                 125 aag tcc ata gat tcg cgt tca agt aac ttt agt gat cgg aac cta cat      432
Lys Ser Ile Asp Ser Arg Ser Ser Asn Phe Ser Asp Arg Asn Leu His
        130                 135                 140 cat ttg gtc cca cag cta cat gat tca aat ttt aaa ggg cca aat cat      480
His Leu Val Pro Gln Leu His Asp Ser Asn Phe Lys Gly Pro Asn His
145                 150                 155                 160 aaa gta tat cat gat atg gta aaa gat aga gtc gct tgc tcg gta gcc      528
Lys Val Tyr His Asp Met Val Lys Asp Arg Val Ala Cys Ser Val Ala
                165                 170                 175 tac ttg gag gat att gaa act gca tgt gac caa gtc gat aat gtt atc      576
Tyr Leu Glu Asp Ile Glu Thr Ala Cys Asp Gln Val Asp Asn Val Ile
                180                 185                 190 cgc gat att tac aag tat tct aaa cct ggt tat att ttt gtt cct gca      624
Arg Asp Ile Tyr Lys Tyr Ser Lys Pro Gly Tyr Ile Phe Val Pro Ala
            195                 200                 205 gat ttt gcg gat atg tct gtt aca tgt gat aat ttg gtt aat gtt cca      672
Asp Phe Ala Asp Met Ser Val Thr Cys Asp Asn Leu Val Asn Val Pro
210                 215                 220 cgt ata tct caa caa gat tgt ata gta tac cct tct gaa aac caa ttg      720
Arg Ile Ser Gln Gln Asp Cys Ile Val Tyr Pro Ser Glu Asn Gln Leu
225                 230                 235                 240 tct gac ata atc aac aag att act agt tgg ata tat tcc agt aaa aca      768
Ser Asp Ile Ile Asn Lys Ile Thr Ser Trp Ile Tyr Ser Ser Lys Thr
                245                 250                 255 cct gcg atc ctt gga gac gta ctg act gat agg tat ggt gtg agt aac      816
Pro Ala Ile Leu Gly Asp Val Leu Thr Asp Arg Tyr Gly Val Ser Asn
                260                 265                 270 ttt ttg aac aag ctt atc tgc aaa act ggg att tgg aat ttt tcc act      864
Phe Leu Asn Lys Leu Ile Cys Lys Thr Gly Ile Trp Asn Phe Ser Thr
            275                 280                 285 gtt atg gga aaa tct gta att gat gag tca aac cca act tat atg ggt      912
Val Met Gly Lys Ser Val Ile Asp Glu Ser Asn Pro Thr Tyr Met Gly
        290                 295                 300 caa tat aat ggt aaa gaa ggt tta aaa caa gtc tat gaa cat ttt gaa      960
Gln Tyr Asn Gly Lys Glu Gly Leu Lys Gln Val Tyr Glu His Phe Glu
305                 310                 315                 320 ctg tgc gac ttg gtc ttg cat ttt gga gtc gac atc aat gaa att aat     1008
Leu Cys Asp Leu Val Leu His Phe Gly Val Asp Ile Asn Glu Ile Asn
                325                 330                 335 aat ggg cat tat act ttt act tat aaa cca aat gct aaa atc att caa     1056
Asn Gly His Tyr Thr Phe Thr Tyr Lys Pro Asn Ala Lys Ile Ile Gln
                340                 345                 350 ttt cat ccg aat tat att cgc ctt gtg gac act agg cag ggc aat gag     1104
Phe His Pro Asn Tyr Ile Arg Leu Val Asp Thr Arg Gln Gly Asn Glu
            355                 360                 365 caa atg ttc aaa gga atc aat ttt gcc cct att tta aaa gaa cta tac     1152
Gln Met Phe Lys Gly Ile Asn Phe Ala Pro Ile Leu Lys Glu Leu Tyr
        370                 375                 380
```

```
aag cgc att gac gtt tct aaa ctt tct ttg caa tat gat tca aat gta    1200
Lys Arg Ile Asp Val Ser Lys Leu Ser Leu Gln Tyr Asp Ser Asn Val
385                 390                 395                 400 act caa tat acg aac gaa aca atg cgg tta gaa gat cct acc aat gga    1248
Thr Gln Tyr Thr Asn Glu Thr Met Arg Leu Glu Asp Pro Thr Asn Gly
                405                 410                 415 caa tca agc att att aca caa gtt cac tta caa aag acg atg cct aaa    1296
Gln Ser Ser Ile Ile Thr Gln Val His Leu Gln Lys Thr Met Pro Lys
            420                 425                 430 ttt ttg aac cct ggt gat gtt gtc gtt tgt gaa aca ggc tct ttt caa    1344
Phe Leu Asn Pro Gly Asp Val Val Val Cys Glu Thr Gly Ser Phe Gln
        435                 440                 445 ttc tct gtt cgt gat ttc gcg ttt cct tcg caa tta aaa tat ata tcg    1392
Phe Ser Val Arg Asp Phe Ala Phe Pro Ser Gln Leu Lys Tyr Ile Ser
    450                 455                 460 caa gga ttt ttc ctt tcc att ggc atg gcc ctt cct gcc gcc cta ggt    1440
Gln Gly Phe Phe Leu Ser Ile Gly Met Ala Leu Pro Ala Ala Leu Gly
465                 470                 475                 480 gtt gga att gcc atg caa gac cac tca aac gct cac atc aat ggt ggc    1488
Val Gly Ile Ala Met Gln Asp His Ser Asn Ala His Ile Asn Gly Gly
                485                 490                 495 aac gta aaa gag gac tat aag cca aga tta att ttg ttt gaa ggt gac    1536
Asn Val Lys Glu Asp Tyr Lys Pro Arg Leu Ile Leu Phe Glu Gly Asp
            500                 505                 510 ggt gca gca cag atg aca atc caa gaa ctg agc acc att ctg aag tgc    1584
Gly Ala Ala Gln Met Thr Ile Gln Glu Leu Ser Thr Ile Leu Lys Cys
        515                 520                 525 aat att cca cta gaa gtt atc att tgg aac aat aac ggc tac act att    1632
Asn Ile Pro Leu Glu Val Ile Ile Trp Asn Asn Asn Gly Tyr Thr Ile
    530                 535                 540 gaa aga gcc atc atg ggc cct acc agg tcg tat aac gac gtt atg tct    1680
Glu Arg Ala Ile Met Gly Pro Thr Arg Ser Tyr Asn Asp Val Met Ser
545                 550                 555                 560 tgg aaa tgg acc aaa cta ttt gaa gca ttc gga gac ttc gac gga aag    1728
Trp Lys Trp Thr Lys Leu Phe Glu Ala Phe Gly Asp Phe Asp Gly Lys
                565                 570                 575 tat act aat agc act ctc att caa tgt ccc tct aaa tta gca ctg aaa    1776
Tyr Thr Asn Ser Thr Leu Ile Gln Cys Pro Ser Lys Leu Ala Leu Lys
            580                 585                 590 ttg gag gag ctt aag aat tca aac aaa aga agc ggg ata gaa ctt tta    1824
Leu Glu Glu Leu Lys Asn Ser Asn Lys Arg Ser Gly Ile Glu Leu Leu
        595                 600                 605 gaa gtc aaa tta ggc gaa ttg gat ttc ccc gaa cag cta aag tgc atg    1872
Glu Val Lys Leu Gly Glu Leu Asp Phe Pro Glu Gln Leu Lys Cys Met
    610                 615                 620 gtt gaa gca gcg gca ctt aaa aga aat aaa aaa tag                    1908
Val Glu Ala Ala Ala Leu Lys Arg Asn Lys Lys
625                 630                 635

<210> SEQ ID NO 32
<211> LENGTH: 635
<212> TYPE: PRT
<213> ORGANISM: Saccharomyces cerevisiae

<400> SEQUENCE: 32

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
```

```
                35                  40                  45
Asp Phe Asn Leu Ser Leu Leu Glu Tyr Leu Tyr Ser Pro Ser Val Glu
 50                  55                  60

Ser Ala Gly Leu Arg Trp Val Gly Thr Cys Asn Glu Leu Asn Ala Ala
 65                  70                  75                  80

Tyr Ala Ala Asp Gly Tyr Ser Arg Tyr Ser Asn Lys Ile Gly Cys Leu
                     85                  90                  95

Ile Thr Thr Tyr Gly Val Gly Glu Leu Ser Ala Leu Asn Gly Ile Ala
                    100                 105                 110

Gly Ser Phe Ala Glu Asn Val Lys Val Leu His Ile Val Gly Val Ala
            115                 120                 125

Lys Ser Ile Asp Ser Arg Ser Ser Asn Phe Ser Asp Arg Asn Leu His
            130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                    165                 170                 175

Tyr Leu Glu Asp Ile Glu Thr Ala Cys Asp Gln Val Asp Asn Val Ile
                180                 185                 190

Arg Asp Ile Tyr Lys Tyr Ser Lys Pro Gly Tyr Ile Phe Val Pro Ala
            195                 200                 205

Asp Phe Ala Asp Met Ser Val Thr Cys Asp Asn Leu Val Asn Val Pro
210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                    245                 250                 255

Pro Ala Ile Leu Gly Asp Val Leu Thr Asp Arg Tyr Gly Val Ser Asn
                260                 265                 270

Phe Leu Asn Lys Leu Ile Cys Lys Thr Gly Ile Trp Asn Phe Ser Thr
            275                 280                 285

Val Met Gly Lys Ser Val Ile Asp Glu Ser Asn Pro Thr Tyr Met Gly
290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                    325                 330                 335

Asn Gly His Tyr Thr Phe Thr Tyr Lys Pro Asn Ala Lys Ile Ile Gln
                340                 345                 350

Phe His Pro Asn Tyr Ile Arg Leu Val Asp Thr Arg Gln Gly Asn Glu
            355                 360                 365

Gln Met Phe Lys Gly Ile Asn Phe Ala Pro Ile Leu Lys Glu Leu Tyr
            370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
                    405                 410                 415

Gln Ser Ser Ile Ile Thr Gln Val His Leu Gln Lys Thr Met Pro Lys
                420                 425                 430

Phe Leu Asn Pro Gly Asp Val Val Cys Glu Thr Gly Ser Phe Gln
            435                 440                 445

Phe Ser Val Arg Asp Phe Ala Phe Pro Ser Gln Leu Lys Tyr Ile Ser
            450                 455                 460
```

```
Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
            515                 520                 525

Asn Ile Pro Leu Glu Val Ile Ile Trp Asn Asn Gly Tyr Thr Ile
        530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
            595                 600                 605

Glu Val Lys Leu Gly Leu Asp Phe Pro Glu Gln Leu Lys Cys Met
    610                 615                 620

Val Glu Ala Ala Leu Lys Arg Asn Lys Lys
625                 630                 635

<210> SEQ ID NO 33
<211> LENGTH: 1830
<212> TYPE: DNA
<213> ORGANISM: Saccharomyces cerevisiae
<220> FEATURE:
<221> NAME/KEY: CDS
<222> LOCATION: (1)..(1830)

<400> SEQUENCE: 33 atg aat tct agc tat aca cag aga tat gca ctg ccg aag tgt ata gca      48
Met Asn Ser Ser Tyr Thr Gln Arg Tyr Ala Leu Pro Lys Cys Ile Ala
1               5                   10                  15 ata tca gat tat ctt ttc cat cgg ctc aac cag ctg aac ata cat acc      96
Ile Ser Asp Tyr Leu Phe His Arg Leu Asn Gln Leu Asn Ile His Thr
            20                  25                  30 ata ttt gga ctc tcc gga gaa ttt agc atg ccg ttg ctg gat aaa cta     144
Ile Phe Gly Leu Ser Gly Glu Phe Ser Met Pro Leu Leu Asp Lys Leu
        35                  40                  45 tac aac att ccg aac tta cga tgg gcc ggt aat tct aat gag tta aat     192
Tyr Asn Ile Pro Asn Leu Arg Trp Ala Gly Asn Ser Asn Glu Leu Asn
    50                  55                  60 gct gcc tac gca gca gat gga tac tca cga cta aaa ggc ttg gga tgt     240
Ala Ala Tyr Ala Ala Asp Gly Tyr Ser Arg Leu Lys Gly Leu Gly Cys
65                  70                  75                  80 ctc ata aca acc ttt ggt gta ggc gaa tta tcg gca atc aat ggc gtg     288
Leu Ile Thr Thr Phe Gly Val Gly Glu Leu Ser Ala Ile Asn Gly Val
                85                  90                  95 gcc gga tct tac gct gaa cat gta gga ata ctt cac ata gtg ggt atg     336
Ala Gly Ser Tyr Ala Glu His Val Gly Ile Leu His Ile Val Gly Met
            100                 105                 110 ccg cca aca agt gca caa acg aaa caa cta cta ctg cat cat act ctg     384
Pro Pro Thr Ser Ala Gln Thr Lys Gln Leu Leu Leu His His Thr Leu
        115                 120                 125 ggc aat ggt gat ttc acg gta ttt cat aga ata gcc agt gat gta gca     432
Gly Asn Gly Asp Phe Thr Val Phe His Arg Ile Ala Ser Asp Val Ala
```

```
                130                 135                 140
tgc tat aca aca ttg att att gac tct gaa tta tgt gcc gac gaa gtc      480
Cys Tyr Thr Thr Leu Ile Ile Asp Ser Glu Leu Cys Ala Asp Glu Val
145                 150                 155                 160 gat aag tgc atc aaa aag gct tgg ata gaa cag agg cca gta tac atg      528
Asp Lys Cys Ile Lys Lys Ala Trp Ile Glu Gln Arg Pro Val Tyr Met
                165                 170                 175 ggc atg cct gtc aac cag gta aat ctc ccg att gaa tca gca agg ctt      576
Gly Met Pro Val Asn Gln Val Asn Leu Pro Ile Glu Ser Ala Arg Leu
            180                 185                 190 aat aca cct ctg gat tta caa ttg cat aaa aac gac cca gac gta gag      624
Asn Thr Pro Leu Asp Leu Gln Leu His Lys Asn Asp Pro Asp Val Glu
        195                 200                 205 aaa gaa gtt att tct cga ata ttg agt ttt ata tac aaa agc cag aat      672
Lys Glu Val Ile Ser Arg Ile Leu Ser Phe Ile Tyr Lys Ser Gln Asn
    210                 215                 220 ccg gca atc atc gta gat gca tgt act agt cga cag aat tta atc gag      720
Pro Ala Ile Ile Val Asp Ala Cys Thr Ser Arg Gln Asn Leu Ile Glu
225                 230                 235                 240 gag act aaa gag ctt tgt aat agg ctt aaa ttt cca gtt ttt gtt aca      768
Glu Thr Lys Glu Leu Cys Asn Arg Leu Lys Phe Pro Val Phe Val Thr
                245                 250                 255 cct atg ggt aag ggt aca gta aac gaa aca gac ccg caa ttt ggg ggc      816
Pro Met Gly Lys Gly Thr Val Asn Glu Thr Asp Pro Gln Phe Gly Gly
            260                 265                 270 gta ttc acg ggc tcg ata tca gcc cca gaa gta aga gaa gta gtt gat      864
Val Phe Thr Gly Ser Ile Ser Ala Pro Glu Val Arg Glu Val Val Asp
        275                 280                 285 ttt gcc gat ttt atc atc gtc att ggt tgc atg ctc tcc gaa ttc agc      912
Phe Ala Asp Phe Ile Ile Val Ile Gly Cys Met Leu Ser Glu Phe Ser
    290                 295                 300 acg tca act ttc cac ttc caa tat aaa act aag aat tgt gcg cta cta      960
Thr Ser Thr Phe His Phe Gln Tyr Lys Thr Lys Asn Cys Ala Leu Leu
305                 310                 315                 320 tat tct aca tct gtg aaa ttg aaa aat gcc aca tat cct gac ttg agc     1008
Tyr Ser Thr Ser Val Lys Leu Lys Asn Ala Thr Tyr Pro Asp Leu Ser
                325                 330                 335 att aaa tta cta cta cag aaa ata tta gca aat ctt gat gaa tct aaa     1056
Ile Lys Leu Leu Leu Gln Lys Ile Leu Ala Asn Leu Asp Glu Ser Lys
            340                 345                 350 ctg tct tac caa cca agc gaa caa ccc agt atg atg gtt cca aga cct     1104
Leu Ser Tyr Gln Pro Ser Glu Gln Pro Ser Met Met Val Pro Arg Pro
        355                 360                 365 tac cca gca gga aat gtc ctc ttg aga caa gaa tgg gtc tgg aat gaa     1152
Tyr Pro Ala Gly Asn Val Leu Leu Arg Gln Glu Trp Val Trp Asn Glu
    370                 375                 380 ata tcc cat tgg ttc caa cca ggt gac ata atc ata aca gaa act ggt     1200
Ile Ser His Trp Phe Gln Pro Gly Asp Ile Ile Ile Thr Glu Thr Gly
385                 390                 395                 400 gct tct gca ttt gga gtt aac cag acc aga ttt ccg gta aat aca cta     1248
Ala Ser Ala Phe Gly Val Asn Gln Thr Arg Phe Pro Val Asn Thr Leu
                405                 410                 415 ggt att tcg caa gct ctt tgg gga tct gtc gga tat aca atg ggg gcg     1296
Gly Ile Ser Gln Ala Leu Trp Gly Ser Val Gly Tyr Thr Met Gly Ala
            420                 425                 430 tgt ctt ggg gca gaa ttt gct gtt caa gag ata aac aag gat aaa ttc     1344
Cys Leu Gly Ala Glu Phe Ala Val Gln Glu Ile Asn Lys Asp Lys Phe
        435                 440                 445 ccc gca act aaa cat aga gtt att ctg ttt atg ggt gac ggt gct ttc     1392
```

```
Pro Ala Thr Lys His Arg Val Ile Leu Phe Met Gly Asp Gly Ala Phe
    450                 455                 460 caa ttg aca gtt caa gaa tta tcc aca att gtt aag tgg gga ttg aca        1440
Gln Leu Thr Val Gln Glu Leu Ser Thr Ile Val Lys Trp Gly Leu Thr
465                 470                 475                 480 cct tat att ttt gtg atg aat aac caa ggt tac tct gtg gac agg ttt        1488
Pro Tyr Ile Phe Val Met Asn Asn Gln Gly Tyr Ser Val Asp Arg Phe
                485                 490                 495 ttg cat cac agg tca gat gct agt tat tac gat atc caa cct tgg aac        1536
Leu His His Arg Ser Asp Ala Ser Tyr Tyr Asp Ile Gln Pro Trp Asn
            500                 505                 510 tac ttg gga tta ttg cga gta ttt ggt tgc acg aac tac gaa acg aaa        1584
Tyr Leu Gly Leu Leu Arg Val Phe Gly Cys Thr Asn Tyr Glu Thr Lys
        515                 520                 525 aaa att att act gtt gga gaa ttc aga tcc atg atc agt gac cca aac        1632
Lys Ile Ile Thr Val Gly Glu Phe Arg Ser Met Ile Ser Asp Pro Asn
530                 535                 540 ttt gcg acc aat gac aaa att cgg atg ata gag att atg cta cca cca        1680
Phe Ala Thr Asn Asp Lys Ile Arg Met Ile Glu Ile Met Leu Pro Pro
545                 550                 555                 560 agg gat gtt cca cag gct ctg ctt gac agg tgg gtg gta gaa aaa gaa        1728
Arg Asp Val Pro Gln Ala Leu Leu Asp Arg Trp Val Val Glu Lys Glu
                565                 570                 575 cag agc aaa caa gtg caa gag gag aac gaa aat tct agc gca gta aat        1776
Gln Ser Lys Gln Val Gln Glu Glu Asn Glu Asn Ser Ser Ala Val Asn
            580                 585                 590 acg cca act cca gaa ttc caa cca ctt cta aaa aaa aat caa gtt gga        1824
Thr Pro Thr Pro Glu Phe Gln Pro Leu Leu Lys Lys Asn Gln Val Gly
        595                 600                 605 tac tga                                                                1830
Tyr
```

<210> SEQ ID NO 34
<211> LENGTH: 609
<212> TYPE: PRT
<213> ORGANISM: Saccharomyces cerevisiae

<400> SEQUENCE: 34

```
Met Asn Ser Ser Tyr Thr Gln Arg Tyr Ala Leu Pro Lys Cys Ile Ala
1               5                   10                  15

Ile Ser Asp Tyr Leu Phe His Arg Leu Asn Gln Leu Asn Ile His Thr
            20                  25                  30

Ile Phe Gly Leu Ser Gly Glu Phe Ser Met Pro Leu Leu Asp Lys Leu
        35                  40                  45

Tyr Asn Ile Pro Asn Leu Arg Trp Ala Gly Asn Ser Asn Glu Leu Asn
50                  55                  60

Ala Ala Tyr Ala Ala Asp Gly Tyr Ser Arg Leu Lys Gly Leu Gly Cys
65                  70                  75                  80

Leu Ile Thr Thr Phe Gly Val Gly Glu Leu Ser Ala Ile Asn Gly Val
                85                  90                  95

Ala Gly Ser Tyr Ala Glu His Val Gly Ile Leu His Ile Val Gly Met
            100                 105                 110

Pro Pro Thr Ser Ala Gln Thr Lys Gln Leu Leu Leu His His Thr Leu
        115                 120                 125

Gly Asn Gly Asp Phe Thr Val Phe His Arg Ile Ala Ser Asp Val Ala
130                 135                 140

Cys Tyr Thr Thr Leu Ile Ile Asp Ser Glu Leu Cys Ala Asp Glu Val
145                 150                 155                 160
```

-continued

Asp Lys Cys Ile Lys Lys Ala Trp Ile Glu Gln Arg Pro Val Tyr Met
            165                 170                 175

Gly Met Pro Val Asn Gln Val Asn Leu Pro Ile Glu Ser Ala Arg Leu
            180                 185                 190

Asn Thr Pro Leu Asp Leu Gln Leu His Lys Asn Asp Pro Asp Val Glu
            195                 200                 205

Lys Glu Val Ile Ser Arg Ile Leu Ser Phe Ile Tyr Lys Ser Gln Asn
            210                 215                 220

Pro Ala Ile Ile Val Asp Ala Cys Thr Ser Arg Gln Asn Leu Ile Glu
225                 230                 235                 240

Glu Thr Lys Glu Leu Cys Asn Arg Leu Lys Phe Pro Val Phe Val Thr
                245                 250                 255

Pro Met Gly Lys Gly Thr Val Asn Glu Thr Asp Pro Gln Phe Gly Gly
                260                 265                 270

Val Phe Thr Gly Ser Ile Ser Ala Pro Glu Val Arg Glu Val Val Asp
            275                 280                 285

Phe Ala Asp Phe Ile Ile Val Ile Gly Cys Met Leu Ser Glu Phe Ser
            290                 295                 300

Thr Ser Thr Phe His Phe Gln Tyr Lys Thr Lys Asn Cys Ala Leu Leu
305                 310                 315                 320

Tyr Ser Thr Ser Val Lys Leu Lys Asn Ala Thr Tyr Pro Asp Leu Ser
                325                 330                 335

Ile Lys Leu Leu Leu Gln Lys Ile Leu Ala Asn Leu Asp Glu Ser Lys
                340                 345                 350

Leu Ser Tyr Gln Pro Ser Glu Gln Pro Ser Met Met Val Pro Arg Pro
            355                 360                 365

Tyr Pro Ala Gly Asn Val Leu Leu Arg Gln Glu Trp Val Trp Asn Glu
            370                 375                 380

Ile Ser His Trp Phe Gln Pro Gly Asp Ile Ile Thr Glu Thr Gly
385                 390                 395                 400

Ala Ser Ala Phe Gly Val Asn Gln Thr Arg Phe Pro Val Asn Thr Leu
                405                 410                 415

Gly Ile Ser Gln Ala Leu Trp Gly Ser Val Gly Tyr Thr Met Gly Ala
                420                 425                 430

Cys Leu Gly Ala Glu Phe Ala Val Gln Glu Ile Asn Lys Asp Lys Phe
                435                 440                 445

Pro Ala Thr Lys His Arg Val Ile Leu Phe Met Gly Asp Gly Ala Phe
450                 455                 460

Gln Leu Thr Val Gln Glu Leu Ser Thr Ile Val Lys Trp Gly Leu Thr
465                 470                 475                 480

Pro Tyr Ile Phe Val Met Asn Asn Gln Gly Tyr Ser Val Asp Arg Phe
                485                 490                 495

Leu His His Arg Ser Asp Ala Ser Tyr Tyr Asp Ile Gln Pro Trp Asn
                500                 505                 510

Tyr Leu Gly Leu Leu Arg Val Phe Gly Cys Thr Asn Tyr Glu Thr Lys
            515                 520                 525

Lys Ile Ile Thr Val Gly Glu Phe Arg Ser Met Ile Ser Asp Pro Asn
530                 535                 540

Phe Ala Thr Asn Asp Lys Ile Arg Met Ile Glu Ile Met Leu Pro Pro
545                 550                 555                 560

Arg Asp Val Pro Gln Ala Leu Leu Asp Arg Trp Val Val Glu Lys Glu
                565                 570                 575

-continued

```
Gln Ser Lys Gln Val Gln Glu Glu Asn Glu Asn Ser Ser Ala Val Asn
            580                 585                 590

Thr Pro Thr Pro Glu Phe Gln Pro Leu Leu Lys Lys Asn Gln Val Gly
        595                 600                 605

Tyr

<210> SEQ ID NO 35
<211> LENGTH: 1665
<212> TYPE: DNA
<213> ORGANISM: Clostridium acetobutylicum
<220> FEATURE:
<221> NAME/KEY: CDS
<222> LOCATION: (1)..(1665)

<400> SEQUENCE: 35 ttg aag agt gaa tac aca att gga aga tat ttg tta gac cgt tta tca    48
Leu Lys Ser Glu Tyr Thr Ile Gly Arg Tyr Leu Leu Asp Arg Leu Ser
1               5                   10                  15 gag ttg ggt att cgg cat atc ttt ggt gta cct gga gat tac aat cta    96
Glu Leu Gly Ile Arg His Ile Phe Gly Val Pro Gly Asp Tyr Asn Leu
            20                  25                  30 tcc ttt tta gac tat ata atg gag tac aaa ggg ata gat tgg gtt gga   144
Ser Phe Leu Asp Tyr Ile Met Glu Tyr Lys Gly Ile Asp Trp Val Gly
        35                  40                  45 aat tgc aat gaa ttg aat gct ggg tat gct gct gat gga tat gca aga   192
Asn Cys Asn Glu Leu Asn Ala Gly Tyr Ala Ala Asp Gly Tyr Ala Arg
    50                  55                  60 ata aat gga att gga gcc ata ctt aca aca ttt ggt gtt gga gaa tta   240
Ile Asn Gly Ile Gly Ala Ile Leu Thr Thr Phe Gly Val Gly Glu Leu
65                  70                  75                  80 agt gcc att aac gca att gct ggg gca tac gct gag caa gtt cca gtt   288
Ser Ala Ile Asn Ala Ile Ala Gly Ala Tyr Ala Glu Gln Val Pro Val
                85                  90                  95 gtt aaa att aca ggt atc ccc aca gca aaa gtt agg gac aat gga tta   336
Val Lys Ile Thr Gly Ile Pro Thr Ala Lys Val Arg Asp Asn Gly Leu
            100                 105                 110 tat gta cac cac aca tta ggt gac gga agg ttt gat cac ttt ttt gaa   384
Tyr Val His His Thr Leu Gly Asp Gly Arg Phe Asp His Phe Phe Glu
        115                 120                 125 atg ttt aga gaa gta aca gtt gct gag gca tta cta agc gaa gaa aat   432
Met Phe Arg Glu Val Thr Val Ala Glu Ala Leu Leu Ser Glu Glu Asn
    130                 135                 140 gca gca caa gaa att gat cgt gtt ctt att tca tgc tgg aga caa aaa   480
Ala Ala Gln Glu Ile Asp Arg Val Leu Ile Ser Cys Trp Arg Gln Lys
145                 150                 155                 160 cgt cct gtt ctt ata aat tta ccg att gat gta tat gat aaa cca att   528
Arg Pro Val Leu Ile Asn Leu Pro Ile Asp Val Tyr Asp Lys Pro Ile
                165                 170                 175 aac aaa cca tta aag cca tta ctc gat tat act att tca agt aac aaa   576
Asn Lys Pro Leu Lys Pro Leu Leu Asp Tyr Thr Ile Ser Ser Asn Lys
            180                 185                 190 gag gct gca tgt gaa ttt gtt aca gaa ata gta cct ata ata aat agg   624
Glu Ala Ala Cys Glu Phe Val Thr Glu Ile Val Pro Ile Ile Asn Arg
        195                 200                 205 gca aaa aag cct gtt att ctt gca gat tat gga gta tat cgt tac caa   672
Ala Lys Lys Pro Val Ile Leu Ala Asp Tyr Gly Val Tyr Arg Tyr Gln
    210                 215                 220 gtt caa cat gtg ctt aaa aac ttg gcc gaa aaa acc gga ttt cct gtg   720
Val Gln His Val Leu Lys Asn Leu Ala Glu Lys Thr Gly Phe Pro Val
225                 230                 235                 240
```

```
gct aca cta agt atg gga aaa ggt gtt ttc aat gaa gca cac cct caa      768
Ala Thr Leu Ser Met Gly Lys Gly Val Phe Asn Glu Ala His Pro Gln
                245                 250                 255 ttt att ggt gtt tat aat ggt gat gta agt tct cct tat tta agg cag      816
Phe Ile Gly Val Tyr Asn Gly Asp Val Ser Ser Pro Tyr Leu Arg Gln
                260                 265                 270 cga gtt gat gaa gca gac tgc att att agc gtt ggt gta aaa ttg acg      864
Arg Val Asp Glu Ala Asp Cys Ile Ile Ser Val Gly Val Lys Leu Thr
                275                 280                 285 gat tca acc aca ggg gga ttt tct cat gga ttt tct aaa agg aat gta      912
Asp Ser Thr Thr Gly Gly Phe Ser His Gly Phe Ser Lys Arg Asn Val
            290                 295                 300 att cac att gat cct ttt tca ata aag gca aaa ggt aaa aaa tat gca      960
Ile His Ile Asp Pro Phe Ser Ile Lys Ala Lys Gly Lys Lys Tyr Ala
305                 310                 315                 320 cct att acg atg aaa gat gct tta aca gaa tta aca agt aaa att gag     1008
Pro Ile Thr Met Lys Asp Ala Leu Thr Glu Leu Thr Ser Lys Ile Glu
                325                 330                 335 cat aga aac ttt gag gat tta gat ata aag cct tac aaa tca gat aat     1056
His Arg Asn Phe Glu Asp Leu Asp Ile Lys Pro Tyr Lys Ser Asp Asn
                340                 345                 350 caa aag tat ttt gca aaa gag aag cca att aca caa aaa cgt ttt ttt     1104
Gln Lys Tyr Phe Ala Lys Glu Lys Pro Ile Thr Gln Lys Arg Phe Phe
                355                 360                 365 gag cgt att gct cac ttt ata aaa gaa aaa gat gta tta tta gca gaa     1152
Glu Arg Ile Ala His Phe Ile Lys Glu Lys Asp Val Leu Leu Ala Glu
            370                 375                 380 cag ggt aca tgc ttt ttt ggt gcg tca acc ata caa cta ccc aaa gat     1200
Gln Gly Thr Cys Phe Phe Gly Ala Ser Thr Ile Gln Leu Pro Lys Asp
385                 390                 395                 400 gca act ttt att ggt caa cct tta tgg gga tct att gga tac aca ctt     1248
Ala Thr Phe Ile Gly Gln Pro Leu Trp Gly Ser Ile Gly Tyr Thr Leu
                405                 410                 415 cct gct tta tta ggt tca caa tta gct gat caa aaa agg cgt aat att     1296
Pro Ala Leu Leu Gly Ser Gln Leu Ala Asp Gln Lys Arg Arg Asn Ile
            420                 425                 430 ctt tta att ggg gat ggt gca ttt caa atg aca gca caa gaa att tca     1344
Leu Leu Ile Gly Asp Gly Ala Phe Gln Met Thr Ala Gln Glu Ile Ser
            435                 440                 445 aca atg ctt cgt tta caa atc aaa cct att att ttt tta att aat aac     1392
Thr Met Leu Arg Leu Gln Ile Lys Pro Ile Ile Phe Leu Ile Asn Asn
450                 455                 460 gat ggt tat aca att gaa cgt gct att cat ggt aga gaa caa gta tat     1440
Asp Gly Tyr Thr Ile Glu Arg Ala Ile His Gly Arg Glu Gln Val Tyr
465                 470                 475                 480 aac aat att caa atg tgg cga tat cat aat gtt cca aag gtt tta ggt     1488
Asn Asn Ile Gln Met Trp Arg Tyr His Asn Val Pro Lys Val Leu Gly
                485                 490                 495 cct aaa gaa tgc agc tta acc ttt aaa gta caa agt gaa act gaa ctt     1536
Pro Lys Glu Cys Ser Leu Thr Phe Lys Val Gln Ser Glu Thr Glu Leu
                500                 505                 510 gaa aag gct ctt tta gtg gca gat aag gat tgt gaa cat ttg att ttt     1584
Glu Lys Ala Leu Leu Val Ala Asp Lys Asp Cys Glu His Leu Ile Phe
            515                 520                 525 ata gaa gtt gtt atg gat cgt tat gat aaa ccc gag cct tta gaa cgt     1632
Ile Glu Val Val Met Asp Arg Tyr Asp Lys Pro Glu Pro Leu Glu Arg
530                 535                 540 ctt tcg aaa cgt ttt gca aat caa aat aat tag                         1665
Leu Ser Lys Arg Phe Ala Asn Gln Asn Asn
545                 550
```

<210> SEQ ID NO 36
<211> LENGTH: 554
<212> TYPE: PRT
<213> ORGANISM: Clostridium acetobutylicum

<400> SEQUENCE: 36

```
Leu Lys Ser Glu Tyr Thr Ile Gly Arg Tyr Leu Leu Asp Arg Leu Ser
1               5                   10                  15
Glu Leu Gly Ile Arg His Ile Phe Gly Val Pro Gly Asp Tyr Asn Leu
            20                  25                  30
Ser Phe Leu Asp Tyr Ile Met Glu Tyr Lys Gly Ile Asp Trp Val Gly
        35                  40                  45
Asn Cys Asn Glu Leu Asn Ala Gly Tyr Ala Ala Asp Gly Tyr Ala Arg
    50                  55                  60
Ile Asn Gly Ile Gly Ala Ile Leu Thr Thr Phe Gly Val Gly Glu Leu
65                  70                  75                  80
Ser Ala Ile Asn Ala Ile Ala Gly Ala Tyr Ala Glu Gln Val Pro Val
                85                  90                  95
Val Lys Ile Thr Gly Ile Pro Thr Ala Lys Val Arg Asp Asn Gly Leu
            100                 105                 110
Tyr Val His His Thr Leu Gly Asp Gly Arg Phe Asp His Phe Phe Glu
        115                 120                 125
Met Phe Arg Glu Val Thr Val Ala Glu Ala Leu Leu Ser Glu Glu Asn
130                 135                 140
Ala Ala Gln Glu Ile Asp Arg Val Leu Ile Ser Cys Trp Arg Gln Lys
145                 150                 155                 160
Arg Pro Val Leu Ile Asn Leu Pro Ile Asp Val Tyr Asp Lys Pro Ile
                165                 170                 175
Asn Lys Pro Leu Lys Pro Leu Leu Asp Tyr Thr Ile Ser Ser Asn Lys
            180                 185                 190
Glu Ala Ala Cys Glu Phe Val Thr Glu Ile Val Pro Ile Ile Asn Arg
        195                 200                 205
Ala Lys Lys Pro Val Ile Leu Ala Asp Tyr Gly Val Tyr Arg Tyr Gln
    210                 215                 220
Val Gln His Val Leu Lys Asn Leu Ala Glu Lys Thr Gly Phe Pro Val
225                 230                 235                 240
Ala Thr Leu Ser Met Gly Lys Gly Val Phe Asn Glu Ala His Pro Gln
                245                 250                 255
Phe Ile Gly Val Tyr Asn Gly Asp Val Ser Ser Pro Tyr Leu Arg Gln
            260                 265                 270
Arg Val Asp Glu Ala Asp Cys Ile Ile Ser Val Gly Val Lys Leu Thr
        275                 280                 285
Asp Ser Thr Thr Gly Gly Phe Ser His Gly Phe Ser Lys Arg Asn Val
    290                 295                 300
Ile His Ile Asp Pro Phe Ser Ile Lys Ala Lys Gly Lys Lys Tyr Ala
305                 310                 315                 320
Pro Ile Thr Met Lys Asp Ala Leu Thr Glu Leu Thr Ser Lys Ile Glu
                325                 330                 335
His Arg Asn Phe Glu Asp Leu Asp Ile Lys Pro Tyr Lys Ser Asp Asn
            340                 345                 350
Gln Lys Tyr Phe Ala Lys Glu Lys Pro Ile Thr Gln Lys Arg Phe Phe
        355                 360                 365
Glu Arg Ile Ala His Phe Ile Lys Glu Lys Asp Val Leu Leu Ala Glu
```

-continued

```
                  370                 375                 380
Gln Gly Thr Cys Phe Phe Gly Ala Ser Thr Ile Gln Leu Pro Lys Asp
385                 390                 395                 400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
                420                 425                 430

Leu Leu Ile Gly Asp Gly Ala Phe Gln Met Thr Ala Gln Glu Ile Ser
                435                 440                 445

Thr Met Leu Arg Leu Gln Ile Lys Pro Ile Ile Phe Leu Ile Asn Asn
            450                 455                 460

Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495

Pro Lys Glu Cys Ser Leu Thr Phe Lys Val Gln Ser Glu Thr Glu Leu
                500                 505                 510

Glu Lys Ala Leu Leu Val Ala Asp Lys Asp Cys Glu His Leu Ile Phe
                515                 520                 525

Ile Glu Val Val Met Asp Arg Tyr Asp Lys Pro Glu Pro Leu Glu Arg
                530                 535                 540

Leu Ser Lys Arg Phe Ala Asn Gln Asn Asn
545                 550
```

<210> SEQ ID NO 37
<211> LENGTH: 1056
<212> TYPE: DNA
<213> ORGANISM: Saccharomyces cerevisiae
<220> FEATURE:
<221> NAME/KEY: CDS
<222> LOCATION: (1)..(1056)

<400> SEQUENCE: 37

```
atg cct tcg caa gtc att cct gaa aaa caa aag gct att gtc ttt tat    48
Met Pro Ser Gln Val Ile Pro Glu Lys Gln Lys Ala Ile Val Phe Tyr
1               5                   10                  15 gag aca gat gga aaa ttg gaa tat aaa gac gtc aca gtt ccg gaa cct    96
Glu Thr Asp Gly Lys Leu Glu Tyr Lys Asp Val Thr Val Pro Glu Pro
            20                  25                  30 aag cct aac gaa att tta gtc cac gtt aaa tat tct ggt gtt tgt cat   144
Lys Pro Asn Glu Ile Leu Val His Val Lys Tyr Ser Gly Val Cys His
        35                  40                  45 agt gac ttg cac gcg tgg cac ggt gat tgg cca ttt caa ttg aaa ttt   192
Ser Asp Leu His Ala Trp His Gly Asp Trp Pro Phe Gln Leu Lys Phe
    50                  55                  60 cca tta atc ggt ggt cac gaa ggt gct ggt gtt gtt gtt aag ttg gga   240
Pro Leu Ile Gly Gly His Glu Gly Ala Gly Val Val Val Lys Leu Gly
65                  70                  75                  80 tct aac gtt aag ggc tgg aaa gtc ggt gat ttt gca ggt ata aaa tgg   288
Ser Asn Val Lys Gly Trp Lys Val Gly Asp Phe Ala Gly Ile Lys Trp
                85                  90                  95 ttg aat ggg act tgc atg tcc tgt gaa tat tgt gaa gta ggt aat gaa   336
Leu Asn Gly Thr Cys Met Ser Cys Glu Tyr Cys Glu Val Gly Asn Glu
            100                 105                 110 tct caa tgt cct tat ttg gat ggt act ggc ttc aca cat gat ggt act   384
Ser Gln Cys Pro Tyr Leu Asp Gly Thr Gly Phe Thr His Asp Gly Thr
        115                 120                 125 ttt caa gaa tac gca act gcc gat gcc gtt caa gct gcc cat att cca   432
```

```
                Phe Gln Glu Tyr Ala Thr Ala Asp Ala Val Gln Ala His Ile Pro
                    130                 135                 140 cca aac gtc aat ctt gct gaa gtt gcc cca atc ttg tgt gca ggt atc              480
Pro Asn Val Asn Leu Ala Glu Val Ala Pro Ile Leu Cys Ala Gly Ile
145                 150                 155                 160 act gtt tat aag gcg ttg aaa aga gcc aat gtg ata cca ggc caa tgg              528
Thr Val Tyr Lys Ala Leu Lys Arg Ala Asn Val Ile Pro Gly Gln Trp
                165                 170                 175 gtc act ata tcc ggt gca tgc ggt ggt ttg ggt tct ctg gca atc caa              576
Val Thr Ile Ser Gly Ala Cys Gly Gly Leu Gly Ser Leu Ala Ile Gln
            180                 185                 190 tac gcc ctt gct atg ggt tac agg gtc att ggt atc gat ggt ggt aat              624
Tyr Ala Leu Ala Met Gly Tyr Arg Val Ile Gly Ile Asp Gly Gly Asn
        195                 200                 205 gcc aag cga aag tta ttt gaa caa tta ggc gga gaa ata ttc atc gat              672
Ala Lys Arg Lys Leu Phe Glu Gln Leu Gly Gly Glu Ile Phe Ile Asp
    210                 215                 220 ttc acg gaa gaa aaa gac att gtt ggt gct ata ata aag gcc act aat              720
Phe Thr Glu Glu Lys Asp Ile Val Gly Ala Ile Ile Lys Ala Thr Asn
225                 230                 235                 240 ggc ggt tct cat gga gtt att aat gtg tct gtt tct gaa gca gct atc              768
Gly Gly Ser His Gly Val Ile Asn Val Ser Val Ser Glu Ala Ala Ile
                245                 250                 255 gag gct tct acg agg tat tgt agg ccc aat ggt act gtc gtc ctg gtt              816
Glu Ala Ser Thr Arg Tyr Cys Arg Pro Asn Gly Thr Val Val Leu Val
                260                 265                 270 ggt atg cca gct cat gct tac tgc aat tcc gat gtt ttc aat caa gtt              864
Gly Met Pro Ala His Ala Tyr Cys Asn Ser Asp Val Phe Asn Gln Val
            275                 280                 285 gta aaa tca atc tcc atc gtt gga tct tgt gtt gga aat aga gct gat              912
Val Lys Ser Ile Ser Ile Val Gly Ser Cys Val Gly Asn Arg Ala Asp
        290                 295                 300 aca agg gag gct tta gat ttc ttc gcc aga ggt ttg atc aaa tct ccg              960
Thr Arg Glu Ala Leu Asp Phe Phe Ala Arg Gly Leu Ile Lys Ser Pro
305                 310                 315                 320 atc cac tta gct ggc cta tcg gat gtt cct gaa att ttt gca aag atg             1008
Ile His Leu Ala Gly Leu Ser Asp Val Pro Glu Ile Phe Ala Lys Met
                325                 330                 335 gag aag ggt gaa att gtt ggt aga tat gtt gtt gag act tct aaa tga             1056
Glu Lys Gly Glu Ile Val Gly Arg Tyr Val Val Glu Thr Ser Lys
                340                 345                 350

<210> SEQ ID NO 38
<211> LENGTH: 351
<212> TYPE: PRT
<213> ORGANISM: Saccharomyces cerevisiae

<400> SEQUENCE: 38

Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
                20                  25                  30

Lys Pro Asn Glu Ile Leu Val His Val Lys Tyr Ser Gly Val Cys His
            35                  40                  45

Ser Asp Leu His Ala Trp His Gly Asp Trp Pro Phe Gln Leu Lys Phe
        50                  55                  60

Pro Leu Ile Gly Gly His Glu Gly Ala Gly Val Val Val Lys Leu Gly
65                  70                  75                  80

Ser Asn Val Lys Gly Trp Lys Val Gly Asp Phe Ala Gly Ile Lys Trp
```

```
                    85                  90                  95
Leu Asn Gly Thr Cys Met Ser Cys Glu Tyr Cys Glu Val Gly Asn Glu
                100                 105                 110

Ser Gln Cys Pro Tyr Leu Asp Gly Thr Gly Phe Thr His Asp Gly Thr
            115                 120                 125

Phe Gln Glu Tyr Ala Thr Ala Asp Ala Val Gln Ala Ala His Ile Pro
        130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
                180                 185                 190

Tyr Ala Leu Ala Met Gly Tyr Arg Val Ile Gly Ile Asp Gly Gly Asn
            195                 200                 205

Ala Lys Arg Lys Leu Phe Glu Gln Leu Gly Gly Glu Ile Phe Ile Asp
        210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
        290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

<210> SEQ ID NO 39
<211> LENGTH: 1725
<212> TYPE: DNA
<213> ORGANISM: Escherichia coli
<220> FEATURE:
<221> NAME/KEY: CDS
<222> LOCATION: (1)..(1725)

<400> SEQUENCE: 39 atg gag atg ttg tct gga gcc gag atg gtc gtc cga tcg ctt atc gat      48
Met Glu Met Leu Ser Gly Ala Glu Met Val Val Arg Ser Leu Ile Asp
1               5                   10                  15 cag ggc gtt aaa caa gta ttc ggt tat ccc gga ggc gca gtc ctt gat      96
Gln Gly Val Lys Gln Val Phe Gly Tyr Pro Gly Gly Ala Val Leu Asp
            20                  25                  30 att tat gat gca ttg cat acc gtg ggt ggt att gat cat gta tta gtt    144
Ile Tyr Asp Ala Leu His Thr Val Gly Gly Ile Asp His Val Leu Val
        35                  40                  45 cgt cat gag cag gcg gcg gtg cat atg gcc gat ggc ctg gcg cgc gcg    192
Arg His Glu Gln Ala Ala Val His Met Ala Asp Gly Leu Ala Arg Ala
    50                  55                  60 acc ggg gaa gtc ggc gtc gtg ctg gta acg tcg ggt cca ggg gcg acc    240
Thr Gly Glu Val Gly Val Val Leu Val Thr Ser Gly Pro Gly Ala Thr
```

```
                65                      70                      75                      80
aat gcg att act ggc atc gcc acc gct tat atg gat tcc att cca tta      288
Asn Ala Ile Thr Gly Ile Ala Thr Ala Tyr Met Asp Ser Ile Pro Leu
                        85                      90                      95 gtt gtc ctt tcc ggg cag gta gcg acc tcg ttg ata ggt tac gat gcc      336
Val Val Leu Ser Gly Gln Val Ala Thr Ser Leu Ile Gly Tyr Asp Ala
                100                     105                     110 ttt cag gag tgc gac atg gtg ggg att tcg cga ccg gtt aaa cac          384
Phe Gln Glu Cys Asp Met Val Gly Ile Ser Arg Pro Val Val Lys His
            115                     120                     125 agt ttt ctg gtt aag caa acg gaa gac att ccg cag gtg ctg aaa aag      432
Ser Phe Leu Val Lys Gln Thr Glu Asp Ile Pro Gln Val Leu Lys Lys
    130                     135                     140 gct ttc tgg ctg gcg gca agt ggt cgc cca gga cca gta gtc gtt gat      480
Ala Phe Trp Leu Ala Ala Ser Gly Arg Pro Gly Pro Val Val Val Asp
145                     150                     155                     160 tta ccg aaa gat att ctt aat ccg gcg aac aaa tta ccc tat gtc tgg      528
Leu Pro Lys Asp Ile Leu Asn Pro Ala Asn Lys Leu Pro Tyr Val Trp
                165                     170                     175 ccg gag tcg gtc agt atg cgt tct tac aat ccc act act acc gga cat      576
Pro Glu Ser Val Ser Met Arg Ser Tyr Asn Pro Thr Thr Thr Gly His
                180                     185                     190 aaa ggg caa att aag cgt gct ctg caa acg ctg gta gcg gca aaa aaa      624
Lys Gly Gln Ile Lys Arg Ala Leu Gln Thr Leu Val Ala Ala Lys Lys
            195                     200                     205 ccg gtt gtc tac gta ggc ggt ggg gca atc acg gcg ggc tgc cat cag      672
Pro Val Val Tyr Val Gly Gly Gly Ala Ile Thr Ala Gly Cys His Gln
    210                     215                     220 cag ttg aaa gaa acg gtg gag gcg ttg aat ctg ccc gtt gtt tgc tca      720
Gln Leu Lys Glu Thr Val Glu Ala Leu Asn Leu Pro Val Val Cys Ser
225                     230                     235                     240 ttg atg ggg ctg ggg gcg ttt ccg gca acg cat cgt cag gca ctg ggc      768
Leu Met Gly Leu Gly Ala Phe Pro Ala Thr His Arg Gln Ala Leu Gly
                245                     250                     255 atg ctg gga atg cac ggt acc tac gaa gcc aat atg acg atg cat aac      816
Met Leu Gly Met His Gly Thr Tyr Glu Ala Asn Met Thr Met His Asn
                260                     265                     270 gcg gat gtg att ttc gcc gtc ggg gta cga ttt gat gac cga acg acg      864
Ala Asp Val Ile Phe Ala Val Gly Val Arg Phe Asp Asp Arg Thr Thr
            275                     280                     285 aac aat ctg gca aag tac tgc cca aat gcc act gtt ctg cat atc gat      912
Asn Asn Leu Ala Lys Tyr Cys Pro Asn Ala Thr Val Leu His Ile Asp
    290                     295                     300 att gat cct act tcc att tct aaa acc gtg act gcg gat atc ccg att      960
Ile Asp Pro Thr Ser Ile Ser Lys Thr Val Thr Ala Asp Ile Pro Ile
305                     310                     315                     320 gtg ggg gat gct cgc cag gtc ctc gaa caa atg ctt gaa ctc ttg tcg      1008
Val Gly Asp Ala Arg Gln Val Leu Glu Gln Met Leu Glu Leu Leu Ser
                325                     330                     335 caa gaa tcc gcc cat caa cca ctg gat gag atc cgc gac tgg tgg cag      1056
Gln Glu Ser Ala His Gln Pro Leu Asp Glu Ile Arg Asp Trp Trp Gln
                340                     345                     350 caa att gaa cag tgg cgc gct cgt cag tgc ctg aaa tat gac act cac      1104
Gln Ile Glu Gln Trp Arg Ala Arg Gln Cys Leu Lys Tyr Asp Thr His
            355                     360                     365 agt gaa aag att aaa ccg cag gcg gtg atc gag act ctt tgg cgg ttg      1152
Ser Glu Lys Ile Lys Pro Gln Ala Val Ile Glu Thr Leu Trp Arg Leu
    370                     375                     380 acg aag gga gac gct tac gtg acg tcc gat gtc ggg cag cac cag atg      1200
```

```
Thr Lys Gly Asp Ala Tyr Val Thr Ser Asp Val Gly Gln His Gln Met
385                 390                 395                 400 ttt gct gca ctt tat tat cca ttc gac aaa ccg cgt cgc tgg atc aat    1248
Phe Ala Ala Leu Tyr Tyr Pro Phe Asp Lys Pro Arg Arg Trp Ile Asn
                405                 410                 415 tcc ggt ggc ctc ggc acg atg ggt ttt ggt tta cct gcg gca ctg ggc    1296
Ser Gly Gly Leu Gly Thr Met Gly Phe Gly Leu Pro Ala Ala Leu Gly
            420                 425                 430 gtc aaa atg gcg ttg cca gaa gaa acc gtg gtt tgc gtc act ggc gac    1344
Val Lys Met Ala Leu Pro Glu Glu Thr Val Val Cys Val Thr Gly Asp
        435                 440                 445 ggc agt att cag atg aac atc cag gaa ctg tct acc gcg ttg caa tac    1392
Gly Ser Ile Gln Met Asn Ile Gln Glu Leu Ser Thr Ala Leu Gln Tyr
450                 455                 460 gag ttg ccc gta ctg gtg gtg aat ctc aat aac cgc tat ctg ggg atg    1440
Glu Leu Pro Val Leu Val Val Asn Leu Asn Asn Arg Tyr Leu Gly Met
465                 470                 475                 480 gtg aag cag tgg cag gac atg atc tat tcc ggc cgt cat tca caa tct    1488
Val Lys Gln Trp Gln Asp Met Ile Tyr Ser Gly Arg His Ser Gln Ser
                485                 490                 495 tat atg caa tcg cta ccc gat ttc gtc cgt ctg gcg gaa gcc tat ggg    1536
Tyr Met Gln Ser Leu Pro Asp Phe Val Arg Leu Ala Glu Ala Tyr Gly
            500                 505                 510 cat gtc ggg atc cag att tct cat ccg cat gag ctg gaa agc aaa ctt    1584
His Val Gly Ile Gln Ile Ser His Pro His Glu Leu Glu Ser Lys Leu
        515                 520                 525 agc gag gcg ctg gaa cag gtg cgc aat aat cgc ctg gtg ttt gtt gat    1632
Ser Glu Ala Leu Glu Gln Val Arg Asn Asn Arg Leu Val Phe Val Asp
530                 535                 540 gtt acc gtc gat ggc agc gag cac gtc tac ccg atg cag att cgc ggg    1680
Val Thr Val Asp Gly Ser Glu His Val Tyr Pro Met Gln Ile Arg Gly
545                 550                 555                 560 ggc gga atg gat gaa atg tgg tta agc aaa acg gag aga acc tga        1725
Gly Gly Met Asp Glu Met Trp Leu Ser Lys Thr Glu Arg Thr
                565                 570

<210> SEQ ID NO 40
<211> LENGTH: 574
<212> TYPE: PRT
<213> ORGANISM: Escherichia coli

<400> SEQUENCE: 40

Met Glu Met Leu Ser Gly Ala Glu Met Val Val Arg Ser Leu Ile Asp
1               5                   10                  15

Gln Gly Val Lys Gln Val Phe Gly Tyr Pro Gly Gly Ala Val Leu Asp
            20                  25                  30

Ile Tyr Asp Ala Leu His Thr Val Gly Gly Ile Asp His Val Leu Val
        35                  40                  45

Arg His Glu Gln Ala Ala Val His Met Ala Asp Gly Leu Ala Arg Ala
    50                  55                  60

Thr Gly Glu Val Gly Val Val Leu Val Thr Ser Gly Pro Gly Ala Thr
65                  70                  75                  80

Asn Ala Ile Thr Gly Ile Ala Thr Ala Tyr Met Asp Ser Ile Pro Leu
                85                  90                  95

Val Val Leu Ser Gly Gln Val Ala Thr Ser Leu Ile Gly Tyr Asp Ala
            100                 105                 110

Phe Gln Glu Cys Asp Met Val Gly Ile Ser Arg Pro Val Val Lys His
        115                 120                 125
```

```
Ser Phe Leu Val Lys Gln Thr Glu Asp Ile Pro Gln Val Leu Lys Lys
    130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175

Pro Glu Ser Val Ser Met Arg Ser Tyr Asn Pro Thr Thr Gly His
                180                 185                 190

Lys Gly Gln Ile Lys Arg Ala Leu Gln Thr Leu Val Ala Ala Lys Lys
            195                 200                 205

Pro Val Val Tyr Val Gly Gly Gly Ala Ile Thr Ala Gly Cys His Gln
210                 215                 220

Gln Leu Lys Glu Thr Val Glu Ala Leu Asn Leu Pro Val Val Cys Ser
225                 230                 235                 240

Leu Met Gly Leu Gly Ala Phe Pro Ala Thr His Arg Gln Ala Leu Gly
                245                 250                 255

Met Leu Gly Met His Gly Thr Tyr Glu Ala Asn Met Thr Met His Asn
                260                 265                 270

Ala Asp Val Ile Phe Ala Val Gly Val Arg Phe Asp Asp Arg Thr Thr
            275                 280                 285

Asn Asn Leu Ala Lys Tyr Cys Pro Asn Ala Thr Val Leu His Ile Asp
290                 295                 300

Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
                325                 330                 335

Gln Glu Ser Ala His Gln Pro Leu Asp Glu Ile Arg Asp Trp Trp Gln
                340                 345                 350

Gln Ile Glu Gln Trp Arg Ala Arg Gln Cys Leu Lys Tyr Asp Thr His
            355                 360                 365

Ser Glu Lys Ile Lys Pro Gln Ala Val Ile Glu Thr Leu Trp Arg Leu
370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
                420                 425                 430

Val Lys Met Ala Leu Pro Glu Glu Thr Val Val Cys Val Thr Gly Asp
            435                 440                 445

Gly Ser Ile Gln Met Asn Ile Gln Glu Leu Ser Thr Ala Leu Gln Tyr
450                 455                 460

Glu Leu Pro Val Leu Val Asn Leu Asn Asn Arg Tyr Leu Gly Met
465                 470                 475                 480

Val Lys Gln Trp Gln Asp Met Ile Tyr Ser Gly Arg His Ser Gln Ser
                485                 490                 495

Tyr Met Gln Ser Leu Pro Asp Phe Val Arg Leu Ala Glu Ala Tyr Gly
                500                 505                 510

His Val Gly Ile Gln Ile Ser His Pro His Glu Leu Glu Ser Lys Leu
            515                 520                 525

Ser Glu Ala Leu Glu Gln Val Arg Asn Asn Arg Leu Val Phe Val Asp
530                 535                 540

Val Thr Val Asp Gly Ser Glu His Val Tyr Pro Met Gln Ile Arg Gly
```

```
                545         550         555         560
                Gly Gly Met Asp Glu Met Trp Leu Ser Lys Thr Glu Arg Thr
                                565                 570

<210> SEQ ID NO 41
<211> LENGTH: 492
<212> TYPE: DNA
<213> ORGANISM: Escherichia coli
<220> FEATURE:
<221> NAME/KEY: CDS
<222> LOCATION: (1)..(492)

<400> SEQUENCE: 41 atg cgc cgg ata tta tca gtc tta ctc gaa aat gaa tca ggc gcg tta         48
Met Arg Arg Ile Leu Ser Val Leu Leu Glu Asn Glu Ser Gly Ala Leu
1               5                   10                  15 tcc cgc gtg att ggc ctt ttt tcc cag cgt ggc tac aac att gaa agc         96
Ser Arg Val Ile Gly Leu Phe Ser Gln Arg Gly Tyr Asn Ile Glu Ser
                20                  25                  30 ctg acc gtt gcg cca acc gac gat ccg aca tta tcg cgt atg acc atc        144
Leu Thr Val Ala Pro Thr Asp Asp Pro Thr Leu Ser Arg Met Thr Ile
            35                  40                  45 cag acc gtg ggc gat gaa aaa gta ctt gag cag atc gaa aag caa tta        192
Gln Thr Val Gly Asp Glu Lys Val Leu Glu Gln Ile Glu Lys Gln Leu
        50                  55                  60 cac aaa ctg gtc gat gtc ttg cgc gtg agt gag ttg ggg cag ggc gcg        240
His Lys Leu Val Asp Val Leu Arg Val Ser Glu Leu Gly Gln Gly Ala
65                  70                  75                  80 cat gtt gag cgg gaa atc atg ctg gtg aaa att cag gcc agc ggt tac        288
His Val Glu Arg Glu Ile Met Leu Val Lys Ile Gln Ala Ser Gly Tyr
                85                  90                  95 ggg cgt gac gaa gtg aaa cgt aat acg gaa ata ttc cgt ggg caa att        336
Gly Arg Asp Glu Val Lys Arg Asn Thr Glu Ile Phe Arg Gly Gln Ile
                100                 105                 110 atc gat gtc aca ccc tcg ctt tat acc gtt caa tta gca ggc acc agc        384
Ile Asp Val Thr Pro Ser Leu Tyr Thr Val Gln Leu Ala Gly Thr Ser
            115                 120                 125 ggt aag ctt gat gca ttt tta gca tcg att cgc gat gtg gcg aaa att        432
Gly Lys Leu Asp Ala Phe Leu Ala Ser Ile Arg Asp Val Ala Lys Ile
        130                 135                 140 gtg gag gtt gct cgc tct ggt gtg gtc gga ctt tcg cgc ggc gat aaa        480
Val Glu Val Ala Arg Ser Gly Val Val Gly Leu Ser Arg Gly Asp Lys
145                 150                 155                 160 ata atg cgt tga                                                         492
Ile Met Arg <210> SEQ ID NO 42
<211> LENGTH: 163
<212> TYPE: PRT
<213> ORGANISM: Escherichia coli

<400> SEQUENCE: 42

Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
                20                  25                  30

Leu Thr Val Ala Pro Thr Asp Asp Pro Thr Leu Ser Arg Met Thr Ile
            35                  40                  45

Gln Thr Val Gly Asp Glu Lys Val Leu Glu Gln Ile Glu Lys Gln Leu
        50                  55                  60
```

```
His Lys Leu Val Asp Val Leu Arg Val Ser Glu Leu Gly Gln Gly Ala
 65                  70                  75                  80

His Val Glu Arg Glu Ile Met Leu Val Lys Ile Gln Ala Ser Gly Tyr
                 85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Asp Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160

Ile Met Arg

<210> SEQ ID NO 43
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 43
```

| | | | | | | | | | | | | | | | | |
|---|---|---|---|---|---|---|---|---|---|---|---|---|---|---|---|---|
| atg | gct | aac | tac | ttc | aat | aca | ctg | aat | ctg | cgc | cag | cag | ctg | gca | cag | 48 |
| Met | Ala | Asn | Tyr | Phe | Asn | Thr | Leu | Asn | Leu | Arg | Gln | Gln | Leu | Ala | Gln | |
| 1   |     |     |     | 5   |     |     |     |     | 10  |     |     |     |     | 15  |     | |
| ctg | ggc | aaa | tgt | cgc | ttt | atg | ggc | cgc | gat | gaa | ttc | gcc | gat | ggc | gcg | 96 |
| Leu | Gly | Lys | Cys | Arg | Phe | Met | Gly | Arg | Asp | Glu | Phe | Ala | Asp | Gly | Ala | |
|     |     | 20  |     |     |     |     | 25  |     |     |     |     | 30  |     |     |     | |
| agc | tac | ctt | cag | ggt | aaa | aaa | gta | gtc | atc | gtc | ggc | tgt | ggc | gca | cag | 144 |
| Ser | Tyr | Leu | Gln | Gly | Lys | Lys | Val | Val | Ile | Val | Gly | Cys | Gly | Ala | Gln | |
|     | 35  |     |     |     |     | 40  |     |     |     |     | 45  |     |     |     |     | |
| ggt | ctg | aac | cag | ggc | ctg | aac | atg | cgt | gat | tct | ggt | ctc | gat | atc | tcc | 192 |
| Gly | Leu | Asn | Gln | Gly | Leu | Asn | Met | Arg | Asp | Ser | Gly | Leu | Asp | Ile | Ser | |
|     | 50  |     |     |     |     | 55  |     |     |     |     | 60  |     |     |     |     | |
| tac | gct | ctg | cgt | aaa | gaa | gcg | att | gcc | gag | aag | cgc | gcg | tcc | tgg | cgt | 240 |
| Tyr | Ala | Leu | Arg | Lys | Glu | Ala | Ile | Ala | Glu | Lys | Arg | Ala | Ser | Trp | Arg | |
| 65  |     |     |     |     | 70  |     |     |     |     | 75  |     |     |     |     | 80  | |
| aaa | gcg | acc | gaa | aat | ggt | ttt | aaa | gtg | ggt | act | tac | gaa | gaa | ctg | atc | 288 |
| Lys | Ala | Thr | Glu | Asn | Gly | Phe | Lys | Val | Gly | Thr | Tyr | Glu | Glu | Leu | Ile | |
|     |     |     |     | 85  |     |     |     |     | 90  |     |     |     |     | 95  |     | |
| cca | cag | gcg | gat | ctg | gtg | att | aac | ctg | acg | ccg | gac | aag | cag | cac | tct | 336 |
| Pro | Gln | Ala | Asp | Leu | Val | Ile | Asn | Leu | Thr | Pro | Asp | Lys | Gln | His | Ser | |
|     |     |     | 100 |     |     |     |     | 105 |     |     |     |     | 110 |     |     | |
| gat | gta | gtg | cgc | acc | gta | cag | cca | ctg | atg | aaa | gac | ggc | gcg | gcg | ctg | 384 |
| Asp | Val | Val | Arg | Thr | Val | Gln | Pro | Leu | Met | Lys | Asp | Gly | Ala | Ala | Leu | |
|     |     |     | 115 |     |     |     |     | 120 |     |     |     |     | 125 |     |     | |
| ggc | tac | tcg | cac | ggt | ttc | aac | atc | gtc | gaa | gtg | ggc | gag | cag | atc | cgt | 432 |
| Gly | Tyr | Ser | His | Gly | Phe | Asn | Ile | Val | Glu | Val | Gly | Glu | Gln | Ile | Arg | |
|     | 130 |     |     |     |     | 135 |     |     |     |     | 140 |     |     |     |     | |
| aaa | gat | atc | acc | gta | gtg | atg | gtt | gcg | ccg | aaa | tgc | cca | ggc | acc | gaa | 480 |
| Lys | Asp | Ile | Thr | Val | Val | Met | Val | Ala | Pro | Lys | Cys | Pro | Gly | Thr | Glu | |
| 145 |     |     |     |     | 150 |     |     |     |     | 155 |     |     |     |     | 160 | |
| gtg | cgt | gaa | gag | tac | aaa | cgt | ggg | ttc | ggc | gta | ccg | acg | ctg | att | gcc | 528 |
| Val | Arg | Glu | Glu | Tyr | Lys | Arg | Gly | Phe | Gly | Val | Pro | Thr | Leu | Ile | Ala | |
|     |     |     |     | 165 |     |     |     |     | 170 |     |     |     |     | 175 |     | |
| gtt | cac | ccg | gaa | aac | gat | ccg | aaa | ggc | gaa | ggc | atg | gcg | att | gcc | aaa | 576 |
| Val | His | Pro | Glu | Asn | Asp | Pro | Lys | Gly | Glu | Gly | Met | Ala | Ile | Ala | Lys | |
|     |     |     | 180 |     |     |     |     | 185 |     |     |     |     | 190 |     |     | |

| | | |
|---|---|---|
| gcc tgg gcg gct gca acc ggt ggt cac cgt gcg ggt gtg ctg gaa tcg<br>Ala Trp Ala Ala Ala Thr Gly Gly His Arg Ala Gly Val Leu Glu Ser<br>    195                    200                  205 | | 624 |
| tcc ttc gtt gcg gaa gtg aaa tct gac ctg atg ggc gag caa acc atc<br>Ser Phe Val Ala Glu Val Lys Ser Asp Leu Met Gly Glu Gln Thr Ile<br>    210                    215                  220 | | 672 |
| ctg tgc ggt atg ttg cag gct ggc tct ctg ctg tgc ttc gac aag ctg<br>Leu Cys Gly Met Leu Gln Ala Gly Ser Leu Leu Cys Phe Asp Lys Leu<br>225                  230                  235                  240 | | 720 |
| gtg gaa gaa ggt acc gat cca gca tac gca gaa aaa ctg att cag ttc<br>Val Glu Glu Gly Thr Asp Pro Ala Tyr Ala Glu Lys Leu Ile Gln Phe<br>                  245                  250                  255 | | 768 |
| ggt tgg gaa acc atc acc gaa gca ctg aaa cag ggc ggc atc acc ctg<br>Gly Trp Glu Thr Ile Thr Glu Ala Leu Lys Gln Gly Gly Ile Thr Leu<br>            260                    265                  270 | | 816 |
| atg atg gac cgt ctc tct aac ccg gcg aaa ctg cgt gct tat gcg ctt<br>Met Met Asp Arg Leu Ser Asn Pro Ala Lys Leu Arg Ala Tyr Ala Leu<br>            275                  280                  285 | | 864 |
| tct gaa cag ctg aaa gag atc atg gca ccc ctg ttc cag aaa cat atg<br>Ser Glu Gln Leu Lys Glu Ile Met Ala Pro Leu Phe Gln Lys His Met<br>290                  295                  300 | | 912 |
| gac gac atc atc tcc ggc gaa ttc tct tcc ggt atg atg gcg gac tgg<br>Asp Asp Ile Ile Ser Gly Glu Phe Ser Ser Gly Met Met Ala Asp Trp<br>305                  310                  315                  320 | | 960 |
| gcc aac gat gat aag aaa ctg ctg acc tgg cgt gaa gag acc ggc aaa<br>Ala Asn Asp Asp Lys Lys Leu Leu Thr Trp Arg Glu Glu Thr Gly Lys<br>                  325                  330                  335 | | 1008 |
| acc gcg ttt gaa acc gcg ccg cag tat gaa ggc aaa atc ggc gag cag<br>Thr Ala Phe Glu Thr Ala Pro Gln Tyr Glu Gly Lys Ile Gly Glu Gln<br>            340                    345                  350 | | 1056 |
| gag tac ttc gat aaa ggc gta ctg atg att gcg atg gtg aaa gcg ggc<br>Glu Tyr Phe Asp Lys Gly Val Leu Met Ile Ala Met Val Lys Ala Gly<br>                  355                  360                  365 | | 1104 |
| gtt gaa ctg gcg ttc gaa acc atg gtc gat tcc ggc atc att gaa gag<br>Val Glu Leu Ala Phe Glu Thr Met Val Asp Ser Gly Ile Ile Glu Glu<br>    370                    375                  380 | | 1152 |
| tct gca tat tat gaa tca ctg cac gag ctg ccg ctg att gcc aac acc<br>Ser Ala Tyr Tyr Glu Ser Leu His Glu Leu Pro Leu Ile Ala Asn Thr<br>385                  390                  395                  400 | | 1200 |
| atc gcc cgt aag cgt ctg tac gaa atg aac gtg gtt atc tct gat acc<br>Ile Ala Arg Lys Arg Leu Tyr Glu Met Asn Val Val Ile Ser Asp Thr<br>                  405                  410                  415 | | 1248 |
| gct gag tac ggt aac tat ctg ttc tct tac gct tgt gtg ccg ttg ctg<br>Ala Glu Tyr Gly Asn Tyr Leu Phe Ser Tyr Ala Cys Val Pro Leu Leu<br>            420                    425                  430 | | 1296 |
| aaa ccg ttt atg gca gag ctg caa ccg ggc gac ctg ggt aaa gct att<br>Lys Pro Phe Met Ala Glu Leu Gln Pro Gly Asp Leu Gly Lys Ala Ile<br>                  435                  440                  445 | | 1344 |
| ccg gaa ggc gcg gta gat aac ggg caa ctg cgt gat gtg aac gaa gcg<br>Pro Glu Gly Ala Val Asp Asn Gly Gln Leu Arg Asp Val Asn Glu Ala<br>    450                    455                  460 | | 1392 |
| att cgc agc cat gcg att gag cag gta ggt aag aaa ctg cgc ggc tat<br>Ile Arg Ser His Ala Ile Glu Gln Val Gly Lys Lys Leu Arg Gly Tyr<br>465                  470                  475                  480 | | 1440 |
| atg aca gat atg aaa cgt att gct gtt gcg ggt taa<br>Met Thr Asp Met Lys Arg Ile Ala Val Ala Gly<br>                  485                  490 | | 1476 |

<210> SEQ ID NO 44
<211> LENGTH: 491

```
<212> TYPE: PRT
<213> ORGANISM: Escherichia coli

<400> SEQUENCE: 44
```

| | | | | | | | | | | | | | | | |
|---|---|---|---|---|---|---|---|---|---|---|---|---|---|---|---|

```
Met Ala Asn Tyr Phe Asn Thr Leu Asn Leu Arg Gln Gln Leu Ala Gln
1               5                  10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
                35                  40                  45

Gly Leu Asn Gln Gly Leu Asn Met Arg Asp Ser Gly Leu Asp Ile Ser
        50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Thr Gly Gly His Arg Ala Gly Val Leu Glu Ser Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400
```

```
Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 45
<211> LENGTH: 1851
<212> TYPE: DNA
<213> ORGANISM: Escherichia coli
<220> FEATURE:
<221> NAME/KEY: CDS
<222> LOCATION: (1)..(1851)

<400> SEQUENCE: 45
```

| | | | | | | | | | | | | | | | | |
|---|---|---|---|---|---|---|---|---|---|---|---|---|---|---|---|---|
| atg | cct | aag | tac | cgt | tcc | gcc | acc | acc | act | cat | ggt | cgt | aat | atg | gcg | 48 |
| Met | Pro | Lys | Tyr | Arg | Ser | Ala | Thr | Thr | Thr | His | Gly | Arg | Asn | Met | Ala | |
| 1 | | | | 5 | | | | | 10 | | | | | 15 | | |
| ggt | gct | cgt | gcg | ctg | tgg | cgc | gcc | acc | gga | atg | acc | gac | gcc | gat | ttc | 96 |
| Gly | Ala | Arg | Ala | Leu | Trp | Arg | Ala | Thr | Gly | Met | Thr | Asp | Ala | Asp | Phe | |
| | | | 20 | | | | | 25 | | | | | 30 | | | |
| ggt | aag | ccg | att | atc | gcg | gtt | gtg | aac | tcg | ttc | acc | caa | ttt | gta | ccg | 144 |
| Gly | Lys | Pro | Ile | Ile | Ala | Val | Val | Asn | Ser | Phe | Thr | Gln | Phe | Val | Pro | |
| | | 35 | | | | | 40 | | | | | 45 | | | | |
| ggt | cac | gtc | cat | ctg | cgc | gat | ctc | ggt | aaa | ctg | gtc | gcc | gaa | caa | att | 192 |
| Gly | His | Val | His | Leu | Arg | Asp | Leu | Gly | Lys | Leu | Val | Ala | Glu | Gln | Ile | |
| | 50 | | | | | 55 | | | | | 60 | | | | | |
| gaa | gcg | gct | ggc | ggc | gtt | gcc | aaa | gag | ttc | aac | acc | att | gcg | gtg | gat | 240 |
| Glu | Ala | Ala | Gly | Gly | Val | Ala | Lys | Glu | Phe | Asn | Thr | Ile | Ala | Val | Asp | |
| 65 | | | | | 70 | | | | | 75 | | | | | 80 | |
| gat | ggg | att | gcc | atg | ggc | cac | ggg | ggg | atg | ctt | tat | tca | ctg | cca | tct | 288 |
| Asp | Gly | Ile | Ala | Met | Gly | His | Gly | Gly | Met | Leu | Tyr | Ser | Leu | Pro | Ser | |
| | | | | 85 | | | | | 90 | | | | | 95 | | |
| cgc | gaa | ctg | atc | gct | gat | tcc | gtt | gag | tat | atg | gtc | aac | gcc | cac | tgc | 336 |
| Arg | Glu | Leu | Ile | Ala | Asp | Ser | Val | Glu | Tyr | Met | Val | Asn | Ala | His | Cys | |
| | | | 100 | | | | | 105 | | | | | 110 | | | |
| gcc | gac | gcc | atg | gtc | tgc | atc | tct | aac | tgc | gac | aaa | atc | acc | ccg | ggg | 384 |
| Ala | Asp | Ala | Met | Val | Cys | Ile | Ser | Asn | Cys | Asp | Lys | Ile | Thr | Pro | Gly | |
| | | 115 | | | | | 120 | | | | | 125 | | | | |
| atg | ctg | atg | gct | tcc | ctg | cgc | ctg | aat | att | ccg | gtg | atc | ttt | gtt | tcc | 432 |
| Met | Leu | Met | Ala | Ser | Leu | Arg | Leu | Asn | Ile | Pro | Val | Ile | Phe | Val | Ser | |
| | 130 | | | | | 135 | | | | | 140 | | | | | |
| ggc | ggc | ccg | atg | gag | gcc | ggg | aaa | acc | aaa | ctt | tcc | gat | cag | atc | atc | 480 |
| Gly | Gly | Pro | Met | Glu | Ala | Gly | Lys | Thr | Lys | Leu | Ser | Asp | Gln | Ile | Ile | |
| 145 | | | | | 150 | | | | | 155 | | | | | 160 | |
| aag | ctc | gat | ctg | gtt | gat | gcg | atg | atc | cag | ggc | gca | gac | ccg | aaa | gta | 528 |
| Lys | Leu | Asp | Leu | Val | Asp | Ala | Met | Ile | Gln | Gly | Ala | Asp | Pro | Lys | Val | |
| | | | | 165 | | | | | 170 | | | | | 175 | | |
| tct | gac | tcc | cag | agc | gat | cag | gtt | gaa | cgt | tcc | gcg | tgt | ccg | acc | tgc | 576 |
| Ser | Asp | Ser | Gln | Ser | Asp | Gln | Val | Glu | Arg | Ser | Ala | Cys | Pro | Thr | Cys | |
| | | | 180 | | | | | 185 | | | | | 190 | | | |
| ggt | tcc | tgc | tcc | ggg | atg | ttt | acc | gct | aac | tca | atg | aac | tgc | ctg | acc | 624 |

```
            Gly Ser Cys Ser Gly Met Phe Thr Ala Asn Ser Met Asn Cys Leu Thr
                    195                 200                 205 gaa gcg ctg ggc ctg tcg cag ccg ggc aac ggc tcg ctg ctg gca acc               672
Glu Ala Leu Gly Leu Ser Gln Pro Gly Asn Gly Ser Leu Leu Ala Thr
210                 215                 220 cac gcc gac cgt aag cag ctg ttc ctt aat gct ggt aaa cgc att gtt               720
His Ala Asp Arg Lys Gln Leu Phe Leu Asn Ala Gly Lys Arg Ile Val
225                 230                 235                 240 gaa ttg acc aaa cgt tat tac gag caa aac gac gaa agt gca ctg ccg               768
Glu Leu Thr Lys Arg Tyr Tyr Glu Gln Asn Asp Glu Ser Ala Leu Pro
            245                 250                 255 cgt aat atc gcc agt aag gcg gcg ttt gaa aac gcc atg acg ctg gat               816
Arg Asn Ile Ala Ser Lys Ala Ala Phe Glu Asn Ala Met Thr Leu Asp
        260                 265                 270 atc gcg atg ggt gga tcg act aac acc gta ctt cac ctg ctg gcg gcg               864
Ile Ala Met Gly Gly Ser Thr Asn Thr Val Leu His Leu Leu Ala Ala
    275                 280                 285 gcg cag gaa gcg gaa atc gac ttc acc atg agt gat atc gat aag ctt               912
Ala Gln Glu Ala Glu Ile Asp Phe Thr Met Ser Asp Ile Asp Lys Leu
290                 295                 300 tcc cgc aag gtt cca cag ctg tgt aaa gtt gcg ccg agc acc cag aaa               960
Ser Arg Lys Val Pro Gln Leu Cys Lys Val Ala Pro Ser Thr Gln Lys
305                 310                 315                 320 tac cat atg gaa gat gtt cac cgt gct ggt ggt gtt atc ggt att ctc              1008
Tyr His Met Glu Asp Val His Arg Ala Gly Gly Val Ile Gly Ile Leu
            325                 330                 335 ggc gaa ctg gat cgc gcg ggg tta ctg aac cgt gat gtg aaa aac gta              1056
Gly Glu Leu Asp Arg Ala Gly Leu Leu Asn Arg Asp Val Lys Asn Val
        340                 345                 350 ctt ggc ctg acg ttg ccg caa acg ctg gaa caa tac gac gtt atg ctg              1104
Leu Gly Leu Thr Leu Pro Gln Thr Leu Glu Gln Tyr Asp Val Met Leu
    355                 360                 365 acc cag gat gac gcg gta aaa aat atg ttc cgc gca ggt cct gca ggc              1152
Thr Gln Asp Asp Ala Val Lys Asn Met Phe Arg Ala Gly Pro Ala Gly
370                 375                 380 att cgt acc aca cag gca ttc tcg caa gat tgc cgt tgg gat acg ctg              1200
Ile Arg Thr Thr Gln Ala Phe Ser Gln Asp Cys Arg Trp Asp Thr Leu
385                 390                 395                 400 gac gac gat cgc gcc aat ggc tgt atc cgc tcg ctg gaa cac gcc tac              1248
Asp Asp Asp Arg Ala Asn Gly Cys Ile Arg Ser Leu Glu His Ala Tyr
            405                 410                 415 agc aaa gac ggc ggc ctg gcg gtg ctc tac ggt aac ttt gcg gaa aac              1296
Ser Lys Asp Gly Gly Leu Ala Val Leu Tyr Gly Asn Phe Ala Glu Asn
        420                 425                 430 ggc tgc atc gtg aaa acg gca ggc gtc gat gac agc atc ctc aaa ttc              1344
Gly Cys Ile Val Lys Thr Ala Gly Val Asp Asp Ser Ile Leu Lys Phe
    435                 440                 445 acc ggc ccg gcg aaa gtg tac gaa agc cag gac gat gcg gta gaa gcg              1392
Thr Gly Pro Ala Lys Val Tyr Glu Ser Gln Asp Asp Ala Val Glu Ala
450                 455                 460 att ctc ggc ggt aaa gtt gtc gcc gga gat gtg gta gta att cgc tat              1440
Ile Leu Gly Gly Lys Val Val Ala Gly Asp Val Val Val Ile Arg Tyr
465                 470                 475                 480 gaa ggc ccg aaa ggc ggt ccg ggg atg cag gaa atg ctc tac cca acc              1488
Glu Gly Pro Lys Gly Gly Pro Gly Met Gln Glu Met Leu Tyr Pro Thr
            485                 490                 495 agc ttc ctg aaa tca atg ggt ctc ggc aaa gcc tgt gcg ctg atc acc              1536
Ser Phe Leu Lys Ser Met Gly Leu Gly Lys Ala Cys Ala Leu Ile Thr
        500                 505                 510
```

| | | | | | | | | | | | | | | | | |
|---|---|---|---|---|---|---|---|---|---|---|---|---|---|---|---|---|
| gac | ggt | cgt | ttc | tct | ggt | ggc | acc | tct | ggt | ctt | tcc | atc | ggc | cac | gtc | 1584 |
| Asp | Gly | Arg | Phe | Ser | Gly | Gly | Thr | Ser | Gly | Leu | Ser | Ile | Gly | His | Val | |
| | | 515 | | | | | 520 | | | | | 525 | | | | |
| tca | ccg | gaa | gcg | gca | agc | ggc | agc | att | ggc | ctg | att | gaa | gat | ggt | | 1632 |
| Ser | Pro | Glu | Ala | Ala | Ser | Gly | Ser | Ile | Gly | Leu | Ile | Glu | Asp | Gly | | |
| | 530 | | | | | 535 | | | | | 540 | | | | | |
| gac | ctg | atc | gct | atc | gac | atc | ccg | aac | cgt | ggc | att | cag | tta | cag | gta | 1680 |
| Asp | Leu | Ile | Ala | Ile | Asp | Ile | Pro | Asn | Arg | Gly | Ile | Gln | Leu | Gln | Val | |
| 545 | | | | | 550 | | | | | 555 | | | | | 560 | |
| agc | gat | gcc | gaa | ctg | gcg | gcg | cgt | cgt | gaa | gcg | cag | gac | gct | cga | ggt | 1728 |
| Ser | Asp | Ala | Glu | Leu | Ala | Ala | Arg | Arg | Glu | Ala | Gln | Asp | Ala | Arg | Gly | |
| | | | | 565 | | | | | 570 | | | | | 575 | | |
| gac | aaa | gcc | tgg | acg | ccg | aaa | aat | cgt | gaa | cgt | cag | gtc | tcc | ttt | gcc | 1776 |
| Asp | Lys | Ala | Trp | Thr | Pro | Lys | Asn | Arg | Glu | Arg | Gln | Val | Ser | Phe | Ala | |
| | | | 580 | | | | | 585 | | | | | 590 | | | |
| ctg | cgt | gct | tat | gcc | agc | ctg | gca | acc | agc | gcc | gac | aaa | ggc | gcg | gtg | 1824 |
| Leu | Arg | Ala | Tyr | Ala | Ser | Leu | Ala | Thr | Ser | Ala | Asp | Lys | Gly | Ala | Val | |
| | 595 | | | | | 600 | | | | | 605 | | | | | |
| cgc | gat | aaa | tcg | aaa | ctg | ggg | ggt | taa | | | | | | | | 1851 |
| Arg | Asp | Lys | Ser | Lys | Leu | Gly | Gly | | | | | | | | | |
| | 610 | | | | | 615 | | | | | | | | | | |

<210> SEQ ID NO 46
<211> LENGTH: 616
<212> TYPE: PRT
<213> ORGANISM: Escherichia coli

<400> SEQUENCE: 46

Met Pro Lys Tyr Arg Ser Ala Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val

```
            225                 230                 235                 240
Glu Leu Thr Lys Arg Tyr Tyr Glu Gln Asn Asp Glu Ser Ala Leu Pro
                    245                 250                 255

Arg Asn Ile Ala Ser Lys Ala Ala Phe Glu Asn Ala Met Thr Leu Asp
                    260                 265                 270

Ile Ala Met Gly Gly Ser Thr Asn Thr Val Leu His Leu Leu Ala Ala
                275                 280                 285

Ala Gln Glu Ala Glu Ile Asp Phe Thr Met Ser Asp Ile Asp Lys Leu
            290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Val Ile Gly Ile Leu
                325                 330                 335

Gly Glu Leu Asp Arg Ala Gly Leu Leu Asn Arg Asp Val Lys Asn Val
                340                 345                 350

Leu Gly Leu Thr Leu Pro Gln Thr Leu Glu Gln Tyr Asp Val Met Leu
                355                 360                 365

Thr Gln Asp Asp Ala Val Lys Asn Met Phe Arg Ala Gly Pro Ala Gly
            370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
                420                 425                 430

Gly Cys Ile Val Lys Thr Ala Gly Val Asp Asp Ser Ile Leu Lys Phe
            435                 440                 445

Thr Gly Pro Ala Lys Val Tyr Glu Ser Gln Asp Asp Ala Val Glu Ala
                450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
                500                 505                 510

Asp Gly Arg Phe Ser Gly Gly Thr Ser Gly Leu Ser Ile Gly His Val
                515                 520                 525

Ser Pro Glu Ala Ala Ser Gly Gly Ser Ile Gly Leu Ile Glu Asp Gly
            530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
                580                 585                 590

Leu Arg Ala Tyr Ala Ser Leu Ala Thr Ser Ala Asp Lys Gly Ala Val
                595                 600                 605

Arg Asp Lys Ser Lys Leu Gly Gly
    610                 615

<210> SEQ ID NO 47
<211> LENGTH: 1545
<212> TYPE: DNA
<213> ORGANISM: Escherichia coli
```

<220> FEATURE:
<221> NAME/KEY: CDS
<222> LOCATION: (1)..(1545)

<400> SEQUENCE: 47

```
atg gct gac tcg caa ccc ctg tcc ggt gct ccg gaa ggt gcc gaa tat        48
Met Ala Asp Ser Gln Pro Leu Ser Gly Ala Pro Glu Gly Ala Glu Tyr
1               5                   10                  15 tta aga gca gtg ctg cgc gcg ccg gtt tac gag gcg gcg cag gtt acg        96
Leu Arg Ala Val Leu Arg Ala Pro Val Tyr Glu Ala Ala Gln Val Thr
                20                  25                  30 ccg cta caa aaa atg gaa aaa ctg tcg tcg cgt ctt gat aac gtc att       144
Pro Leu Gln Lys Met Glu Lys Leu Ser Ser Arg Leu Asp Asn Val Ile
            35                  40                  45 ctg gtg aag cgc gaa gat cgc cag cca gtg cac agc ttt aag ctg cgc       192
Leu Val Lys Arg Glu Asp Arg Gln Pro Val His Ser Phe Lys Leu Arg
        50                  55                  60 ggc gca tac gcc atg atg gcg ggc ctg acg gaa gaa cag aaa gcg cac       240
Gly Ala Tyr Ala Met Met Ala Gly Leu Thr Glu Glu Gln Lys Ala His
65                  70                  75                  80 ggc gtg atc act gct tct gcg ggt aac cac gcg cag ggc gtc gcg ttt       288
Gly Val Ile Thr Ala Ser Ala Gly Asn His Ala Gln Gly Val Ala Phe
                85                  90                  95 tct tct gcg cgg tta ggc gtg aag gcc ctg atc gtt atg cca acc gcc       336
Ser Ser Ala Arg Leu Gly Val Lys Ala Leu Ile Val Met Pro Thr Ala
                100                 105                 110 acc gcc gac atc aaa gtc gac gcg gtg cgc ggc ttc ggc ggc gaa gtg       384
Thr Ala Asp Ile Lys Val Asp Ala Val Arg Gly Phe Gly Gly Glu Val
            115                 120                 125 ctg ctc cac ggc gcg aac ttt gat gaa gcg aaa gcc aaa gcg atc gaa       432
Leu Leu His Gly Ala Asn Phe Asp Glu Ala Lys Ala Lys Ala Ile Glu
        130                 135                 140 ctg tca cag cag cag ggg ttc acc tgg gtg ccg ccg ttc gac cat ccg       480
Leu Ser Gln Gln Gln Gly Phe Thr Trp Val Pro Pro Phe Asp His Pro
145                 150                 155                 160 atg gtg att gcc ggg caa ggc acg ctg gcg ctg gaa ctg ctc cag cag       528
Met Val Ile Ala Gly Gln Gly Thr Leu Ala Leu Glu Leu Leu Gln Gln
                165                 170                 175 gac gcc cat ctc gac cgc gta ttt gtg cca gtc ggc ggc ggt ggt ctg       576
Asp Ala His Leu Asp Arg Val Phe Val Pro Val Gly Gly Gly Gly Leu
            180                 185                 190 gct gct ggc gtg gcg gtg ctg atc aaa caa ctg atg ccg caa atc aaa       624
Ala Ala Gly Val Ala Val Leu Ile Lys Gln Leu Met Pro Gln Ile Lys
        195                 200                 205 gtg atc gcc gta gaa gcg gaa gac tcc gcc tgc ctg aaa gca gcg ctg       672
Val Ile Ala Val Glu Ala Glu Asp Ser Ala Cys Leu Lys Ala Ala Leu
210                 215                 220 gat gcg ggt cat ccg gtt gat ctg ccg cgc gta ggg cta ttt gct gaa       720
Asp Ala Gly His Pro Val Asp Leu Pro Arg Val Gly Leu Phe Ala Glu
225                 230                 235                 240 ggc gta gcg gta aaa cgc atc ggt gac gaa acc ttc cgt tta tgc cag       768
Gly Val Ala Val Lys Arg Ile Gly Asp Glu Thr Phe Arg Leu Cys Gln
                245                 250                 255 gag tat ctc gac gac atc atc acc gtc gat agc gat gcg atc tgt gcg       816
Glu Tyr Leu Asp Asp Ile Ile Thr Val Asp Ser Asp Ala Ile Cys Ala
            260                 265                 270 gcg atg aag gat tta ttc gaa gat gtg cgc gcg gtg gcg gaa ccc tct       864
Ala Met Lys Asp Leu Phe Glu Asp Val Arg Ala Val Ala Glu Pro Ser
        275                 280                 285 ggc gcg ctg gcg ctg gcg gga atg aaa aaa tat atc gcc ctg cac aac       912
```

```
Gly Ala Leu Ala Leu Ala Gly Met Lys Lys Tyr Ile Ala Leu His Asn
            290                 295                 300 att cgc ggc gaa cgg ctg gcg cat att ctt tcc ggt gcc aac gtg aac      960
Ile Arg Gly Glu Arg Leu Ala His Ile Leu Ser Gly Ala Asn Val Asn
305                 310                 315                 320 ttc cac ggc ctg cgc tac gtc tca gaa cgc tgc gaa ctg ggc gaa cag     1008
Phe His Gly Leu Arg Tyr Val Ser Glu Arg Cys Glu Leu Gly Glu Gln
                325                 330                 335 cgt gaa gcg ttg ttg gcg gtg acc att ccg gaa gaa aaa ggc agc ttc     1056
Arg Glu Ala Leu Leu Ala Val Thr Ile Pro Glu Glu Lys Gly Ser Phe
            340                 345                 350 ctc aaa ttc tgc caa ctg ctt ggc ggg cgt tcg gtc acc gag ttc aac     1104
Leu Lys Phe Cys Gln Leu Leu Gly Gly Arg Ser Val Thr Glu Phe Asn
        355                 360                 365 tac cgt ttt gcc gat gcc aaa aac gcc tgc atc ttt gtc ggt gtg cgc     1152
Tyr Arg Phe Ala Asp Ala Lys Asn Ala Cys Ile Phe Val Gly Val Arg
370                 375                 380 ctg agc cgc ggc ctc gaa gag cgc aaa gaa att ttg cag atg ctc aac     1200
Leu Ser Arg Gly Leu Glu Glu Arg Lys Glu Ile Leu Gln Met Leu Asn
385                 390                 395                 400 gac ggc ggc tac agc gtg gtt gat ctc tcc gac gac gaa atg gcg aag     1248
Asp Gly Gly Tyr Ser Val Val Asp Leu Ser Asp Asp Glu Met Ala Lys
                405                 410                 415 cta cac gtg cgc tat atg gtc ggc gga cgt cca tcg cat ccg ttg cag     1296
Leu His Val Arg Tyr Met Val Gly Gly Arg Pro Ser His Pro Leu Gln
            420                 425                 430 gaa cgc ctc tac agc ttc gaa ttc ccg gaa tca ccg ggc gcg ctg ctg     1344
Glu Arg Leu Tyr Ser Phe Glu Phe Pro Glu Ser Pro Gly Ala Leu Leu
        435                 440                 445 cgc ttc ctc aac acg ctg ggt acg tac tgg aac att tct ttg ttc cac     1392
Arg Phe Leu Asn Thr Leu Gly Thr Tyr Trp Asn Ile Ser Leu Phe His
450                 455                 460 tat cgc agc cat ggc acc gac tac ggg cgc gta ctg gcg gcg ttc gaa     1440
Tyr Arg Ser His Gly Thr Asp Tyr Gly Arg Val Leu Ala Ala Phe Glu
465                 470                 475                 480 ctt ggc gac cat gaa ccg gat ttc gaa acc cgg ctg aat gag ctg ggc     1488
Leu Gly Asp His Glu Pro Asp Phe Glu Thr Arg Leu Asn Glu Leu Gly
                485                 490                 495 tac gat tgc cac gac gaa acc aat aac ccg gcg ttc agg ttc ttt ttg     1536
Tyr Asp Cys His Asp Glu Thr Asn Asn Pro Ala Phe Arg Phe Phe Leu
            500                 505                 510 gcg ggt tag                                                          1545
Ala Gly <210> SEQ ID NO 48
<211> LENGTH: 514
<212> TYPE: PRT
<213> ORGANISM: Escherichia coli

<400> SEQUENCE: 48

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
```

```
                65                  70                  75                  80
        Gly Val Ile Thr Ala Ser Ala Gly Asn His Ala Gln Gly Val Ala Phe
                            85                  90                  95

Ser Ser Ala Arg Leu Gly Val Lys Ala Leu Ile Val Met Pro Thr Ala
                           100                 105                 110

Thr Ala Asp Ile Lys Val Asp Ala Val Arg Gly Phe Gly Gly Glu Val
                           115                 120                 125

Leu Leu His Gly Ala Asn Phe Asp Glu Ala Lys Ala Lys Ala Ile Glu
                    130                 135                 140

Leu Ser Gln Gln Gln Gly Phe Thr Trp Val Pro Pro Phe Asp His Pro
        145                 150                 155                 160

Met Val Ile Ala Gly Gln Gly Thr Leu Ala Leu Glu Leu Leu Gln Gln
                            165                 170                 175

Asp Ala His Leu Asp Arg Val Phe Val Pro Val Gly Gly Gly Gly Leu
                    180                 185                 190

Ala Ala Gly Val Ala Val Leu Ile Lys Gln Leu Met Pro Gln Ile Lys
                    195                 200                 205

Val Ile Ala Val Glu Ala Glu Asp Ser Ala Cys Leu Lys Ala Ala Leu
        210                 215                 220

Asp Ala Gly His Pro Val Asp Leu Pro Arg Val Gly Leu Phe Ala Glu
        225                 230                 235                 240

Gly Val Ala Val Lys Arg Ile Gly Asp Glu Thr Phe Arg Leu Cys Gln
                            245                 250                 255

Glu Tyr Leu Asp Asp Ile Ile Thr Val Asp Ser Asp Ala Ile Cys Ala
                    260                 265                 270

Ala Met Lys Asp Leu Phe Glu Asp Val Arg Ala Val Ala Glu Pro Ser
                    275                 280                 285

Gly Ala Leu Ala Leu Ala Gly Met Lys Lys Tyr Ile Ala Leu His Asn
                    290                 295                 300

Ile Arg Gly Glu Arg Leu Ala His Ile Leu Ser Gly Ala Asn Val Asn
        305                 310                 315                 320

Phe His Gly Leu Arg Tyr Val Ser Glu Arg Cys Glu Leu Gly Glu Gln
                            325                 330                 335

Arg Glu Ala Leu Leu Ala Val Thr Ile Pro Glu Glu Lys Gly Ser Phe
                            340                 345                 350

Leu Lys Phe Cys Gln Leu Leu Gly Gly Arg Ser Val Thr Glu Phe Asn
                    355                 360                 365

Tyr Arg Phe Ala Asp Ala Lys Asn Ala Cys Ile Phe Val Gly Val Arg
                    370                 375                 380

Leu Ser Arg Gly Leu Glu Glu Arg Lys Glu Ile Leu Gln Met Leu Asn
        385                 390                 395                 400

Asp Gly Gly Tyr Ser Val Val Asp Leu Ser Asp Asp Glu Met Ala Lys
                    405                 410                 415

Leu His Val Arg Tyr Met Val Gly Gly Arg Pro Ser His Pro Leu Gln
                    420                 425                 430

Glu Arg Leu Tyr Ser Phe Glu Phe Pro Glu Ser Pro Gly Ala Leu Leu
                    435                 440                 445

Arg Phe Leu Asn Thr Leu Gly Thr Tyr Trp Asn Ile Ser Leu Phe His
        450                 455                 460

Tyr Arg Ser His Gly Thr Asp Tyr Gly Arg Val Leu Ala Ala Phe Glu
        465                 470                 475                 480

Leu Gly Asp His Glu Pro Asp Phe Glu Thr Arg Leu Asn Glu Leu Gly
                    485                 490                 495
```

```
Tyr Asp Cys His Asp Glu Thr Asn Asn Pro Ala Phe Arg Phe Phe Leu
            500                 505                 510
Ala Gly
```

<210> SEQ ID NO 49
<211> LENGTH: 1572
<212> TYPE: DNA
<213> ORGANISM: Escherichia coli
<220> FEATURE:
<221> NAME/KEY: CDS
<222> LOCATION: (1)..(1572)

<400> SEQUENCE: 49

```
atg agc cag caa gtc att att ttc gat acc aca ttg cgc gac ggt gaa      48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg      96
Gln Ala Leu Gln Ala Ser Leu Ser Val Lys Glu Lys Leu Gln Ile Ala
                20                  25                  30 ctg gcc ctt gag cgt atg ggt gtt gac gtg atg gaa gtc ggt ttc ccc     144
Leu Ala Leu Glu Arg Met Gly Val Asp Val Met Glu Val Gly Phe Pro
            35                  40                  45 gtc tct tcg ccg ggc gat ttt gaa tcg gtg caa acc atc gcc cgc cag     192
Val Ser Ser Pro Gly Asp Phe Glu Ser Val Gln Thr Ile Ala Arg Gln
        50                  55                  60 gtt aaa aac agc cgc gta tgt gcg tta gct cgc tgc gtg gaa aaa gat     240
Val Lys Asn Ser Arg Val Cys Ala Leu Ala Arg Cys Val Glu Lys Asp
65                  70                  75                  80 atc gac gtg gcg gcc gaa tcc ctg aaa gtc gcc gaa gcc ttc cgt att     288
Ile Asp Val Ala Ala Glu Ser Leu Lys Val Ala Glu Ala Phe Arg Ile
                85                  90                  95 cat acc ttt att gcc act tcg cca atg cac atc gcc acc aag ctg cgc     336
His Thr Phe Ile Ala Thr Ser Pro Met His Ile Ala Thr Lys Leu Arg
                100                 105                 110 agc acg ctg gac gag gtg atc gaa cgc gct atc tat atg gtg aaa cgc     384
Ser Thr Leu Asp Glu Val Ile Glu Arg Ala Ile Tyr Met Val Lys Arg
            115                 120                 125 gcc cgt aat tac acc gat gat gtt gaa ttt tct tgc gaa gat gcc ggg     432
Ala Arg Asn Tyr Thr Asp Asp Val Glu Phe Ser Cys Glu Asp Ala Gly
        130                 135                 140 cgt aca ccc att gcc gat ctg gcg cga gtg gtc gaa gcg gcg att aat     480
Arg Thr Pro Ile Ala Asp Leu Ala Arg Val Val Glu Ala Ala Ile Asn
145                 150                 155                 160 gcc ggt gcc acc acc atc aac att ccg gac acc gtg ggc tac acc atg     528
Ala Gly Ala Thr Thr Ile Asn Ile Pro Asp Thr Val Gly Tyr Thr Met
                165                 170                 175 ccg ttt gag ttc gcc gga atc atc agc ggc ctg tat gaa cgc gtg cct     576
Pro Phe Glu Phe Ala Gly Ile Ile Ser Gly Leu Tyr Glu Arg Val Pro
                180                 185                 190 aac atc gac aaa gcc att atc tcc gta cat acc cac gat gat ttg ggc     624
Asn Ile Asp Lys Ala Ile Ile Ser Val His Thr His Asp Asp Leu Gly
            195                 200                 205 ctg gcg gtc gga aac tca ctg gcg gcg gta cat gcc ggt gca cgc cag     672
Leu Ala Val Gly Asn Ser Leu Ala Ala Val His Ala Gly Ala Arg Gln
        210                 215                 220 gtg gaa ggc gca atg aac ggg atc ggc gag cgt gcc gga aac tgt tcc     720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac     768
Leu Glu Glu Val Ile Met Ala Ile Lys Val Arg Lys Asp Ile Leu Asn
```

```
                  245                 250                 255
gtc cac acc gcc att aat cac cag gag ata tgg cgc acc agc cag tta    816
Val His Thr Ala Ile Asn His Gln Glu Ile Trp Arg Thr Ser Gln Leu
        260                 265                 270 gtt agc cag att tgt aat atg ccg atc ccg gca aac aaa gcc att gtt    864
Val Ser Gln Ile Cys Asn Met Pro Ile Pro Ala Asn Lys Ala Ile Val
    275                 280                 285 ggc agc ggc gca ttc gca cac tcc tcc ggt ata cac cag gat ggc gtg    912
Gly Ser Gly Ala Phe Ala His Ser Ser Gly Ile His Gln Asp Gly Val
290                 295                 300 ctg aaa aac cgc gaa aac tac gaa atc atg aca cca gaa tct att ggt    960
Leu Lys Asn Arg Glu Asn Tyr Glu Ile Met Thr Pro Glu Ser Ile Gly
305                 310                 315                 320 ctg aac caa atc cag ctg aat ctg acc tct cgt tcg ggg cgt gcg gcg   1008
Leu Asn Gln Ile Gln Leu Asn Leu Thr Ser Arg Ser Gly Arg Ala Ala
                325                 330                 335 gtg aaa cat cgc atg gat gag atg ggg tat aaa gaa agt gaa tat aat   1056
Val Lys His Arg Met Asp Glu Met Gly Tyr Lys Glu Ser Glu Tyr Asn
            340                 345                 350 tta gac aat ttg tac gat gct ttc ctg aag ctg gcg gac aaa aaa ggt   1104
Leu Asp Asn Leu Tyr Asp Ala Phe Leu Lys Leu Ala Asp Lys Lys Gly
        355                 360                 365 cag gtg ttt gat tac gat ctg gag gcg ctg gcc ttc atc ggt aag cag   1152
Gln Val Phe Asp Tyr Asp Leu Glu Ala Leu Ala Phe Ile Gly Lys Gln
370                 375                 380 caa gaa gag ccg gag cat ttc cgt ctg gat tac ttc agc gtg cag tct   1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa   1248
Gly Ser Asn Asp Ile Ala Thr Ala Ala Val Lys Leu Ala Cys Gly Glu
                405                 410                 415 gaa gtc aaa gca gaa gcc gcc aac ggt aac ggt ccg gtc gat gcc gtc   1296
Glu Val Lys Ala Glu Ala Ala Asn Gly Asn Gly Pro Val Asp Ala Val
            420                 425                 430 tat cag gca att aac cgc atc act gaa tat aac gtc gaa ctg gtg aaa   1344
Tyr Gln Ala Ile Asn Arg Ile Thr Glu Tyr Asn Val Glu Leu Val Lys
        435                 440                 445 tac agc ctg acc gcc aaa ggc cac ggt aaa gat gcg ctg ggt cag gtg   1392
Tyr Ser Leu Thr Ala Lys Gly His Gly Lys Asp Ala Leu Gly Gln Val
450                 455                 460 gat atc gtc gct aac tac aac ggt cgc cgc ttc cac ggc gtc ggc ctg   1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg   1488
Ala Thr Asp Ile Val Glu Ser Ser Ala Lys Ala Met Val His Val Leu
                485                 490                 495 aac aat atc tgg cgt gcc gca gaa gtc gaa aaa gag ttg caa cgc aaa   1536
Asn Asn Ile Trp Arg Ala Ala Glu Val Glu Lys Glu Leu Gln Arg Lys
            500                 505                 510 gct caa cac aac gaa aac aac aag gaa acc gtg tga                    1572
Ala Gln His Asn Glu Asn Asn Lys Glu Thr Val
        515                 520

<210> SEQ ID NO 50
<211> LENGTH: 523
<212> TYPE: PRT
<213> ORGANISM: Escherichia coli

<400> SEQUENCE: 50

Met Ser Gln Gln Val Ile Ile Phe Asp Thr Thr Leu Arg Asp Gly Glu
```

-continued

```
1               5                    10                   15
Gln Ala Leu Gln Ala Ser Leu Ser Val Lys Glu Lys Leu Gln Ile Ala
                20                  25                  30
Leu Ala Leu Glu Arg Met Gly Val Asp Val Met Glu Val Gly Phe Pro
                35                  40                  45
Val Ser Ser Pro Gly Asp Phe Glu Ser Val Gln Thr Ile Ala Arg Gln
    50                  55                  60
Val Lys Asn Ser Arg Val Cys Ala Leu Ala Arg Cys Val Glu Lys Asp
65                  70                  75                  80
Ile Asp Val Ala Ala Glu Ser Leu Lys Val Ala Glu Ala Phe Arg Ile
                85                  90                  95
His Thr Phe Ile Ala Thr Ser Pro Met His Ile Ala Thr Lys Leu Arg
                100                 105                 110
Ser Thr Leu Asp Glu Val Ile Glu Arg Ala Ile Tyr Met Val Lys Arg
                115                 120                 125
Ala Arg Asn Tyr Thr Asp Asp Val Glu Phe Ser Cys Glu Asp Ala Gly
                130                 135                 140
Arg Thr Pro Ile Ala Asp Leu Ala Arg Val Val Glu Ala Ala Ile Asn
145                 150                 155                 160
Ala Gly Ala Thr Thr Ile Asn Ile Pro Asp Thr Val Gly Tyr Thr Met
                165                 170                 175
Pro Phe Glu Phe Ala Gly Ile Ile Ser Gly Leu Tyr Glu Arg Val Pro
                180                 185                 190
Asn Ile Asp Lys Ala Ile Ile Ser Val His Thr His Asp Asp Leu Gly
                195                 200                 205
Leu Ala Val Gly Asn Ser Leu Ala Ala Val His Ala Gly Ala Arg Gln
                210                 215                 220
Val Glu Gly Ala Met Asn Gly Ile Gly Glu Arg Ala Gly Asn Cys Ser
225                 230                 235                 240
Leu Glu Glu Val Ile Met Ala Ile Lys Val Arg Lys Asp Ile Leu Asn
                245                 250                 255
Val His Thr Ala Ile Asn His Gln Glu Ile Trp Arg Thr Ser Gln Leu
                260                 265                 270
Val Ser Gln Ile Cys Asn Met Pro Ile Pro Ala Asn Lys Ala Ile Val
                275                 280                 285
Gly Ser Gly Ala Phe Ala His Ser Ser Gly Ile His Gln Asp Gly Val
                290                 295                 300
Leu Lys Asn Arg Glu Asn Tyr Glu Ile Met Thr Pro Glu Ser Ile Gly
305                 310                 315                 320
Leu Asn Gln Ile Gln Leu Asn Leu Thr Ser Arg Ser Gly Arg Ala Ala
                325                 330                 335
Val Lys His Arg Met Asp Glu Met Gly Tyr Lys Glu Ser Glu Tyr Asn
                340                 345                 350
Leu Asp Asn Leu Tyr Asp Ala Phe Leu Lys Leu Ala Asp Lys Lys Gly
                355                 360                 365
Gln Val Phe Asp Tyr Asp Leu Glu Ala Leu Ala Phe Ile Gly Lys Gln
                370                 375                 380
Gln Glu Glu Pro Glu His Phe Arg Leu Asp Tyr Phe Ser Val Gln Ser
385                 390                 395                 400
Gly Ser Asn Asp Ile Ala Thr Ala Ala Val Lys Leu Ala Cys Gly Glu
                405                 410                 415
Glu Val Lys Ala Glu Ala Ala Asn Gly Asn Gly Pro Val Asp Ala Val
                420                 425                 430
```

```
                Tyr Gln Ala Ile Asn Arg Ile Thr Glu Tyr Asn Val Glu Leu Val Lys
                            435                 440                 445

Tyr Ser Leu Thr Ala Lys Gly His Gly Lys Asp Ala Leu Gly Gln Val
                    450                 455                 460

Asp Ile Val Ala Asn Tyr Asn Gly Arg Arg Phe His Gly Val Gly Leu
                465                 470                 475                 480

Ala Thr Asp Ile Val Glu Ser Ser Ala Lys Ala Met Val His Val Leu
                                485                 490                 495

Asn Asn Ile Trp Arg Ala Ala Glu Val Glu Lys Glu Leu Gln Arg Lys
                            500                 505                 510

Ala Gln His Asn Glu Asn Asn Lys Glu Thr Val
                            515                 520

<210> SEQ ID NO 51
                <211> LENGTH: 1095
                <212> TYPE: DNA
                <213> ORGANISM: Escherichia coli
                <220> FEATURE:
                <221> NAME/KEY: CDS
                <222> LOCATION: (1)..(1095)

<400> SEQUENCE: 51
```

| | | |
|---|---|---|
| gtg atg tcg aag aat tac cat att gcc gta ttg ccg ggg gac ggt att<br>Val Met Ser Lys Asn Tyr His Ile Ala Val Leu Pro Gly Asp Gly Ile<br>1               5                   10                  15 | | 48 |
| ggt ccg gaa gtg atg acc cag gcg ctg aaa gtg ctg gat gcc gtg cgc<br>Gly Pro Glu Val Met Thr Gln Ala Leu Lys Val Leu Asp Ala Val Arg<br>                20                  25                  30 | | 96 |
| aac cgc ttt gcg atg cgc atc acc acc agc cat tac gat gta ggc ggc<br>Asn Arg Phe Ala Met Arg Ile Thr Thr Ser His Tyr Asp Val Gly Gly<br>            35                  40                  45 | | 144 |
| gca gcc att gat aac cac ggg caa cca ctg ccg cct gcg acg gtt gaa<br>Ala Ala Ile Asp Asn His Gly Gln Pro Leu Pro Pro Ala Thr Val Glu<br>        50                  55                  60 | | 192 |
| ggt tgt gag caa gcc gat gcc gtg ctg ttt ggc tcg gta ggc ggc ccg<br>Gly Cys Glu Gln Ala Asp Ala Val Leu Phe Gly Ser Val Gly Gly Pro<br>65                  70                  75                  80 | | 240 |
| aag tgg gaa cat tta cca cca gac cag caa cca gaa cgc ggc gcg ctg<br>Lys Trp Glu His Leu Pro Pro Asp Gln Gln Pro Glu Arg Gly Ala Leu<br>                85                  90                  95 | | 288 |
| ctg cct ctg cgt aag cac ttc aaa tta ttc agc aac ctg cgc ccg gca<br>Leu Pro Leu Arg Lys His Phe Lys Leu Phe Ser Asn Leu Arg Pro Ala<br>            100                 105                 110 | | 336 |
| aaa ctg tat cag ggg ctg gaa gca ttc tgt ccg ctg cgt gca gac att<br>Lys Leu Tyr Gln Gly Leu Glu Ala Phe Cys Pro Leu Arg Ala Asp Ile<br>        115                 120                 125 | | 384 |
| gcc gca aac ggc ttc gac atc ctg tgt gtg cgc gaa ctg acc ggc ggc<br>Ala Ala Asn Gly Phe Asp Ile Leu Cys Val Arg Glu Leu Thr Gly Gly<br>    130                 135                 140 | | 432 |
| atc tat ttc ggt cag cca aaa ggc cgc gaa ggt agc gga caa tat gaa<br>Ile Tyr Phe Gly Gln Pro Lys Gly Arg Glu Gly Ser Gly Gln Tyr Glu<br>145                 150                 155                 160 | | 480 |
| aaa gcc ttt gat acc gag gtg tat cac cgt ttt gag atc gaa cgt atc<br>Lys Ala Phe Asp Thr Glu Val Tyr His Arg Phe Glu Ile Glu Arg Ile<br>                165                 170                 175 | | 528 |
| gcc cgc atc gcg ttt gaa tct gct cgc aag cgt cgc cac aaa gtg acg<br>Ala Arg Ile Ala Phe Glu Ser Ala Arg Lys Arg Arg His Lys Val Thr<br>            180                 185                 190 | | 576 |
| tcg atc gat aaa gcc aac gtg ctg caa tcc tct att tta tgg cgg gag<br> | | 624 |

```
Ser Ile Asp Lys Ala Asn Val Leu Gln Ser Ser Ile Leu Trp Arg Glu
        195                 200                 205 atc gtt aac gag atc gcc acg gaa tac ccg gat gtc gaa ctg gcg cat      672
Ile Val Asn Glu Ile Ala Thr Glu Tyr Pro Asp Val Glu Leu Ala His
        210                 215                 220 atg tac atc gac aac gcc acc atg cag ctg att aaa gat cca tca cag      720
Met Tyr Ile Asp Asn Ala Thr Met Gln Leu Ile Lys Asp Pro Ser Gln
225                 230                 235                 240 ttt gac gtt ctg ctg tgc tcc aac ctg ttt ggc gac att ctg tct gac      768
Phe Asp Val Leu Leu Cys Ser Asn Leu Phe Gly Asp Ile Leu Ser Asp
                245                 250                 255 gag tgc gca atg atc act ggc tcg atg ggg atg ttg cct tcc gcc agc      816
Glu Cys Ala Met Ile Thr Gly Ser Met Gly Met Leu Pro Ser Ala Ser
            260                 265                 270 ctg aac gag caa ggt ttt gga ctg tat gaa ccg gcg ggc ggc tcg gca      864
Leu Asn Glu Gln Gly Phe Gly Leu Tyr Glu Pro Ala Gly Gly Ser Ala
        275                 280                 285 cca gat atc gca ggc aaa aac atc gcc aac ccg att gca caa atc ctt      912
Pro Asp Ile Ala Gly Lys Asn Ile Ala Asn Pro Ile Ala Gln Ile Leu
    290                 295                 300 tcg ctg gca ctg ctg ctg cgt tac agc ctg gat gcc gat gat gcg gct      960
Ser Leu Ala Leu Leu Leu Arg Tyr Ser Leu Asp Ala Asp Asp Ala Ala
305                 310                 315                 320 tgc gcc att gaa cgc gcc att aac cgc gca tta gaa gaa ggc att cgc     1008
Cys Ala Ile Glu Arg Ala Ile Asn Arg Ala Leu Glu Glu Gly Ile Arg
                325                 330                 335 acc ggg gat tta gcc cgt ggc gct gcc gcc gtt agt acc gat gaa atg     1056
Thr Gly Asp Leu Ala Arg Gly Ala Ala Ala Val Ser Thr Asp Glu Met
            340                 345                 350 ggc gat atc att gcc cgc tat gta gca gaa ggg gtg taa                 1095
Gly Asp Ile Ile Ala Arg Tyr Val Ala Glu Gly Val
        355                 360

<210> SEQ ID NO 52
<211> LENGTH: 364
<212> TYPE: PRT
<213> ORGANISM: Escherichia coli

<400> SEQUENCE: 52

Val Met Ser Lys Asn Tyr His Ile Ala Val Leu Pro Gly Asp Gly Ile
1               5                   10                  15

Gly Pro Glu Val Met Thr Gln Ala Leu Lys Val Leu Asp Ala Val Arg
            20                  25                  30

Asn Arg Phe Ala Met Arg Ile Thr Thr Ser His Tyr Asp Val Gly Gly
        35                  40                  45

Ala Ala Ile Asp Asn His Gly Gln Pro Leu Pro Pro Ala Thr Val Glu
    50                  55                  60

Gly Cys Glu Gln Ala Asp Ala Val Leu Phe Gly Ser Val Gly Gly Pro
65                  70                  75                  80

Lys Trp Glu His Leu Pro Pro Asp Gln Pro Glu Arg Gly Ala Leu
                85                  90                  95

Leu Pro Leu Arg Lys His Phe Lys Leu Phe Ser Asn Leu Arg Pro Ala
            100                 105                 110

Lys Leu Tyr Gln Gly Leu Glu Ala Phe Cys Pro Leu Arg Ala Asp Ile
        115                 120                 125

Ala Ala Asn Gly Phe Asp Ile Leu Cys Val Arg Glu Leu Thr Gly Gly
    130                 135                 140

Ile Tyr Phe Gly Gln Pro Lys Gly Arg Glu Gly Ser Gly Gln Tyr Glu
```

```
                145                 150                 155                 160
            Lys Ala Phe Asp Thr Glu Val Tyr His Arg Phe Glu Ile Glu Arg Ile
                            165                 170                 175

Ala Arg Ile Ala Phe Glu Ser Ala Arg Lys Arg His Lys Val Thr
                        180                 185                 190

Ser Ile Asp Lys Ala Asn Val Leu Gln Ser Ser Ile Leu Trp Arg Glu
                        195                 200                 205

Ile Val Asn Glu Ile Ala Thr Glu Tyr Pro Asp Val Glu Leu Ala His
                        210                 215                 220

Met Tyr Ile Asp Asn Ala Thr Met Gln Leu Ile Lys Asp Pro Ser Gln
            225                 230                 235                 240

Phe Asp Val Leu Leu Cys Ser Asn Leu Phe Gly Asp Ile Leu Ser Asp
                            245                 250                 255

Glu Cys Ala Met Ile Thr Gly Ser Met Gly Met Leu Pro Ser Ala Ser
                            260                 265                 270

Leu Asn Glu Gln Gly Phe Gly Leu Tyr Glu Pro Ala Gly Gly Ser Ala
                        275                 280                 285

Pro Asp Ile Ala Gly Lys Asn Ile Ala Asn Pro Ile Ala Gln Ile Leu
                        290                 295                 300

Ser Leu Ala Leu Leu Leu Arg Tyr Ser Leu Asp Ala Asp Asp Ala Ala
            305                 310                 315                 320

Cys Ala Ile Glu Arg Ala Ile Asn Arg Ala Leu Glu Glu Gly Ile Arg
                            325                 330                 335

Thr Gly Asp Leu Ala Arg Gly Ala Ala Ala Val Ser Thr Asp Glu Met
                            340                 345                 350

Gly Asp Ile Ile Ala Arg Tyr Val Ala Glu Gly Val
                        355                 360

<210> SEQ ID NO 53
<211> LENGTH: 1401
<212> TYPE: DNA
<213> ORGANISM: Escherichia coli
<220> FEATURE:
<221> NAME/KEY: CDS
<222> LOCATION: (1)..(1401)

<400> SEQUENCE: 53 atg gct aag acg tta tac gaa aaa ttg ttc gac gct cac gtt gtg tac      48
Met Ala Lys Thr Leu Tyr Glu Lys Leu Phe Asp Ala His Val Val Tyr
1               5                   10                  15 gaa gcc gaa aac gaa acc cca ctg tta tat atc gac cgc cac ctg gtg      96
Glu Ala Glu Asn Glu Thr Pro Leu Leu Tyr Ile Asp Arg His Leu Val
                20                  25                  30 cat gaa gtg acc tca ccg cag gcg ttc gat ggt ctg cgc gcc cac ggt     144
His Glu Val Thr Ser Pro Gln Ala Phe Asp Gly Leu Arg Ala His Gly
            35                  40                  45 cgc ccg gta cgt cag ccg ggc aaa acc ttc gct acc atg gat cac aac     192
Arg Pro Val Arg Gln Pro Gly Lys Thr Phe Ala Thr Met Asp His Asn
        50                  55                  60 gtc tct acc cag acc aaa gac att aat gcc tgc ggt gaa atg gcg cgt     240
Val Ser Thr Gln Thr Lys Asp Ile Asn Ala Cys Gly Glu Met Ala Arg
65                  70                  75                  80 atc cag atg cag gaa ctg atc aaa aac tgc aaa gaa ttt ggc gtc gaa     288
Ile Gln Met Gln Glu Leu Ile Lys Asn Cys Lys Glu Phe Gly Val Glu
                85                  90                  95 ctg tat gac ctg aat cac ccg tat cag ggg atc gtc cac gta atg ggg     336
Leu Tyr Asp Leu Asn His Pro Tyr Gln Gly Ile Val His Val Met Gly
            100                 105                 110
```

```
ccg gaa cag ggc gtc acc ttg ccg ggg atg acc att gtc tgc ggc gac       384
Pro Glu Gln Gly Val Thr Leu Pro Gly Met Thr Ile Val Cys Gly Asp
            115                 120                 125 tcg cat acc gcc acc cac ggc gcg ttt ggc gca ctg gcc ttt ggt atc       432
Ser His Thr Ala Thr His Gly Ala Phe Gly Ala Leu Ala Phe Gly Ile
    130                 135                 140 ggc act tcc gaa gtt gaa cac gta ctg gca acg caa acc ctg aaa cag       480
Gly Thr Ser Glu Val Glu His Val Leu Ala Thr Gln Thr Leu Lys Gln
145                 150                 155                 160 ggc cgc gca aaa acc atg aaa att gaa gtc cag ggc aaa gcc gcg ccg       528
Gly Arg Ala Lys Thr Met Lys Ile Glu Val Gln Gly Lys Ala Ala Pro
                165                 170                 175 ggc att acc gca aaa gat atc gtg ctg gca att atc ggt aaa acc ggt       576
Gly Ile Thr Ala Lys Asp Ile Val Leu Ala Ile Ile Gly Lys Thr Gly
            180                 185                 190 agc gca ggc ggc acc ggg cat gtg gtg gag ttt tgc ggc gaa gca atc       624
Ser Ala Gly Gly Thr Gly His Val Val Glu Phe Cys Gly Glu Ala Ile
        195                 200                 205 cgt gat tta agc atg gaa ggt cgt atg acc ctg tgc aat atg gca atc       672
Arg Asp Leu Ser Met Glu Gly Arg Met Thr Leu Cys Asn Met Ala Ile
210                 215                 220 gaa atg ggc gca aaa gcc ggt ctg gtt gca ccg gac gaa acc acc ttt       720
Glu Met Gly Ala Lys Ala Gly Leu Val Ala Pro Asp Glu Thr Thr Phe
225                 230                 235                 240 aac tat gtc aaa ggc cgt ctg cat gcg ccg aaa ggc aaa gat ttc gac       768
Asn Tyr Val Lys Gly Arg Leu His Ala Pro Lys Gly Lys Asp Phe Asp
                245                 250                 255 gac gcc gtt gcc tac tgg aaa acc ctg caa acc gac gaa ggc gca act       816
Asp Ala Val Ala Tyr Trp Lys Thr Leu Gln Thr Asp Glu Gly Ala Thr
            260                 265                 270 ttc gat acc gtt gtc act ctg caa gca gaa gaa att tca ccg cag gtc       864
Phe Asp Thr Val Val Thr Leu Gln Ala Glu Glu Ile Ser Pro Gln Val
        275                 280                 285 acc tgg ggc acc aat ccc ggc cag gtg att tcc gtg aac gac aat att       912
Thr Trp Gly Thr Asn Pro Gly Gln Val Ile Ser Val Asn Asp Asn Ile
        290                 295                 300 ccc gat ccg gct tcg ttt gcc gat ccg gtt gaa cgc gcg tcg gca gaa       960
Pro Asp Pro Ala Ser Phe Ala Asp Pro Val Glu Arg Ala Ser Ala Glu
305                 310                 315                 320 aaa gcg ctg gcc tat atg ggg ctg aaa ccg ggt att ccg ctg acc gaa      1008
Lys Ala Leu Ala Tyr Met Gly Leu Lys Pro Gly Ile Pro Leu Thr Glu
                325                 330                 335 gtg gct atc gac aaa gtg ttt atc ggt tcc tgt acc aac tcg cgc att      1056
Val Ala Ile Asp Lys Val Phe Ile Gly Ser Cys Thr Asn Ser Arg Ile
            340                 345                 350 gaa gat tta cgc gcg gca gcg gag atc gcc aaa ggg cga aaa gtc gcg      1104
Glu Asp Leu Arg Ala Ala Ala Glu Ile Ala Lys Gly Arg Lys Val Ala
        355                 360                 365 cca ggc gtg cag gca ctg gtg gtt ccc ggc tct ggc ccg gta aaa gcc      1152
Pro Gly Val Gln Ala Leu Val Val Pro Gly Ser Gly Pro Val Lys Ala
    370                 375                 380 cag gcg gaa gcg gaa ggt ctg gat aaa atc ttt att gaa gcc ggt ttt      1200
Gln Ala Glu Ala Glu Gly Leu Asp Lys Ile Phe Ile Glu Ala Gly Phe
385                 390                 395                 400 gaa tgg cgc ttg cct ggc tgc tca atg tgt ctg gcg atg aac aac gac      1248
Glu Trp Arg Leu Pro Gly Cys Ser Met Cys Leu Ala Met Asn Asn Asp
                405                 410                 415 cgt ctg aat ccg ggc gaa cgt tgt gcc tcc acc agc aac cgt aac ttt      1296
Arg Leu Asn Pro Gly Glu Arg Cys Ala Ser Thr Ser Asn Arg Asn Phe
```

```
                    420                425                430
gaa ggc cgc cag ggg cgc ggc ggg cgc acg cat ctg gtc agc ccg gca    1344
Glu Gly Arg Gln Gly Arg Gly Gly Arg Thr His Leu Val Ser Pro Ala
        435                440                445 atg gct gcc gct gct gct gtg acc gga cat ttc gcc gac att cgc aac    1392
Met Ala Ala Ala Ala Ala Val Thr Gly His Phe Ala Asp Ile Arg Asn
450                455                460 att aaa taa                                                         1401
Ile Lys
465

<210> SEQ ID NO 54
<211> LENGTH: 466
<212> TYPE: PRT
<213> ORGANISM: Escherichia coli

<400> SEQUENCE: 54

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300
```

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Glu Ile Ala Lys Gly Arg Lys Val Ala
        355                 360                 365

Pro Gly Val Gln Ala Leu Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Arg Thr His Leu Val Ser Pro Ala
        435                 440                 445

Met Ala Ala Ala Ala Val Thr Gly His Phe Ala Asp Ile Arg Asn
450                 455                 460

Ile Lys
465

<210> SEQ ID NO 55
<211> LENGTH: 606
<212> TYPE: DNA
<213> ORGANISM: Escherichia coli
<220> FEATURE:
<221> NAME/KEY: CDS
<222> LOCATION: (1)..(606)

<400> SEQUENCE: 55 atg gca gag aaa ttt atc aaa cac aca ggc ctg gtg gtt ccg ctg gat    48
Met Ala Glu Lys Phe Ile Lys His Thr Gly Leu Val Val Pro Leu Asp
1               5                   10                  15 gcc gcc aat gtc gat acc gat gca atc atc ccg aaa cag ttt ttg cag    96
Ala Ala Asn Val Asp Thr Asp Ala Ile Ile Pro Lys Gln Phe Leu Gln
                20                  25                  30 aaa gtg acc cgt acg ggt ttt ggc gcg cat ctg ttt aac gac tgg cgt   144
Lys Val Thr Arg Thr Gly Phe Gly Ala His Leu Phe Asn Asp Trp Arg
            35                  40                  45 ttt ctg gat gaa aaa ggc caa cag cca aac ccg gac ttc gtg ctg aac   192
Phe Leu Asp Glu Lys Gly Gln Gln Pro Asn Pro Asp Phe Val Leu Asn
        50                  55                  60 ttc ccg cag tat cag ggc gct tcc att ttg ctg gca cga gaa aac ttc   240
Phe Pro Gln Tyr Gln Gly Ala Ser Ile Leu Leu Ala Arg Glu Asn Phe
65                  70                  75                  80 ggc tgt ggc tct tcg cgt gag cac gcg ccc tgg gca ttg acc gac tac   288
Gly Cys Gly Ser Ser Arg Glu His Ala Pro Trp Ala Leu Thr Asp Tyr
                85                  90                  95 ggt ttt aaa gtg gtg att gcg ccg agt ttt gct gac atc ttc tac ggc   336
Gly Phe Lys Val Val Ile Ala Pro Ser Phe Ala Asp Ile Phe Tyr Gly
            100                 105                 110 aat agc ttt aac aac cag ctg ctg ccg gtg aaa tta agc gat gca gaa   384
Asn Ser Phe Asn Asn Gln Leu Leu Pro Val Lys Leu Ser Asp Ala Glu
        115                 120                 125 gtg gac gaa ctg ttt gcg ctg gtg aaa gct aat ccg ggg atc cat ttc   432
Val Asp Glu Leu Phe Ala Leu Val Lys Ala Asn Pro Gly Ile His Phe
130                 135                 140

```
gac gtg gat ctg gaa gcg caa gag gtg aaa gcg gga gag aaa acc tat    480
Asp Val Asp Leu Glu Ala Gln Glu Val Lys Ala Gly Glu Lys Thr Tyr
145                 150                 155                 160 cgc ttt acc atc gat gcc ttc cgc cgc cac tgc atg atg aac ggt ctg    528
Arg Phe Thr Ile Asp Ala Phe Arg Arg His Cys Met Met Asn Gly Leu
                165                 170                 175 gac agt att ggg ctt acc ttg cag cac gac gac gcc att gcc gct tat    576
Asp Ser Ile Gly Leu Thr Leu Gln His Asp Asp Ala Ile Ala Ala Tyr
            180                 185                 190 gaa gca aaa caa cct gcg ttt atg aat taa                            606
Glu Ala Lys Gln Pro Ala Phe Met Asn
        195                 200
```

<210> SEQ ID NO 56
<211> LENGTH: 201
<212> TYPE: PRT
<213> ORGANISM: Escherichia coli

<400> SEQUENCE: 56

```
Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200
```

<210> SEQ ID NO 57
<211> LENGTH: 1476
<212> TYPE: DNA
<213> ORGANISM: Methanococcus jannaschii
<220> FEATURE:
<221> NAME/KEY: CDS
<222> LOCATION: (1)..(1476)

<400> SEQUENCE: 57

```
atg atg gta agg ata ttt gat aca aca ctt aga gat gga gag caa aca    48
Met Met Val Arg Ile Phe Asp Thr Thr Leu Arg Asp Gly Glu Gln Thr
1               5                   10                  15
```

| | | | | | | | | | | | | | | | |
|---|---|---|---|---|---|---|---|---|---|---|---|---|---|---|---|
| cca | gga | gtt | tct | tta | aca | cca | aat | gat | aag | tta | gag | ata | gca | aaa | aaa | 96 |
| Pro | Gly | Val | Ser | Leu | Thr | Pro | Asn | Asp | Lys | Leu | Glu | Ile | Ala | Lys | Lys | |
| | | | 20 | | | | 25 | | | | 30 | | | | | |
| ttg | gat | gag | ctt | gga | gtt | gat | gtt | ata | gag | gca | ggt | tca | gct | ata | act | 144 |
| Leu | Asp | Glu | Leu | Gly | Val | Asp | Val | Ile | Glu | Ala | Gly | Ser | Ala | Ile | Thr | |
| | | 35 | | | | 40 | | | | 45 | | | | | | |
| tca | aaa | gga | gag | aga | gaa | gga | ata | aaa | tta | ata | aca | aaa | gaa | ggt | tta | 192 |
| Ser | Lys | Gly | Glu | Arg | Glu | Gly | Ile | Lys | Leu | Ile | Thr | Lys | Glu | Gly | Leu | |
| | 50 | | | | 55 | | | | 60 | | | | | | | |
| aat | gca | gaa | atc | tgc | tca | ttt | gtt | aga | gct | tta | cct | gta | gat | att | gat | 240 |
| Asn | Ala | Glu | Ile | Cys | Ser | Phe | Val | Arg | Ala | Leu | Pro | Val | Asp | Ile | Asp | |
| 65 | | | | 70 | | | | 75 | | | | 80 | | | | |
| gct | gcc | tta | gaa | tgt | gat | gta | gat | agt | gtc | cat | tta | gta | gtg | cca | aca | 288 |
| Ala | Ala | Leu | Glu | Cys | Asp | Val | Asp | Ser | Val | His | Leu | Val | Val | Pro | Thr | |
| | | | 85 | | | | 90 | | | | 95 | | | | | |
| tct | cca | ata | cac | atg | aaa | tat | aag | ctt | aga | aaa | aca | gaa | gat | gag | gtt | 336 |
| Ser | Pro | Ile | His | Met | Lys | Tyr | Lys | Leu | Arg | Lys | Thr | Glu | Asp | Glu | Val | |
| | | | 100 | | | | 105 | | | | 110 | | | | | |
| tta | gag | aca | gct | tta | aag | gct | gta | gag | tat | gct | aaa | gaa | cat | gga | ttg | 384 |
| Leu | Glu | Thr | Ala | Leu | Lys | Ala | Val | Glu | Tyr | Ala | Lys | Glu | His | Gly | Leu | |
| | | 115 | | | | 120 | | | | 125 | | | | | | |
| att | gtt | gag | tta | tct | gca | gag | gat | gca | aca | aga | agt | gat | gta | aat | ttc | 432 |
| Ile | Val | Glu | Leu | Ser | Ala | Glu | Asp | Ala | Thr | Arg | Ser | Asp | Val | Asn | Phe | |
| | 130 | | | | 135 | | | | 140 | | | | | | | |
| tta | ata | aaa | cta | ttt | aat | gaa | ggg | gaa | aag | gtt | gga | gca | gac | aga | gtt | 480 |
| Leu | Ile | Lys | Leu | Phe | Asn | Glu | Gly | Glu | Lys | Val | Gly | Ala | Asp | Arg | Val | |
| 145 | | | | 150 | | | | 155 | | | | 160 | | | | |
| tgt | gtt | tgt | gac | aca | gta | gga | gtt | tta | act | cca | caa | aag | agt | cag | gaa | 528 |
| Cys | Val | Cys | Asp | Thr | Val | Gly | Val | Leu | Thr | Pro | Gln | Lys | Ser | Gln | Glu | |
| | | | 165 | | | | 170 | | | | 175 | | | | | |
| tta | ttt | aaa | aaa | ata | act | gaa | aat | gtt | aat | tta | ccg | gtc | tca | gtt | cat | 576 |
| Leu | Phe | Lys | Lys | Ile | Thr | Glu | Asn | Val | Asn | Leu | Pro | Val | Ser | Val | His | |
| | | | 180 | | | | 185 | | | | 190 | | | | | |
| tgc | cac | aac | gac | ttt | gga | atg | gct | act | gct | aat | act | tgc | tca | gca | gtt | 624 |
| Cys | His | Asn | Asp | Phe | Gly | Met | Ala | Thr | Ala | Asn | Thr | Cys | Ser | Ala | Val | |
| | | 195 | | | | 200 | | | | 205 | | | | | | |
| tta | ggt | gga | gct | gtt | cag | tgc | cac | gta | aca | gtt | aat | ggt | att | gga | gag | 672 |
| Leu | Gly | Gly | Ala | Val | Gln | Cys | His | Val | Thr | Val | Asn | Gly | Ile | Gly | Glu | |
| | 210 | | | | 215 | | | | 220 | | | | | | | |
| aga | gca | gga | aat | gcc | tca | ttg | gaa | gag | gtt | gtt | gct | gct | tta | aaa | ata | 720 |
| Arg | Ala | Gly | Asn | Ala | Ser | Leu | Glu | Glu | Val | Val | Ala | Ala | Leu | Lys | Ile | |
| 225 | | | | 230 | | | | 235 | | | | 240 | | | | |
| ctc | tat | ggc | tat | gat | act | aag | ata | aag | atg | gaa | aag | tta | tat | gag | gtt | 768 |
| Leu | Tyr | Gly | Tyr | Asp | Thr | Lys | Ile | Lys | Met | Glu | Lys | Leu | Tyr | Glu | Val | |
| | | | 245 | | | | 250 | | | | 255 | | | | | |
| tca | aga | att | gtc | tca | aga | ttg | atg | aaa | ctt | cct | gtt | cca | cca | aat | aaa | 816 |
| Ser | Arg | Ile | Val | Ser | Arg | Leu | Met | Lys | Leu | Pro | Val | Pro | Pro | Asn | Lys | |
| | | | 260 | | | | 265 | | | | 270 | | | | | |
| gca | att | gtt | ggg | gac | aat | gca | ttt | gct | cat | gaa | gca | gga | ata | cat | gtt | 864 |
| Ala | Ile | Val | Gly | Asp | Asn | Ala | Phe | Ala | His | Glu | Ala | Gly | Ile | His | Val | |
| | | 275 | | | | 280 | | | | 285 | | | | | | |
| gat | gga | tta | ata | aaa | aat | act | gaa | acc | tat | gag | cca | ata | aaa | cca | gaa | 912 |
| Asp | Gly | Leu | Ile | Lys | Asn | Thr | Glu | Thr | Tyr | Glu | Pro | Ile | Lys | Pro | Glu | |
| | 290 | | | | 295 | | | | 300 | | | | | | | |
| atg | gtt | ggg | aat | aga | aga | aga | att | att | ttg | ggt | aag | cat | tct | ggt | aga | 960 |
| Met | Val | Gly | Asn | Arg | Arg | Arg | Ile | Ile | Leu | Gly | Lys | His | Ser | Gly | Arg | |
| 305 | | | | 310 | | | | 315 | | | | 320 | | | | |
| aaa | gct | tta | aaa | tac | aaa | ctt | gat | ttg | atg | ggc | ata | aac | gtt | agt | gat | 1008 |
| Lys | Ala | Leu | Lys | Tyr | Lys | Leu | Asp | Leu | Met | Gly | Ile | Asn | Val | Ser | Asp | |
| | | | 325 | | | | 330 | | | | 335 | | | | | |

```
gag caa tta aat aaa ata tat gaa aga gtt aaa gaa ttt ggg gat ttg    1056
Glu Gln Leu Asn Lys Ile Tyr Glu Arg Val Lys Glu Phe Gly Asp Leu
        340                 345                 350 ggt aaa tac att tca gac gct gat ttg ttg gct ata gtt aga gaa gtt    1104
Gly Lys Tyr Ile Ser Asp Ala Asp Leu Leu Ala Ile Val Arg Glu Val
355                 360                 365 act gga aaa ttg gta gaa gag aaa atc aaa tta gat gaa tta act gtt    1152
Thr Gly Lys Leu Val Glu Glu Lys Ile Lys Leu Asp Glu Leu Thr Val
    370                 375                 380 gta tct gga aat aaa ata aca cca att gca tct gtt aaa ctc cat tat    1200
Val Ser Gly Asn Lys Ile Thr Pro Ile Ala Ser Val Lys Leu His Tyr
385                 390                 395                 400 aaa gga gaa gat ata act tta ata gaa act gct tat ggt gtt gga ccg    1248
Lys Gly Glu Asp Ile Thr Leu Ile Glu Thr Ala Tyr Gly Val Gly Pro
                405                 410                 415 gta gat gca gca ata aat gct gtg aga aag gca ata agt gga gtt gca    1296
Val Asp Ala Ala Ile Asn Ala Val Arg Lys Ala Ile Ser Gly Val Ala
            420                 425                 430 gat att aag ttg gta gag tat aga gtt gaa gca att ggt gga gga act    1344
Asp Ile Lys Leu Val Glu Tyr Arg Val Glu Ala Ile Gly Gly Gly Thr
        435                 440                 445 gat gcg tta ata gag gtt gtt gtt aaa tta aga aaa gga act gaa att    1392
Asp Ala Leu Ile Glu Val Val Val Lys Leu Arg Lys Gly Thr Glu Ile
    450                 455                 460 gtt gaa gtt aga aaa tca gac gct gat ata ata agg gct tct gta gat    1440
Val Glu Val Arg Lys Ser Asp Ala Asp Ile Ile Arg Ala Ser Val Asp
465                 470                 475                 480 gct gta atg gaa gga atc aat atg tta ttg aat taa                    1476
Ala Val Met Glu Gly Ile Asn Met Leu Leu Asn
                485                 490

<210> SEQ ID NO 58
<211> LENGTH: 491
<212> TYPE: PRT
<213> ORGANISM: Methanococcus jannaschii

<400> SEQUENCE: 58

Met Met Val Arg Ile Phe Asp Thr Thr Leu Arg Asp Gly Glu Gln Thr
1               5                   10                  15

Pro Gly Val Ser Leu Thr Pro Asn Asp Lys Leu Glu Ile Ala Lys Lys
            20                  25                  30

Leu Asp Glu Leu Gly Val Asp Val Ile Glu Ala Gly Ser Ala Ile Thr
        35                  40                  45

Ser Lys Gly Glu Arg Glu Gly Ile Lys Leu Ile Thr Lys Glu Gly Leu
    50                  55                  60

Asn Ala Glu Ile Cys Ser Phe Val Arg Ala Leu Pro Val Asp Ile Asp
65                  70                  75                  80

Ala Ala Leu Glu Cys Asp Val Asp Ser Val His Leu Val Val Pro Thr
                85                  90                  95

Ser Pro Ile His Met Lys Tyr Lys Leu Arg Lys Thr Glu Asp Glu Val
            100                 105                 110

Leu Glu Thr Ala Leu Lys Ala Val Glu Tyr Ala Lys Glu His Gly Leu
        115                 120                 125

Ile Val Glu Leu Ser Ala Glu Asp Ala Thr Arg Ser Asp Val Asn Phe
    130                 135                 140

Leu Ile Lys Leu Phe Asn Glu Gly Glu Lys Val Gly Ala Asp Arg Val
145                 150                 155                 160
```

```
Cys Val Cys Asp Thr Val Gly Val Leu Thr Pro Gln Lys Ser Gln Glu
            165                 170                 175

Leu Phe Lys Lys Ile Thr Glu Asn Val Asn Leu Pro Val Ser Val His
            180                 185                 190

Cys His Asn Asp Phe Gly Met Ala Thr Ala Asn Thr Cys Ser Ala Val
            195                 200                 205

Leu Gly Gly Ala Val Gln Cys His Val Thr Val Asn Gly Ile Gly Glu
            210                 215                 220

Arg Ala Gly Asn Ala Ser Leu Glu Glu Val Ala Ala Leu Lys Ile
225                 230                 235                 240

Leu Tyr Gly Tyr Asp Thr Lys Ile Lys Met Glu Lys Leu Tyr Glu Val
            245                 250                 255

Ser Arg Ile Val Ser Arg Leu Met Lys Leu Pro Val Pro Pro Asn Lys
            260                 265                 270

Ala Ile Val Gly Asp Asn Ala Phe Ala His Glu Ala Gly Ile His Val
            275                 280                 285

Asp Gly Leu Ile Lys Asn Thr Glu Thr Tyr Glu Pro Ile Lys Pro Glu
            290                 295                 300

Met Val Gly Asn Arg Arg Arg Ile Ile Leu Gly Lys His Ser Gly Arg
305                 310                 315                 320

Lys Ala Leu Lys Tyr Lys Leu Asp Leu Met Gly Ile Asn Val Ser Asp
            325                 330                 335

Glu Gln Leu Asn Lys Ile Tyr Glu Arg Val Lys Glu Phe Gly Asp Leu
            340                 345                 350

Gly Lys Tyr Ile Ser Asp Ala Asp Leu Leu Ala Ile Val Arg Glu Val
            355                 360                 365

Thr Gly Lys Leu Val Glu Glu Lys Ile Lys Leu Asp Glu Leu Thr Val
            370                 375                 380

Val Ser Gly Asn Lys Ile Thr Pro Ile Ala Ser Val Lys Leu His Tyr
385                 390                 395                 400

Lys Gly Glu Asp Ile Thr Leu Ile Glu Thr Ala Tyr Gly Val Gly Pro
            405                 410                 415

Val Asp Ala Ala Ile Asn Ala Val Arg Lys Ala Ile Ser Gly Val Ala
            420                 425                 430

Asp Ile Lys Leu Val Glu Tyr Arg Val Glu Ala Ile Gly Gly Gly Thr
            435                 440                 445

Asp Ala Leu Ile Glu Val Val Lys Leu Arg Lys Gly Thr Glu Ile
            450                 455                 460

Val Glu Val Arg Lys Ser Asp Ala Asp Ile Ile Arg Ala Ser Val Asp
465                 470                 475                 480

Ala Val Met Glu Gly Ile Asn Met Leu Leu Asn
            485                 490

<210> SEQ ID NO 59
<211> LENGTH: 264
<212> TYPE: DNA
<213> ORGANISM: Escherichia coli
<220> FEATURE:
<221> NAME/KEY: CDS
<222> LOCATION: (1)..(264)

<400> SEQUENCE: 59 atg atg caa cat cag gtc aat gta tcg gct cgc ttc aat cca gaa acc      48
Met Met Gln His Gln Val Asn Val Ser Ala Arg Phe Asn Pro Glu Thr
1               5                   10                  15 tta gaa cgt gtt tta cgc gtg gtg cgt cat cgt ggt ttc cac gtc tgc      96
```

```
Leu Glu Arg Val Leu Arg Val Val Arg His Arg Gly Phe His Val Cys
             20                  25                  30 tca atg aat atg gcc gcc gcc agc gat gca caa aat ata aat atc gaa    144
Ser Met Asn Met Ala Ala Ala Ser Asp Ala Gln Asn Ile Asn Ile Glu
         35                  40                  45 ttg acc gtt gcc agc cca cgg tcg gtc gac tta ctg ttt agt cag tta    192
Leu Thr Val Ala Ser Pro Arg Ser Val Asp Leu Leu Phe Ser Gln Leu
 50                  55                  60 aat aaa ctg gtg gac gtc gca cac gtt gcc atc tgc cag agc aca acc    240
Asn Lys Leu Val Asp Val Ala His Val Ala Ile Cys Gln Ser Thr Thr
 65                  70                  75                  80 aca tca caa caa atc cgc gcc tga                                    264
Thr Ser Gln Gln Ile Arg Ala
             85

<210> SEQ ID NO 60
<211> LENGTH: 87
<212> TYPE: PRT
<213> ORGANISM: Escherichia coli

<400> SEQUENCE: 60

Met Met Gln His Gln Val Asn Val Ser Ala Arg Phe Asn Pro Glu Thr
 1               5                  10                  15

Leu Glu Arg Val Leu Arg Val Val Arg His Arg Gly Phe His Val Cys
             20                  25                  30

Ser Met Asn Met Ala Ala Ala Ser Asp Ala Gln Asn Ile Asn Ile Glu
         35                  40                  45

Leu Thr Val Ala Ser Pro Arg Ser Val Asp Leu Leu Phe Ser Gln Leu
 50                  55                  60

Asn Lys Leu Val Asp Val Ala His Val Ala Ile Cys Gln Ser Thr Thr
 65                  70                  75                  80

Thr Ser Gln Gln Ile Arg Ala
             85

<210> SEQ ID NO 61
<211> LENGTH: 582
<212> TYPE: DNA
<213> ORGANISM: Escherichia coli
<220> FEATURE:
<221> NAME/KEY: CDS
<222> LOCATION: (1)..(582)

<400> SEQUENCE: 61 ttg ttg tta aaa caa ctg tcg gat cgt aaa cct gcg gat tgc gtc gtg     48
Leu Leu Leu Lys Gln Leu Ser Asp Arg Lys Pro Ala Asp Cys Val Val
 1               5                  10                  15 acc aca gat gtg ggg cag cac cag atg tgg gct gcg cag cac atc gcc     96
Thr Thr Asp Val Gly Gln His Gln Met Trp Ala Ala Gln His Ile Ala
             20                  25                  30 cac act cgc ccg gaa aat ttc atc acc tcc agc ggt tta ggt acc atg    144
His Thr Arg Pro Glu Asn Phe Ile Thr Ser Ser Gly Leu Gly Thr Met
         35                  40                  45 ggt ttt ggt tta ccg gcg gcg gtt ggc gca caa gtc gcg cga ccg aac    192
Gly Phe Gly Leu Pro Ala Ala Val Gly Ala Gln Val Ala Arg Pro Asn
 50                  55                  60 gat acc gtt gtc tgt atc tcc ggt gac ggc tct ttc atg atg aat gtg    240
Asp Thr Val Val Cys Ile Ser Gly Asp Gly Ser Phe Met Met Asn Val
 65                  70                  75                  80 caa gag ctg ggc acc gta aaa cgc aag cag tta ccg ttg aaa atc gtc    288
Gln Glu Leu Gly Thr Val Lys Arg Lys Gln Leu Pro Leu Lys Ile Val
             85                  90                  95
```

```
tta ctc gat aac caa cgg tta ggg atg gtt cga caa tgg cag caa ctg      336
Leu Leu Asp Asn Gln Arg Leu Gly Met Val Arg Gln Trp Gln Gln Leu
            100                 105                 110 ttt ttt cag gaa cga tac agc gaa acc acc ctt act gat aac ccc gat      384
Phe Phe Gln Glu Arg Tyr Ser Glu Thr Thr Leu Thr Asp Asn Pro Asp
        115                 120                 125 ttc ctc atg tta gcc agc gcc ttc ggc atc cat ggc caa cac atc acc      432
Phe Leu Met Leu Ala Ser Ala Phe Gly Ile His Gly Gln His Ile Thr
130                 135                 140 cgg aaa gac cag gtt gaa gcg gca ctc gac acc atg ctg aac agt gat      480
Arg Lys Asp Gln Val Glu Ala Ala Leu Asp Thr Met Leu Asn Ser Asp
145                 150                 155                 160 ggg cca tac ctg ctt cat gtc tca atc gac gaa ctt gag aac gtc tgg      528
Gly Pro Tyr Leu Leu His Val Ser Ile Asp Glu Leu Glu Asn Val Trp
                165                 170                 175 ccg ctg gtg ccg cct ggc gcc agt aat tca gaa atg ttg gag aaa tta      576
Pro Leu Val Pro Pro Gly Ala Ser Asn Ser Glu Met Leu Glu Lys Leu
            180                 185                 190 tca tga                                                              582
Ser

<210> SEQ ID NO 62
<211> LENGTH: 193
<212> TYPE: PRT
<213> ORGANISM: Escherichia coli

<400> SEQUENCE: 62

Leu Leu Leu Lys Gln Leu Ser Asp Arg Lys Pro Ala Asp Cys Val Val
1               5                   10                  15

Thr Thr Asp Val Gly Gln His Gln Met Trp Ala Ala Gln His Ile Ala
            20                  25                  30

His Thr Arg Pro Glu Asn Phe Ile Thr Ser Ser Gly Leu Gly Thr Met
        35                  40                  45

Gly Phe Gly Leu Pro Ala Ala Val Gly Ala Gln Val Ala Arg Pro Asn
    50                  55                  60

Asp Thr Val Val Cys Ile Ser Gly Asp Gly Ser Phe Met Met Asn Val
65                  70                  75                  80

Gln Glu Leu Gly Thr Val Lys Arg Lys Gln Leu Pro Leu Lys Ile Val
                85                  90                  95

Leu Leu Asp Asn Gln Arg Leu Gly Met Val Arg Gln Trp Gln Gln Leu
            100                 105                 110

Phe Phe Gln Glu Arg Tyr Ser Glu Thr Thr Leu Thr Asp Asn Pro Asp
        115                 120                 125

Phe Leu Met Leu Ala Ser Ala Phe Gly Ile His Gly Gln His Ile Thr
130                 135                 140

Arg Lys Asp Gln Val Glu Ala Ala Leu Asp Thr Met Leu Asn Ser Asp
145                 150                 155                 160

Gly Pro Tyr Leu Leu His Val Ser Ile Asp Glu Leu Glu Asn Val Trp
                165                 170                 175

Pro Leu Val Pro Pro Gly Ala Ser Asn Ser Glu Met Leu Glu Lys Leu
            180                 185                 190

Ser

<210> SEQ ID NO 63
<211> LENGTH: 291
<212> TYPE: DNA
<213> ORGANISM: Escherichia coli
```

```
<220> FEATURE:
<221> NAME/KEY: CDS
<222> LOCATION: (1)..(291)

<400> SEQUENCE: 63 atg caa aac aca act cat gac aac gta att ctg gag ctc acc gtt cgc      48
Met Gln Asn Thr Thr His Asp Asn Val Ile Leu Glu Leu Thr Val Arg
1               5                   10                  15 aac cat ccg ggc gta atg acc cac gtt tgt ggc ctt ttt gcc cgc cgc      96
Asn His Pro Gly Val Met Thr His Val Cys Gly Leu Phe Ala Arg Arg
                20                  25                  30 gct ttt aac gtt gaa ggc att ctt tgt ctg ccg att cag gac agc gac     144
Ala Phe Asn Val Glu Gly Ile Leu Cys Leu Pro Ile Gln Asp Ser Asp
            35                  40                  45 aaa agc cat atc tgg cta ctg gtc aat gac gac cag cgt ctg gag cag     192
Lys Ser His Ile Trp Leu Leu Val Asn Asp Asp Gln Arg Leu Glu Gln
    50                  55                  60 atg ata agc caa atc gat aag ctg gaa gat gtc gtg aaa gtg cag cgt     240
Met Ile Ser Gln Ile Asp Lys Leu Glu Asp Val Val Lys Val Gln Arg
65                  70                  75                  80 aat cag tcc gat ccg acg atg ttt aac aag atc gcg gtg ttt ttt cag     288
Asn Gln Ser Asp Pro Thr Met Phe Asn Lys Ile Ala Val Phe Phe Gln
                85                  90                  95 taa                                                                  291

<210> SEQ ID NO 64
<211> LENGTH: 96
<212> TYPE: PRT
<213> ORGANISM: Escherichia coli

<400> SEQUENCE: 64

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
                20                  25                  30

Ala Phe Asn Val Glu Gly Ile Leu Cys Leu Pro Ile Gln Asp Ser Asp
            35                  40                  45

Lys Ser His Ile Trp Leu Leu Val Asn Asp Asp Gln Arg Leu Glu Gln
    50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95

<210> SEQ ID NO 65
<211> LENGTH: 1689
<212> TYPE: DNA
<213> ORGANISM: Escherichia coli
<220> FEATURE:
<221> NAME/KEY: CDS
<222> LOCATION: (1)..(1689)

<400> SEQUENCE: 65 atg gca agt tcg ggc aca aca tcg acg cgt aag cgc ttt acc ggc gca      48
Met Ala Ser Ser Gly Thr Thr Ser Thr Arg Lys Arg Phe Thr Gly Ala
1               5                   10                  15 gaa ttt atc gtt cat ttc ctg gaa cag cag ggc att aag att gtg aca      96
Glu Phe Ile Val His Phe Leu Glu Gln Gln Gly Ile Lys Ile Val Thr
                20                  25                  30 ggc att ccg ggc ggt tct atc ctg cct gtt tac gat gcc tta agc caa     144
Gly Ile Pro Gly Gly Ser Ile Leu Pro Val Tyr Asp Ala Leu Ser Gln
```

|     |     |     |     |     |     |     |     |     |     |     |     |     |     |     |     |     |
|---|---|---|---|---|---|---|---|---|---|---|---|---|---|---|---|---|
|     |     |     | 35  |     |     |     | 40  |     |     |     | 45  |     |     |     |     |     |
| agc | acg | caa | atc | cgc | cat | att | ctg | gcc | cgt | cat | gaa | cag | ggc | gcg | ggc | 192 |
| Ser | Thr | Gln | Ile | Arg | His | Ile | Leu | Ala | Arg | His | Glu | Gln | Gly | Ala | Gly |     |
|     |     | 50  |     |     |     |     | 55  |     |     |     |     | 60  |     |     |     |     |
| ttt | atc | gct | cag | gga | atg | gcg | cgc | acc | gac | ggt | aaa | ccg | gcg | gtc | tgt | 240 |
| Phe | Ile | Ala | Gln | Gly | Met | Ala | Arg | Thr | Asp | Gly | Lys | Pro | Ala | Val | Cys |     |
| 65  |     |     |     |     | 70  |     |     |     |     | 75  |     |     |     |     | 80  |     |
| atg | gcc | tgt | agc | gga | ccg | ggt | gcg | act | aac | ctg | gtg | acc | gcc | att | gcc | 288 |
| Met | Ala | Cys | Ser | Gly | Pro | Gly | Ala | Thr | Asn | Leu | Val | Thr | Ala | Ile | Ala |     |
|     |     |     |     | 85  |     |     |     |     | 90  |     |     |     |     | 95  |     |     |
| gat | gcg | cgg | ctg | gac | tcc | atc | ccg | ctg | att | tgc | atc | act | ggt | cag | gtt | 336 |
| Asp | Ala | Arg | Leu | Asp | Ser | Ile | Pro | Leu | Ile | Cys | Ile | Thr | Gly | Gln | Val |     |
|     |     |     | 100 |     |     |     |     | 105 |     |     |     |     | 110 |     |     |     |
| ccc | gcc | tcg | atg | atc | ggc | acc | gac | gcc | ttc | cag | gaa | gtg | gac | acc | tac | 384 |
| Pro | Ala | Ser | Met | Ile | Gly | Thr | Asp | Ala | Phe | Gln | Glu | Val | Asp | Thr | Tyr |     |
|     |     | 115 |     |     |     |     | 120 |     |     |     |     | 125 |     |     |     |     |
| ggc | atc | tct | atc | ccc | atc | acc | aaa | cac | aac | tat | ctg | gtc | aga | cat | atc | 432 |
| Gly | Ile | Ser | Ile | Pro | Ile | Thr | Lys | His | Asn | Tyr | Leu | Val | Arg | His | Ile |     |
|     | 130 |     |     |     |     | 135 |     |     |     |     | 140 |     |     |     |     |     |
| gaa | gaa | ctc | ccg | cag | gtc | atg | agc | gat | gcc | ttc | cgc | att | gcg | caa | tca | 480 |
| Glu | Glu | Leu | Pro | Gln | Val | Met | Ser | Asp | Ala | Phe | Arg | Ile | Ala | Gln | Ser |     |
| 145 |     |     |     |     | 150 |     |     |     |     | 155 |     |     |     |     | 160 |     |
| ggc | cgc | cca | ggc | ccg | gtg | tgg | ata | gac | att | cct | aag | gat | gtg | caa | acg | 528 |
| Gly | Arg | Pro | Gly | Pro | Val | Trp | Ile | Asp | Ile | Pro | Lys | Asp | Val | Gln | Thr |     |
|     |     |     |     | 165 |     |     |     |     | 170 |     |     |     |     | 175 |     |     |
| gca | gtt | ttt | gag | att | gaa | aca | cag | ccc | gct | atg | gca | gaa | aaa | gcc | gcc | 576 |
| Ala | Val | Phe | Glu | Ile | Glu | Thr | Gln | Pro | Ala | Met | Ala | Glu | Lys | Ala | Ala |     |
|     |     |     | 180 |     |     |     |     | 185 |     |     |     |     | 190 |     |     |     |
| gcc | ccc | gcc | ttt | agc | gaa | gaa | agc | att | cgt | gac | gca | gcg | atg | att |     | 624 |
| Ala | Pro | Ala | Phe | Ser | Glu | Glu | Ser | Ile | Arg | Asp | Ala | Ala | Met | Ile |     |     |
|     | 195 |     |     |     |     | 200 |     |     |     |     | 205 |     |     |     |     |     |
| aac | gct | gcc | aaa | cgc | ccg | gtg | ctt | tat | ctg | ggc | ggc | ggt | gtg | atc | aat | 672 |
| Asn | Ala | Ala | Lys | Arg | Pro | Val | Leu | Tyr | Leu | Gly | Gly | Gly | Val | Ile | Asn |     |
|     | 210 |     |     |     |     | 215 |     |     |     |     | 220 |     |     |     |     |     |
| gcg | ccc | gca | cgg | gtg | cgt | gaa | ctg | gcg | gag | aaa | gcg | caa | ctg | cct | acc | 720 |
| Ala | Pro | Ala | Arg | Val | Arg | Glu | Leu | Ala | Glu | Lys | Ala | Gln | Leu | Pro | Thr |     |
| 225 |     |     |     |     | 230 |     |     |     |     | 235 |     |     |     |     | 240 |     |
| acc | atg | act | tta | atg | gcg | ctg | ggc | atg | ttg | cca | aaa | gcg | cat | ccg | ttg | 768 |
| Thr | Met | Thr | Leu | Met | Ala | Leu | Gly | Met | Leu | Pro | Lys | Ala | His | Pro | Leu |     |
|     |     |     |     | 245 |     |     |     |     | 250 |     |     |     |     | 255 |     |     |
| tcg | ctg | ggt | atg | ctg | ggg | atg | cac | ggc | gtg | cgc | agc | acc | aac | tat | att | 816 |
| Ser | Leu | Gly | Met | Leu | Gly | Met | His | Gly | Val | Arg | Ser | Thr | Asn | Tyr | Ile |     |
|     |     |     | 260 |     |     |     |     | 265 |     |     |     |     | 270 |     |     |     |
| ttg | cag | gag | gcg | gat | ttg | ttg | ata | gtg | ctc | ggt | gcg | cgt | ttt | gat | gac | 864 |
| Leu | Gln | Glu | Ala | Asp | Leu | Leu | Ile | Val | Leu | Gly | Ala | Arg | Phe | Asp | Asp |     |
|     |     | 275 |     |     |     |     | 280 |     |     |     |     | 285 |     |     |     |     |
| cgg | gcg | att | ggc | aaa | acc | gag | cag | ttc | tgt | ccg | aat | gcc | aaa | atc | att | 912 |
| Arg | Ala | Ile | Gly | Lys | Thr | Glu | Gln | Phe | Cys | Pro | Asn | Ala | Lys | Ile | Ile |     |
|     | 290 |     |     |     |     | 295 |     |     |     |     | 300 |     |     |     |     |     |
| cat | gtc | gat | atc | gac | cgt | gca | gag | ctg | ggt | aaa | atc | aag | cag | ccg | cac | 960 |
| His | Val | Asp | Ile | Asp | Arg | Ala | Glu | Leu | Gly | Lys | Ile | Lys | Gln | Pro | His |     |
| 305 |     |     |     |     | 310 |     |     |     |     | 315 |     |     |     |     | 320 |     |
| gtg | gcg | att | cag | gcg | gat | gtt | gat | gac | gtg | ctg | gcg | cag | ttg | atc | ccg | 1008 |
| Val | Ala | Ile | Gln | Ala | Asp | Val | Asp | Asp | Val | Leu | Ala | Gln | Leu | Ile | Pro |     |
|     |     |     |     | 325 |     |     |     |     | 330 |     |     |     |     | 335 |     |     |
| ctg | gtg | gaa | gcg | caa | ccg | cgt | gca | gag | tgg | cac | cag | ttg | gta | gcg | gat | 1056 |
| Leu | Val | Glu | Ala | Gln | Pro | Arg | Ala | Glu | Trp | His | Gln | Leu | Val | Ala | Asp |     |
|     |     |     | 340 |     |     |     |     | 345 |     |     |     |     | 350 |     |     |     |
| ttg | cag | cgt | gag | ttt | ccg | tgt | cca | atc | ccg | aaa | gcg | tgc | gat | ccg | tta | 1104 |

-continued

```
Leu Gln Arg Glu Phe Pro Cys Pro Ile Pro Lys Ala Cys Asp Pro Leu
            355                 360                 365 agc cat tac ggc ctg atc aac gcc gtt gcc gcc tgt gtc gat gac aat    1152
Ser His Tyr Gly Leu Ile Asn Ala Val Ala Ala Cys Val Asp Asp Asn
370                 375                 380 gca att atc acc acc gac gtt ggt cag cat cag atg tgg acc gcg caa    1200
Ala Ile Ile Thr Thr Asp Val Gly Gln His Gln Met Trp Thr Ala Gln
385                 390                 395                 400 gct tat ccg ctc aat cgc cca cgc cag tgg ctg acc tcc ggt ggg ctg    1248
Ala Tyr Pro Leu Asn Arg Pro Arg Gln Trp Leu Thr Ser Gly Gly Leu
                405                 410                 415 ggc acg atg ggt ttt ggc ctg cct gcg gcg att ggc gct gcg ctg gcg    1296
Gly Thr Met Gly Phe Gly Leu Pro Ala Ala Ile Gly Ala Ala Leu Ala
            420                 425                 430 aac ccg gat cgc aaa gtg ttg tgt ttc tcc ggc gac ggc agc ctg atg    1344
Asn Pro Asp Arg Lys Val Leu Cys Phe Ser Gly Asp Gly Ser Leu Met
        435                 440                 445 atg aat att cag gag atg gcg acc gcc agt gaa aat cag ctg gat gtc    1392
Met Asn Ile Gln Glu Met Ala Thr Ala Ser Glu Asn Gln Leu Asp Val
450                 455                 460 aaa atc att ctg atg aac aac gaa gcg ctg ggg ctg gtg cat cag caa    1440
Lys Ile Ile Leu Met Asn Asn Glu Ala Leu Gly Leu Val His Gln Gln
465                 470                 475                 480 cag agt ctg ttc tac gag caa ggc gtt ttt gcc gcc acc tat ccg ggc    1488
Gln Ser Leu Phe Tyr Glu Gln Gly Val Phe Ala Ala Thr Tyr Pro Gly
                485                 490                 495 aaa atc aac ttt atg cag att gcc gcc gga ttc ggc ctc gaa acc tgt    1536
Lys Ile Asn Phe Met Gln Ile Ala Ala Gly Phe Gly Leu Glu Thr Cys
            500                 505                 510 gat ttg aat aac gaa gcc gat ccg cag gct tca ttg cag gaa atc atc    1584
Asp Leu Asn Asn Glu Ala Asp Pro Gln Ala Ser Leu Gln Glu Ile Ile
        515                 520                 525 aat cgc cct ggc ccg gcg ctg atc cat gtg cgc att gat gcc gaa gaa    1632
Asn Arg Pro Gly Pro Ala Leu Ile His Val Arg Ile Asp Ala Glu Glu
530                 535                 540 aaa gtt tac ccg atg gtg ccg cca ggt gcg gcg aat act gaa atg gtg    1680
Lys Val Tyr Pro Met Val Pro Pro Gly Ala Ala Asn Thr Glu Met Val
545                 550                 555                 560 ggg gaa taa                                                        1689
Gly Glu
```

<210> SEQ ID NO 66
<211> LENGTH: 562
<212> TYPE: PRT
<213> ORGANISM: Escherichia coli

<400> SEQUENCE: 66

```
Met Ala Ser Ser Gly Thr Thr Ser Thr Arg Lys Arg Phe Thr Gly Ala
1               5                   10                  15

Glu Phe Ile Val His Phe Leu Glu Gln Gln Gly Ile Lys Ile Val Thr
            20                  25                  30

Gly Ile Pro Gly Gly Ser Ile Leu Pro Val Tyr Asp Ala Leu Ser Gln
        35                  40                  45

Ser Thr Gln Ile Arg His Ile Leu Ala Arg His Glu Gln Gly Ala Gly
    50                  55                  60

Phe Ile Ala Gln Gly Met Ala Arg Thr Asp Gly Lys Pro Ala Val Cys
65                  70                  75                  80

Met Ala Cys Ser Gly Pro Gly Ala Thr Asn Leu Val Thr Ala Ile Ala
            85                  90                  95
```

```
Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
        115                 120                 125

Gly Ile Ser Ile Pro Ile Thr Lys His Asn Tyr Leu Val Arg His Ile
    130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Met Ile
        195                 200                 205

Asn Ala Ala Lys Arg Pro Val Leu Tyr Leu Gly Gly Gly Val Ile Asn
    210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
            260                 265                 270

Leu Gln Glu Ala Asp Leu Leu Ile Val Leu Gly Ala Arg Phe Asp Asp
        275                 280                 285

Arg Ala Ile Gly Lys Thr Glu Gln Phe Cys Pro Asn Ala Lys Ile Ile
    290                 295                 300

His Val Asp Ile Asp Arg Ala Glu Leu Gly Lys Ile Lys Gln Pro His
305                 310                 315                 320

Val Ala Ile Gln Ala Asp Val Asp Val Leu Ala Gln Leu Ile Pro
                325                 330                 335

Leu Val Glu Ala Gln Pro Arg Ala Glu Trp His Gln Leu Val Ala Asp
            340                 345                 350

Leu Gln Arg Glu Phe Pro Cys Pro Ile Pro Lys Ala Cys Asp Pro Leu
        355                 360                 365

Ser His Tyr Gly Leu Ile Asn Ala Val Ala Ala Cys Val Asp Asp Asn
    370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
            420                 425                 430

Asn Pro Asp Arg Lys Val Leu Cys Phe Ser Gly Asp Gly Ser Leu Met
        435                 440                 445

Met Asn Ile Gln Glu Met Ala Thr Ala Ser Glu Asn Gln Leu Asp Val
    450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
                485                 490                 495

Lys Ile Asn Phe Met Gln Ile Ala Ala Gly Phe Gly Leu Glu Thr Cys
            500                 505                 510
```

```
Asp Leu Asn Asn Glu Ala Asp Pro Gln Ala Ser Leu Gln Glu Ile Ile
        515                 520                 525

Asn Arg Pro Gly Pro Ala Leu Ile His Val Arg Ile Asp Ala Glu Glu
    530                 535                 540

Lys Val Tyr Pro Met Val Pro Pro Gly Ala Ala Asn Thr Glu Met Val
545                 550                 555                 560

Gly Glu

<210> SEQ ID NO 67
<211> LENGTH: 2577
<212> TYPE: DNA
<213> ORGANISM: Clostridium acetobutylicum
<220> FEATURE:
<221> NAME/KEY: CDS
<222> LOCATION: (1)..(2577)

<400> SEQUENCE: 67
```

| | | | | | | | | | | | | | | | | |
|---|---|---|---|---|---|---|---|---|---|---|---|---|---|---|---|---|
| atg | aaa | gtt | aca | aat | caa | aaa | gaa | cta | aaa | caa | aag | cta | aat | gaa | ttg | 48 |
| Met | Lys | Val | Thr | Asn | Gln | Lys | Glu | Leu | Lys | Gln | Lys | Leu | Asn | Glu | Leu | |
| 1 | | | | 5 | | | | | 10 | | | | | 15 | | |
| aga | gaa | gcg | caa | aag | aag | ttt | gca | acc | tat | act | caa | gag | caa | gtt | gat | 96 |
| Arg | Glu | Ala | Gln | Lys | Lys | Phe | Ala | Thr | Tyr | Thr | Gln | Glu | Gln | Val | Asp | |
| | | | 20 | | | | | 25 | | | | | 30 | | | |
| aaa | att | ttt | aaa | caa | tgt | gcc | ata | gcc | gca | gct | aaa | gaa | aga | ata | aac | 144 |
| Lys | Ile | Phe | Lys | Gln | Cys | Ala | Ile | Ala | Ala | Ala | Lys | Glu | Arg | Ile | Asn | |
| | | 35 | | | | | 40 | | | | | 45 | | | | |
| tta | gct | aaa | tta | gca | gta | gaa | gaa | aca | gga | ata | ggt | ctt | gta | gaa | gat | 192 |
| Leu | Ala | Lys | Leu | Ala | Val | Glu | Glu | Thr | Gly | Ile | Gly | Leu | Val | Glu | Asp | |
| | 50 | | | | | 55 | | | | | 60 | | | | | |
| aaa | att | ata | aaa | aat | cat | ttt | gca | gca | gaa | tat | ata | tac | aat | aaa | tat | 240 |
| Lys | Ile | Ile | Lys | Asn | His | Phe | Ala | Ala | Glu | Tyr | Ile | Tyr | Asn | Lys | Tyr | |
| 65 | | | | | 70 | | | | | 75 | | | | | 80 | |
| aaa | aat | gaa | aaa | act | tgt | ggc | ata | ata | gac | cat | gac | gat | tct | tta | ggc | 288 |
| Lys | Asn | Glu | Lys | Thr | Cys | Gly | Ile | Ile | Asp | His | Asp | Asp | Ser | Leu | Gly | |
| | | | | 85 | | | | | 90 | | | | | 95 | | |
| ata | aca | aag | gtt | gct | gaa | cca | att | gga | att | gtt | gca | gcc | ata | gtt | cct | 336 |
| Ile | Thr | Lys | Val | Ala | Glu | Pro | Ile | Gly | Ile | Val | Ala | Ala | Ile | Val | Pro | |
| | | | 100 | | | | | 105 | | | | | 110 | | | |
| act | act | aat | cca | act | tcc | aca | gca | att | ttc | aaa | tca | tta | att | tct | tta | 384 |
| Thr | Thr | Asn | Pro | Thr | Ser | Thr | Ala | Ile | Phe | Lys | Ser | Leu | Ile | Ser | Leu | |
| | | 115 | | | | | 120 | | | | | 125 | | | | |
| aaa | aca | aga | aac | gca | ata | ttc | ttt | tca | cca | cat | cca | cgt | gca | aaa | aaa | 432 |
| Lys | Thr | Arg | Asn | Ala | Ile | Phe | Phe | Ser | Pro | His | Pro | Arg | Ala | Lys | Lys | |
| | 130 | | | | | 135 | | | | | 140 | | | | | |
| tct | aca | att | gct | gca | gca | aaa | tta | att | tta | gat | gca | gct | gtt | aaa | gca | 480 |
| Ser | Thr | Ile | Ala | Ala | Ala | Lys | Leu | Ile | Leu | Asp | Ala | Ala | Val | Lys | Ala | |
| 145 | | | | | 150 | | | | | 155 | | | | | 160 | |
| gga | gca | cct | aaa | aat | ata | ata | ggc | tgg | ata | gat | gag | cca | tca | ata | gaa | 528 |
| Gly | Ala | Pro | Lys | Asn | Ile | Ile | Gly | Trp | Ile | Asp | Glu | Pro | Ser | Ile | Glu | |
| | | | | 165 | | | | | 170 | | | | | 175 | | |
| ctt | tct | caa | gat | ttg | atg | agt | gaa | gct | gat | ata | ata | tta | gca | aca | gga | 576 |
| Leu | Ser | Gln | Asp | Leu | Met | Ser | Glu | Ala | Asp | Ile | Ile | Leu | Ala | Thr | Gly | |
| | | | 180 | | | | | 185 | | | | | 190 | | | |
| ggt | cct | tca | atg | gtt | aaa | gcg | gcc | tat | tca | tct | gga | aaa | cct | gca | att | 624 |
| Gly | Pro | Ser | Met | Val | Lys | Ala | Ala | Tyr | Ser | Ser | Gly | Lys | Pro | Ala | Ile | |
| | | 195 | | | | | 200 | | | | | 205 | | | | |
| ggt | gtt | gga | gca | gga | aat | aca | cca | gca | ata | ata | gat | gag | agt | gca | gat | 672 |
| Gly | Val | Gly | Ala | Gly | Asn | Thr | Pro | Ala | Ile | Ile | Asp | Glu | Ser | Ala | Asp | |
| | 210 | | | | | 215 | | | | | 220 | | | | | |
| ata | gat | atg | gca | gta | agc | tcc | ata | att | tta | tca | aag | act | tat | gac | aat | 720 |

```
             Ile Asp Met Ala Val Ser Ser Ile Ile Leu Ser Lys Thr Tyr Asp Asn
             225                 230                 235                 240 gga gta ata tgc gct tct gaa caa tca ata tta gtt atg aat tca ata         768
Gly Val Ile Cys Ala Ser Glu Gln Ser Ile Leu Val Met Asn Ser Ile
                    245                 250                 255 tac gaa aaa gtt aaa gag gaa ttt gta aaa cga gga tca tat ata ctc         816
Tyr Glu Lys Val Lys Glu Glu Phe Val Lys Arg Gly Ser Tyr Ile Leu
                260                 265                 270 aat caa aat gaa ata gct aaa ata aaa gaa act atg ttt aaa aat gga         864
Asn Gln Asn Glu Ile Ala Lys Ile Lys Glu Thr Met Phe Lys Asn Gly
            275                 280                 285 gct att aat gct gac ata gtt gga aaa tct gct tat ata att gct aaa         912
Ala Ile Asn Ala Asp Ile Val Gly Lys Ser Ala Tyr Ile Ile Ala Lys
        290                 295                 300 atg gca gga att gaa gtt cct caa act aca aag ata ctt ata ggc gaa         960
Met Ala Gly Ile Glu Val Pro Gln Thr Thr Lys Ile Leu Ile Gly Glu
305                 310                 315                 320 gta caa tct gtt gaa aaa agc gag ctg ttc tca cat gaa aaa cta tca        1008
Val Gln Ser Val Glu Lys Ser Glu Leu Phe Ser His Glu Lys Leu Ser
                325                 330                 335 cca gta ctt gca atg tat aaa gtt aag gat ttt gat gaa gct cta aaa        1056
Pro Val Leu Ala Met Tyr Lys Val Lys Asp Phe Asp Glu Ala Leu Lys
            340                 345                 350 aag gca caa agg cta ata gaa tta ggt gga agt gga cac acg tca tct        1104
Lys Ala Gln Arg Leu Ile Glu Leu Gly Gly Ser Gly His Thr Ser Ser
        355                 360                 365 tta tat ata gat tca caa aac aat aag gat aaa gtt aaa gaa ttt gga        1152
Leu Tyr Ile Asp Ser Gln Asn Asn Lys Asp Lys Val Lys Glu Phe Gly
370                 375                 380 tta gca atg aaa act tca agg aca ttt att aac atg cct tct tca cag        1200
Leu Ala Met Lys Thr Ser Arg Thr Phe Ile Asn Met Pro Ser Ser Gln
385                 390                 395                 400 gga gca agc gga gat tta tac aat ttt gcg ata gca cca tca ttt act        1248
Gly Ala Ser Gly Asp Leu Tyr Asn Phe Ala Ile Ala Pro Ser Phe Thr
                405                 410                 415 ctt gga tgc ggc act tgg gga gga aac tct gta tcg caa aat gta gag        1296
Leu Gly Cys Gly Thr Trp Gly Gly Asn Ser Val Ser Gln Asn Val Glu
            420                 425                 430 cct aaa cat tta tta aat att aaa agt gtt gct gaa aga agg gaa aat        1344
Pro Lys His Leu Leu Asn Ile Lys Ser Val Ala Glu Arg Arg Glu Asn
        435                 440                 445 atg ctt tgg ttt aaa gtg cca caa aaa ata tat ttt aaa tat gga tgt        1392
Met Leu Trp Phe Lys Val Pro Gln Lys Ile Tyr Phe Lys Tyr Gly Cys
450                 455                 460 ctt aga ttt gca tta aaa gaa tta aaa gat atg aat aag aaa aga gcc        1440
Leu Arg Phe Ala Leu Lys Glu Leu Lys Asp Met Asn Lys Lys Arg Ala
465                 470                 475                 480 ttt ata gta aca gat aaa gat ctt ttt aaa ctt gga tat gtt aat aaa        1488
Phe Ile Val Thr Asp Lys Asp Leu Phe Lys Leu Gly Tyr Val Asn Lys
                485                 490                 495 ata aca aag gta cta gat gag ata gat att aaa tac agt ata ttt aca        1536
Ile Thr Lys Val Leu Asp Glu Ile Asp Ile Lys Tyr Ser Ile Phe Thr
            500                 505                 510 gat att aaa tct gat cca act att gat tca gta aaa aaa ggt gct aaa        1584
Asp Ile Lys Ser Asp Pro Thr Ile Asp Ser Val Lys Lys Gly Ala Lys
        515                 520                 525 gaa atg ctt aac ttt gaa cct gat act ata atc tct att ggt ggt gga        1632
Glu Met Leu Asn Phe Glu Pro Asp Thr Ile Ile Ser Ile Gly Gly Gly
530                 535                 540
```

```
tcg cca atg gat gca gca aag gtt atg cac ttg tta tat gaa tat cca    1680
Ser Pro Met Asp Ala Ala Lys Val Met His Leu Leu Tyr Glu Tyr Pro
545                 550                 555                 560 gaa gca gaa att gaa aat cta gct ata aac ttt atg gat ata aga aag    1728
Glu Ala Glu Ile Glu Asn Leu Ala Ile Asn Phe Met Asp Ile Arg Lys
            565                 570                 575 aga ata tgc aat ttc cct aaa tta ggt aca aag gcg att tca gta gct    1776
Arg Ile Cys Asn Phe Pro Lys Leu Gly Thr Lys Ala Ile Ser Val Ala
        580                 585                 590 att cct aca act gct ggt acc ggt tca gag gca aca cct ttt gca gtt    1824
Ile Pro Thr Thr Ala Gly Thr Gly Ser Glu Ala Thr Pro Phe Ala Val
    595                 600                 605 ata act aat gat gaa aca gga atg aaa tac cct tta act tct tat gaa    1872
Ile Thr Asn Asp Glu Thr Gly Met Lys Tyr Pro Leu Thr Ser Tyr Glu
610                 615                 620 ttg acc cca aac atg gca ata ata gat act gaa tta atg tta aat atg    1920
Leu Thr Pro Asn Met Ala Ile Ile Asp Thr Glu Leu Met Leu Asn Met
625                 630                 635                 640 cct aga aaa tta aca gca gca act gga ata gat gca tta gtt cat gct    1968
Pro Arg Lys Leu Thr Ala Ala Thr Gly Ile Asp Ala Leu Val His Ala
            645                 650                 655 ata gaa gca tat gtt tcg gtt atg gct acg gat tat act gat gaa tta    2016
Ile Glu Ala Tyr Val Ser Val Met Ala Thr Asp Tyr Thr Asp Glu Leu
        660                 665                 670 gcc tta aga gca ata aaa atg ata ttt aaa tat ttg cct aga gcc tat    2064
Ala Leu Arg Ala Ile Lys Met Ile Phe Lys Tyr Leu Pro Arg Ala Tyr
    675                 680                 685 aaa aat ggg act aac gac att gaa gca aga gaa aaa atg gca cat gcc    2112
Lys Asn Gly Thr Asn Asp Ile Glu Ala Arg Glu Lys Met Ala His Ala
690                 695                 700 tct aat att gcg ggg atg gca ttt gca aat gct ttc tta ggt gta tgc    2160
Ser Asn Ile Ala Gly Met Ala Phe Ala Asn Ala Phe Leu Gly Val Cys
705                 710                 715                 720 cat tca atg gct cat aaa ctt ggg gca atg cat cac gtt cca cat gga    2208
His Ser Met Ala His Lys Leu Gly Ala Met His His Val Pro His Gly
            725                 730                 735 att gct tgt gct gta tta ata gaa gaa gtt att aaa tat aac gct aca    2256
Ile Ala Cys Ala Val Leu Ile Glu Glu Val Ile Lys Tyr Asn Ala Thr
        740                 745                 750 gac tgt cca aca aag caa aca gca ttc cct caa tat aaa tct cct aat    2304
Asp Cys Pro Thr Lys Gln Thr Ala Phe Pro Gln Tyr Lys Ser Pro Asn
    755                 760                 765 gct aag aga aaa tat gct gaa att gca gag tat ttg aat tta aag ggt    2352
Ala Lys Arg Lys Tyr Ala Glu Ile Ala Glu Tyr Leu Asn Leu Lys Gly
770                 775                 780 act agc gat acc gaa aag gta aca gcc tta ata gaa gct att tca aag    2400
Thr Ser Asp Thr Glu Lys Val Thr Ala Leu Ile Glu Ala Ile Ser Lys
785                 790                 795                 800 tta aag ata gat ttg agt att cca caa aat ata agt gcc gct gga ata    2448
Leu Lys Ile Asp Leu Ser Ile Pro Gln Asn Ile Ser Ala Ala Gly Ile
            805                 810                 815 aat aaa aaa gat ttt tat aat acg cta gat aaa atg tca gag ctt gct    2496
Asn Lys Lys Asp Phe Tyr Asn Thr Leu Asp Lys Met Ser Glu Leu Ala
        820                 825                 830 ttt gat gac caa tgt aca aca gct aat cct agg tat cca ctt ata agt    2544
Phe Asp Asp Gln Cys Thr Thr Ala Asn Pro Arg Tyr Pro Leu Ile Ser
    835                 840                 845 gaa ctt aag gat atc tat ata aaa tca ttt taa                        2577
Glu Leu Lys Asp Ile Tyr Ile Lys Ser Phe
850                 855
```

<210> SEQ ID NO 68
<211> LENGTH: 858
<212> TYPE: PRT
<213> ORGANISM: Clostridium acetobutylicum

<400> SEQUENCE: 68

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly

```
               370                 375                 380
Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
                420                 425                 430

Pro Lys His Leu Leu Asn Ile Lys Ser Val Ala Glu Arg Arg Glu Asn
                435                 440                 445

Met Leu Trp Phe Lys Val Pro Gln Lys Ile Tyr Phe Lys Tyr Gly Cys
                450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
                500                 505                 510

Asp Ile Lys Ser Asp Pro Thr Ile Asp Ser Val Lys Lys Gly Ala Lys
                515                 520                 525

Glu Met Leu Asn Phe Glu Pro Asp Thr Ile Ile Ser Ile Gly Gly Gly
                530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
                580                 585                 590

Ile Pro Thr Thr Ala Gly Thr Gly Ser Glu Ala Thr Pro Phe Ala Val
                595                 600                 605

Ile Thr Asn Asp Glu Thr Gly Met Lys Tyr Pro Leu Thr Ser Tyr Glu
                610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
                660                 665                 670

Ala Leu Arg Ala Ile Lys Met Ile Phe Lys Tyr Leu Pro Arg Ala Tyr
                675                 680                 685

Lys Asn Gly Thr Asn Asp Ile Glu Ala Arg Glu Lys Met Ala His Ala
                690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
                740                 745                 750

Asp Cys Pro Thr Lys Gln Thr Ala Phe Pro Gln Tyr Lys Ser Pro Asn
                755                 760                 765

Ala Lys Arg Lys Tyr Ala Glu Ile Ala Glu Tyr Leu Asn Leu Lys Gly
                770                 775                 780

Thr Ser Asp Thr Glu Lys Val Thr Ala Leu Ile Glu Ala Ile Ser Lys
785                 790                 795                 800
```

```
Leu Lys Ile Asp Leu Ser Ile Pro Gln Asn Ile Ser Ala Ala Gly Ile
            805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
            835                 840                 845

Glu Leu Lys Asp Ile Tyr Ile Lys Ser Phe
    850                 855

<210> SEQ ID NO 69
<211> LENGTH: 1551
<212> TYPE: DNA
<213> ORGANISM: Leptospira interrogans
<220> FEATURE:
<221> NAME/KEY: CDS
<222> LOCATION: (1)..(1551)

<400> SEQUENCE: 69 atg aca aaa gta gaa act cga ttg gaa att tta gac gta act ttg aga      48
Met Thr Lys Val Glu Thr Arg Leu Glu Ile Leu Asp Val Thr Leu Arg
1               5                   10                  15 gac ggg gag cag acc aga ggg gtc agt ttt tcc act tcc gaa aaa cta      96
Asp Gly Glu Gln Thr Arg Gly Val Ser Phe Ser Thr Ser Glu Lys Leu
            20                  25                  30 aat atc gca aaa ttt cta tta caa aaa cta aat gta gat cgg gta gag     144
Asn Ile Ala Lys Phe Leu Leu Gln Lys Leu Asn Val Asp Arg Val Glu
        35                  40                  45 att gcg tct gca aga gtt tct aaa ggg gaa ttg gaa acg gtc caa aaa     192
Ile Ala Ser Ala Arg Val Ser Lys Gly Glu Leu Glu Thr Val Gln Lys
    50                  55                  60 atc atg gaa tgg gct gca aca gaa cag ctt acg gaa aga atc gaa atc     240
Ile Met Glu Trp Ala Ala Thr Glu Gln Leu Thr Glu Arg Ile Glu Ile
65                  70                  75                  80 tta ggt ttt gta gac ggg aat aaa acc gta gat tgg atc aaa gat agt     288
Leu Gly Phe Val Asp Gly Asn Lys Thr Val Asp Trp Ile Lys Asp Ser
                85                  90                  95 ggg gct aag gtt tta aat ctt ttg act aag gga tcg ctt cat cat tta     336
Gly Ala Lys Val Leu Asn Leu Leu Thr Lys Gly Ser Leu His His Leu
            100                 105                 110 gaa aaa caa tta ggc aaa act ccg aaa gaa ttc ttt aca gac gtt tct     384
Glu Lys Gln Leu Gly Lys Thr Pro Lys Glu Phe Phe Thr Asp Val Ser
        115                 120                 125 ttt gta ata gaa tac gcg atc aaa agc gga ctt aaa ata aac gta tat     432
Phe Val Ile Glu Tyr Ala Ile Lys Ser Gly Leu Lys Ile Asn Val Tyr
    130                 135                 140 tta gaa gat tgg tcc aac ggt ttc aga aac agt cca gat tac gtc aaa     480
Leu Glu Asp Trp Ser Asn Gly Phe Arg Asn Ser Pro Asp Tyr Val Lys
145                 150                 155                 160 tcg ctc gta gaa cat cta agt aaa gaa cat ata gaa aga att ttt ctt     528
Ser Leu Val Glu His Leu Ser Lys Glu His Ile Glu Arg Ile Phe Leu
                165                 170                 175 cca gac acg tta ggc gtt ctt tcg cca gaa gag acg ttt caa gga gtg     576
Pro Asp Thr Leu Gly Val Leu Ser Pro Glu Glu Thr Phe Gln Gly Val
            180                 185                 190 gat tca ctc att caa aaa tac ccg gat att cat ttt gaa ttt cac gga     624
Asp Ser Leu Ile Gln Lys Tyr Pro Asp Ile His Phe Glu Phe His Gly
        195                 200                 205 cat aac gac tac gat ctt tcc gtg gca aat agt ctt caa gcg att cgt     672
His Asn Asp Tyr Asp Leu Ser Val Ala Asn Ser Leu Gln Ala Ile Arg
    210                 215                 220
```

| | | |
|---|---|---|
| gcc gga gtc aaa ggt ctt cac gct tct ata aat ggt ctc gga gaa aga<br>Ala Gly Val Lys Gly Leu His Ala Ser Ile Asn Gly Leu Gly Glu Arg<br>225                          230                     235                   240 | 720 |
| gcc gga aat act ccg ttg gaa gca ctc gta acc acg att cat gat aag<br>Ala Gly Asn Thr Pro Leu Glu Ala Leu Val Thr Thr Ile His Asp Lys<br>                245                     250                     255 | 768 |
| tct aac tct aaa acg aac ata aac gaa att gca att acg gaa gca agc<br>Ser Asn Ser Lys Thr Asn Ile Asn Glu Ile Ala Ile Thr Glu Ala Ser<br>                260                     265                     270 | 816 |
| cgt ctt gta gaa gta ttc agc gga aaa aga att tct gca aat aga ccg<br>Arg Leu Val Glu Val Phe Ser Gly Lys Arg Ile Ser Ala Asn Arg Pro<br>       275                     280                     285 | 864 |
| atc gta gga gaa gac gtg ttt act cag acc gcg gga gta cac gca gac<br>Ile Val Gly Glu Asp Val Phe Thr Gln Thr Ala Gly Val His Ala Asp<br>290                          295                     300 | 912 |
| gga gac aaa aaa gga aat tta tac gca aat cct att tta ccg gaa aga<br>Gly Asp Lys Lys Gly Asn Leu Tyr Ala Asn Pro Ile Leu Pro Glu Arg<br>305                          310                     315                   320 | 960 |
| ttt ggt agg aaa aga agt tac gcg tta ggc aaa ctt gca ggt aag gcg<br>Phe Gly Arg Lys Arg Ser Tyr Ala Leu Gly Lys Leu Ala Gly Lys Ala<br>                     325                     330                     335 | 1008 |
| agt atc tcc gaa aat gta aaa caa ctc gga atg gtt tta agt gaa gtg<br>Ser Ile Ser Glu Asn Val Lys Gln Leu Gly Met Val Leu Ser Glu Val<br>                340                     345                     350 | 1056 |
| gtt tta caa aag gtt tta gaa agg gtg atc gaa tta gga gat cag aat<br>Val Leu Gln Lys Val Leu Glu Arg Val Ile Glu Leu Gly Asp Gln Asn<br>       355                     360                     365 | 1104 |
| aaa cta gtg aca cct gaa gat ctt cca ttt atc att gcg gac gtt tct<br>Lys Leu Val Thr Pro Glu Asp Leu Pro Phe Ile Ile Ala Asp Val Ser<br>370                          375                     380 | 1152 |
| gga aga acc gga gaa aag gta ctt aca atc aaa tct tgt aat att cat<br>Gly Arg Thr Gly Glu Lys Val Leu Thr Ile Lys Ser Cys Asn Ile His<br>385                          390                     395                   400 | 1200 |
| tcc gga att gga att cgt cct cac gca caa att gaa ttg gaa tat cag<br>Ser Gly Ile Gly Ile Arg Pro His Ala Gln Ile Glu Leu Glu Tyr Gln<br>                405                     410                     415 | 1248 |
| gga aag att cat aag gaa att tct gaa gga gac gga ggg tat gat gcg<br>Gly Lys Ile His Lys Glu Ile Ser Glu Gly Asp Gly Gly Tyr Asp Ala<br>                     420                     425                     430 | 1296 |
| ttt atg aat gca ctt act aaa att acg aat cgc ctc ggt att agt att<br>Phe Met Asn Ala Leu Thr Lys Ile Thr Asn Arg Leu Gly Ile Ser Ile<br>                435                     440                     445 | 1344 |
| cct aaa ttg ata gat tac gaa gta agg att cct cct ggt gga aaa aca<br>Pro Lys Leu Ile Asp Tyr Glu Val Arg Ile Pro Pro Gly Gly Lys Thr<br>450                          455                     460 | 1392 |
| gat gca ctt gta gaa act agg atc acc tgg aac aag tcc tta gat tta<br>Asp Ala Leu Val Glu Thr Arg Ile Thr Trp Asn Lys Ser Leu Asp Leu<br>465                          470                     475                   480 | 1440 |
| gaa gag gac cag act ttc aaa acg atg gga gtt cat ccg gat caa acg<br>Glu Glu Asp Gln Thr Phe Lys Thr Met Gly Val His Pro Asp Gln Thr<br>                   485                     490                     495 | 1488 |
| gtt gca gcg gtt cat gca act gaa aag atg ctc aat caa att cta caa<br>Val Ala Ala Val His Ala Thr Glu Lys Met Leu Asn Gln Ile Leu Gln<br>                  500                     505                     510 | 1536 |
| cca tgg caa atc taa<br>Pro Trp Gln Ile<br>       515 | 1551 |

<210> SEQ ID NO 70

<211> LENGTH: 516
<212> TYPE: PRT
<213> ORGANISM: Leptospira interrogans

<400> SEQUENCE: 70

```

```
                385                 390                 395                 400
            Ser Gly Ile Gly Ile Arg Pro His Ala Gln Ile Glu Leu Glu Tyr Gln
                            405                 410                 415
            Gly Lys Ile His Lys Glu Ile Ser Glu Gly Asp Gly Gly Tyr Asp Ala
                            420                 425                 430
            Phe Met Asn Ala Leu Thr Lys Ile Thr Asn Arg Leu Gly Ile Ser Ile
                        435                 440                 445
            Pro Lys Leu Ile Asp Tyr Glu Val Arg Ile Pro Pro Gly Gly Lys Thr
                450                 455                 460
            Asp Ala Leu Val Glu Thr Arg Ile Thr Trp Asn Lys Ser Leu Asp Leu
            465                 470                 475                 480
            Glu Glu Asp Gln Thr Phe Lys Thr Met Gly Val His Pro Asp Gln Thr
                                485                 490                 495
            Val Ala Ala Val His Ala Thr Glu Lys Met Leu Asn Gln Ile Leu Gln
                            500                 505                 510
            Pro Trp Gln Ile
                    515

<210> SEQ ID NO 71
<211> LENGTH: 1398
<212> TYPE: DNA
<213> ORGANISM: Leptospira interrogans
<220> FEATURE:
<221> NAME/KEY: CDS
<222> LOCATION: (1)..(1398)

<400> SEQUENCE: 71 atg aag aca atg ttc gaa aaa att tgg gaa gat cat cta gtc gga gaa      48
Met Lys Thr Met Phe Glu Lys Ile Trp Glu Asp His Leu Val Gly Glu
1               5                   10                  15 cta gat gct gga tcc tat cta atc tat ata gat cgc cat ctc att cat      96
Leu Asp Ala Gly Ser Tyr Leu Ile Tyr Ile Asp Arg His Leu Ile His
                20                  25                  30 gaa gtt aca agt cct cag gcg ttt gaa gga ctt aaa ctt gca ggc aga     144
Glu Val Thr Ser Pro Gln Ala Phe Glu Gly Leu Lys Leu Ala Gly Arg
            35                  40                  45 aag gtt cgt cgt cct gaa gct act ttt gcc aca atg gat cat aac gtt     192
Lys Val Arg Arg Pro Glu Ala Thr Phe Ala Thr Met Asp His Asn Val
        50                  55                  60 tct act aga aca cgt gat tta agt ctg gcc gat cct gtt tcc gca att     240
Ser Thr Arg Thr Arg Asp Leu Ser Leu Ala Asp Pro Val Ser Ala Ile
65                  70                  75                  80 caa atg cag act tta aaa aag aac tgc gac gaa aac gga atc cgc gtt     288
Gln Met Gln Thr Leu Lys Lys Asn Cys Asp Glu Asn Gly Ile Arg Val
                85                  90                  95 tat gat ttt caa aac cct gac caa gga atc att cac gta atc gct cct     336
Tyr Asp Phe Gln Asn Pro Asp Gln Gly Ile Ile His Val Ile Ala Pro
                100                 105                 110 gaa atg gga ctg act cat cct gga atg aca atc gta tgc gga gat tct     384
Glu Met Gly Leu Thr His Pro Gly Met Thr Ile Val Cys Gly Asp Ser
            115                 120                 125 cat act tct aca cac ggt gcg ttt ggt gcg ctt gct ttc ggg atc gga     432
His Thr Ser Thr His Gly Ala Phe Gly Ala Leu Ala Phe Gly Ile Gly
        130                 135                 140 acc agc gaa gta gag cac gtt ctt gcg act caa acc tta gtt caa aaa     480
Thr Ser Glu Val Glu His Val Leu Ala Thr Gln Thr Leu Val Gln Lys
145                 150                 155                 160 aga gca aaa aca atg gag att aga gtc gat gga aaa ctt tcc gat aag     528
Arg Ala Lys Thr Met Glu Ile Arg Val Asp Gly Lys Leu Ser Asp Lys
```

-continued

```
                    165                 170                 175
gtc aca gca aaa gac atc att ctt gcg atc att gga aaa att gga acc      576
Val Thr Ala Lys Asp Ile Ile Leu Ala Ile Ile Gly Lys Ile Gly Thr
            180                 185                 190 gca ggt gcg aca ggt tat gtg atc gaa tat aga ggt tct gca att caa      624
Ala Gly Ala Thr Gly Tyr Val Ile Glu Tyr Arg Gly Ser Ala Ile Gln
            195                 200                 205 gcc ctc agt atg gaa gct aga atg act att tgt aat atg tct atc gaa      672
Ala Leu Ser Met Glu Ala Arg Met Thr Ile Cys Asn Met Ser Ile Glu
    210                 215                 220 gcg gga gct aga gca ggt tta atc gca cca gat gaa act act ttt aat      720
Ala Gly Ala Arg Ala Gly Leu Ile Ala Pro Asp Glu Thr Thr Phe Asn
225                 230                 235                 240 tat att caa gga aag gac ttt tct cca aaa gga gtc gaa tgg gat ctt      768
Tyr Ile Gln Gly Lys Asp Phe Ser Pro Lys Gly Val Glu Trp Asp Leu
            245                 250                 255 gcg gtc aaa aaa tgg aaa cac tat gta acg gac gaa ggt gct aaa ttt      816
Ala Val Lys Lys Trp Lys His Tyr Val Thr Asp Glu Gly Ala Lys Phe
            260                 265                 270 gat aga acc gta att ctt cat gca gat gaa atc gct cct atg gta act      864
Asp Arg Thr Val Ile Leu His Ala Asp Glu Ile Ala Pro Met Val Thr
            275                 280                 285 tgg gga act tct ccc agt cag gtt gtt tcg ata aaa gga gtc gtt cca      912
Trp Gly Thr Ser Pro Ser Gln Val Val Ser Ile Lys Gly Val Val Pro
    290                 295                 300 gat cca aaa gat gca aat gat ccg gtg gaa aaa att gga att gag tct      960
Asp Pro Lys Asp Ala Asn Asp Pro Val Glu Lys Ile Gly Ile Glu Ser
305                 310                 315                 320 gcg ctt aaa tat atg gat ctc aaa tcg ggc cag aag ata gaa gac att     1008
Ala Leu Lys Tyr Met Asp Leu Lys Ser Gly Gln Lys Ile Glu Asp Ile
            325                 330                 335 tca att aat aaa gtg ttt atc ggt tcc tgt act aat tct aga atc gaa     1056
Ser Ile Asn Lys Val Phe Ile Gly Ser Cys Thr Asn Ser Arg Ile Glu
            340                 345                 350 gat tta aga gcg gcc gct gct acc gta aaa gga aaa aaa gtt tcc tct     1104
Asp Leu Arg Ala Ala Ala Ala Thr Val Lys Gly Lys Lys Val Ser Ser
            355                 360                 365 aag gtt cag gcg att gtg gtt ccc ggt tca ggc aga gtc aaa cgt cag     1152
Lys Val Gln Ala Ile Val Val Pro Gly Ser Gly Arg Val Lys Arg Gln
370                 375                 380 gcg gaa caa gaa ggt ctg gat aaa att ttt acc gcg gcc ggt ttt gaa     1200
Ala Glu Gln Glu Gly Leu Asp Lys Ile Phe Thr Ala Ala Gly Phe Glu
385                 390                 395                 400 tgg aga aat cca ggc tgt tct atg tgt ctt gcg atg aac gac gac gta     1248
Trp Arg Asn Pro Gly Cys Ser Met Cys Leu Ala Met Asn Asp Asp Val
            405                 410                 415 tta gaa ccg gga gat cgt tgt gct tct act tct aac cga aac ttt gaa     1296
Leu Glu Pro Gly Asp Arg Cys Ala Ser Thr Ser Asn Arg Asn Phe Glu
            420                 425                 430 ggt cgt caa gga aaa ggt gga aga acc cat cta gta gga ccg gaa atg     1344
Gly Arg Gln Gly Lys Gly Gly Arg Thr His Leu Val Gly Pro Glu Met
            435                 440                 445 gcc gcc gcc gcg gct atc gaa ggc cat ttt gtg gat att cga aac tgg     1392
Ala Ala Ala Ala Ala Ile Glu Gly His Phe Val Asp Ile Arg Asn Trp
450                 455                 460 aaa taa                                                              1398
Lys
465
```

<210> SEQ ID NO 72
<211> LENGTH: 465
<212> TYPE: PRT
<213> ORGANISM: Leptospira interrogans

<400> SEQUENCE: 72

| | | | | | | | | | | | | | | |
|---|---|---|---|---|---|---|---|---|---|---|---|---|---|---|
| Met | Lys | Thr | Met | Phe | Lys | Ile | Trp | Glu | Asp | His | Leu | Val | Gly | Glu |
| 1 | | | | 5 | | | | | 10 | | | | | 15 |
| Leu | Asp | Ala | Gly | Ser | Tyr | Leu | Ile | Tyr | Ile | Asp | Arg | His | Leu | Ile | His |
| | | | 20 | | | | | 25 | | | | | 30 | | |
| Glu | Val | Thr | Ser | Pro | Gln | Ala | Phe | Glu | Gly | Leu | Lys | Leu | Ala | Gly | Arg |
| | | 35 | | | | | 40 | | | | | 45 | | | |
| Lys | Val | Arg | Arg | Pro | Glu | Ala | Thr | Phe | Ala | Thr | Met | Asp | His | Asn | Val |
| 50 | | | | | 55 | | | | | 60 | | | | | |
| Ser | Thr | Arg | Thr | Arg | Asp | Leu | Ser | Leu | Ala | Asp | Pro | Val | Ser | Ala | Ile |
| 65 | | | | | 70 | | | | | 75 | | | | | 80 |
| Gln | Met | Gln | Thr | Leu | Lys | Lys | Asn | Cys | Asp | Glu | Asn | Gly | Ile | Arg | Val |
| | | | | 85 | | | | | 90 | | | | | 95 | |
| Tyr | Asp | Phe | Gln | Asn | Pro | Asp | Gln | Gly | Ile | Ile | His | Val | Ile | Ala | Pro |
| | | | 100 | | | | | 105 | | | | | 110 | | |
| Glu | Met | Gly | Leu | Thr | His | Pro | Gly | Met | Thr | Ile | Val | Cys | Gly | Asp | Ser |
| | | 115 | | | | | 120 | | | | | 125 | | | |
| His | Thr | Ser | Thr | His | Gly | Ala | Phe | Gly | Ala | Leu | Ala | Phe | Gly | Ile | Gly |
| 130 | | | | | 135 | | | | | 140 | | | | | |
| Thr | Ser | Glu | Val | Glu | His | Val | Leu | Ala | Thr | Gln | Thr | Leu | Val | Gln | Lys |
| 145 | | | | | 150 | | | | | 155 | | | | | 160 |
| Arg | Ala | Lys | Thr | Met | Glu | Ile | Arg | Val | Asp | Gly | Lys | Leu | Ser | Asp | Lys |
| | | | | 165 | | | | | 170 | | | | | 175 | |
| Val | Thr | Ala | Lys | Asp | Ile | Ile | Leu | Ala | Ile | Gly | Lys | Ile | Gly | Thr |
| | | | 180 | | | | | 185 | | | | | 190 | | |
| Ala | Gly | Ala | Thr | Gly | Tyr | Val | Ile | Glu | Tyr | Arg | Gly | Ser | Ala | Ile | Gln |
| | | 195 | | | | | 200 | | | | | 205 | | | |
| Ala | Leu | Ser | Met | Glu | Ala | Arg | Met | Thr | Ile | Cys | Asn | Met | Ser | Ile | Glu |
| 210 | | | | | 215 | | | | | 220 | | | | | |
| Ala | Gly | Ala | Arg | Ala | Gly | Leu | Ile | Ala | Pro | Asp | Glu | Thr | Thr | Phe | Asn |
| 225 | | | | | 230 | | | | | 235 | | | | | 240 |
| Tyr | Ile | Gln | Gly | Lys | Asp | Phe | Ser | Pro | Lys | Gly | Val | Glu | Trp | Asp | Leu |
| | | | | 245 | | | | | 250 | | | | | 255 | |
| Ala | Val | Lys | Lys | Trp | Lys | His | Tyr | Val | Thr | Asp | Glu | Gly | Ala | Lys | Phe |
| | | | 260 | | | | | 265 | | | | | 270 | | |
| Asp | Arg | Thr | Val | Ile | Leu | His | Ala | Asp | Glu | Ile | Ala | Pro | Met | Val | Thr |
| | | 275 | | | | | 280 | | | | | 285 | | | |
| Trp | Gly | Thr | Ser | Pro | Ser | Gln | Val | Val | Ser | Ile | Lys | Gly | Val | Val | Pro |
| 290 | | | | | 295 | | | | | 300 | | | | | |
| Asp | Pro | Lys | Asp | Ala | Asn | Asp | Pro | Val | Glu | Lys | Ile | Gly | Ile | Glu | Ser |
| 305 | | | | | 310 | | | | | 315 | | | | | 320 |
| Ala | Leu | Lys | Tyr | Met | Asp | Leu | Lys | Ser | Gly | Gln | Lys | Ile | Glu | Asp | Ile |
| | | | | 325 | | | | | 330 | | | | | 335 | |
| Ser | Ile | Asn | Lys | Val | Phe | Ile | Gly | Ser | Cys | Thr | Asn | Ser | Arg | Ile | Glu |
| | | | 340 | | | | | 345 | | | | | 350 | | |
| Asp | Leu | Arg | Ala | Ala | Ala | Thr | Val | Lys | Gly | Lys | Val | Ser | Ser |
| | | 355 | | | | | 360 | | | | | 365 | | | |
| Lys | Val | Gln | Ala | Ile | Val | Val | Pro | Gly | Ser | Gly | Arg | Val | Lys | Arg | Gln |
| 370 | | | | | 375 | | | | | 380 | | | | | |

```
Ala Glu Gln Glu Gly Leu Asp Lys Ile Phe Thr Ala Ala Gly Phe Glu
385                 390                 395                 400

Trp Arg Asn Pro Gly Cys Ser Met Cys Leu Ala Met Asn Asp Asp Val
            405                 410                 415

Leu Glu Pro Gly Asp Arg Cys Ala Ser Thr Ser Asn Arg Asn Phe Glu
        420                 425                 430

Gly Arg Gln Gly Lys Gly Arg Thr His Leu Val Gly Pro Glu Met
    435                 440                 445

Ala Ala Ala Ala Ile Glu Gly His Phe Val Asp Ile Arg Asn Trp
450                 455                 460

Lys
465

<210> SEQ ID NO 73
<211> LENGTH: 621
<212> TYPE: DNA
<213> ORGANISM: Leptospira interrogans
<220> FEATURE:
<221> NAME/KEY: CDS
<222> LOCATION: (1)..(621)

<400> SEQUENCE: 73 atg aaa ccc ttt act ata tta aat gga att gcc gcc tta ctg gac aga     48
Met Lys Pro Phe Thr Ile Leu Asn Gly Ile Ala Ala Leu Leu Asp Arg
1               5                   10                  15 ccc aac gtg gat acg gat cag atc att cca aaa caa ttt tta cgg aag     96
Pro Asn Val Asp Thr Asp Gln Ile Ile Pro Lys Gln Phe Leu Arg Lys
            20                  25                  30 ata gaa cga acc ggt ttc gga gtt cat ctg ttt cac gat tgg aga tac    144
Ile Glu Arg Thr Gly Phe Gly Val His Leu Phe His Asp Trp Arg Tyr
        35                  40                  45 tta gac gac gcg ggt acc aaa ctc aat cct gat ttt tcc ctc aat caa    192
Leu Asp Asp Ala Gly Thr Lys Leu Asn Pro Asp Phe Ser Leu Asn Gln
    50                  55                  60 gaa cga tat aag gga gct tct atc ctt atc acc aga gat aac ttt ggt    240
Glu Arg Tyr Lys Gly Ala Ser Ile Leu Ile Thr Arg Asp Asn Phe Gly
65                  70                  75                  80 tgt gga tct tcc aga gaa cac gct cct tgg gct tta gaa gac tac ggg    288
Cys Gly Ser Ser Arg Glu His Ala Pro Trp Ala Leu Glu Asp Tyr Gly
                85                  90                  95 ttt agg gca atc att gct cct tct tac gcg gat att ttt ttc aac aac    336
Phe Arg Ala Ile Ile Ala Pro Ser Tyr Ala Asp Ile Phe Phe Asn Asn
            100                 105                 110 tgc ttt aaa aac gga atg ctt cca gtc att tta aaa tcg gaa gaa gta    384
Cys Phe Lys Asn Gly Met Leu Pro Val Ile Leu Lys Ser Glu Glu Val
        115                 120                 125 gaa gag ctg ttc cat ttg gtt tcg act aac gta gga gcg aaa gtc ata    432
Glu Glu Leu Phe His Leu Val Ser Thr Asn Val Gly Ala Lys Val Ile
    130                 135                 140 gtg gat ctg gac aaa caa act gta acc gga ccg act gga aaa ata tat    480
Val Asp Leu Asp Lys Gln Thr Val Thr Gly Pro Thr Gly Lys Ile Tyr
145                 150                 155                 160 tat ttt gaa gtg gat tct ttt cgt aaa tac tgt ctt tat aac gga ctt    528
Tyr Phe Glu Val Asp Ser Phe Arg Lys Tyr Cys Leu Tyr Asn Gly Leu
                165                 170                 175 gat gac ata ggt cta act cta aaa caa gaa agt aaa att gga gag ttt    576
Asp Asp Ile Gly Leu Thr Leu Lys Gln Glu Ser Lys Ile Gly Glu Phe
            180                 185                 190 gaa aaa aag cag aaa gaa gtt gaa cct tgg tta tac gcc ata taa        621
Glu Lys Lys Gln Lys Glu Val Glu Pro Trp Leu Tyr Ala Ile
        195                 200                 205
```

<210> SEQ ID NO 74
<211> LENGTH: 206
<212> TYPE: PRT
<213> ORGANISM: Leptospira interrogans

<400> SEQUENCE: 74

```
Met Lys Pro Phe Thr Ile Leu Asn Gly Ile Ala Ala Leu Leu Asp Arg
1               5                   10                  15
Pro Asn Val Asp Thr Asp Gln Ile Ile Pro Lys Gln Phe Leu Arg Lys
            20                  25                  30
Ile Glu Arg Thr Gly Phe Gly Val His Leu Phe His Asp Trp Arg Tyr
        35                  40                  45
Leu Asp Asp Ala Gly Thr Lys Leu Asn Pro Asp Phe Ser Leu Asn Gln
    50                  55                  60
Glu Arg Tyr Lys Gly Ala Ser Ile Leu Ile Thr Arg Asp Asn Phe Gly
65                  70                  75                  80
Cys Gly Ser Ser Arg Glu His Ala Pro Trp Ala Leu Glu Asp Tyr Gly
                85                  90                  95
Phe Arg Ala Ile Ile Ala Pro Ser Tyr Ala Asp Ile Phe Phe Asn Asn
            100                 105                 110
Cys Phe Lys Asn Gly Met Leu Pro Val Ile Leu Lys Ser Glu Glu Val
        115                 120                 125
Glu Glu Leu Phe His Leu Val Ser Thr Asn Val Gly Ala Lys Val Ile
    130                 135                 140
Val Asp Leu Asp Lys Gln Thr Val Thr Gly Pro Thr Gly Lys Ile Tyr
145                 150                 155                 160
Tyr Phe Glu Val Asp Ser Phe Arg Lys Tyr Cys Leu Tyr Asn Gly Leu
                165                 170                 175
Asp Asp Ile Gly Leu Thr Leu Lys Gln Glu Ser Lys Ile Gly Glu Phe
            180                 185                 190
Glu Lys Lys Gln Lys Glu Val Glu Pro Trp Leu Tyr Ala Ile
        195                 200                 205
```

<210> SEQ ID NO 75
<211> LENGTH: 1077
<212> TYPE: DNA
<213> ORGANISM: Leptospira interrogans
<220> FEATURE:
<221> NAME/KEY: CDS
<222> LOCATION: (1)..(1077)

<400> SEQUENCE: 75

```
atg aag aat gta gca gta ctt tca gga gac gga atc gga ccg gaa gtc      48
Met Lys Asn Val Ala Val Leu Ser Gly Asp Gly Ile Gly Pro Glu Val
1               5                   10                  15 atg gag ata gcc atc tcc gtt ttg aaa aag gct ctc ggt gca aaa gtt      96
Met Glu Ile Ala Ile Ser Val Leu Lys Lys Ala Leu Gly Ala Lys Val
            20                  25                  30 tcc gag ttt caa ttt aaa gaa gga ttt gta ggt gga atc gca atc gat     144
Ser Glu Phe Gln Phe Lys Glu Gly Phe Val Gly Gly Ile Ala Ile Asp
        35                  40                  45 aaa act gga cac cca ctt cca ccg gaa act ctt aaa cta tgt gaa gaa     192
Lys Thr Gly His Pro Leu Pro Pro Glu Thr Leu Lys Leu Cys Glu Glu
    50                  55                  60 tct tcc gca att ctt ttc gga agt gtg gga ggt cct aaa tgg gaa aca     240
Ser Ser Ala Ile Leu Phe Gly Ser Val Gly Gly Pro Lys Trp Glu Thr
65                  70                  75                  80
```

| | | |
|---|---|---|
| ctc cct ccg gaa aaa caa ccg gaa cga ggg gca ctt cta cct ttg aga<br>Leu Pro Pro Glu Lys Gln Pro Glu Arg Gly Ala Leu Leu Pro Leu Arg<br>                    85                     90                    95 | 288 | |
| aaa cat ttt gat cta ttt gca aac tta aga cct gcg atc att tat cca<br>Lys His Phe Asp Leu Phe Ala Asn Leu Arg Pro Ala Ile Ile Tyr Pro<br>                 100                   105                 110 | 336 | |
| gag ttg aaa aat gct tct cca gtt cgt tct gat att att gga aac gga<br>Glu Leu Lys Asn Ala Ser Pro Val Arg Ser Asp Ile Ile Gly Asn Gly<br>             115                   120                  125 | 384 | |
| tta gat att ctc ata tta aga gag tta acc gga gga att tat ttt gga<br>Leu Asp Ile Leu Ile Leu Arg Glu Leu Thr Gly Gly Ile Tyr Phe Gly<br>130                    135                   140 | 432 | |
| caa cca aaa gga aga gaa gga tca ggt cag gaa gaa ttt gca tac gac<br>Gln Pro Lys Gly Arg Glu Gly Ser Gly Gln Glu Glu Phe Ala Tyr Asp<br>145                    150                   155                 160 | 480 | |
| acg atg aag tat tcc aga aga gaa atc gaa agg att gct aaa gtc gca<br>Thr Met Lys Tyr Ser Arg Arg Glu Ile Glu Arg Ile Ala Lys Val Ala<br>                 165                   170                 175 | 528 | |
| ttc cag gcg gcc aga aaa aga aat aat aaa gtg act agt atc gat aaa<br>Phe Gln Ala Ala Arg Lys Arg Asn Asn Lys Val Thr Ser Ile Asp Lys<br>                 180                   185                 190 | 576 | |
| gca aac gtc ttg act act tcc gtt ttt tgg aag gaa gta gta atc gaa<br>Ala Asn Val Leu Thr Thr Ser Val Phe Trp Lys Glu Val Val Ile Glu<br>             195                   200                  205 | 624 | |
| ttg cat aag aaa gaa ttt tca gac gtc caa ttg aat cat ctt tat gtg<br>Leu His Lys Lys Glu Phe Ser Asp Val Gln Leu Asn His Leu Tyr Val<br>210                    215                   220 | 672 | |
| gac aat gcg gcg atg cag tta atc gta aat ccg aaa caa ttc gac gtg<br>Asp Asn Ala Ala Met Gln Leu Ile Val Asn Pro Lys Gln Phe Asp Val<br>225                    230                   235                 240 | 720 | |
| gtt ctt tgt gag aat atg ttt ggt gat att ctt tcg gac gag gct tcc<br>Val Leu Cys Glu Asn Met Phe Gly Asp Ile Leu Ser Asp Glu Ala Ser<br>                   245                   250                 255 | 768 | |
| atc att acg ggt tca atc gga atg ctt cct tct gcc tct ctt tcc gaa<br>Ile Ile Thr Gly Ser Ile Gly Met Leu Pro Ser Ala Ser Leu Ser Glu<br>                 260                   265                 270 | 816 | |
| tct gga ttt gga ttg tat gaa cct tct ggt ggt tct gcg ccg gac ata<br>Ser Gly Phe Gly Leu Tyr Glu Pro Ser Gly Gly Ser Ala Pro Asp Ile<br>             275                   280                  285 | 864 | |
| gcc gga aaa gga gtg gca aat ccg att gct caa gta ttg agt gcg gcg<br>Ala Gly Lys Gly Val Ala Asn Pro Ile Ala Gln Val Leu Ser Ala Ala<br>290                    295                   300 | 912 | |
| ttg atg tta cgt tat tct ttt tct atg gaa gaa gaa gca aac aag ata<br>Leu Met Leu Arg Tyr Ser Phe Ser Met Glu Glu Glu Ala Asn Lys Ile<br>305                    310                   315                 320 | 960 | |
| gaa acc gcc gtg cgt aaa acg att gcc tcc gga aaa aga acc aga gac<br>Glu Thr Ala Val Arg Lys Thr Ile Ala Ser Gly Lys Arg Thr Arg Asp<br>                 325                   330                 335 | 1008 | |
| ata gcg gaa gta gga tct acg atc gta gga act aaa gaa atc ggt caa<br>Ile Ala Glu Val Gly Ser Thr Ile Val Gly Thr Lys Glu Ile Gly Gln<br>             340                   345                 350 | 1056 | |
| ttg atc gaa tcc ttt ctc taa<br>Leu Ile Glu Ser Phe Leu<br>             355 | 1077 | |

<210> SEQ ID NO 76
<211> LENGTH: 358
<212> TYPE: PRT
<213> ORGANISM: Leptospira interrogans

```
<400> SEQUENCE: 76

Met Lys Asn Val Ala Val Leu Ser Gly Asp Gly Ile Gly Pro Glu Val
1               5                   10                  15

Met Glu Ile Ala Ile Ser Val Leu Lys Lys Ala Leu Gly Ala Lys Val
            20                  25                  30

Ser Glu Phe Gln Phe Lys Glu Gly Phe Val Gly Gly Ile Ala Ile Asp
        35                  40                  45

Lys Thr Gly His Pro Leu Pro Pro Glu Thr Leu Lys Leu Cys Glu Glu
    50                  55                  60

Ser Ser Ala Ile Leu Phe Gly Ser Val Gly Gly Pro Lys Trp Glu Thr
65                  70                  75                  80

Leu Pro Pro Glu Lys Gln Pro Glu Arg Gly Ala Leu Leu Pro Leu Arg
                85                  90                  95

Lys His Phe Asp Leu Phe Ala Asn Leu Arg Pro Ala Ile Ile Tyr Pro
            100                 105                 110

Glu Leu Lys Asn Ala Ser Pro Val Arg Ser Asp Ile Ile Gly Asn Gly
        115                 120                 125

Leu Asp Ile Leu Ile Leu Arg Glu Leu Thr Gly Gly Ile Tyr Phe Gly
130                 135                 140

Gln Pro Lys Gly Arg Glu Gly Ser Gly Gln Glu Glu Phe Ala Tyr Asp
145                 150                 155                 160

Thr Met Lys Tyr Ser Arg Arg Glu Ile Glu Arg Ile Ala Lys Val Ala
                165                 170                 175

Phe Gln Ala Ala Arg Lys Arg Asn Asn Lys Val Thr Ser Ile Asp Lys
            180                 185                 190

Ala Asn Val Leu Thr Thr Ser Val Phe Trp Lys Glu Val Val Ile Glu
        195                 200                 205

Leu His Lys Lys Glu Phe Ser Asp Val Gln Leu Asn His Leu Tyr Val
210                 215                 220

Asp Asn Ala Ala Met Gln Leu Ile Val Asn Pro Lys Gln Phe Asp Val
225                 230                 235                 240

Val Leu Cys Glu Asn Met Phe Gly Asp Ile Leu Ser Asp Glu Ala Ser
                245                 250                 255

Ile Ile Thr Gly Ser Ile Gly Met Leu Pro Ser Ala Ser Leu Ser Glu
            260                 265                 270

Ser Gly Phe Gly Leu Tyr Glu Pro Ser Gly Gly Ser Ala Pro Asp Ile
        275                 280                 285

Ala Gly Lys Gly Val Ala Asn Pro Ile Ala Gln Val Leu Ser Ala Ala
290                 295                 300

Leu Met Leu Arg Tyr Ser Phe Ser Met Glu Glu Ala Asn Lys Ile
305                 310                 315                 320

Glu Thr Ala Val Arg Lys Thr Ile Ala Ser Gly Lys Arg Thr Arg Asp
                325                 330                 335

Ile Ala Glu Val Gly Ser Thr Ile Val Gly Thr Lys Glu Ile Gly Gln
            340                 345                 350

Leu Ile Glu Ser Phe Leu
        355

<210> SEQ ID NO 77
<211> LENGTH: 1161
<212> TYPE: DNA
<213> ORGANISM: Escherichia coli
<220> FEATURE:
<221> NAME/KEY: CDS
<222> LOCATION: (1)..(1161)
```

<400> SEQUENCE: 77

| | | | | | | | | | | | | | | | | |
|---|---|---|---|---|---|---|---|---|---|---|---|---|---|---|---|---|
| atg | aca | tcg | gaa | aac | ccg | tta | ctg | gcg | ctg | cga | gag | aaa | atc | agc | gcg | 48 |
| Met | Thr | Ser | Glu | Asn | Pro | Leu | Leu | Ala | Leu | Arg | Glu | Lys | Ile | Ser | Ala | |
| 1 | | | | 5 | | | | | 10 | | | | | 15 | | |
| ctg | gat | gaa | aaa | tta | tta | gcg | tta | ctg | gca | gaa | cgg | cgc | gaa | ctg | gcc | 96 |
| Leu | Asp | Glu | Lys | Leu | Leu | Ala | Leu | Leu | Ala | Glu | Arg | Arg | Glu | Leu | Ala | |
| | | | 20 | | | | | 25 | | | | | 30 | | | |
| gtc | gag | gtg | gga | aaa | gcc | aaa | ctg | ctc | tcg | cat | cgc | ccg | gta | cgt | gat | 144 |
| Val | Glu | Val | Gly | Lys | Ala | Lys | Leu | Leu | Ser | His | Arg | Pro | Val | Arg | Asp | |
| | | | 35 | | | | | 40 | | | | | 45 | | | |
| att | gat | cgt | gaa | cgc | gat | ttg | ctg | gaa | aga | tta | att | acg | ctc | ggt | aaa | 192 |
| Ile | Asp | Arg | Glu | Arg | Asp | Leu | Leu | Glu | Arg | Leu | Ile | Thr | Leu | Gly | Lys | |
| | 50 | | | | | 55 | | | | | 60 | | | | | |
| gcg | cac | cat | ctg | gac | gcc | cat | tac | att | act | cgc | ctg | ttc | cag | ctc | atc | 240 |
| Ala | His | His | Leu | Asp | Ala | His | Tyr | Ile | Thr | Arg | Leu | Phe | Gln | Leu | Ile | |
| 65 | | | | | 70 | | | | | 75 | | | | | 80 | |
| att | gaa | gat | tcc | gta | tta | act | cag | cag | gct | ttg | ctc | caa | caa | cat | ctc | 288 |
| Ile | Glu | Asp | Ser | Val | Leu | Thr | Gln | Gln | Ala | Leu | Leu | Gln | Gln | His | Leu | |
| | | | | 85 | | | | | 90 | | | | | 95 | | |
| aat | aaa | att | aat | ccg | cac | tca | gca | cgc | atc | gct | ttt | ctc | ggc | ccc | aaa | 336 |
| Asn | Lys | Ile | Asn | Pro | His | Ser | Ala | Arg | Ile | Ala | Phe | Leu | Gly | Pro | Lys | |
| | | | 100 | | | | | 105 | | | | | 110 | | | |
| ggt | tct | tat | tcc | cat | ctt | gcg | gcg | cgc | cag | tat | gct | gcc | cgt | cac | ttt | 384 |
| Gly | Ser | Tyr | Ser | His | Leu | Ala | Ala | Arg | Gln | Tyr | Ala | Ala | Arg | His | Phe | |
| | | | | 115 | | | | | 120 | | | | | 125 | | |
| gag | caa | ttc | att | gaa | agt | ggc | tgc | gcc | aaa | ttt | gcc | gat | att | ttt | aat | 432 |
| Glu | Gln | Phe | Ile | Glu | Ser | Gly | Cys | Ala | Lys | Phe | Ala | Asp | Ile | Phe | Asn | |
| | 130 | | | | | 135 | | | | | 140 | | | | | |
| cag | gtg | gaa | acc | ggc | cag | gcc | gac | tat | gcc | gtc | gta | ccg | att | gaa | aat | 480 |
| Gln | Val | Glu | Thr | Gly | Gln | Ala | Asp | Tyr | Ala | Val | Val | Pro | Ile | Glu | Asn | |
| 145 | | | | | 150 | | | | | 155 | | | | | 160 | |
| acc | agc | tcc | ggt | gcc | ata | aac | gac | gtt | tac | gat | ctg | ctg | caa | cat | acc | 528 |
| Thr | Ser | Ser | Gly | Ala | Ile | Asn | Asp | Val | Tyr | Asp | Leu | Leu | Gln | His | Thr | |
| | | | | 165 | | | | | 170 | | | | | 175 | | |
| agc | ttg | tcg | att | gtt | ggc | gag | atg | acg | tta | act | atc | gac | cat | tgt | ttg | 576 |
| Ser | Leu | Ser | Ile | Val | Gly | Glu | Met | Thr | Leu | Thr | Ile | Asp | His | Cys | Leu | |
| | | | 180 | | | | | 185 | | | | | 190 | | | |
| ttg | gtc | tcc | ggc | act | act | gat | tta | tcc | acc | atc | aat | acg | gtc | tac | agc | 624 |
| Leu | Val | Ser | Gly | Thr | Thr | Asp | Leu | Ser | Thr | Ile | Asn | Thr | Val | Tyr | Ser | |
| | | | | 195 | | | | | 200 | | | | | 205 | | |
| cat | ccg | cag | cca | ttc | cag | caa | tgc | agc | aaa | ttc | ctt | aat | cgt | tat | ccg | 672 |
| His | Pro | Gln | Pro | Phe | Gln | Gln | Cys | Ser | Lys | Phe | Leu | Asn | Arg | Tyr | Pro | |
| | 210 | | | | | 215 | | | | | 220 | | | | | |
| cac | tgg | aag | att | gaa | tat | acc | gaa | agt | acg | tct | gcg | gca | atg | gaa | aag | 720 |
| His | Trp | Lys | Ile | Glu | Tyr | Thr | Glu | Ser | Thr | Ser | Ala | Ala | Met | Glu | Lys | |
| 225 | | | | | 230 | | | | | 235 | | | | | 240 | |
| gtt | gca | cag | gca | aaa | tca | ccg | cat | gtt | gct | gcg | tta | gga | agc | gaa | gct | 768 |
| Val | Ala | Gln | Ala | Lys | Ser | Pro | His | Val | Ala | Ala | Leu | Gly | Ser | Glu | Ala | |
| | | | | 245 | | | | | 250 | | | | | 255 | | |
| ggc | ggc | act | ttg | tac | ggt | ttg | cag | gta | ctg | gag | cgt | att | gaa | gca | aat | 816 |
| Gly | Gly | Thr | Leu | Tyr | Gly | Leu | Gln | Val | Leu | Glu | Arg | Ile | Glu | Ala | Asn | |
| | | | 260 | | | | | 265 | | | | | 270 | | | |
| cag | cga | caa | aac | ttc | acc | cga | ttt | gtg | gtg | ttg | gcg | cgt | aaa | gcc | att | 864 |
| Gln | Arg | Gln | Asn | Phe | Thr | Arg | Phe | Val | Val | Leu | Ala | Arg | Lys | Ala | Ile | |
| | | 275 | | | | | 280 | | | | | 285 | | | | |
| aac | gtg | tct | gat | cag | gtt | ccg | gcg | aaa | acc | acg | ttg | tta | atg | gcg | acc | 912 |
| Asn | Val | Ser | Asp | Gln | Val | Pro | Ala | Lys | Thr | Thr | Leu | Leu | Met | Ala | Thr | |
| | 290 | | | | | 295 | | | | | 300 | | | | | |

```
ggg caa caa gcc ggt gcg ctg gtt gaa gcg ttg ctg gta ctg cgc aac    960
Gly Gln Gln Ala Gly Ala Leu Val Glu Ala Leu Leu Val Leu Arg Asn
305                 310                 315                 320 cac aat ctg att atg acc cgt ctg gaa tca cgc ccg att cac ggt aat   1008
His Asn Leu Ile Met Thr Arg Leu Glu Ser Arg Pro Ile His Gly Asn
                325                 330                 335 cca tgg gaa gag atg ttc tat ctg gat att cag gcc aat ctt gaa tca   1056
Pro Trp Glu Glu Met Phe Tyr Leu Asp Ile Gln Ala Asn Leu Glu Ser
            340                 345                 350 gcg gaa atg caa aaa gca ttg aaa gag tta ggg gaa atc acc cgt tca   1104
Ala Glu Met Gln Lys Ala Leu Lys Glu Leu Gly Glu Ile Thr Arg Ser
        355                 360                 365 atg aag gta ttg ggc tgt tac cca agt gag aac gta gtg cct gtt gat   1152
Met Lys Val Leu Gly Cys Tyr Pro Ser Glu Asn Val Val Pro Val Asp
    370                 375                 380 cca acc tga                                                       1161
Pro Thr
385

<210> SEQ ID NO 78
<211> LENGTH: 386
<212> TYPE: PRT
<213> ORGANISM: Escherichia coli

<400> SEQUENCE: 78

Met Thr Ser Glu Asn Pro Leu Ala Leu Arg Glu Lys Ile Ser Ala
1               5                   10                  15

Leu Asp Glu Lys Leu Leu Ala Leu Leu Ala Glu Arg Arg Glu Leu Ala
                20                  25                  30

Val Glu Val Gly Lys Ala Lys Leu Leu Ser His Arg Pro Val Arg Asp
            35                  40                  45

Ile Asp Arg Glu Arg Asp Leu Leu Glu Arg Leu Ile Thr Leu Gly Lys
        50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
        195                 200                 205

His Pro Gln Pro Phe Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255
```

```
Gly Gly Thr Leu Tyr Gly Leu Gln Val Leu Glu Arg Ile Glu Ala Asn
            260                 265                 270

Gln Arg Gln Asn Phe Thr Arg Phe Val Leu Ala Arg Lys Ala Ile
        275                 280                 285

Asn Val Ser Asp Gln Val Pro Ala Lys Thr Thr Leu Leu Met Ala Thr
        290                 295                 300

Gly Gln Gln Ala Gly Ala Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335

Pro Trp Glu Glu Met Phe Tyr Leu Asp Ile Gln Ala Asn Leu Glu Ser
            340                 345                 350

Ala Glu Met Gln Lys Ala Leu Lys Glu Leu Gly Glu Ile Thr Arg Ser
        355                 360                 365

Met Lys Val Leu Gly Cys Tyr Pro Ser Glu Asn Val Val Pro Val Asp
        370                 375                 380

Pro Thr
385

<210> SEQ ID NO 79
<211> LENGTH: 1122
<212> TYPE: DNA
<213> ORGANISM: Escherichia coli
<220> FEATURE:
<221> NAME/KEY: CDS
<222> LOCATION: (1)..(1122)

<400> SEQUENCE: 79 atg gtt gct gaa ttg acc gca tta cgc gat caa att gat gaa gtc gat      48
Met Val Ala Glu Leu Thr Ala Leu Arg Asp Gln Ile Asp Glu Val Asp
1               5                   10                  15 aaa gcg ctg ctg aat tta tta gcg aag cgt ctg gaa ctg gtt gct gaa      96
Lys Ala Leu Leu Asn Leu Leu Ala Lys Arg Leu Glu Leu Val Ala Glu
                20                  25                  30 gtg ggc gag gtg aaa agc cgc ttt gga ctg cct att tat gtt ccg gag     144
Val Gly Glu Val Lys Ser Arg Phe Gly Leu Pro Ile Tyr Val Pro Glu
            35                  40                  45 cgc gag gca tct atg ttg gcc tcg cgt cgt gca gag gcg gaa gct ctg     192
Arg Glu Ala Ser Met Leu Ala Ser Arg Arg Ala Glu Ala Glu Ala Leu
        50                  55                  60 ggt gta ccg cca gat ctg att gag gat gtt ttg cgt cgg gtg atg cgt     240
Gly Val Pro Pro Asp Leu Ile Glu Asp Val Leu Arg Arg Val Met Arg
65                  70                  75                  80 gaa tct tac tcc agt gaa aac gac aaa gga ttt aaa aca ctt tgt ccg     288
Glu Ser Tyr Ser Ser Glu Asn Asp Lys Gly Phe Lys Thr Leu Cys Pro
                85                  90                  95 tca ctg cgt ccg gtg gtt atc gtc ggc ggt ggc ggt cag atg gga cgc     336
Ser Leu Arg Pro Val Val Ile Val Gly Gly Gly Gly Gln Met Gly Arg
            100                 105                 110 ctg ttc gag aag atg ctg acc ctc tcg ggt tat cag gtg cgg att ctg     384
Leu Phe Glu Lys Met Leu Thr Leu Ser Gly Tyr Gln Val Arg Ile Leu
        115                 120                 125 gag caa cat gac tgg gat cga gcg gct gat att gtt gcc gat gcc gga     432
Glu Gln His Asp Trp Asp Arg Ala Ala Asp Ile Val Ala Asp Ala Gly
    130                 135                 140 atg gtg att gtt agt gtg cca atc cac gtt act gag caa gtt att ggc     480
Met Val Ile Val Ser Val Pro Ile His Val Thr Glu Gln Val Ile Gly
145                 150                 155                 160
```

```
aaa tta ccg cct tta ccg aaa gat tgt att ctg gtc gat ctg gca tca      528
Lys Leu Pro Pro Leu Pro Lys Asp Cys Ile Leu Val Asp Leu Ala Ser
            165                 170                 175 gtg aaa aat ggg cca tta cag gcc atg ctg gtg gcg cat gat ggt ccg      576
Val Lys Asn Gly Pro Leu Gln Ala Met Leu Val Ala His Asp Gly Pro
        180                 185                 190 gtg ctg ggg cta cac ccg atg ttc ggt ccg gac agc ggt agc ctg gca      624
Val Leu Gly Leu His Pro Met Phe Gly Pro Asp Ser Gly Ser Leu Ala
    195                 200                 205 aag caa gtt gtg gtc tgg tgt gat gga cgt aaa ccg gaa gca tac caa      672
Lys Gln Val Val Val Trp Cys Asp Gly Arg Lys Pro Glu Ala Tyr Gln
210                 215                 220 tgg ttt ctg gag caa att cag gtc tgg ggc gct cgg ctg cat cgt att      720
Trp Phe Leu Glu Gln Ile Gln Val Trp Gly Ala Arg Leu His Arg Ile
225                 230                 235                 240 agc gcc gtc gag cac gat cag aat atg gcg ttt att cag gca ctg cgc      768
Ser Ala Val Glu His Asp Gln Asn Met Ala Phe Ile Gln Ala Leu Arg
            245                 250                 255 cac ttt gct act ttt gct tac ggg ctg cac ctg gca gaa gaa aat gtt      816
His Phe Ala Thr Phe Ala Tyr Gly Leu His Leu Ala Glu Glu Asn Val
        260                 265                 270 cag ctt gag caa ctt ctg gcg ctc tct tcg ccg att tac cgc ctt gag      864
Gln Leu Glu Gln Leu Leu Ala Leu Ser Ser Pro Ile Tyr Arg Leu Glu
    275                 280                 285 ctg gcg atg gtc ggg cga ctg ttt gct cag gat ccg cag ctt tat gcc      912
Leu Ala Met Val Gly Arg Leu Phe Ala Gln Asp Pro Gln Leu Tyr Ala
290                 295                 300 gac atc att atg tcg tca gag cgt aat ctg gcg tta atc aaa cgt tac      960
Asp Ile Ile Met Ser Ser Glu Arg Asn Leu Ala Leu Ile Lys Arg Tyr
305                 310                 315                 320 tat aag cgt ttc ggc gag gcg att gag ttg ctg gag cag ggc gat aag     1008
Tyr Lys Arg Phe Gly Glu Ala Ile Glu Leu Leu Glu Gln Gly Asp Lys
            325                 330                 335 cag gcg ttt att gac agt ttc cgc aag gtg gag cac tgg ttc ggc gat     1056
Gln Ala Phe Ile Asp Ser Phe Arg Lys Val Glu His Trp Phe Gly Asp
        340                 345                 350 tac gca cag cgt ttt cag agt gaa agc cgc gtg tta ttg cgt cag gcg     1104
Tyr Ala Gln Arg Phe Gln Ser Glu Ser Arg Val Leu Leu Arg Gln Ala
    355                 360                 365 aat gac aat cgc cag taa                                              1122
Asn Asp Asn Arg Gln
    370

<210> SEQ ID NO 80
<211> LENGTH: 373
<212> TYPE: PRT
<213> ORGANISM: Escherichia coli

<400> SEQUENCE: 80

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80
```

```
Glu Ser Tyr Ser Ser Glu Asn Asp Lys Gly Phe Lys Thr Leu Cys Pro
             85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
            115                 120                 125

Glu Gln His Asp Trp Asp Arg Ala Ala Asp Ile Val Ala Asp Ala Gly
            130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
            195                 200                 205

Lys Gln Val Val Val Trp Cys Asp Gly Arg Lys Pro Glu Ala Tyr Gln
            210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
            275                 280                 285

Leu Ala Met Val Gly Arg Leu Phe Ala Gln Asp Pro Gln Leu Tyr Ala
            290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
            325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
            355                 360                 365

Asn Asp Asn Arg Gln
    370
```

<210> SEQ ID NO 81
<211> LENGTH: 1716
<212> TYPE: DNA
<213> ORGANISM: Bacillus subtilis
<220> FEATURE:
<221> NAME/KEY: CDS
<222> LOCATION: (1)..(1716)

<400> SEQUENCE: 81

```
atg ttg aca aaa gca aca aaa gaa caa aaa tcc ctt gtg aaa aac aga    48
Met Leu Thr Lys Ala Thr Lys Glu Gln Lys Ser Leu Val Lys Asn Arg
1               5                   10                  15 ggg gcg gag ctt gtt gtt gat tgc tta gtg gag caa ggt gtc aca cat    96
Gly Ala Glu Leu Val Val Asp Cys Leu Val Glu Gln Gly Val Thr His
                20                  25                  30 gta ttt ggc att cca ggt gca aaa att gat gcg gta ttt gac gct tta   144
Val Phe Gly Ile Pro Gly Ala Lys Ile Asp Ala Val Phe Asp Ala Leu
            35                  40                  45
```

```
caa gat aaa gga cct gaa att atc gtt gcc cgg cac gaa caa aac gca      192
Gln Asp Lys Gly Pro Glu Ile Ile Val Ala Arg His Glu Gln Asn Ala
    50                  55                  60 gca ttc atg gcc caa gca gtc ggc cgt tta act gga aaa ccg gga gtc      240
Ala Phe Met Ala Gln Ala Val Gly Arg Leu Thr Gly Lys Pro Gly Val
65                  70                  75                  80 gtg tta gtc aca tca gga ccg ggt gcc tct aac ttg gca aca ggc ctg      288
Val Leu Val Thr Ser Gly Pro Gly Ala Ser Asn Leu Ala Thr Gly Leu
                85                  90                  95 ctg aca gcg aac act gaa gga gac cct gtc gtt gcg ctt gct gga aac      336
Leu Thr Ala Asn Thr Glu Gly Asp Pro Val Val Ala Leu Ala Gly Asn
            100                 105                 110 gtg atc cgt gca gat cgt tta aaa cgg aca cat caa tct ttg gat aat      384
Val Ile Arg Ala Asp Arg Leu Lys Arg Thr His Gln Ser Leu Asp Asn
        115                 120                 125 gcg gcg cta ttc cag ccg att aca aaa tac agt gta gaa gtt caa gat      432
Ala Ala Leu Phe Gln Pro Ile Thr Lys Tyr Ser Val Glu Val Gln Asp
    130                 135                 140 gta aaa aat ata ccg gaa gct gtt aca aat gca ttt agg ata gcg tca      480
Val Lys Asn Ile Pro Glu Ala Val Thr Asn Ala Phe Arg Ile Ala Ser
145                 150                 155                 160 gca ggg cag gct ggg gcc gct ttt gtg agc ttt ccg caa gat gtt gtg      528
Ala Gly Gln Ala Gly Ala Ala Phe Val Ser Phe Pro Gln Asp Val Val
                165                 170                 175 aat gaa gtc aca aat acg aaa aac gtg cgt gct gtt gca gcg cca aaa      576
Asn Glu Val Thr Asn Thr Lys Asn Val Arg Ala Val Ala Ala Pro Lys
            180                 185                 190 ctc ggt cct gca gca gat gat gca atc agt gcg gcc ata gca aaa atc      624
Leu Gly Pro Ala Ala Asp Asp Ala Ile Ser Ala Ala Ile Ala Lys Ile
        195                 200                 205 caa aca gca aaa ctt cct gtc gtt ttg gtc ggc atg aaa ggc gga aga      672
Gln Thr Ala Lys Leu Pro Val Val Leu Val Gly Met Lys Gly Gly Arg
    210                 215                 220 ccg gaa gca att aaa gcg gtt cgc aag ctt ttg aaa aag gtt cag ctt      720
Pro Glu Ala Ile Lys Ala Val Arg Lys Leu Leu Lys Lys Val Gln Leu
225                 230                 235                 240 cca ttt gtt gaa aca tat caa gct gcc ggt acc ctt tct aga gat tta      768
Pro Phe Val Glu Thr Tyr Gln Ala Ala Gly Thr Leu Ser Arg Asp Leu
                245                 250                 255 gag gat caa tat ttt ggc cgt atc ggt ttg ttc cgc aac cag cct ggc      816
Glu Asp Gln Tyr Phe Gly Arg Ile Gly Leu Phe Arg Asn Gln Pro Gly
            260                 265                 270 gat tta ctg cta gag cag gca gat gtt gtt ctg acg atc ggc tat gac      864
Asp Leu Leu Leu Glu Gln Ala Asp Val Val Leu Thr Ile Gly Tyr Asp
        275                 280                 285 ccg att gaa tat gat ccg aaa ttc tgg aat atc aat gga gac cgg aca      912
Pro Ile Glu Tyr Asp Pro Lys Phe Trp Asn Ile Asn Gly Asp Arg Thr
    290                 295                 300 att atc cat tta gac gag att atc gct gac att gat cat gct tac cag      960
Ile Ile His Leu Asp Glu Ile Ile Ala Asp Ile Asp His Ala Tyr Gln
305                 310                 315                 320 cct gat ctt gaa ttg atc ggt gac att ccg tcc acg atc aat cat atc     1008
Pro Asp Leu Glu Leu Ile Gly Asp Ile Pro Ser Thr Ile Asn His Ile
                325                 330                 335 gaa cac gat gct gtg aaa gtg gaa ttt gca gag cgt gag cag aaa atc     1056
Glu His Asp Ala Val Lys Val Glu Phe Ala Glu Arg Glu Gln Lys Ile
            340                 345                 350 ctt tct gat tta aaa caa tat atg cat gaa ggt gag cag gtg cct gca     1104
Leu Ser Asp Leu Lys Gln Tyr Met His Glu Gly Glu Gln Val Pro Ala
```

```
                355                 360                 365
gat tgg aaa tca gac aga gcg cac cct ctt gaa atc gtt aaa gag ttg    1152
Asp Trp Lys Ser Asp Arg Ala His Pro Leu Glu Ile Val Lys Glu Leu
370                 375                 380 cgt aat gca gtc gat gat cat gtt aca gta act tgc gat atc ggt tcg    1200
Arg Asn Ala Val Asp Asp His Val Thr Val Thr Cys Asp Ile Gly Ser
385                 390                 395                 400 cac gcc att tgg atg tca cgt tat ttc cgc agc tac gag ccg tta aca    1248
His Ala Ile Trp Met Ser Arg Tyr Phe Arg Ser Tyr Glu Pro Leu Thr
                405                 410                 415 tta atg atc agt aac ggt atg caa aca ctc ggc gtt gcg ctt cct tgg    1296
Leu Met Ile Ser Asn Gly Met Gln Thr Leu Gly Val Ala Leu Pro Trp
            420                 425                 430 gca atc ggc gct tca ttg gtg aaa ccg gga gaa aaa gtg gtt tct gtc    1344
Ala Ile Gly Ala Ser Leu Val Lys Pro Gly Glu Lys Val Val Ser Val
        435                 440                 445 tct ggt gac ggc ggt ttc tta ttc tca gca atg gaa tta gag aca gca    1392
Ser Gly Asp Gly Gly Phe Leu Phe Ser Ala Met Glu Leu Glu Thr Ala
450                 455                 460 gtt cga cta aaa gca cca att gta cac att gta tgg aac gac agc aca    1440
Val Arg Leu Lys Ala Pro Ile Val His Ile Val Trp Asn Asp Ser Thr
465                 470                 475                 480 tat gac atg gtt gca ttc cag caa ttg aaa aaa tat aac cgt aca tct    1488
Tyr Asp Met Val Ala Phe Gln Gln Leu Lys Lys Tyr Asn Arg Thr Ser
                485                 490                 495 gcg gtc gat ttc gga aat atc gat atc gtg aaa tat gcg gaa agc ttc    1536
Ala Val Asp Phe Gly Asn Ile Asp Ile Val Lys Tyr Ala Glu Ser Phe
            500                 505                 510 gga gca act ggc ttg cgc gta gaa tca cca gac cag ctg gca gat gtt    1584
Gly Ala Thr Gly Leu Arg Val Glu Ser Pro Asp Gln Leu Ala Asp Val
        515                 520                 525 ctg cgt caa ggc atg aac gct gaa ggt cct gtc atc atc gat gtc ccg    1632
Leu Arg Gln Gly Met Asn Ala Glu Gly Pro Val Ile Ile Asp Val Pro
530                 535                 540 gtt gac tac agt gat aac att aat tta gca agt gac aag ctt ccg aaa    1680
Val Asp Tyr Ser Asp Asn Ile Asn Leu Ala Ser Asp Lys Leu Pro Lys
545                 550                 555                 560 gaa ttc ggg gaa ctc atg aaa acg aaa gct ctc tag                    1716
Glu Phe Gly Glu Leu Met Lys Thr Lys Ala Leu
                565                 570

<210> SEQ ID NO 82
<211> LENGTH: 571
<212> TYPE: PRT
<213> ORGANISM: Bacillus subtilis

<400> SEQUENCE: 82

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95
```

```
Leu Thr Ala Asn Thr Glu Gly Asp Pro Val Ala Leu Ala Gly Asn
            100                 105                 110

Val Ile Arg Ala Asp Arg Leu Lys Arg Thr His Gln Ser Leu Asp Asn
    115                 120                 125

Ala Ala Leu Phe Gln Pro Ile Thr Lys Tyr Ser Val Glu Val Gln Asp
130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510
```

```
Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

<210> SEQ ID NO 83
<211> LENGTH: 48
<212> TYPE: DNA
<213> ORGANISM: Artificial Sequence
<220> FEATURE:
<223> OTHER INFORMATION: Oligonucleotide Primer Sequence

<400> SEQUENCE: 83
ctagagctcg aaggagatat accatgaaac cagtaacgtt atacgatg      48

<210> SEQ ID NO 84
<211> LENGTH: 29
<212> TYPE: DNA
<213> ORGANISM: Artificial Sequence
<220> FEATURE:
<223> OTHER INFORMATION: Oligonucleotide Primer Sequence

<400> SEQUENCE: 84
ctagagctct cactgcccgc tttccagtc      29

<210> SEQ ID NO 85
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 85
cgagcggtac catgcatatt acatacgatc tgccgg      36

<210> SEQ ID NO 86
<211> LENGTH: 36
<212> TYPE: DNA
<213> ORGANISM: Artificial Sequence
<220> FEATURE:
<223> OTHER INFORMATION: Oligonucleotide Primer Sequence

<400> SEQUENCE: 86
acgcagtcga cttaagcgtc aacgaaaccg gtgatt      36

<210> SEQ ID NO 87
<211> LENGTH: 37
<212> TYPE: DNA
<213> ORGANISM: Artificial Sequence
<220> FEATURE:
<223> OTHER INFORMATION: Oligonucleotide Primer Sequence

<400> SEQUENCE: 87
tcaggtacca tgcgagtgtt gaagttcggc ggtacat      37

<210> SEQ ID NO 88
<211> LENGTH: 39
<212> TYPE: DNA
<213> ORGANISM: Artificial Sequence
<220> FEATURE:
<223> OTHER INFORMATION: Oligonucleotide Primer Sequence

```
<400> SEQUENCE: 88
tcaaagcttt tactgatgat tcatcatcaa tttacgcaa                                              39
```

BIOFUEL PRODUCTION BY RECOMBINANT MICROORGANISMS

CROSS REFERENCE TO RELATED APPLICATIONS

This application is a divisional of U.S. patent application Ser. No. 12/028,727, filed Feb. 8, 2008 (now U.S. Pat. No. 8,975,049), which claims priority to U.S. Provisional Application Ser. No. 60/900,477 filed Feb. 9, 2007, Ser. No. 60/900,546, filed Feb. 9, 2007, Ser. No. 60/921,927, filed Apr. 4, 2007, and Ser. No. 60/956,634, filed Aug. 17, 2007, the disclosures of which are incorporated herein by reference.

TECHNICAL FIELD

Metabolically-modified microorganisms and methods of producing such organisms are provided. Also provided are methods of producing biofuels by contacting a suitable substrate with a metabolically-modified microorganism and enzymatic preparations there from.

BACKGROUND

Demand for biofuels as a substitute for petroleum is expected to increase because of economic and environmental concerns. The common bio-fuel, ethanol, is not ideal because it has a lower energy density than gasoline and must be mixed with gasoline at a limited concentration range in order to serve as a transportation fuel. Ethanol is also hygroscopic and corrosive, which poses a problem for storage and distribution systems.

SUMMARY

The disclosure provides a recombinant microorganism that produces an alcohol selected from the group consisting of: (a) 1-propanol, (b) isobutanol and having a yield of about 0.12 to about 0.41 grams of isobutanol per gram of glucose; (c) 1-butanol, (d) 2-methyl 1-butanol, (e) 3-methyl 1-butanol, and (f) 2-phenylethanol, wherein the alcohol is produced from a metabolite comprising 2-keto acid. In one embodiment, the organism produced less than about 240 mg/L of ethanol at about 112 hrs of culture. In another embodiment the alcohol production profile of the microorganism is substantially identical to the alcohol production profile of the microorganism designated SA237 or CRS-BuOH23, when cultured under similar conditions. In yet another embodiment, the yield of isobutanol is from about 0.33 to about 0.36 grams of isobutanol per gram of glucose or is about 0.36 to 0.40 grams of isobutanol per gram of glucose at about 16 to about 64 hours of culture. In yet a further embodiment, the yield of ethanol per gram of glucose is less than about 0.0037 g/g. In one embodiment, the microorganism comprises reduced ethanol production capability compared to a parental microorganism. In yet another embodiment, the microorganism comprises a reduction or inhibition in the conversion of acetyl-coA to ethanol. In yet a further embodiment, the recombinant microorganism comprises a reduction of an ethanol dehydrogenase thereby providing a reduced ethanol production capability. In one embodiment, the microorganism comprises expression or elevated expression of an enzyme that converts pyruvate to alpha-keto-isovalerate. In a further embodiment, the enzyme is 2-keto-acid decarboxylase (e.g., Pdc, Pdcl, Pdc5, Pdc6, Aro10, Thi3, Kivd, and KdcA, a homolog or variant of any of the foregoing, and a polypeptide having at least 60% identity to any one of the foregoing and having 2-keto-acid decarboxylase activity). In another embodiment, the 2-keto-acid decarboxylase is encoded by a polynucleotide having at least 60% identity to a nucleic acid selected from the group consisting of pdc, pdc1, pdc5, pdc6, aro10, thi3, kivd, kdcA, a homolog or variant of any of the foregoing, or a fragment thereof and wherein the polynucleotide encodes a polypeptide having 2-keto acid decarboxylase activity. In a specific embodiment, the 2-keto-acid decarboxylase is encoded by a polynucleotide derived from a kivd gene, or homolog thereof. In one embodiment, the microorganism comprises elevated expression or activity of a 2-keto-acid decarboxylase and an alcohol dehydrogenase, as compared to a parental microorganism. In one embodiment, the alcohol dehydrogenase is selected from the group consisting of Adh1, Adh2, Adh3, Adh4, Adh5, Adh6, Sfa1, a homolog or variant of any of the foregoing, and a polypeptide having at least 60% identity to any one of the foregoing and having alcohol dehydrogenase activity. In yet another embodiment, the alcohol dehydrogenase is encoded by a polynucleotide having at least 60% identity to a nucleic acid selected from the group consisting of an adh1, adh2, adh3, adh4, adh5, adh6, sfa1 gene, and a homolog of any of the foregoing and wherein the polynucleotide encodes a protein having 2-alcohol dehydrogenase activity. In one embodiment, the recombinant microorganism comprises one or more deletions or knockouts in a gene encoding an enzyme that catalyzes the conversion of acetyl-coA to ethanol, catalyzes the conversion of pyruvate to lactate, catalyzes the conversion of fumarate to succinate, catalyzes the conversion of acetyl-coA and phosphate to coA and acetyl phosphate, catalyzes the conversion of acetyl-coA and formate to coA and pyruvate, condensation of the acetyl group of acetyl-CoA with 3-methyl-2-oxobutanoate (2-oxoisovalerate), isomerization between 2-isopropylmalate and 3-isopropylmalate, catalyzes the conversion of alpha-keto acid to branched chain amino acids, synthesis of Phe Tyr Asp or Leu, catalyzes the conversion of pyruvate to acetly-coA, catalyzes the formation of branched chain amino acids, catalyzes the formation of alpha-ketobutyrate from threonine, catalyzes the first step in methionine biosynthesis, and catalyzes the catabolism of threonine. For example, the microorganism can comprise one or more gene deletions selected from the group consisting of adhE, ldhA, frdBC, fnr, pta, pflB, leuA, leuB, leuC, leuD, ilvE, tyrB, poxB, ilvB, ilvI, ilvA, metA, tdh, homologs of any of the foregoing and naturally occurring variants of any of the foregoing. In a specific embodiment, a genotype of the microorganism is selected from the group consisting of: (a) a deletion or knockout selected from the group consisting of ΔadhE, ΔldhA, Δpta, ΔleuA, ΔleuB, ΔleuC, ΔleuD, ΔpoxB, ΔilvB, ΔilvI, ΔmetA, Δtdh and any combination thereof and comprising an expression or increased expression of kivd, ThrABC and adh2, wherein the microorganism produces 1-propanol; (b) a deletion or knockout selected from the group consisting of ΔadhE, ΔldhA, ΔfrdB, ΔfrdC, Δfnr, Δpta, ΔpflB, ΔleuA, ΔilvE, ΔpoxB, ΔilvA, and any combination thereof and comprising an expression or increased expression of kivd, ThrABC and adh2 wherein the microorganism produces isobutanol; (c) a deletion or knockout selected from the group consisting of ΔadhE, ΔldhA, Δpta, ΔpoxB, ΔilvB, ΔilvI, ΔmetA, Δtdh, and any combination thereof and comprising an expression or increased expression of kivd, ThrABC and adh2 wherein the microorganism produces 1-butanol; (d) a deletion or knockout selected from the group consisting of ΔilvB, ΔilvI, ΔmetA, Δtdh, and any combination thereof and comprising an expression or increased expression of kivd, ThrABC and adh2 wherein the microorganism produces 2-methyl 1-butanol; (e) a deletion or knockout selected from the group consisting of ΔadhE, ΔldhA, ΔfrdB, ΔfrdC, Δfnr, Δpta, ΔpflB, ΔilvE, ΔtyrB, and any combination thereof and comprising an expression or increased expression of kivd, ThrABC and adh2 wherein the microorganism produces 3-methyl 1-butanol; and (f) a deletion or knockout selected from the group consisting of ΔadhE, ΔldhA, ΔfrdB, ΔfrdC, Δfnr, Δpta, ΔpflB, ΔleuA, ΔilvE, ΔpoxB, ΔilvA, and any combination thereof and comprising an expression or increased expression of kivd, ThrABC and adh2 wherein the microorganism produces 2-pehylethanol. In a further embodiment, the ThrABC comprises a feedback resistant ThrA*. In one embodiment, the recombinant microorganism comprises a phenotype of the micoorganism designated SA237 or CRS-BuOH23.

Provided herein are metabolically-modified microorganisms that include recombinant biochemical pathways useful for producing biofuels such as isobutanol, 2-methyl-1-butanol, 3-methyl-1-butanol, 2-phenylethanol, 1-propanol, or 1-butanol via conversion of a suitable substrate by a metabolically engineered microorganism. Also provided are methods of producing biofuels using microorganisms described herein.

In one embodiment, a recombinant microorganism that produces an alcohol is provided. The alcohol can be 1-propanol, isobutanol, 1-butanol, 2-methyl-1-butanol, 3-methyl-1-butanol or 2-phenylethanol. In general, the alcohol may be produced fermentatively or non-fermentatively (i.e., with or without the presence of oxygen) from a metabolite comprising 2-keto acid. In some aspects, the 2-keto acid includes 2-ketobutyrate, 2-ketoisovalerate, 2-ketovalerate, 2-keto-3-methylvalerate, 2-keto-4-methyl-pentanoate, or phenylpyruvate. In other aspects, the recombinant microorganism includes elevated expression or activity of a 2-keto-acid decarboxylase and an alcohol dehydrogenase, as compared to a parental microorganism. The 2-keto-acid decarboxylase may be Pdc6 from *Saccharomyces cerevisiae*, Aro10 from *Saccharomyces cerevisiae*, Thi3 from *Saccharomyces cerevisiae*, Kivd from *Lactococcus lactis*, or Pdc from *Clostridium acetobutylicum*, or homologs thereof. The 2-keto-acid decarboxylase can be encoded by a polynucleotide derived from a gene selected from PDC6 from *S. cerevisiae*, ARO10 from *S. cerevisiae*, THIS from *S. cerevisiae*, kivd from *L. lactis*, or pdc from *C. acetobutylicum*, or homologs thereof. In some aspects, the alcohol dehydrogenase may be Adh2 from *S. cerevisiae*, or homologs thereof, encoded by a polynucleotide derived from the ADH2 gene from *S. cerevisiae*. In another embodiment, a recombinant microorganism that produces isobutanol is provided. The microorganism includes elevated expression or activity of acetohydroxy acid synthase, acetohydroxy acid isomeroreductase, dihydroxy-acid dehydratase, 2-keto-acid decarboxylase, and alcohol dehydrogenase, as compared to a parental microorganism. In some aspects, the microorganism can include elevated expression of acetolactate synthase, acetohydroxy acid isomeroreductase, dihydroxy-acid dehydratase, 2-keto-acid decarboxylase, and alcohol dehydrogenase. In some aspects, the recombinant microorganism further includes an elevated level of pyruvate as compared to a parental microorganism. Accordingly, the recombinant microorganism may further include the deletion or inhibition of expression of an adhE, ldh, frd, fnr, pflB, ackA, or pta gene, or any combination thereof. In particular, the recombinant microorganism can include a deletion of adh, ldh, frd alone or in combination with fnr, fnr and pta, or pta and pflB. In some aspects, the recombinant microorganism may further include deletion of a portion of the recombinant microorganism genome, such as nucleotides from about 1,397,551 to about 1,439,877 of the *E. coli* genome. In one aspect, the acetohydroxy acid synthase may be encoded by a polynucleotide derived from the ilvIH operon, ilvBN operon, ilvGM in *E. coli*, or the alsS gene from *Bacillus subtilis*, or homologs thereof. The ilvI gene of the ilvIH operon encodes an acetohydroxyacid synthase large subunit polypeptide and the ilvH gene of the ilvIH operon encodes an acetohydroxyacid synthase small subunit polypeptide. In another aspect, the acetohydroxy acid isomeroreductase may be encoded by a polynucleotide derived from an ilvC gene in *E. coli*, or homologs thereof. In another aspect, the dihydroxy-acid dehydratase may be encoded by a polynucleotide derived from an ilvD gene, or homologs thereof. In yet another aspect, the 2-keto-acid decarboxylase may be encoded by a polynucleotide derived from a kivd gene from *Lactococcus lactis* or homologs thereof, or an ARO10 gene from *S. cerevisiae*, or homologs thereof. In a further aspect, the alcohol dehydrogenase may be encoded by a polynucleotide derived from an ADH2 gene from *S. cerevisiae*, or homologs thereof.

In general the ilvIH operon of *Escherichia coli* encodes acetohydroxy acid synthase, the first enzyme in the isoleucine, valine and leucine biosynthetic pathway. The acetohydroxy acid synthase III isozyme, which catalyzes the first common step in the biosynthesis of isoleucine, leucine, and valine in *Escherichia coli* K-12, is composed of two subunits, the ilvI (acetohydroxyacid synthase III large subunit) and ilvH (acetohydroxyacid synthase small subunit) gene products. The ilvC gene of *Escherichia coli* encodes acetohydroxy acid isomeroreductase, the second enzyme in the parallel isoleucine-valine biosynthetic pathway. The ilvD gene of *Escherichia coli* encodes dihydroxy-acid dehydratase, the third enzyme in the isoleucine-valine biosynthetic pathway. In some aspects the recombinant microorganism included an elevated expression of acetolactate synthase. The acetolactate synthase can be AlsS from *Bacillus subtilis*.

In one embodiment, a recombinant microorganism that produces 1-butanol is provided. The microorganism includes elevated expression or activity of 2-isopropylmalate synthase, beta-isopropylmalate dehydrogenase, isopropylmalate isomerase, and threonine dehydratase, as compared to a parental microorganism. In another embodiment, the recombinant microorganism further includes increased levels of 2-ketovalerate, as compared to a parental microorganism. In another embodiment, the recombinant microorganism further includes decreased levels of 2-ketoisovalerate, 2-keto-3-methyl-valerate, or 2-keto-4-methyl-pentanoate, or any combination thereof, as compared to a parental microorganism. Accordingly, the microorganism may further include the deletion or inhibition of expression of an ilvD gene, as compared to a parental microorganism. In one aspect, the 2-isopropylmalate synthase may be encoded by a polynucleotide derived from a leuA gene, or homologs thereof. In another aspect, the beta-isopropylmalate dehydrogenase may be encoded by a polynucleotide derived from a leuB gene, or homologs thereof. In yet another aspect, the isopropylmalate isomerase may be encoded by a polynucleotide derived from a leuCD operon, or homologs thereof. In general the leuC gene of the leuCD operon encodes an isopropylmalate isomerase large subunit polypeptide and the leuD gene of the leuCD operon encodes an isopropylmalate isomerase small subunit polypeptide. In another aspect, the threonine dehydratase may be encoded by a polynucleotide derived from an ilvA gene, or homologs thereof. In yet another aspect, the threonine dehydratase may be encoded by a polynucleotide derived from a tdcB gene, or homologs thereof. In yet another embodiment, the recombinant microorganism may further include elevated expression or activity of phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, or threonine dehydratase, or any combination thereof, as compared to a parental microorganism. In some aspects, the phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, and threonine dehydratase, are encoded by a polynucleotide derived from the ppc, pyc, aspC, thrA, asd, thrB, thrC, sdaAB, and tdcB genes, respectively, or homologs thereof.

In one embodiment, a recombinant microorganism that produces 1-propanol is provided. The microorganism includes elevated expression or activity of alpha-isopropylmalate synthase, LeuB of *Leptospira interrogans*, isopropylmalate isomerase, and threonine dehydratase, as compared to a parental microorganism. In one aspect, the alpha-isopropylmalate synthase may be encoded by a polynucleotide derived from a cimA gene, or homologs thereof. The cimA gene may be a *Leptospira interrogans* cimA gene or *Methanocaldococcus jannaschii* cimA gene. In another aspect, the beta-isopropylmalate dehydrogenase may be encoded by a polynucleotide derived from a leuB gene, or homologs thereof. In another aspect, the isopropylmalate isomerase may be encoded by a polynucleotide derived from a leuCD operon, or homologs thereof. In yet another embodiment, the recombinant microorganism may further include elevated expression or activity of phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, or threonine dehydratase, or any combination thereof, as compared to a parental microorganism. In some aspects, the phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, and threonine dehydratase, are encoded by a polynucleotide derived from the ppc, pyc, aspC, thrA, asd, thrB, thrC, sdaAB, and tdcB genes, respectively, or homologs thereof.

In another embodiment, a recombinant microorganism that produces 2-methyl 1-butanol is provided. The microorganism includes elevated expression or activity of threonine dehydratase, acetohydroxy acid synthase, acetohydroxy acid isomeroreductase, dihydroxy-acid dehydratase, 2-keto-acid decarboxylase, and alcohol dehydrogenase, as compared to a parental microorganism, wherein the recombinant microorganism produces 2-methyl 1-butanol. In some aspects, the threonine dehydratase may be encoded by a polynucleotide derived from an ilvA gene, or homologs thereof. In another aspect, the threonine dehydratase may be encoded by a polynucleotide derived from a tdcB gene, or homologs thereof. In another embodiment, the recombinant microorganism further includes increased levels of 2-keto-3-methyl-valerate, as compared to a parental microorganism. In yet another aspect, the 2-keto-acid decarboxylase may be encoded by a polynucleotide derived from a kivd gene, or homologs thereof, or a PDC6 gene, or homologs thereof, or THI3 gene, or homologs thereof.

In another embodiment, a recombinant microorganism that produces 3-methyl 1-butanol is provided. The microorganism includes elevated expression or activity of acetohydroxy acid synthase or acetolactate synthase, acetohydroxy acid isomeroreductase, dihydroxy-acid dehydratase, 2-isopropylmalate synthase, isopropylmalate isomerase, beta-isopropylmalate dehydrogenase, 2-keto-acid decarboxylase, and alcohol dehydrogenase, as compared to a parental microorganism. In some aspects, the acetohydroxy acid synthase may be encoded by a polynucleotide derived from an ilvIH operon, or homologs thereof. In another aspect, the acetolactate synthase may be encoded by a polynucleotide derived from an alsS gene, or homologs thereof. In another aspect, the acetolactate synthase may be encoded by a polynucleotide derived from an ilvMG operon, or homologs thereof. In another embodiment, the recombinant microorganism further includes increased levels of 2-ketoisocaproate, as compared to a parental microorganism. In yet another aspect, the acetolactate synthase may be encoded by a polynucleotide derived from an ilvNB operon, or homologs thereof.

In another embodiment, a recombinant microorganism that produces phenylethanol is provided. The microorganism includes elevated expression or activity of chorismate mutase P/prephenate dehydratase, chorismate mutase T/prephenate dehydrogenase, 2-keto-acid decarboxylase and alcohol dehydrogenase, as compared to a parental microorganism. In one aspect, the chorismate mutase P/prephenate dehydratase may be encoded by a polynucleotide derived from a pheA gene, or homologs thereof. In another aspect, the chorismate mutase T/prephenate dehydrogenase may be encoded by a polynucleotide derived from a tyrA gene, or homologs thereof. In yet another embodiment, the recombinant microorganism further includes increased levels of phenylpyruvate, as compared to a parental microorganism.

In one embodiment, a method of producing a recombinant microorganism that converts a suitable substrate or metabolic intermediate to 1-butanol is provided. The method includes transforming a microorganism with one or more recombinant polynucleotides encoding polypeptides comprising 2-isopropylmalate synthase activity, beta-isopropylmalate dehydrogenase activity, isopropylmalate isomerase activity, and threonine dehydratase activity.

In another embodiment, a method of producing a recombinant microorganism that converts a suitable substrate or metabolic intermediate to isobutanol, is provided. The method includes transforming a microorganism with one or more recombinant polynucleotides encoding polypeptides comprising acetohydroxy acid synthase activity, acetohydroxy acid isomeroreductase activity, dihydroxy-acid dehydratase activity, 2-keto-acid decarboxylase activity, and alcohol dehydrogenase activity.

In another embodiment, a method of producing a recombinant microorganism that converts a suitable substrate or metabolic intermediate to 1-propanol, is provided. The method includes transforming a microorganism with one or more recombinant polynucleotides encoding polypeptides comprising alpha-isopropylmalate synthase activity, beta-isopropylmalate dehydrogenase activity, isopropylmalate isomerase activity, and threonine dehydratase activity.

In one embodiment, a method of producing a recombinant microorganism that converts a suitable substrate or metabolic intermediate to 2-methyl 1-butanol, is provided. The method includes transforming a microorganism with one or more recombinant polynucleotides encoding polypeptides comprising threonine dehydratase activity, acetohydroxy acid synthase activity, acetohydroxy acid isomeroreductase activity, dihydroxy-acid dehydratase activity, 2-keto-acid decarboxylase activity, and alcohol dehydrogenase activity.

In another embodiment, a method of producing a recombinant microorganism that converts a suitable substrate or metabolic intermediate to 3-methyl 1-butanol, is provided. The method includes transforming a microorganism with one or more recombinant polynucleotides encoding polypeptides comprising acetohydroxy acid synthase activity or acetolactate synthase activity, acetohydroxy acid isomeroreductase activity, dihydroxy-acid dehydratase activity, 2-isopropylmalate synthase activity, isopropylmalate isomerase activity, beta-isopropylmalate dehydrogenase activity, 2-keto-acid decarboxylase activity, and alcohol dehydrogenase activity.

In another embodiment, a method of producing a recombinant microorganism that converts a suitable substrate or metabolic intermediate to phenylethanol, is provided. The method includes transforming a microorganism with one or more recombinant polynucleotides encoding polypeptides comprising chorismate mutase P/prephenate dehydratase activity, chorismate mutase T/prephenate dehydrogenase activity, 2-keto-acid decarboxylase activity, and alcohol dehydrogenase activity.

In another embodiment, a method of producing an alcohol, is provided. The method includes providing a recombinant microorganism provided herein; culturing the microorganism of in the presence of a suitable substrate or metabolic intermediate and under conditions suitable for the conversion of the substrate to an alcohol; and detecting the production of the alcohol. In various aspects, the alcohol is selected from 1-propanol, isobutanol, 1-butanol, 2-methyl 1-butanol, 3-methyl 1-butanol, and 2-phenylethanol. In another aspect, the substrate or metabolic intermediate includes a 2-keto acid, such as 2-ketobutyrate, 2-ketoisovalerate, 2-ketovalerate, 2-keto 3-methylvalerate, 2-keto 4-methyl-pentanoate, or phenylpyruvate.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 2A-C depicts modified amino acid biosynthesis pathways for improved isobutanol and 1-butanol production. Panel A shows isobutanol production with or without the engineered ilvIHCD pathway. Left panel: isobutanol production; Right panel: isobutanol yield per g of glucose. Theoretical maximum yield of isobutanol is 0.41 g/g. Panel B shows 1-butanol production with or without the engineered ilvA-leuABCD pathway from glucose. Left panel: 1-butanol production; Right panel: 1-propanol production in the same strain. Panel C shows 1-butanol production with L-threonine addition. Left panel: 1-butanol production; Right panel: 1-propanol production from the same strain.

FIG. 15 depicts a nucleic acid sequence (SEQ ID NO:27) derived from a kivd gene encoding a polypeptide having 2-keto-acid decarboxylase activity.

FIG. 16 depicts a nucleic acid sequence (SEQ ID NO:29) derived from a PDC6 gene encoding a polypeptide having 2-keto-acid decarboxylase activity.

FIG. 17 depicts a nucleic acid sequence (SEQ ID NO:31) derived from an ARO10 gene encoding a polypeptide having 2-keto-acid decarboxylase activity.

FIG. 18 depicts a nucleic acid sequence (SEQ ID NO:33) derived from a THI3 gene encoding a polypeptide having 2-keto-acid decarboxylase activity.

FIG. 19 depicts a nucleic acid sequence (SEQ ID NO:35) derived from a pdc gene encoding a polypeptide having 2-keto-acid decarboxylase activity.

FIG. 20 depicts a nucleic acid sequence (SEQ ID NO:37) derived from an ADH2 gene encoding a polypeptide having alcohol dehydrogenase activity.

FIG. 21 depicts a nucleic acid sequence (SEQ ID NO:39) derived from an ilvI gene encoding a polypeptide having acetolactate synthase large subunit activity.

FIG. 22 depicts a nucleic acid sequence (SEQ ID NO:41) derived from an ilvH gene encoding a polypeptide having acetolactate synthase small subunit activity.

FIG. 23 depicts a nucleic acid sequence (SEQ ID NO:43) derived from an ilvC gene encoding a polypeptide having acetohydroxy acid isomeroreductase activity.

FIG. 24 depicts a nucleic acid sequence (SEQ ID NO:45) derived from an ilvD gene encoding a polypeptide having dihydroxy-acid dehydratase activity.

FIG. 25 depicts a nucleic acid sequence (SEQ ID NO:47) derived from an ilvA gene encoding a polypeptide having threonine dehydratase activity.

FIG. 26 depicts a nucleic acid sequence (SEQ ID NO:49) derived from a leuA gene encoding a polypeptide having 2-isopropylmalate synthase activity.

FIG. 27 depicts a nucleic acid sequence (SEQ ID NO:51) derived from a leuB gene encoding a polypeptide having beta-isopropylmalate dehydrogenase activity.

FIG. 28 depicts a nucleic acid sequence (SEQ ID NO:53) derived from a leuC gene encoding a polypeptide having isopropylmalate isomerase large subunit activity.

FIG. 29 depicts a nucleic acid sequence (SEQ ID NO:55) derived from a leuD gene encoding a polypeptide having isopropylmalate isomerase small subunit activity.

FIG. 30 depicts a nucleic acid sequence (SEQ ID NO:57) derived from a cimA gene encoding a polypeptide having alpha-isopropylmalate synthase activity.

FIG. 31 depicts a nucleic acid sequence (SEQ ID NO:59) derived from an ilvM gene encoding a polypeptide having acetolactate synthase large subunit activity.

FIG. 32 depicts a nucleic acid sequence (SEQ ID NO:61) derived from an ilvG gene encoding a polypeptide having acetolactate synthase small subunit activity.

FIG. 33 depicts a nucleic acid sequence (SEQ ID NO:63) derived from an ilvN gene encoding a polypeptide having acetolactate synthase large subunit activity.

FIG. 34 depicts a nucleic acid sequence (SEQ ID NO:65) derived from an ilvB gene encoding a polypeptide having acetolactate synthase small subunit activity.

FIG. 35 depicts a nucleic acid sequence (SEQ ID NO:67) derived from an adhE2 gene encoding a polypeptide having alcohol dehydrogenase activity.

FIG. 36 depicts a nucleic acid sequence (SEQ ID NO:69) derived from a Li-cimA gene encoding a polypeptide having alpha-isopropylmalate synthase activity.

FIG. 37 depicts a nucleic acid sequence (SEQ ID NO:71) derived from a Li-leuC gene encoding a polypeptide having isopropylmalate isomerase large subunit activity.

FIG. 38 depicts a nucleic acid sequence (SEQ ID NO:73) derived from a Li-leuD gene encoding a polypeptide having isopropylmalate isomerase small subunit activity.

FIG. 39 depicts a nucleic acid sequence (SEQ ID NO:75) derived from a Li-leuB gene encoding a polypeptide having beta-isopropylmalate dehydrogenase activity.

FIG. 40 depicts a nucleic acid sequence (SEQ ID NO:77) derived from a pheA gene encoding a polypeptide having chorismate mutase P/prephenate dehydratase activity.

FIG. 41 depicts a nucleic acid sequence (SEQ ID NO:79) derived from a TyrA gene encoding a polypeptide having chorismate mutase T/prephenate dehydratase activity.

FIG. 42 depicts a nucleic acid sequence (SEQ ID NO:81) derived from an alsS gene encoding a polypeptide having acetolactate synthase activity.

FIG. 44 depicts the comparison of isobutanol production in normal shake flasks and in screw cap flasks.

FIG. 47A-B shows an initial production of 3-methyl-1-butanol. Checkered columns indicate isobutanol; solid columns are for 3-methyl-1-butanol. (A) 3-methyl-1-butanol production in JCL16. Strains carrying either ilvIH (EC) or alsS (BS) with chromosomal or plasmid based expression of leuABCD were assayed for alcohol production. (B) 3-methyl-1-butanol production in JCL260. Strains carrying either ilvIH (IAA92) or alsS (IAA85) were tested for alcohol production.

FIG. 54A-E shows a time course of propanol, butanol and metabolic by-products in CRS-BuOH 23. A. Production of 1-propanol and 1-butanol. Filled diamonds represent butanol and opened diamonds indicate propanol. B. Production of the major by-product acetate. C. Production of the minor by-products pyruvate, lactate and ethanol. Filled diamond represents pyruvate, opened square represents lactate, and cross represents ethanol. D. Consumption of glucose. E. Growth of CRS-BuOH 23 in the 100 hour time period.

Like reference symbols in the various drawings indicate like elements.

DETAILED DESCRIPTION

Figure 1A:
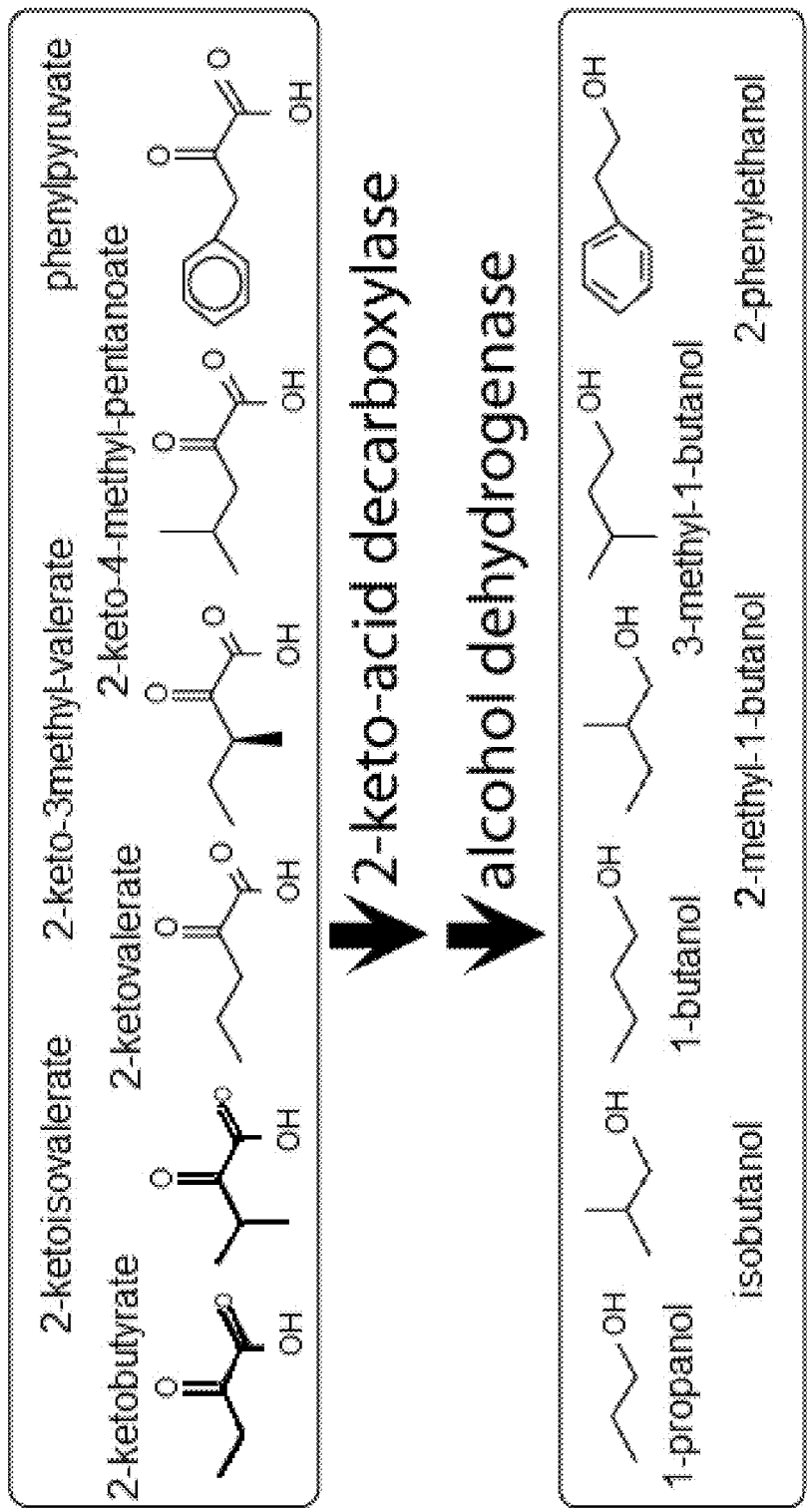
FIG. 1A-C depicts pathways useful in understanding the disclosure. (A) depicts an exemplary synthetic non-fermentative pathway using 2-keto acid metabolism for alcohol production. (B) depicts an exemplary alcohol production pathway in genetically engineered *E. coli*. Gray arrowheads represent the 2-keto acid degradation pathway. Enzymes, LeuABCD, IlvA, and IlvIHCD represent amino acid biosynthesis pathways. Double lines represent a side-reaction of amino acid biosynthesis pathways. (C) depicts a general pathway of a microorganism and identifies enzymes that can be disrupted or knocked out in the organism to improve flux in a desired direction (e.g., increase flux for the synthesis of pyruvate, and decrease flux of pyruvate to other competitive pathways).

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

Butanol is hydrophobic and less volatile than ethanol. 1-Butanol has an energy density closer to gasoline. Butanol at 85 percent strength can be used in cars without any change to the engine (unlike ethanol) and it produces more power than ethanol and almost as much power as gasoline. Butanol is also used as a solvent in chemical and textile processes, organic synthesis and as a chemical intermediate. Butanol also is used as a component of hydraulic and brake fluids and as a base for perfumes.

Isobutanol has the same advantages as 1-butanol over ethanol, with the added advantage that isobutanol has a higher octane number than 1-butanol because of its branched carbon chain. 1-Butanol has been produced as a fermentation product and used as a motor fuel, but isobutanol has never been produced from a renewable source in high yield and has not been considered as a gasoline substitute, even though it has been used as an engine additive.

The native producers of 1-butanol, such as *Clostridium acetobutylicum*, also produce byproducts such as acetone, ethanol, and butyrate as fermentation products. However, these microorganisms are relatively difficult to manipulate. Genetic manipulation tools for these organisms are not as efficient as those for user-friendly hosts such as *E. coli* and physiology and their metabolic regulation are much less understood, prohibiting rapid progress towards high-efficiency production. Furthermore, no native microorganisms have been identified to produce from glucose other higher alcohols such as isobutanol, 2-methyl 1-butanol, 3-methyl 1-butanol, and 2-phenylethanol to industrially relevant quantities, despite the small amounts that have been identified as microbial byproducts.

The production of isobutanol and other fusel alcohols by various yeast species, including *Saccharomyces cerevisiae* is of special interest to the distillers of alcoholic beverage, for whom fusel alcohols constitute often undesirable off-notes. Production of isobutanol in wild-type yeasts has been documented on various growth media, ranging from grape must from winemaking (Romano, et al., Metabolic diversity of *Saccharomyces cerevisiae* strains from spontaneously fermented grape musts, 19:311-315, 2003), in which 12-219 mg/L isobutanol were produced, to supplemented minimal media (Oliviera, et al. (2005) World Journal of Microbiology and Biotechnology 21:1569-1576), producing 16-34 mg/L isobutanol. Work from Dickinson, et al. (J Biol Chem. 272 (43):26871-8, 1997) has identified the enzymatic steps utilized in a pathway converting branch-chain amino acids (e.g., valine or leucine) to isobutanol.

The disclosure provides metabolically engineered microorganisms comprising biochemical pathways for the production of higher alcohols including isobutanol, 1-butanol, 1-propanol, 2-methyl-1-butanol, 3-methyl-1-butanol and 2-phenylethanol from a suitable substrate. A metabolically engineered microorganism of the disclosure comprises one or more recombinant polynucleotides within the genome of the organism or external to the genome within the organism. The microorganism can comprise a reduction, disruption or knockout of a gene found in the wild-type organism and/or introduction of a heterologous polynucleotide.

The disclosure also includes metabolically engineered biosynthetic pathways that utilize an organism's native amino acid pathway. Biofuel production utilizing the organism's native amino acid pathways offers several advantages. Not only does it avoid the difficulty of expressing a large set of foreign genes but it also minimizes the possible accumulation of toxic intermediates. Contrary to the butanol production pathway found in many species of *Clostridium*, the engineered amino acid biosynthetic routes for biofuel production circumvent the need to involve oxygen-sensitive enzymes and CoA-dependent intermediates. The disclosure provides a much more host-friendly biofuel production system utilizing the organism's native metabolites in the amino acid biosynthetic pathway to produce biofuels.

In one aspect, the disclosure provides a recombinant microorganism comprising elevated expression of at least one target enzyme as compared to a parental microorganism or encodes an enzyme not found in the parental organism. In another or further aspect, the microorganism comprises a reduction, disruption or knockout of at least one gene encoding an enzyme that competes with a metabolite necessary for the production of a desired higher alcohol product. The recombinant microorganism produces at least one metabolite involved in a biosynthetic pathway for the production of isobutanol, 1-butanol, 1-propanol, 2-methyl-1-butanol, 3-methyl-1-butanol or 2-phenylethanol. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of isobutanol, 1-butanol, 1-propanol, 2-methyl-1-butanol, 3-methyl-1-butanol or 2-phenylethanol. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure.

As used herein, the term "metabolically engineered" or "metabolic engineering" involves rational pathway design and assembly of biosynthetic genes, genes associated with operons, and control elements of such polynucleotides, for the production of a desired metabolite, such as a 2-keto acid or higher alcohol, in a microorganism. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one aspect, where the polynucleotide is xenogenetic to the host organism, the polynucleotide can be codon optimized.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

For example, L-leucine is synthesized through biosynthetic pathway inherent to L-leucine which diverges from the intermediate (2-ketoisovalerate) of L-valine biosynthesis system. In Escherichia, the L-valine biosynthesis and biosynthesis inherent to L-leucine are carried out by a group of enzymes encoded by ilvGMEDA operon and those encoded by leuABCD operon, respectively.

The leuABCD operon includes leuA, leuB, leuC and leuD genes. Among them, leuA encodes α-isopropylmalate synthase, leuB encodes β-isopropylmalate dehydrogenase, leuC and leuD encodes α-isopropylmalate isomerase. Of these enzymes, α-isopropylmalate synthase catalyzes the synthetic reaction from α-ketoisovalerate to α-isopropylmalate, α-isopropylmalate isomerase catalyzes the isomerization reaction from α-isopropylmalate to β-isopropylmalate and β-isopropylmalate dehydrogenase catalyzes the dehydrogenation reaction from β-isopropylmalate to α-ketoisocaproic acid which is the final intermediate of L-leucine biosynthesis. Escherichia possess four kinds of transaminases, namely, transaminase A (aspartate-glutamate aminotransferase) encoded by aspC gene, transaminase B (BCAA aminotransferase) encoded by ilvE gene which is included in ilvGMEDA operon, transaminase C (alanine-valine aminotransferase) encoded by avtA gene and transaminase D (tyrosine aminotransferase) encoded by tyrB gene. These enzymes participate in various amination reactions. Of these enzymes, transaminase B and transaminase D catalyze the abovementioned amination reaction from α-ketoisocaproic acid to L-leucine. Transaminase C and transaminase D catalyze the final step of L-valine biosynthetic pathway, which includes a common pathway among the L-valine biosynthesis and L-leucine biosynthesis.

Also, the expression of leuABCD operon is repressed by L-leucine. Expression of ilvBN gene encoding acetohydroxy acid synthase I suffers concerted repression by L-valine and L-leucine, expression of ilvGM gene encoding acetohydroxy acid synthase II suffers concerted repression by L-isoleucine, L-valine and L-leucine, and expression of ilvIH gene encoding acetohydroxy acid synthase III suffers repression by L-leucine.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein. A "biomass derived sugar" includes, but is not limited to, molecules such as glucose, sucrose, mannose, xylose, and arabinose. The term biomass derived sugar encompasses suitable carbon substrates ordinarily used by microorganisms, such as 6 carbon sugars, including but not limited to glucose, lactose, sorbose, fructose, idose, galactose and mannose all in either D or L form, or a combination of 6 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

The term "alcohol" includes for example 1-propanol, isobutanol, 1-butanol, 2-methyl 1-butanol, 3-methyl 1-butanol or 2-phenylethanol. The term "1-butanol" or "n-butanol" generally refers to a straight chain isomer with the alcohol functional group at the terminal carbon. The straight chain isomer with the alcohol at an internal carbon is sec-butanol or 2-butanol. The branched isomer with the alcohol at a terminal carbon is isobutanol, and the branched isomer with the alcohol at the internal carbon is tert-butanol.

Recombinant microorganisms provided herein can express a plurality of target enzymes involved in pathways for the production of, for example, 1-propanol, isobutanol, 1-butanol, 2-methyl 1-butanol, 3-methyl 1-butanol or 2-phenylethanol, from using a suitable carbon substrate.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. In an illustrative embodiment, the introduction of genetic material into a parental microorganism results in a new or modified ability to produce an alcohol such as 1-propanol, isobutanol, 1-butanol, 2-methyl 1-butanol, 3-methyl 1-butanol or 2-phenylethanol. The genetic material introduced into the parental microorganism contains gene(s), or parts of genes, coding for one or more of the enzymes involved in a biosynthetic pathway for the production of an alcohol and may also include additional elements for the expression and/or regulation of expression of these genes, e.g. promoter sequences.

An engineered or modified microorganism can also include in the alternative or in addition to the introduction of a genetic material into a host or parental micoorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produced a new or greater quantities of an interacellular metabolite, improve the flux of a metabolite down a desired pathway, and/or reduce the production of undesirable by-products).

The disclosure demonstrates that the expression of one or more heterologous polynucleotide or over-expression of one or more heterologous polynucleotide encoding a polypeptide having ketoacid decarboxylase and a polypeptide having alcohol dehydrogenase in the presence of a polypeptide having α-isopropylmalate synthase, a polypeptide having β-isopropylmalate dehydrogenase, a polypeptide having α-isopropylmalate isomerase, a polypeptide having threonine dehydratease, a polypeptide having homoserine dehydrogenase activity, a polypeptide having homoserine kinase activity, and a polypeptide having threonine synthase activity.

For example, the disclosure demonstrates that with over-expression of the heterologous kivd and adh2 and the E. coli ilvA, leuA, leuB, leuC, leuD (or a Leu operon, e.g., leuABCD), and thrA, thrB, thrC or a Thr operon (e.g., thrABC, the thrA may be a feedback resistive polypeptide such as thrA*) the production of 1-butanol and 1-propanol can be obtained. The production of 1-butanol uses 2-ketovalerate, which involves the intermediate 2-ketobutyrate and the unnatural norvaline biosynthetic pathway. Since Kivd has similar affinity towards both 2-ketoacids and 2-ketobutyrate is a secondary substrate for LeuA, 1-propanol was co-produced with 1-butanol in similar amounts.

Microorganisms provided herein are modified to produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-keto acid) in, or an end product (e.g., 1-propanol, isobutanol, 1-butanol, 2-methyl 1-butanol, 3-methyl 1-butanol or 2-phenylethanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Figure 1B:
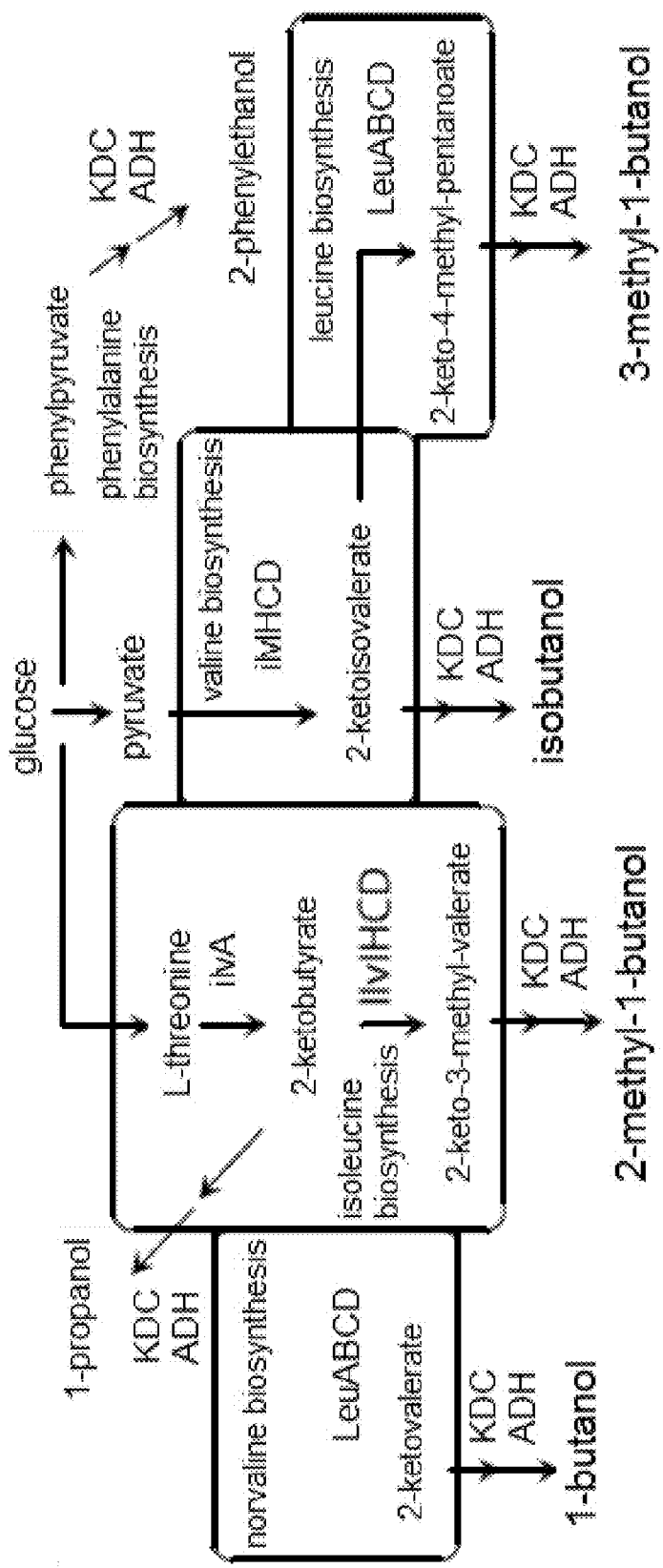
Figure 1C:
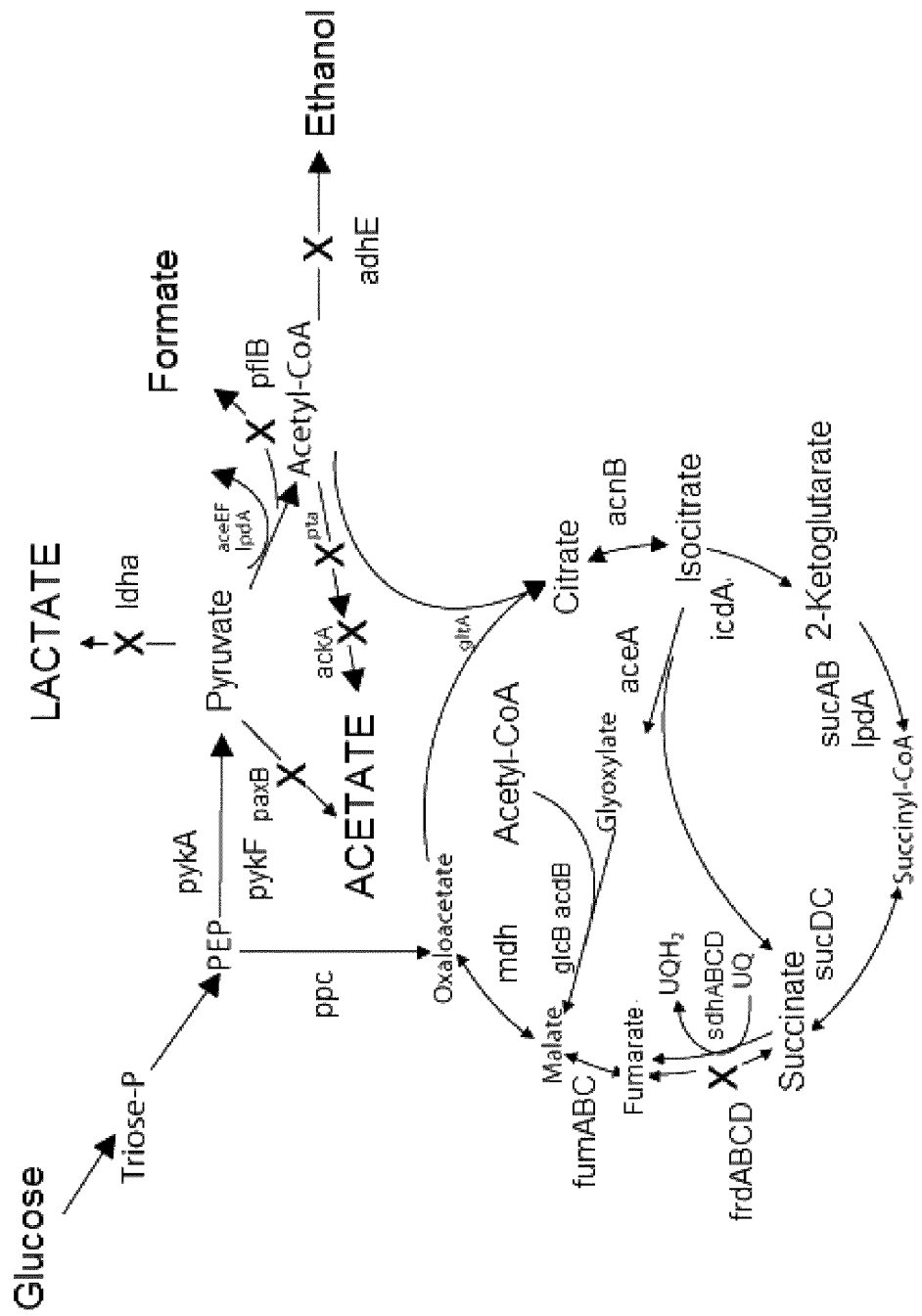

Exemplary metabolites include glucose, pyruvate, 1-propanol, isobutanol, 1-butanol, 2-methyl 1-butanol, 3-methyl 1-butanol or 2-phenylethanol, and 2-keto acids. As depicted in FIG. 1A, exemplary 2-keto acid intermediates include 2-ketobutyrate, 2-ketoisovalerate, 2-ketovalerate, 2-keto 3-methylvalerate, 2-keto 4-methyl-pentanoate, and phenylpyruvate. The exemplary 2-keto acids shown in FIG. 1A may be used as metabolic intermediates in the production of 1-propanol, isobutanol, 1-butanol, 2-methyl 1-butanol, 3-methyl 1-butanol or 2-phenylethanol. For example, as shown in FIG. 1B a recombinant microorganism metabolically engineered to provide elevated expression of 2-isopropylmalate synthase, beta-isopropylmalate dehydrogenase and isopropylmalate isomerase enzymes encoded by, for example, a Leu operon (e.g., LeuABCD) produces 2-ketovalerate from 2-ketobutyrate. The 2-ketovalerate metabolite may be used to produce 1-butanol by additional enzymes produced by the metabolically modified microorganism. Additionally, 1-propanol and 2-methyl 1-butanol can be produced from 2-ketobutyrate and 2-keto-3-methyl-valerate by a recombinant microorganism metabolically engineered to express or over-express acetohydroxy acid synthase, alpha-ketoacid decarboxylase, and alcohol dehydrogenase enzymes encoded by, for example, ilvIHDC, kdc and adh genes. Further, the metabolite 2-ketoisovalerate can be produced by a recombinant microorganism metabolically engineered to express or over-express acetohydroxy acid synthase enzymes encoded by, for example, ilvIHCD genes. This metabolite can then be used in the production of isobutanol or 3-methyl 1-butanol. The metabolites pyruvate and phenylpyruvate can be used to produce 2-phenylethanol by a recombinant microorganism metabolically engineered to express or over-express alpha-ketoacid decarboxylase, and alcohol dehydrogenase enzymes encoded by, for example, kdc and adh. Additional metabolites and genes are shown in FIG. 1B.

Accordingly, provided herein are recombinant microorganisms that produce isobutanol and in some aspects may include the elevated expression of target enzymes such as acetohydroxy acid synthase (e.g., ilvIH operon), acetohydroxy acid isomeroreductase (e.g., ilvC), dihydroxy-acid dehydratase (e.g., ilvD), 2-keto-acid decarboxylase (e.g., PDC6, ARO10, THI3, kivd, or pdc), and alcohol dehydrogenase (e.g., ADH2). The microorganism may further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, to increase the availability of pyruvate or reduce enzymes that compete for a metabolite in a desired biosynthetic pathway. In some aspects the recombinant microorganism may include the elevated expression of acetolactate synthase (e.g., alsS), acteohydroxy acid isomeroreductase (e.g., ilvC), dihydroxy-acid dehydratase (e.g., ilvD), 2-keto acid decarboxylase (e.g., PDC6, ARO10, TH13, kivd, or pdc), and alcohol dehydrogenase (e.g., ADH2). With reference to alcohol dehydrogenases, although ethanol dehydrogenase is an alcohol dehydrogenase, the synthesis of ethanol is undesireable as a by-product in the biosynthetic pathways. Accordingly, reference to an increase in alcohol dehydrogenase activity or expression in a microorganism specifically excludes ethanol dehydrogenase activity.

Also provided are recombinant microorganisms that produce 1-butanol and may include the elevated expression of target enzymes such as 2-isopropylmalate synthase (e.g., leuA), beta-isopropylmalate dehydrogenase (e.g., leuB), isopropylmalate isomerase (e.g., leuC, leuD, or leuCD operon), threonine dehydratase (e.g., ilvA). The microorganism may further include decreased levels of 2-ketoisovalerate, 2-keto-3-methyl-valerate, or 2-keto-4-methyl-pentanoate, or any combination thereof, as compared to a parental microorganism. In addition, the microorganism may include a disruption, deletion or knockout of expression of a dihydroxy-acid dehydratase (e.g. ilvD gene), as compared to a parental microorganism. A recombinant microorganism that produces 1-butanol may include further elevated expression or activity of phosphoenolpyruvate carboxylase, pyruvate carboxylase, aspartate aminotransferase, homoserine dehydrogenase, aspartate-semialdehyde dehydrogenase, homoserine kinase, threonine synthase, L-serine dehydratase, and/or threonine dehydratase, encoded by a nucleic acid sequences derived from the ppc, pyc, aspC, thrA, asd, thrB, thrC, sdaAB, and tdcB genes, respectively, or homologs thereof.

Also provided are recombinant microorganisms that produce 1-propanol and may include the elevated expression of target enzymes such as alpha-isopropylmalate synthase (e.g., cimA), beta-isopropylmalate dehydrogenase (e.g., leuB), isopropylmalate isomerase (e.g., leuCD operon) and threonine dehydratase.

Also provided are recombinant microorganisms that produce 2-methyl 1-butanol and may include the elevated expression of target enzymes such as threonine dehydratase (e.g., ilvA or tdcB), acetohydroxy acid synthase (e.g., ilvIH operon), acetohydroxy acid isomeroreductase (e.g., ilvC), dihydroxy-acid dehydratase (e.g., ilvD), 2-keto-acid decarboxylase (e.g., PDC6, ARO10, THIS, kivd, and/or pdc, and alcohol dehydrogenase (e.g., ADH2).

Also provided are recombinant microorganisms that produce 3-methyl 1-butanol and may include the elevated expression of target enzymes such as acetolactate synthase (e.g., alsS), acetohydroxy acid synthase (e.g., ilvIH), acetolactate synthase (e.g., ilvMG) or (e.g., ilvNB), acetohydroxy acid isomeroreductase (e.g., ilvC), dihydroxy-acid dehydratase (e.g., ilvD), 2-isopropylmalate synthase (leuA), isopropylmalate isomerase (e.g., leuC, D or leuCD operon), beta-isopropylmalate dehydrogenase (e.g., leuB), 2-ketoacid decarboxylase (e.g., kivd, PDC6, or THI3), and alcohol dehydrogenase (e.g., ADH2).

Also provided are recombinant microorganisms that produce phenylethanol and may include the elevated expression of target enzymes such as chorismate mutase P/prephenate dehydratase (e.g., pheA), chorismate mutase T/prephenate dehydrogenase (e.g., tyrA), 2-keto-acid decarboxylase (e.g., kivd, PDC6, or THI3), and alcohol dehydrogenase (e.g., ADH2).

As previously noted the target enzymes described throughout this disclosure generally produce metabolites. For example, the enzymes 2-isopropylmalate synthase (leuA), beta-isopropylmalate dehydrogenase (leuB), and isopropylmalate isomerase (leuC, leuD or leuCD operon) may produce 2-ketovalerate from a substrate that includes 2-ketobutyrate. In addition, the target enzymes described throughout this disclosure are encoded by polynucleotides. For example, threonine dehydratase can be encoded by a polynucleotide derived from an ilvA gene. Acetohydroxy acid synthase can be encoded by a polynucleotide derived from an ilvIH operon. Acetohydroxy acid isomeroreductase can be encoded by a polynucleotide derived from an ilvC gene. Dihydroxy-acid dehydratase can be encoded by a polynucleotide derived from an ilvD gene. 2-keto-acid decarboxylase can be encoded by a polynucleotide derived from a PDC6, ARO10, THI3, kivd, and/or pdc gene. Alcohol dehydrogenase can be encoded by a polynucleotide derived from an ADH2 gene. Additional enzymes and exemplary genes are described throughout this document. Homologs of the various polypeptides and polynucleotides can be derived from any biologic source that provides a suitable polynucleotide encoding a suitable enzyme. Homologs, for example, can be identified by reference to various databases.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a function enzyme activity using methods known in the art.

Due to the inherent degeneracy of the genetic code, other polynucleotides which encode substantially the same or a functionally equivalent polypeptide can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites (e.g., keto thiolase, acetyl-CoA acetyltransferase, hydroxybutyryl CoA dehydrogenase, crotonase, crotonyl-CoA reductase, butyryl-coA dehydrogenase, alcohol dehydrogenase (ADH)) are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.)

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For example, reference to a kivd gene includes homologs (e.g., pdc6, aro10, thI3, pdc, kdcA, pdc1, pdc5) from other organisms encoding an enzyme having substantially similar enzymatic activity, as well as genes having at least 30, 40, 50, 60, 70, 80, 85, 90, 95, 98, or 99% identity to the referenced gene and which encodes an enzyme having substantially similar enzymatic activity as the referenced gene. For example, pyruvate decarboxylase of *Kluyveromyces lactis* has 37% identity to Kivd at the amino acids level; kivd and thI3 are 32% identical at the nucleic acid level; Alcohol dehydrogenase of *Schizosaccharomyces pombe* has 52% identity to ADH2 of *Saccharomyces cerevisiae* at the amino acid sequence level; *S. cerevisiae* adh2 and *Lactococcus Lactis* adh are 49% identical; KIVD (*Lactococcus lactis*) and PDC6 (*Saccharomyces cerevisiae*) share 36% identity (Positives=322/562 (57%), Gaps=24/562 (4%)); KIVD (*Lactococcus lactis* and THI3 (*Saccharomyces cerevisiae*) share 32% identity (Positives=307/571 (53%), Gaps=35/571 (6%)); kivd (*Lactococcus lactis*) and ARO10 (*Saccharomyces cerevisiae*) share 30% identikit (Positives=296/598 (49%), Gaps=65/598 (10%)); ARO10 (*Saccharomyces cerevisiae*) and PDC6 (*Saccharomyces cerevisiae*) share 34% identity (Positives=320/616 (51%), Gaps=61/616 (9%)); ARO10 (*Saccharomyces cerevisiae*) and THI3 (*Saccharomyces cerevisiae*) share 30% identity (Positives=304/599 (50%), Gaps=48/599 (8%)); ARO10 (*Saccharomyces cerevisiae*) and Pyruvate decarboxylase (*Clostridium acetobutylicum* ATCC 824) share 30% identity (Positives=291/613 (47%), Gaps=73/613 (11%)); PDC6 ((*Saccharomyces cerevisiae*) and THI3 (*Saccharomyces cerevisiae*) share 50% identikit (Positives=402/561 (71%), Gaps=17/561 (3%)); PDC6 (*Saccharomyces cerevisiae*) and Pyruvate decarboxylase (*Clostridium acetobutylicum* ATCC 824) share 38% identity (Positives=328/570 (57%), Gaps=30/570 (5%)); and THI3 (*Saccharomyces cerevisiae*) and Pyruvate decarboxylase (*Clostridium acetobutylicum* ATCC 824) share 35% identity (Positives=284/521 (54%), Gaps=25/521 (4%)). Sequence for each of the genes and polypeptides/enzymes listed herein can be readily identified using databases available on the World-Wide-Web (see, e.g., http://)eecoli.kaist.ac.kr/main.html). In addition, the amino acid sequence and nucleic acid sequence can be readily compared for identity using commonly used algorithms in the art.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

The following table and the disclosure provides non-limiting examples of genes and homologs for each gene having polynucleotide and polypeptide sequences available to the skilled person in the art.

TABLE 1

Depicts recombinant pathways for the production of various higher alcohols ("+" = expression, increase expression or activity/"−" = reduced expression or activity or knockout*).

| Enzyme | Exemplary Gene(s) | isobutanol | 1-butanol (via L-threonine) | 1-butanol (via pyruvate) | 1-propanol (via L-threonine) | 1-propanol (via pyruvate) | 3-M-1-butanol (via pyruvate) | 2-M-1-butanol (via L-threonine) |
|---|---|---|---|---|---|---|---|---|
| Ethanol Dehydrogenase | adhE | − | − | − | − | − | − | − |
| Lactate Dehydrogenase | ldhA | − | − | − | − | − | − | − |
| Fumarate reductase | frdBC | − | | | | | − | − |
| | fnr | − | | | | | − | − |
| acetate kinase | ackA | − | − | − | − | − | − | − |
| Phosphate acetyltransferase | pta | − | − | − | − | − | − | − |
| Formate acetyltransferase | pflB | − | | | | | − | − |
| α-isopropylmalate synthase | leuA | − | + | + | | | + | |
| β-isopropylmalate dehydrogenase, | leuB | | + | + | − | + | + | |
| α-isopropylmalate isomerase | leuC | | + | + | | + | + | |
| α-isopropylmalate isomerase | leuD | | + | + | | + | | |
| BCAA aminotransferase | ilvE | − | | | | | − | |
| tyrosine aminotransferase | tyrB, tyrAT | | | | | | − | |
| pyruvate dehydrogenase | poxB | − | − | − | − | − | | |
| acetolactate synthase | ilvB | | − | − | − | − | | |
| acetolactate synthase | ilvI, alsS | | − | − | − | − | | |
| threonine dehydratase | ilvA, tdcB | − | + | + | + | + | | + |
| homoserine transsuccinylase | metA | | − | − | − | − | | − |
| L-threonine 3-dehydrogenase | tdh | | − | − | −□ | − | | − |
| acetohydroxy acid synthase | ilvHI, ilvNB, ilvGM, alsS | + | | | | | + | + |
| acetohydroxy acid isomeroredutase | ilvC, ilv5 | + | | | | | + | + |
| dihydroxy-acid dehyratase | ilvD, ilv3 | + | | | | | + | + |
| 2-ketoacid decarboxylase | pdc6, aro10, thI3, kivd, pdc, kdcA, pdc1, pdc5 | + | + | + | + | + | + | + |
| alcohol dehydrogenase | adh1, adh2, adh3, adh4, adh5, adh6, sfa1 | + | + | + | + | + | + | + |
| citramalate synthase | cimA | | | + | | + | | |

*knockout or a reduction in expression are optional in the synthesis of the product, however, such knockouts increase various substrate intermediates and improve yield.

Tables 2-9 set forth reaction pathways for various recombinant microorganism of the disclosure including a list of exemplary genes and homologs and organism source.

TABLE 2

Isobutanol production pathway (via pyruvate)

Reaction 1 pyruvate –> 2-acetolactate
Genes ilvHI (*E. coli*), ilvNB (*E. coli*), ilvGM (*E. coli*), alsS (*Bacillus subtilis*) or homologs thereof
Reaction 2

2-acetolactate –> 2,3-dihydroxy-isovalerate
Genes ilvC (*E. coli*) or homologs thereof TABLE 2-continued Isobutanol production pathway (via pyruvate)

Reaction 3

2,3-dihydroxy-isovalerate –> 2-keto-isovalerate
Genes ilvD (*E. coli*) or homologs thereof
Reaction 4

2-keto-isovalerate –> isobutrylaldehyde
Genes kivd (*Lactococcus lactis*), kdcA (*Lactococcus lactis*), PDC1 (*Saccharomyces cerevisiae*), PDC5 (*Saccharomyces cerevisiae*), PDC6 (*Saccharomyces cerevisiae*) THI3 (*Saccharomyces cerevisiae*), ARO10 (*Saccharomyces cerevisiae*) or homologs thereof
Reaction 5 isobutrylaldehyde –> isobutanol

TABLE 2-continued

Isobutanol production pathway (via pyruvate)

Genes

ADH1 (*Saccharomyces cerevisiae*), ADH2 (*Saccharomyces cerevisiae*), ADH3(*Saccharomyces cerevisiae*), ADH4 (*Saccharomyces cerevisiae*), ADH5(*Saccharomyces cerevisiae*), ADH6 (*Saccharomyces cerevisiae*), SFA1 (*Saccharomyces cerevisiae*) or homologs thereof

TABLE 3

1-butanol production pathway via L-threonine

Reaction 1

L-threonine -> 2-keto-butyrate
Genes ilvA(*E. coli*), tdcB(*E. coli*) or homologs thereof
Reaction 2

2-keto-butyrate -> 2-ethylmalate
Genes leuA(*E. coli*) or homologs thereof
Reaction 3

2-ethylmalate -> 3-ethylmalate
Genes leuCD(*E. coli*) or homologs thereof
Reaction 4

3-ethylmalate -> 2-ethyl-3-oxosuccinate
Genes leuB(*E. coli*) or homologs thereof
Reaction 5

2-ethyl-3-oxosuccinate -> 2-keto-valerate
Gene n/a (spontaneous reaction)
Reaction 6

2-keto-valerate -> butrylaldehyde
Genes kivd(*Lactococcus lactis*), kdcA(*Lactococcus lactis*), PDC1(*Saccharomyces cerevisiae*), PDC5(*Saccharomyces cerevisiae*), PDC6(*Saccharomyces cerevisiae*) THI3 (*Saccharomyces cerevisiae*), ARO10(*Saccharomyces cerevisiae*) or homologs thereof
Reaction 7 butrylaldehyde -> 1-butanol
Genes

ADH1 (*Saccharomyces cerevisiae*), ADH2(*Saccharomyces cerevisiae*), ADH3(*Saccharomyces cerevisiae*), ADH4(*Saccharomyces cerevisiae*), ADH5(*Saccharomyces cerevisiae*), ADH6(*Saccharomyces cerevisiae*), SFA1 (*Saccharomyces cerevisiae*) or homologs thereof

TABLE 4

1-butanol production pathway via pyruvate

Reaction 1

Pyruvate + Acetyl-CoA -> (R)-citramalate
Genes cimA(*Methanocaldococcus jannaschii*), cimA(*Leptospira interrogans*) or homologs thereof

TABLE 4-continued 1-butanol production pathway via pyruvate

Reaction 2

(R)-citramalate -> citraconate
Genes leuCD(*Leptospira interrogans*), leuCD(*E. coli*) or homologs thereof
Reaction 3 citraconate -> β-methyl-D-malate
Genes leuCD(*Leptospira interrogans*), leuCD(*E. coli*) or homologs thereof
Reaction 4

β-methyl-D-malate -> 2-keto-butyrate
Genes leuB(*Leptospira interrogans*), leuB(*E. coli*) or homologs thereof
Reaction 5

2-keto-butyrate -> 2-ethylmalate
Genes leuA(*E. coli*) or homologs thereof
Reaction 3

2-ethylmalate -> 3-ethylmalate
Genes leuCD(*E. coli*) or homologs thereof
Reaction 4

3-ethylmalate -> 2-ethyl-3-oxosuccinate
Genes leuB(*E. coli*) or homologs thereof
Reaction 5

2-ethyl-3-oxosuccinate -> 2-keto-valerate
Genes (spontaneous)
Reaction 6

2-keto-valerate -> butrylaldehyde
Genes kivd(*Lactococcus lactis*), kdcA(*Lactococcus lactis*), PDC1(*Saccharomyces cerevisiae*), PDC5(*Saccharomyces cerevisiae*), PDC6(*Saccharomyces cerevisiae*) THI3 (*Saccharomyces cerevisiae*), ARO10(*Saccharomyces cerevisiae*) or homologs thereof
Reaction 7 butrylaldehyde -> 1-butanol
Genes

ADH1(*Saccharomyces cerevisiae*), ADH2(*Saccharomyces cerevisiae*), ADH3(*Saccharomyces cerevisiae*), ADH4(*Saccharomyces cerevisiae*), ADH5(*Saccharomyces cerevisiae*), ADH6(*Saccharomyces cerevisiae*), SFA1 (*Saccharomyces cerevisiae*) or homologs thereof

TABLE 5

1-propanol production pathway via L-threonine

Reaction 1

L-threonine -> 2-keto-butyrate
Genes ilvA(*E. coli*), tdcB(*E. coli*) or homologs thereof
Reaction 2

2-keto-butyrate -> propyl aldehyde

TABLE 5-continued

1-propanol production pathway via L-threonine

Genes kivd(*Lactococcus lactis*), kdcA(*Lactococcus lactis*), PDC1(*Saccharomyces cerevisiae*), PDC5(*Saccharomyces cerevisiae*), PDC6(*Saccharomyces cerevisiae*), THI3 (*Saccharomyces cerevisiae*), ARO10(*Saccharomyces cerevisiae*) or homologs thereof
Reaction 3 propyl aldehyde -> 1-propanol
Genes

ADH1(*Saccharomyces cerevisiae*), ADH2(*Saccharomyces cerevisiae*), ADH3(*Saccharomyces cerevisiae*), ADH4(*Saccharomyces cerevisiae*), ADH5(*Saccharomyces cerevisiae*), ADH6(*Saccharomyces cerevisiae*), SFA1 (*Saccharomyces cerevisiae*) or homologs thereof

TABLE 6

1-propanol production pathway via pyruvate

Reaction 1

Pyruvate + Acetyl-CoA -> (R)-citramalate
Genes cimA(*Methanocaldococcus jannaschii*), cimA(*Leptospira interrogans*) or homologs thereof
Reaction 2

(R)-citramalate -> citraconate
Genes leuCD(*Leptospira interrogans*), leuCD(*E. coli*) or homologs thereof
Reaction 3 citraconate -> β-methyl-D-malate
Genes leuCD(*Leptospira interrogans*), leuCD(*E. coli*) or homologs thereof
Reaction 4

β-methyl-D-malate -> 2-keto-butyrate
Genes leuB(*Leptospira interrogans*), leuB(*E. coli*) or homologs thereof
Reaction 5

2-keto-butyral -> butrylaldehyde
Genes kivd(*Lactococcus lactis*), kdcA(*Lactococcus lactis*), PDC1(*Saccharomyces cerevisiae*), PDC5(*Saccharomyces cerevisiae*), PDC6(*Saccharomyces cerevisiae*), THI3(*Saccharomyces cerevisiae*), ARO10(*Saccharomyces cerevisiae*) or homologs thereof
Reaction 7 butrylaldehyde -> 1-butanol
Genes

ADH1(*Saccharomyces cerevisiae*), ADH2(*Saccharomyces cerevisiae*), ADH3(*Saccharomyces cerevisiae*), ADH4(*Saccharomyces cerevisiae*), ADH5(*Saccharomyces cerevisiae*), ADH6(*Saccharomyces cerevisiae*), SFA1 (*Saccharomyces cerevisiae*) or homologs thereof

TABLE 7

2-methyl-1-butanol production pathway (via L-threonine)

Reaction 1

L-threonine -> 2-keto-butyrate

TABLE 7-continued

2-methyl-1-butanol production pathway (via L-threonine)

Genes ilvA(*E. coli*), tdcB(*E. coli*) or homologs thereof
Reaction 2

2-keto-butyrate -> 2-aceto-2-hydroxy-butyrate
Genes ilvHI(*E. coli*), ilvNB(*E. coli*), ilvGM(*E. coli*), alsS(*Bacillus subtilis*) or homologs thereof
Reaction 3

2-aceto-2-hydroxy-butyrate -> 2,3-dihydroxy-3-methylvalerate
Genes ilvC(*E. coli*) or homologs thereof
Reaction 4

2,3-dihydroxy-3-methylvalerate -> 2-keto-3-methyl-valerate
Genes ilvD(*E. coli*) or homologs thereof
Reaction 5

2-keto-3-methyl-valerate -> 2-methylbutyraldehyde
Genes kivd(*Lactococcus lactis*), kdcA(*Lactococcus lactis*), PDC1(*Saccharomyces cerevisiae*), PDC5(*Saccharomyces cerevisiae*), PDC6(*Saccharomyces cerevisiae*), THI3 (*Saccharomyces cerevisiae*), ARO10(*Saccharomyces cerevisiae*) or homologs thereof
Reaction 6

2-methylbutyraldehyde -> 2-methyl-1-butanol
Genes

ADH1(*Saccharomyces cerevisiae*), ADH2(*Saccharomyces cerevisiae*), ADH3(*Saccharomyces cerevisiae*), ADH4(*Saccharomyces cerevisiae*), ADH5(*Saccharomyces cerevisiae*), ADH6(*Saccharomyces cerevisiae*), SFA1 (*Saccharomyces cerevisiae*) or homologs thereof

TABLE 8

3-methyl-1-butanol production pathway (via pyruvate)

Reaction 1 pyruvate -> 2-acetolactate
Gene ilvHI(*E. coli*), ilvNB(*E. coli*), ilvGM(*E. coli*), alsS(*Bacillus subtilis*) or homologs thereof
Reaction 2

2-acetolactate -> 2,3-dihydroxy-isovalerate
Genes ilvC(*E. coli*) or homologs thereof
Reaction 3

2,3-dihydroxy-isovalerate -> 2-keto-isovalerate
Genes ilvD(*E. coli*) or homologs thereof
Reaction 4

2-keto-isovalerate -> 2-isopropylmalate
Genes leuA(*E. coli*) or homologs thereof
Reaction 5

2-isopropylmalate -> 3-isopropylmalate

TABLE 8-continued

3-methyl-1-butanol production pathway (via pyruvate)

Genes leuCD(*E. coli*) or homologs thereof
Reaction 6

3-isopropylmalate -> 2-isopropyl-3-oxosuccinate
Genes leuB(*E. coli*) or homologs thereof
Reaction 7

2-isopropyl-3-oxosuccinate -> 2-ketoisocaproate
Genes (spontaneous)
Reaction 8

2-ketoisocaproate -> 3-methylbutyraldehyde
Genes kivd(*Lactococcus lactis*), kdcA(*Lactococcus lactis*), PDC1(*Saccharomyces cerevisiae*), PDC5(*Saccharomyces cerevisiae*), PDC6(*Saccharomyces cerevisiae*) THI3 (*Saccharomyces cerevisiae*), ARO10(*Saccharomyces cerevisiae*) or homologs thereof
Reaction 9

3-methylbutyraldehyde -> 3-methyl-1-butanol
Genes

ADH1(*Saccharomyces cerevisiae*), ADH2(*Saccharomyces cerevisiae*), ADH3(*Saccharomyces cerevisiae*), ADH4(*Saccharomyces cerevisiae*), ADH5(*Saccharomyces cerevisiae*), ADH6(*Saccharomyces cerevisiae*), SFA1 (*Saccharomyces cerevisiae*) or homologs thereof

TABLE 9 phenyl-ethanol production pathway (via chorismate)

Reaction 1 chorismate -> prephenate
Genes tyrA(*E. coli*), pheA(*E. coli*) or homologs thereof
Reaction 2 prephenate -> phenylpyruvate
Genes pheA(*E. coli*) or homologs thereof
Reaction 3 phenylpyruvate -> phenylaldehyde
Genes kivd(*Lactococcus lactis*), kdcA(*Lactococcus lactis*), PDC1(*Saccharomyces cerevisiae*), PDC5(*Saccharomyces cerevisiae*), PDC6(*Saccharomyces cerevisiae*) THI3 (*Saccharomyces cerevisiae*), ARO10(*Saccharomyces cerevisiae*) or homologs thereof
Reaction 4 phenylaldehyde -> 2-phenylethanol
Genes

ADH1(*Saccharomyces cerevisiae*), ADH2(*Saccharomyces cerevisiae*), ADH3(*Saccharomyces cerevisiae*), ADH4(*Saccharomyces cerevisiae*), ADH5(*Saccharomyces cerevisiae*), ADH6(*Saccharomyces cerevisiae*), SFA1 (*Saccharomyces cerevisiae*) or homologs thereof The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Ethanol Dehydrogenase (also referred to as Aldehyde-alcohol dehydrogenase) is encoded in *E. coli* by adhE. adhE comprises three activities: alcohol dehydrogenase (ADH); acetaldehyde/acetyl-CoA dehydrogenase (ACDH); pyruvate-formate-lyase deactivase (PFL deactivase); PFL deactivase activity catalyzes the quenching of the pyruvate-formate-lyase catalyst in an iron, NAD, and CoA dependent reaction. Homologs are known in the art (see, e.g., aldehyde-alcohol dehydrogenase (*Polytomella* sp. *Pringsheim* 198.80) gi|40644910|emb|CAD42653.2|(40644910); aldehyde-alcohol dehydrogenase (*Clostridium botulinum* A str. ATCC 3502) gi|148378348|ref|YP_001252889.1|(148378348); aldehyde-alcohol dehydrogenase (*Yersinia pestis* CO92) gi|16122410|ref|NP_405723.1|(16122410); aldehyde-alcohol dehydrogenase (*Yersinia pseudotuberculosis* IP 32953) gi|51596429|ref|YP_070620.1|(51596429); aldehyde-alcohol dehydrogenase (*Yersinia pestis* CO92) gi|115347889|emb|CAL20810.1|(115347889); aldehyde-alcohol dehydrogenase (*Yersinia pseudotuberculosis* IP 32953) gi|51589711|emb|CAH21341.1|(51589711); Aldehyde-alcohol dehydrogenase (*Escherichia coli* CFT073) gi|26107972|gb|AAN80172.1|AE016760_31(26107972); aldehyde-alcohol dehydrogenase (*Yersinia pestis* biovar *Microtus* str. 91001) gi|45441777|ref|NP_993316.1| (45441777); aldehyde-alcohol dehydrogenase (*Yersinia pestis* biovar *Microtus* str. 91001) gi|45436639|gb|AAS62193.1| (45436639); aldehyde-alcohol dehydrogenase (*Clostridium perfringens* ATCC 13124) gi|110798574|ref|YP_697219.1| (110798574); aldehyde-alcohol dehydrogenase (*Shewanella oneidensis* MR-1) gi|24373696|ref|NP_717739.1| (24373696); aldehyde-alcohol dehydrogenase (*Clostridium botulinum* A str. ATCC 19397) gi|153932445|ref|YP_001382747.1|(153932445); aldehyde-alcohol dehydrogenase (*Yersinia pestis* biovar *Antiqua* str. E1979001) gi|165991833|gb|EDR44134.1| (165991833); aldehyde-alcohol dehydrogenase (*Clostridium botulinum* A str. Hall) gi|153937530|ref|YP_001386298.1| (153937530); aldehyde-alcohol dehydrogenase (*Clostridium perfringens* ATCC 13124) gi|110673221|gb|ABG82208.1| (110673221); aldehyde-alcohol dehydrogenase (*Clostridium botulinum* A str. Hall) gi|152933444|gb|ABS38943.1| (152933444); aldehyde-alcohol dehydrogenase (*Yersinia pestis* biovar *Orientalis* str. F1991016) gi|165920640|gb|EDR37888.1|(165920640); aldehyde-alcohol dehydrogenase (*Yersinia pestis* biovar *Orientalis* str. IP275) gi|165913933|gb|EDR32551.1|(165913933); aldehyde-alcohol dehydrogenase (*Yersinia pestis* Angola) gi|162419116|ref|YP_001606617.1|(162419116); aldehyde-alcohol dehydrogenase (*Clostridium botulinum* F str. Langeland) gi|153940830|ref|YP_001389712.1| (153940830); aldehyde-alcohol dehydrogenase (*Escherichia coli* HS) gi|157160746|ref|YP_001458064.1|(157160746); aldehyde-alcohol dehydrogenase (*Escherichia coli* E24377A) gi|157155679|ref|YP_001462491.1| (157155679); aldehyde-alcohol dehydrogenase (*Yersinia enterocolitica* subsp. *enterocolitica* 8081) gi|123442494|ref|YP_001006472.1|(123442494); aldehyde-alcohol dehydrogenase (*Synechococcus* sp. JA-3-3Ab) gi|86605191|ref|YP_473954.1|(86605191); aldehyde-alcohol dehydrogenase (*Listeria monocytogenes* str. 4b F2365) gi|46907864|ref|YP_014253.1|(46907864); aldehyde-alcohol dehydrogenase (*Enterococcus faecalis* V583) gi|29375484|ref|NP_814638.1|(29375484); aldehyde-alcohol dehydrogenase (*Streptococcus agalactiae* 2603V/R)

gi|22536238|ref|NP_687089.1|(22536238); aldehyde-alcohol dehydrogenase (*Clostridium botulinum* A str. ATCC 19397) gi|152928489|gb|ABS33989.1|(152928489); aldehyde-alcohol dehydrogenase (*Escherichia coli* E24377A) gi|157077709|gb|ABV17417.1|(157077709); aldehyde-alcohol dehydrogenase (*Escherichia coli* HS) gi|157066426|gb|ABV05681.1|(157066426); aldehyde-alcohol dehydrogenase (*Clostridium botulinum* F str. Langeland) gi|152936726|gb|ABS42224.1|(152936726); aldehyde-alcohol dehydrogenase (*Yersinia pestis* CA88-4125) gi|149292312|gb|EDM42386.1|(149292312); aldehyde-alcohol dehydrogenase (*Yersinia enterocolitica* subsp. *enterocolitica* 8081) gi|122089455|emb|CAL12303.1|(122089455); aldehyde-alcohol dehydrogenase (*Chlamydomonas reinhardtii*) gi|92084840|emb|CAF04128.1|(92084840); aldehyde-alcohol dehydrogenase (*Synechococcus* sp. JA-3-3Ab) gi|86553733|gb|ABC98691.1|(86553733); aldehyde-alcohol dehydrogenase (*Shewanella oneidensis* MR-1) gi|24348056|gb|AAN55183.1|AE015655_9(24348056); aldehyde-alcohol dehydrogenase (*Enterococcus faecalis* V583) gi|29342944|gb|AAO80708.1|(29342944); aldehyde-alcohol dehydrogenase (*Listeria monocytogenes* str. 4b F2365) gi|46881133|gb|AAT04430.1|(46881133); aldehyde-alcohol dehydrogenase (*Listeria monocytogenes* str. 1/2a F6854) gi|47097587|ref|ZP_00235115.1|(47097587); aldehyde-alcohol dehydrogenase (*Listeria monocytogenes* str. 4b H7858) gi|47094265|ref|ZP_00231973.1|(47094265); aldehyde-alcohol dehydrogenase (*Listeria monocytogenes* str. 4b H7858) gi|47017355|gb|EAL08180.1|(47017355); aldehyde-alcohol dehydrogenase (*Listeria monocytogenes* str. 1/2a F6854) gi|47014034|gb|EAL05039.1|(47014034); aldehyde-alcohol dehydrogenase (*Streptococcus agalactiae* 2603V/R) gi|22533058|gb|AAM98961.1|AE014194_6 (22533058)p; aldehyde-alcohol dehydrogenase (*Yersinia pestis* biovar *Antiqua* str. E1979001) gi|166009278|ref|ZP_02230176.1|(166009278); aldehyde-alcohol dehydrogenase (*Yersinia pestis* biovar *Orientalis* str. IP275) gi|165938272|ref|ZP_02226831.1|(165938272); aldehyde-alcohol dehydrogenase (*Yersinia pestis* biovar *Orientalis* str. F1991016) gi|165927374|ref|ZP_02223206.1|(165927374); aldehyde-alcohol dehydrogenase (*Yersinia pestis* Angola) gi|162351931|gb|ABX85879.1|(162351931); aldehyde-alcohol dehydrogenase (*Yersinia pseudotuberculosis* IP 31758) gi|153949366|ref|YP_001400938.1|(153949366); aldehyde-alcohol dehydrogenase (*Yersinia pseudotuberculosis* IP 31758) gi|152960861|gb|ABS48322.1|(152960861); aldehyde-alcohol dehydrogenase (*Yersinia pestis* CA88-4125) gi|149365899|ref|ZP_01887934.1|(149365899); Acetaldehyde dehydrogenase (acetylating) (*Escherichia coli* CFT073) gi|26247570|ref|NP_753610.1|(26247570); aldehyde-alcohol dehydrogenase (includes: alcohol dehydrogenase; acetaldehyde dehydrogenase (acetylating) (EC 1.2.1.10) (acdh); pyruvate-formate-lyase deactivase (pfl deactivase)) (*Clostridium botulinum* A str. ATCC 3502) gi|148287832|emb|CAL81898.1|(148287832); aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152980|sp|P0A9Q7.2|ADHE_ECOLI (71152980); aldehyde-alcohol dehydrogenase (includes: alcohol dehydrogenase and acetaldehyde dehydrogenase, and pyruvate-formate-lyase deactivase (*Erwinia carotovora* subsp. atroseptica SCRI1043) gi|50121254|ref|YP_050421.1|(50121254); aldehyde-alcohol dehydrogenase (includes: alcohol dehydrogenase and acetaldehyde dehydrogenase, and pyruvate-formate-lyase deactivase (*Erwinia carotovora* subsp. atroseptica SCRI1043) gi|49611780|emb|CAG75229.1|(49611780); Aldehyde-alcohol dehydrogenase (Includes: Alcohol dehydrogenase (ADH); Acetaldehyde dehydrogenase (acetylating) (ACDH)) gi|19858620|sp|P33744.31ADHE_CLOAB (19858620); Aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152683|sp|P0A9Q8.2|ADHE_ECO57 (71152683); aldehyde-alcohol dehydrogenase (includes: alcohol dehydrogenase; acetaldehyde dehydrogenase (acetylating); pyruvate-formate-lyase deactivase (*Clostridium difficile* 630) gi|126697906|ref|YP_001086803.1|(126697906); aldehyde-alcohol dehydrogenase (includes: alcohol dehydrogenase; acetaldehyde dehydrogenase (acetylating); pyruvate-formate-lyase deactivase (*Clostridium difficile* 630) gi|115249343|emb|CAJ67156.1|(115249343); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|37526388|ref|NP_929732.1|(37526388); aldehyde-alcohol dehydrogenase 2 (includes: alcohol dehydrogenase; acetaldehyde dehydrogenase) (*Streptococcus pyogenes* str. Manfredo) gi|134271169|emb|CAM29381.1|(134271169); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|36785819|emb|CAE14870.1|(36785819); aldehyde-alcohol dehydrogenase (includes: alcohol dehydrogenase and pyruvate-formate-lyase deactivase (*Clostridium difficile* 630) gi|126700586|ref|YP_001089483.1|(126700586); aldehyde-alcohol dehydrogenase (includes: alcohol dehydrogenase and pyruvate-formate-lyase deactivase (*Clostridium difficile* 630) gi|115252023|emb|CAJ69859.1|(115252023); aldehyde-alcohol dehydrogenase 2 (*Streptococcus pyogenes* str. Manfredo) gi|139472923|ref|YP_001127638.1|(139472923); aldehyde-alcohol dehydrogenase E (*Clostridium perfringens* str. 13) gi|18311513|ref|NP_563447.1|(18311513); aldehyde-alcohol dehydrogenase E (*Clostridium perfringens* str. 13) gi|18146197|dbj|BAB82237.1|(18146197); Aldehyde-alcohol dehydrogenase, ADHE1 (*Clostridium acetobutylicum* ATCC 824) gi|5004739|ref|NP_149199.1|(15004739); Aldehyde-alcohol dehydrogenase, ADHE1 (*Clostridium acetobutylicum* ATCC 824) gi|14994351|gb|AAK76781.1|AE001438_34(14994351); Aldehyde-alcohol dehydrogenase 2 (Includes: Alcohol dehydrogenase (ADH); acetaldehyde/acetyl-CoA dehydrogenase (ACDH)) gi|2492737|sp|Q24803.1|ADH2_ENTHI (2492737); alcohol dehydrogenase (*Salmonella enterica* subsp. *enterica* serovar *Typhi* str. CT18) gi|16760134|ref|NP_455751.1|(16760134); and alcohol dehydrogenase (*Salmonella enterica* subsp. *enterica* serovar *Typhi*) gi|16502428|emb|CAD08384.1|(16502428)), each sequence associated with the accession number is incorporated herein by reference in its entirety.

Lactate Dehydrogenase (also referred to as D-lactate dehydrogenase and fermentive dehydrognase) is encoded in *E. coli* by ldhA and catalyzes the NADH-dependent conversion of pyruvate to D-lactate. ldhA homologs and variants are known. In fact there are currently 1664 bacterial lactate dehydrogenases available through NCBI. For example, such homologs and variants include, for example, D-lactate dehydrogenase (D-LDH) (Fermentative lactate dehydrogenase)

gi|1730102|sp|P52643.1|LDHD_ECOLI (1730102); D-lactate dehydrogenase gi|1049265|gb|AAB51772.1|(1049265); D-lactate dehydrogenase (*Escherichia coli* APEC O1) gi|117623655|ref|YP_852568.1|(117623655); D-lactate dehydrogenase (*Escherichia coli* CFT073) gi|26247689|ref|NP_753729.1|(26247689); D-lactate dehydrogenase (*Escherichia coli* O157:H7 EDL933) gi|15801748|ref|NP_287766.1|(15801748); D-lactate dehydrogenase (*Escherichia coli* APEC O1) gi|115512779|gb|ABJ00854.1|(115512779); D-lactate dehydrogenase (*Escherichia coli* CFT073) gi|26108091|gb|AAN80291.1|AE016760_150 (26108091); fermentative D-lactate dehydrogenase, NAD-dependent (*Escherichia coli* K12) gi|16129341|ref|NP_415898.1| (16129341); fermentative D-lactate dehydrogenase, NAD-dependent (*Escherichia coli* UTI89) gi|91210646|ref|YP_540632.1|(91210646); fermentative D-lactate dehydrogenase, NAD-dependent (*Escherichia coli* K12) gi|1787645|gb|AAC74462.1|(1787645); fermentative D-lactate dehydrogenase, NAD-dependent (*Escherichia coli* W3110) gi|89108227|ref|AP 002007.1|(89108227); fermentative D-lactate dehydrogenase, NAD-dependent (*Escherichia coli* W3110) gi|1742259|dbj|BAA14990.1|(1742259); fermentative D-lactate dehydrogenase, NAD-dependent (*Escherichia coli* UTI89) gi|91072220|gb|ABE07101.1| (91072220); fermentative D-lactate dehydrogenase, NAD-dependent (*Escherichia coli* O157:H7 EDL933) gi|12515320|gb|AAG56380.1|AE005366_6 (12515320); fermentative D-lactate dehydrogenase (*Escherichia coli* O157:H7 str. Sakai) gi|13361468|dbj|BAB35425.1| (13361468); COG1052: Lactate dehydrogenase and related dehydrogenases (*Escherichia coli* 101-1) gi|83588593|ref|ZP_00927217.1|(83588593); COG1052: Lactate dehydrogenase and related dehydrogenases (*Escherichia coli* 53638) gi|75515985|ref|ZP_00738103.1| (75515985); COG1052: Lactate dehydrogenase and related dehydrogenases (*Escherichia coli* E22) gi|75260157|ref|ZP_00731425.1|(75260157); COG1052: Lactate dehydrogenase and related dehydrogenases (*Escherichia coli* F11) gi|75242656|ref|ZP_00726400.1|(75242656); COG1052: Lactate dehydrogenase and related dehydrogenases (*Escherichia coli* E110019) gi|75237491|ref|ZP_00721524.1|(75237491); COG1052: Lactate dehydrogenase and related dehydrogenases (*Escherichia coli* B7A) gi|75231601|ref|ZP_00717959.1| (75231601); and COG1052: Lactate dehydrogenase and related dehydrogenases (*Escherichia coli* B171) gi|75211308|ref|ZP_00711407.1|(75211308), each sequence associated with the accession number is incorporated herein by reference in its entirety.

Two membrane-bound, FAD-containing enzymes are responsible for the catalysis of fumarate and succinate interconversion; the fumarate reductase is used in anaerobic growth, and the succinate dehydrogenase is used in aerobic growth. Fumarate reductase comprises multiple subunits (e.g., frdA, B, and C in *E. coli*). Modification of any one of the subunits can result in the desired activity herein. For example, a knockout of frdB, frdC or frdBC is useful in the methods of the disclosure. Frd homologs and variants are known. For example, homologs and variants includes, for example, Fumarate reductase subunit D (Fumarate reductase 13 kDa hydrophobic protein) gi|67463543|sp|P0A8Q3.1|FRDD_ECOLI (67463543); Fumarate reductase subunit C (Fumarate reductase 15 kDa hydrophobic protein) gi|1346037|sp|P20923.2|FRDC_PROVU (1346037); Fumarate reductase subunit D (Fumarate reductase 13 kDa hydrophobic protein) gi|20499|sp|P20924.1|FRDD_PROVU (120499); Fumarate reductase subunit C (Fumarate reductase 15 kDa hydrophobic protein) gi|67463538|sp|P0A8Q0.1|FRDC_ECOLI (67463538); fumarate reductase iron-sulfur subunit (*Escherichia coli*) gi|145264|gb|AAA23438.1|(145264); fumarate reductase flavoprotein subunit (*Escherichia coli*) gi|145263|gb|AAA23437.1|(145263); Fumarate reductase flavoprotein subunit gi|37538290|sp|P17412.3|FRDA_WOLSU (37538290); Fumarate reductase flavoprotein subunit gi|20489|sp|P00363.3|FRDA_ECOLI (120489); Fumarate reductase flavoprotein subunit gi|20490|sp|P20922.1|FRDA_PROVU (120490); Fumarate reductase flavoprotein subunit precursor (Flavocytochrome c) (Flavocytochrome c3) (Fcc3) gi|119370087|sp|Q07WU7.2|FRDA_SHEFN (119370087); Fumarate reductase iron-sulfur subunit gi|81175308|sp|P0AC47.2|FRDB_ECOLI (81175308); Fumarate reductase flavoprotein subunit (Flavocytochrome c) (Flavocytochrome c3) (Fcc3) gi|119370088|sp|P0C278.1|FRDA_SHEFR (119370088); Frd operon uncharacterized protein C gi|40663|sp|P20927.1|YFRC_PROVU (140663); Frd operon probable iron-sulfur subunit A gi|40661|sp|P20925.1|YFRA_PROVU (140661); Fumarate reductase iron-sulfur subunit gi|20493|sp|P20921.2|FRDB_PROVU(120493); Fumarate reductase flavoprotein subunit gi|2494617|sp|O06913.2|FRDA_HELPY (2494617); Fumarate reductase flavoprotein subunit precursor (Iron(III)-induced flavocytochrome C3) (Ifc3) gi|13878499|sp|Q9Z4P0.1|FRD2_SHEFN (13878499); Fumarate reductase flavoprotein subunit gi|54041009|sp|P64174.1|FRDA_MYCTU (54041009); Fumarate reductase flavoprotein subunit gi|54037132|sp|P64175.1|FRDA_MYCBO (54037132); Fumarate reductase flavoprotein subunit gi|12230114|sp|Q9ZMP0.1|FRDA_HELPJ (12230114); Fumarate reductase flavoprotein subunit gi|1169737|sp|P44894.1|FRDA_HAEIN (1169737); fumarate reductase flavoprotein subunit (*Wolinella succinogenes*) gi|13160058|emb|CAA04214.2|(13160058); Fumarate reductase flavoprotein subunit precursor (Flavocytochrome c) (FL cyt) gi|25452947|sp|P83223.2|FRDA_SHEON (25452947); fumarate reductase iron-sulfur subunit (*Wolinella succinogenes*) gi|2282000|emb|CAA04215.1| (2282000); and fumarate reductase cytochrome b subunit (*Wolinella succinogenes*) gi|2281998|emb|CAA04213.1| (2281998), each sequence associated with the accession number is incorporated herein by reference in its entirety.

Acetate kinase is encoded in *E. coli* by ackA. AckA is involved in conversion of acetyl-coA to acetate. Specifically, ackA catalyzes the conversion of acetyl-phophate to acetate. AckA homologs and variants are known. The NCBI database list approximately 1450 polypeptides as bacterial acetate kinases. For example, such homologs and variants include acetate kinase (*Streptomyces coelicolor* A3(2)) gi|21223784|ref|NP_629563.1| (21223784); acetate kinase (*Streptomyces coelicolor* A3(2)) gi|6808417|emb|CAB70654.1| (6808417); acetate kinase (*Streptococcus pyogenes* M1 GAS) gi|15674332|ref|NP_268506.1| (15674332); acetate kinase (*Campylobacter jejuni* subsp. *jejuni* NCTC 11168) gi|15792038|ref|NP_281861.1|(15792038); acetate kinase (*Streptococcus pyogenes* M1 GAS) gi|13621416|gb|AAK33227.1|(13621416); acetate kinase (Rhodopirellula baltica SH 1) gi|32476009|ref|NP_869003.1|(32476009); acetate kinase (Rhodopirellula baltica SH 1) gi|32472045|ref|NP_865039.1|(32472045); acetate kinase (Campylobacter jejuni subsp. jejuni NCTC 11168) gi|112360034|emb|CAL34826.1|(112360034); acetate kinase (Rhodopirellula baltica SH 1) gi|32446553|emb|CAD76388.1|(32446553); acetate kinase (Rhodopirellula baltica SH 1) gi|32397417|emb|CAD72723.1|(32397417); AckA (Clostridium kluyveri DSM 555) gi|153954016|ref|YP_001394781.1|(153954016); acetate kinase (Bifidobacterium longum NCC2705) gi|23465540|ref|NP_696143.1|(23465540); AckA (Clostridium kluyveri DSM 555) gi|146346897|gb|EDK33433.1|(146346897); Acetate kinase (Corynebacterium diphtheriae) gi|38200875|emb|CAE50580.1|(38200875); acetate kinase (Bifidobacterium longum NCC2705) gi|23326203|gb|AAN24779.1(23326203); Acetate kinase (Acetokinase) gi|67462089|sp|P0A6A3.1|ACKA_ECOLI (67462089); and AckA (Bacillus licheniformis DSM 13) gi|52349315|gb|AAU41949.1|(52349315), the sequences associated with such accession numbers are incorporated herein by reference.

Phosphate acetyltransferase is encoded in E. coli by pta. PTA is involved in conversion of acetate to acetyl-CoA. Specifically, PTA catalyzes the conversion of acetyl-coA to acetyl-phosphate. PTA homologs and variants are known. There are approximately 1075 bacterial phosphate acetyltransferases available on NCBI. For example, such homologs and variants include phosphate acetyltransferase Pta (Rickettsia felis URRWXCal2) gi|67004021|gb|AAY60947.1 (67004021); phosphate acetyltransferase (Buchnera aphidicola str. Cc (Cinara cedri)) gi|116256910|gb|ABJ90592.1| (116256910); pta (Buchnera aphidicola str. Cc (Cinara cedri)) gi|116515056|ref|YP_802685.1|(116515056); pta (Wigglesworthia glossinidia endosymbiont of Glossina brevipalpis) gi|25166135|dbj|BAC24326.1(25166135); Pta (Pasteurella multocida subsp. multocida str. Pm70) gi|12720993|gb|AAK02789.1|(12720993); Pta (Rhodospirillum rubrum) gi|25989720|gb|AAN75024.1|(25989720); pta (Listeria welshimeri serovar 6b str. SLCC5334) gi|116742418|emb|CAK21542.1(116742418); Pta (Mycobacterium avium subsp. paratuberculosis K-10) gi|41398816|gb|AAS06435.1|(41398816); phosphate acetyltransferase (pta) (Borrelia burgdorferi B31) gi|15594934|ref|NP_212723.1|(15594934); phosphate acetyltransferase (pta) (Borrelia burgdorferi B31) gi|2688508|gb|AAB91518.1|(2688508); phosphate acetyltransferase (pta) (Haemophilus influenzae Rd KW20) gi|1574131|gb|AAC22857.1|(1574131); Phosphate acetyltransferase Pta (Rickettsia bellii RML369-C) gi|91206026|ref|YP_538381.1|(91206026); Phosphate acetyltransferase Pta (Rickettsia bellii RML369-C) gi|91206025|ref|YP_538380.1|(91206025); phosphate acetyltransferase pta (Mycobacterium tuberculosis F11) gi|148720131|gb|ABRO4756.1|(148720131); phosphate acetyltransferase pta (Mycobacterium tuberculosis str. Haarlem) gi|134148886|gbEBA40931.1|(134148886); phosphate acetyltransferase pta (Mycobacterium tuberculosis C) gi|124599819|gb|EAY58829.1|(124599819); Phosphate acetyltransferase Pta (Rickettsia bellii RML369-C) gi|91069570|gb|ABE05292.1(91069570); Phosphate acetyltransferase Pta (Rickettsia bellii RML369-C) gi|91069569|gb|ABE05291.1|(91069569); phosphate acetyltransferase (pta) (Treponema pallidum subsp. pallidum str. Nichols) gi|15639088|ref|NP_218534.1|(15639088); and phosphate acetyltransferase (pta) (Treponema pallidum subsp. pallidum str. Nichols) gi|3322356|gb|AAC65090.1| (3322356), each sequence associated with the accession number is incorporated herein by reference in its entirety.

Pyruvate-formate lyase (Formate acetyltransferase) is an enzyme that catalyzes the conversion of pyruvate to acetly-coA and formate. It is induced by pfl-activating enzyme under anaerobic conditions by generation of an organic free radical and decreases significantly during phosphate limitation. Formate acetyltransferase is encoded in E. coli by pflB. PFLB homologs and variants are known. For examples, such homologs and variants include, for example, Formate acetyltransferase 1 (Pyruvate formate-lyase 1) gi|129879|sp|P09373.2|PFLB_ECOLI (129879); formate acetyltransferase 1 (Yersinia pestis CO92) gi|16121663|ref|NP_404976.1|(16121663); formate acetyltransferase 1 (Yersinia pseudotuberculosis IP 32953) gi|51595748|ref|YP_069939.1|(51595748); formate acetyltransferase 1 (Yersinia pestis biovar Microtus str. 91001) gi|45441037|ref|NP_992576.1|(45441037); formate acetyltransferase 1 (Yersinia pestis CO92) gi|115347142|emb|CAL20035.1|(115347142); formate acetyltransferase 1 (Yersinia pestis biovar Microtus str. 91001) gi|45435896|gb|AAS61453.1|(45435896); formate acetyltransferase 1 (Yersinia pseudotuberculosis IP 32953) gi|51589030|emb|CAH20648.1|(51589030); formate acetyltransferase 1 (Salmonella enterica subsp. enterica serovar Typhi str. CT18) gi|16759843|ref|NP_455460.1| (16759843); formate acetyltransferase 1 (Salmonella enterica subsp. enterica serovar Paratyphi A str. ATCC 9150) gi|56413977|ref|YP_151052.1|(56413977); formate acetyltransferase 1 (Salmonella enterica subsp. enterica serovar Typhi) gi|16502136|emb|CAD05373.1|(16502136); formate acetyltransferase 1 (Salmonella enterica subsp. enterica serovar Paratyphi A str. ATCC 9150) gi|56128234|gb|AAV77740.1|(56128234); formate acetyltransferase 1 (Shigella dysenteriae Sd197) gi|82777577|ref|YP_403926.1|(82777577); formate acetyltransferase 1 (Shigella flexneri 2a str. 2457T) gi|30062438|ref|NP_836609.1|(30062438); formate acetyltransferase 1 (Shigella flexneri 2a str. 2457T) gi|30040684|gb|AAP16415.1|(30040684); formate acetyltransferase 1 (Shigella flexneri 5 str. 8401) gi|110614459|gb|ABF03126.1(110614459); formate acetyltransferase 1 (Shigella dysenteriae Sd197) gi|81241725|gb|ABB62435.1|(81241725); formate acetyltransferase 1 (Escherichia coli O157:H7 EDL933) gi|12514066|gb|AAG55388.1|AE005279_8(12514066); formate acetyltransferase 1 (Yersinia pestis KIM) gi|22126668|ref|NP_670091.1|(22126668); formate acetyltransferase 1 (Streptococcus agalactiae A909) gi|76787667|ref|YP_330335.1|(76787667); formate acetyltransferase 1 (Yersinia pestis KIM) gi|21959683|gb|AAM86342.1|AE013882_3(21959683); formate acetyltransferase 1 (Streptococcus agalactiae A909) gi|76562724|gb|ABA45308.1|(76562724); formate acetyltransferase 1 (Yersinia enterocolitica subsp. enterocolitica 8081) gi|123441844|ref|YP_001005827.1|(123441844); formate acetyltransferase 1 (Shigella flexneri 5 str. 8401) gi|110804911|ref|YP_688431.1|(110804911); formate acetyltransferase 1 (Escherichia coli UTI89) gi|91210004|ref|YP_539990.1|(91210004); formate acetyltransferase 1 (Shigella boydii Sb227) gi|82544641|ref|YP_408588.1|(82544641); formate acetyltransferase 1 (Shigella sonnei Ss046) gi|74311459|ref|YP_309878.1|(74311459); formate acetyltransferase 1 (*Klebsiella pneumoniae* subsp. *pneumoniae* MGH 78578) gi|152969488|ref|YP_001334597.1| (152969488); formate acetyltransferase 1 (*Salmonella enterica* subsp. *enterica* serovar *Typhi* Ty2) gi|29142384|ref|NP_805726.1|(29142384); formate acetyltransferase 1 (*Shigella flexneri* 2a str. 301) gi|24112311|ref|NP_706821.1|(24112311); formate acetyltransferase 1 (*Escherichia coli* O157:H7 EDL933) gi|15800764|ref|NP_286778.1|(15800764); formate acetyltransferase 1 (*Klebsiella pneumoniae* subsp. *pneumoniae* MGH 78578) gi|50954337|gb|ABR76367.1|(150954337); formate acetyltransferase 1 (*Yersinia pestis* CA88-4125) gi|149366640|ref|ZP_01888674.1|(149366640); formate acetyltransferase 1 (*Yersinia pestis* CA88-4125) gi|149291014|gb|EDM41089.1|(149291014); formate acetyltransferase 1 (*Yersinia enterocolitica* subsp. *enterocolitica* 8081) gi|122088805|emb|CAL11611.1| (122088805); formate acetyltransferase 1 (*Shigella sonnei* Ss046) gi|73854936|gb|AAZ87643.1|(73854936); formate acetyltransferase 1 (*Escherichia coli* UTI89) gi|91071578|gb|ABE06459.1|(91071578); formate acetyltransferase 1 (*Salmonella enterica* subsp. *enterica* serovar *Typhi* Ty2) gi|29138014|gb|AAO69575.1|(29138014); formate acetyltransferase 1 (*Shigella boydii* Sb227) gi|81246052|gb|ABB66760.1(81246052); formate acetyltransferase 1 (*Shigella flexneri* 2a str. 301) gi|24051169|gb|AAN42528.1|(24051169); formate acetyltransferase 1 (*Escherichia coli* O157:H7 str. Sakai) gi|13360445|dbj|BAB34409.1|(13360445); formate acetyltransferase 1 (*Escherichia coli* O157:H7 str. Sakai) gi|15830240|ref|NP_309013.1|(15830240); formate acetyltransferase I (pyruvate formate-lyase 1) (*Photorhabdus luminescens* subsp. *laumondii* TTO1) gi|36784986|emb|CAE13906.1|(36784986); formate acetyltransferase I (pyruvate formate-lyase 1) (*Photorhabdus luminescens* subsp. *laumondii* TTO1) gi|37525558|ref|NP_928902.1|(37525558); formate acetyltransferase (*Staphylococcus aureus* subsp. *aureus* Mu50) gi|14245993|dbj|BAB56388.1|(14245993); formate acetyltransferase (*Staphylococcus aureus* subsp. *aureus* Mu50) gi|15923216|ref|NP_370750.1|(15923216); Formate acetyltransferase (Pyruvate formate-lyase) gi|81706366|sp|Q7A7X6.1|PFLB_STAAN (81706366); Formate acetyltransferase (Pyruvate formate-lyase) gi|81782287|sp|Q99WZ7.1|PFLB_STAAM (81782287); Formate acetyltransferase (Pyruvate formate-lyase) gi|81704726|sp|Q7A1W9.1|PFLB_STAAW (81704726); formate acetyltransferase (*Staphylococcus aureus* subsp. *aureus* Mu3) gi|156720691|dbj|BAF77108.1|(156720691); formate acetyltransferase (*Erwinia carotovora* subsp. *atroseptica* SCRI1043) gi|50121521|ref|YP_050688.1| (50121521); formate acetyltransferase (*Erwinia carotovora* subsp. *atroseptica* SCRI1043) gi|49612047|emb|CAG75496.1|(49612047); formate acetyltransferase (*Staphylococcus aureus* subsp. *aureus* str. Newman) gi|50373174|dbj|BAF66434.1|(150373174); formate acetyltransferase (*Shewanella oneidensis* MR-1) gi|24374439|ref|NP_718482.1|(24374439); formate acetyltransferase (*Shewanella oneidensis* MR-1) gi|24349015|gb|AAN55926.1|AE015730_3(24349015); formate acetyltransferase (*Actinobacillus pleuropneumoniae* serovar 3 str. JL03) gi|165976461|ref|YP_001652054.1| (165976461); formate acetyltransferase (*Actinobacillus pleuropneumoniae* serovar 3 str. JL03) gi|165876562|gb|ABY69610.1|(165876562); formate acetyltransferase (*Staphylococcus aureus* subsp. *aureus* MW2) gi|212033651|dbj|BAB94066.1|(21203365); formate acetyltransferase (*Staphylococcus aureus* subsp. *aureus* N315) gi|13700141|dbj|BAB41440.1|(13700141); formate acetyltransferase (*Staphylococcus aureus* subsp. *aureus* str. Newman) gi|151220374|ref|YP_001331197.1| (151220374); formate acetyltransferase (*Staphylococcus aureus* subsp. *aureus* Mu3) gi|156978556|ref|YP_001440815.1|(156978556); formate acetyltransferase (*Synechococcus* sp. JA-2-3B'a(2-13)) gi|86607744|ref|YP_476506.1|(86607744); formate acetyltransferase (*Synechococcus* sp. JA-3-3Ab) gi|86605195|ref|YP_473958.1|(86605195); formate acetyltransferase (*Streptococcus pneumoniae* D39) gi|116517188|ref|YP_815928.1|(116517188); formate acetyltransferase (*Synechococcus* sp. JA-2-3B'a(2-13)) gi|86556286|gb|ABD01243.1|(86556286); formate acetyltransferase (*Synechococcus* sp. JA-3-3Ab) gi|86553737|gb|ABC98695.1|(86553737); formate acetyltransferase (*Clostridium novyi* NT) gi|118134908|gb|ABK61952.1|(118134908); formate acetyltransferase (*Staphylococcus aureus* subsp. *aureus* MRSA252) gi|49482458|ref|YP_039682.1|(49482458); and formate acetyltransferase (*Staphylococcus aureus* subsp. *aureus* MRSA252) gi|49240587|emb|CAG39244.1| (49240587), each sequence associated with the accession number is incorporated herein by reference in its entirety.

Alpha isopropylmalate synthase (EC 2.3.3.13, sometimes referred to a 2-isopropylmalate synthase, alpha-IPM synthetase) catalyzes the condensation of the acetyl group of acetyl-CoA with 3-methyl-2-oxobutanoate (2-oxoisovalerate) to form 3-carboxy-3-hydroxy-4-methylpentanoate (2-isopropylmalate). Alpha isopropylmalate synthase is encoded in *E. coli* by leuA. LeuA homologs and variants are known. For example, such homologs and variants include, for example, 2-isopropylmalate synthase (*Corynebacterium glutamicum*) gi|452382|emb|CAA50295.1|(452382); 2-isopropylmalate synthase (*Escherichia coli* K12) gi|16128068|ref|NP_414616.1|(16128068); 2-isopropylmalate synthase (*Escherichia coli* K12) gi|1786261|gb|AAC73185.1|(1786261); 2-isopropylmalate synthase (*Arabidopsis thaliana*) gi|15237194|ref|NP_197692.1|(15237194); 2-isopropylmalate synthase (*Arabidopsis thaliana*) gi|42562149|ref|NP_173285.2|(42562149); 2-isopropylmalate synthase (*Arabidopsis thaliana*) gi|15221125|ref|NP_177544.1|(15221125); 2-isopropylmalate synthase (*Streptomyces coelicolor* A3(2)) gi|32141173|ref|NP_733575.1|(32141173); 2-isopropylmalate synthase (*Rhodopirellula baltica* SH 1) gi|32477692|ref|NP_870686.1|(32477692); 2-isopropylmalate synthase (*Rhodopirellula baltica* SH 1) gi|32448246|emb|CAD77763.1|(32448246); 2-isopropylmalate synthase (Akkermansia muciniphila ATCC BAA-835) gi|166241432|gb|EDR53404.1|(166241432); 2-isopropylmalate synthase (Herpetosiphon *aurantiacus* ATCC 23779) gi|159900959|ref|YP_001547206.1|(159900959); 2-isopropylmalate synthase (Dinoroseobacter shibae DFL 12) gi|159043149|ref|YP_001531943.1|(159043149); 2-isopropylmalate synthase (Salinispora arenicola CNS-205) gi|159035933|ref|YP_001535186.1|(159035933); 2-isopropylmalate synthase (Clavibacter *michiganensis* subsp. *michiganensis* NCPPB 382) gi|148272757|ref|YP_001222318.1| (148272757); 2-isopropylmalate synthase (*Escherichia coli* B) gi|124530643|ref|ZP_01701227.1|(124530643); 2-isopropylmalate synthase (*Escherichia coli* C str. ATCC 8739) gi|124499067|gb|EAY46563.1|(124499067); 2-isopropylmalate synthase (*Bordetella pertussis* Tohama I) gi|33591386|ref|NP_879030.1|(33591386); 2-isopropylmalate synthase (Polynucleobacter necessarius STIR1) gi|164564063|ref|ZP_02209880.1|(164564063); 2-isopropylmalate synthase (Polynucleobacter necessarius STIR1) gi|164506789|gb|EDQ94990.1|(164506789); and 2-isopropylmalate synthase (Bacillus weihenstephanensis KBAB4) gi|163939313|ref|YP_001644197.1|(163939313), any sequence associated with the accession number is incorporated herein by reference in its entirety.

BCAA aminotranferases catalyze the formation of branched chain amino acids (BCAA). A number of such aminotranferases are known and are exemplified by ilvE in *E. coli*. Exemplary homologs and variants include sequences designated by the following accession numbers: ilvE (*Microcystis aeruginosa* PCC 7806) gi|159026756|emb|CAO86637.1|(159026756); IlvE (*Escherichia coli*) gi|87117962|gb|ABD20288.1|(87117962); IlvE (*Escherichia coli*) gi|87117960|gb|ABD20287.1| (87117960); IlvE (*Escherichia coli*) gi|87117958|gb|ABD20286.1|(87117958); IlvE (*Shigella flexneri*) gi|87117956|gb|ABD20285.1|(87117956); IlvE (*Shigella flexneri*) gi|87117954|gb|ABD20284.1| (87117954); IlvE (*Shigella flexneri*) gi|87117952|gb|ABD20283.1|(87117952); IlvE (*Shigella flexneri*) gi|87117950|gb|ABD20282.1|(87117950); IlvE (*Shigella flexneri*) gi|87117948|gb|ABD20281.1| (87117948); IlvE (*Shigella flexneri*) gi|87117946|gb|ABD20280.1|(87117946); IlvE (*Shigella flexneri*) gi|87117944|gb|ABD20279.1|(87117944); IlvE (*Shigella flexneri*) gi|87117942|gb|ABD20278.1| (87117942); IlvE (*Shigella flexneri*) gi|87117940|gb|ABD20277.1|(87117940); livE (*Shigella flexneri*) gi|87117938|gb|ABD20276.1|(87117938); IlvE (*Shigella dysenteriae*) gi|87117936|gb|ABD20275.1| (87117936); livE (*Shigella dysenteriae*) gi|87117934|gb|ABD20274.1|(87117934); IlvE (*Shigella dysenteriae*) gi|87117932|gb|ABD20273.1|(87117932); IlvE (*Shigella dysenteriae*) gi|87117930|gb|ABD20272.1| (87117930); and livE (*Shigella dysenteriae*) gi|87117928|gb|ABD20271.1|(87117928), each sequence associated with the accession number is incorporated herein by reference.

Tyrosine aminotransferases catalyzes transamination for both dicarboxylic and aromatic amino-acid substrates. A tyrosine aminotransferase of *E. coli* is encoded by the gene tyrB. TyrB homologs and variants are known. For example, such homologs and variants include tyrB (*Bordetella petrii*) gi|163857093|ref|YP_001631391.1|(163857093); tyrB (*Bordetella petrii*) gi|163260821|emb|CAP43123.1| (163260821); aminotransferase gi|551844|gb|AAA24704.1| (551844); aminotransferase (*Bradyrhizobium* sp. BTAi1) gi|146404387|gb|ABQ32893.1|(146404387); tyrosine aminotransferase TyrB (*Salmonella enterica*) gi|4775574|emb|CAB40973.2|(4775574); tyrosine aminotransferase (*Salmonella typhimurium* LT2) gi|16422806|gb|AAL23072.1|(16422806); and tyrosine aminotransferase gi|148085|gb|AAA24703.1|(148085), each sequence of which is incorporated herein by reference.

Pyruvate oxidase catalyzes the conversion of pyruvate to acetate and $CO_2$. In *E. coli*, pyruvate oxidase is encoded by poxB. PoxB and homologs and variants thereof include, for example, pyruvate oxidase; PoxB (*Escherichia coli*) gi|685128|gb|AAB31180.1|||bbm|348451|bbs|154716 (685128); PoxB (*Pseudomonas fluorescens*) gi|32815820|gb|AAP88293.1|(32815820); poxB (*Escherichia coli*) gi|25269169|emb|CAD57486.1|(25269169); pyruvate dehydrogenase (*Salmonella enterica* subsp. *enterica* serovar *Typhi*) gi|6502101|emb|CAD05337.1| (16502101); pyruvate oxidase (*Lactobacillus plantarum*) gi|41691702|gb|AAS10156.1|(41691702); pyruvate dehydrogenase (*Bradyrhizobium japonicum*) gi|20257167|gb|AAM12352.1|(20257167); pyruvate dehydrogenase (*Yersinia pestis* KIM) gi|22126698|ref|NP_670121.1|(22126698); pyruvate dehydrogenase (cytochrome) (*Yersinia pestis* biovar *Antiqua* str. B42003004) gi|166211240|ref|ZP_02237275.1| (166211240); pyruvate dehydrogenase (cytochrome) (*Yersinia pestis* biovar *Antiqua* str. B42003004) gi|166207011|gb|EDR51491.1|(166207011); pyruvate dehydrogenase (*Pseudomonas syringae* pv. tomato str. DC3000) gi|28869703|ref|NP_792322.1|(28869703); pyruvate dehydrogenase (*Salmonella typhimurium* LT2) gi|16764297|ref|NP_459912.1|(16764297); pyruvate dehydrogenase (*Salmonella enterica* subsp. *enterica* serovar *Typhi* str. CT18) gi|16759808|ref|NP_455425.1|(16759808); pyruvate dehydrogenase (cytochrome) (*Coxiella burnetii* Dugway 5J108-111) gi|154706110|ref|YP_001424132.1| (154706110); pyruvate dehydrogenase (*Clavibacter michiganensis* subsp. *michiganensis* NCPPB 382) gi|148273312|ref|YP_001222873.1|(148273312); pyruvate oxidase (*Lactobacillus acidophilus* NCFM) gi|58338213|ref|YP_194798.1|(58338213); and pyruvate dehydrogenase (*Yersinia pestis* C092) gi|16121638|ref|NP_404951.1|(16121638), the sequences of each accession number are incorporated herein by reference.

L-threonine 3-dehydrogenase (EC 1.1.1.103) catalyzes the conversion of L-threonine to L-2-amino-3-oxobutanoate. The gene tdh encodes an L-threonine 3-dehydrogenase. There are approximately 700 L-threonine 3-dehydrogenases from bacterial organism recognized in NCBI. Various homologs and variants of tdh include, for example, L-threonine 3-dehydrogenase gi|135560|sp|P07913.1|TDH_ECOLI (135560); L-threonine 3-dehydrogenase gi|166227854|sp|A4TSC6.1|TDH_YERPP (166227854); L-threonine 3-dehydrogenase gi|166227853|sp|A1JHX8.1|TDH_YERE8 (166227853); L-threonine 3-dehydrogenase gi|166227852|sp|A6UBM6.1|TDH_SINMW (166227852); L-threonine 3-dehydrogenase gi|166227851|sp|A1RE07.1|TDH_SHESW (166227851); L-threonine 3-dehydrogenase gi|166227850|sp|A0L2Q3.1|TDH_SHESA (166227850); L-threonine 3-dehydrogenase gi|166227849|sp|A4YCC5.1|TDH_SHEPC (166227849); L-threonine 3-dehydrogenase gi|166227848|sp|A3QJC8.1|TDH_SHELP (166227848); L-threonine 3-dehydrogenase gi|166227847|sp|A6WUG6.1|TDH_SHEB8 (166227847); L-threonine 3-dehydrogenase gi|166227846|sp|A3CYN0.1|TDH_SHEB5 (166227846); L-threonine 3-dehydrogenase gi|166227845|sp|A1S1Q3.1|TDH_SHEAM (166227845); L-threonine 3-dehydrogenase gi|166227844|sp|A4FND4.1|TDH_SACEN (166227844); L-threonine 3-dehydrogenase gi|166227843|sp|A1SVW5.1|TDH_PSYIN (166227843); L-threonine 3-dehydrogenase gi|166227842|sp|A5IGK7.1|TDH_LEGPC(166227842); L-threonine 3-dehydrogenase gi|166227841|sp|A6TFL2.1|TDH_KLEP7 (166227841); L-threonine 3-dehydrogenase gi|166227840|sp|A4IZ92.1|TDH_FRATW (166227840); L-threonine 3-dehydrogenase gi|166227839|sp|A0Q5K3.1|TDH_FRATN (166227839);

L-threonine 3-dehydrogenase gi|166227838|sp|A7NDM9.1|TDH_FRATF (166227838); L-threonine 3-dehydrogenase gi|166227837|sp|A7MID0.1TDH_ENTS8 (166227837); and L-threonine 3-dehydrogenase gi|166227836|sp|A1AHF3.1|TDH_ECOK1(166227836), the sequences associated with each accession number are incorporated herein by reference.

Acetohydroxy acid synthases (e.g. ilvH) and acetolactate synthases (e.g., alsS, ilvB, ilvI) catalyze the synthesis of the branched-chain amino acids (valine, leucine, and isoleucine). IlvH encodes an acetohydroxy acid synthase in *E. coli* (see, e.g., acetohydroxy acid synthase AHAS III (IlvH) (*Escherichia coli*) gi|40846|emb|CAA38855.1|(40846), incorporated herein by reference). Homologs and variants as well as operons comprising ilvH are known and include, for example, ilvH (*Microcystis aeruginosa* PCC 7806) gi|159026908|emb|CAO89159.1|(159026908); IlvH (*Bacillus amyloliquefaciens* FZB42) gi|154686966|ref|YP_001422127.1|(154686966); IlvH (*Bacillus amyloliquefaciens* FZB42) gi|154352817|gb|ABS74896.1|(154352817); IlvH (*Xenorhabdus nematophila*) gi|131054140|gb|ABO32787.1| (131054140); IlvH (*Salmonella typhimurium*) gi|7631124|gb|AAF65177.11AF117227_2 (7631124), ilvN (*Listeria innocua*) gi|16414606|emb|CAC97322.1| (16414606); ilvN (*Listeria monocytogenes*) gi|16411438|emb|CAD00063.1|(16411438); acetohydroxy acid synthase (*Caulobacter crescentus*) gi|408939|gb|AAA23048.1| (408939); acetohydroxy acid synthase I, small subunit (*Salmonella enterica* subsp. *enterica* serovar *Typhi*) gi|16504830|emb|CAD03199.1| (16504830); acetohydroxy acid synthase, small subunit (*Tropheryma whipplei* TW08/27) gi|28572714|ref|NP_789494.1|(28572714); acetohydroxy acid synthase, small subunit (*Tropheryma whipplei* TW08/27) gi|28410846|emb|CAD67232.1|(28410846); acetohydroxy acid synthase I, small subunit (*Salmonella enterica* subsp. *enterica* serovar Paratyphi A str. ATCC 9150) gi|56129933|gb|AAV79439.1|(56129933); acetohydroxy acid synthase small subunit; acetohydroxy acid synthase, small subunit gi|551779|gb|AAA62430.1|(551779); acetohydroxy acid synthase I, small subunit (*Salmonella enterica* subsp. *enterica* serovar *Typhi* Ty2) gi|29139650|gb|AAO71216.1|(29139650); acetohydroxy acid synthase small subunit (*Streptomyces cinnamonensis*) gi|5733116|gb|AAD49432.1|AF175526_1(5733116); acetohydroxy acid synthase large subunit; and acetohydroxy acid synthase, large subunit gi|400334|gb|AAA62429.1| (400334), the sequences associated with the accession numbers are incorporated herein by reference. Acetolactate synthase genes include alsS and ilvI. Homologs of ilvI and alsS are known and include, for example, acetolactate synthase small subunit (*Bifidobacterium longum* NCC2705) gi|23325489|gb|AAN24137.1|(23325489); acetolactate synthase small subunit (*Geobacillus stearothermophilus*) gi|19918933|gb|AAL99357.1|(19918933); acetolactate synthase (*Azoarcus* sp. BH72) gi|119671178|emb|CAL95091.1| (119671178); Acetolactate synthase small subunit (*Corynebacterium diphtheriae*) gi|38199954|emb|CAE49622.1| (38199954); acetolactate synthase (*Azoarcus* sp. BH72) gi|119669739|emb|CAL93652.1|(119669739); acetolactate synthase small subunit (*Corynebacterium jeikeium* K411) gi|68263981|emb|CAI37469.1|(68263981); acetolactate synthase small subunit (*Bacillus subtilis*) gi|1770067|emb|CAA99562.1|(1770067); Acetolactate synthase isozyme 1 small subunit (AHAS-I) (Acetohydroxy-acid synthase I small subunit) (ALS-I) gi|83309006|sp|P0ADF8.1|ILVN_ECOLI (83309006); acetolactate synthase large subunit (*Geobacillus stearothermophilus*) gi|19918932|gb|AAL99356.1|(19918932); and Acetolactate synthase, small subunit (*Thermoanaerobacter tengcongensis* MB4) gi|20806556|ref|NP_621727.1| (20806556), the sequences associated with the accession numbers are incorporated herein by reference. There are approximately 1120 ilvB homologs and variants listed in NCBI.

Acetohydroxy acid isomeroreductase is the second enzyme in parallel pathways for the biosynthesis of isoleucine and valine. IlvC encodes an acetohydroxy acid isomeroreductase in *E. coli*. Homologs and variants of ilvC are known and include, for example, acetohydroxyacid reductoisomerase (*Schizosaccharomyces pombe* 972h-) gi|162312317|ref|NP_001018845.2|(162312317); acetohydroxyacid reductoisomerase (*Schizosaccharomyces pombe*) gi|3116142|emb|CAA18891.1|(3116142); acetohydroxyacid reductoisomerase (*Saccharomyces cerevisiae* YJM789) gi|151940879|gb|EDN59261.1|(151940879); Ilv5p: acetohydroxyacid reductoisomerase (*Saccharomyces cerevisiae*) gi|609403|gb|AAB67753.1|(609403); ACL198Wp (*Ashbya gossypii* ATCC 10895) gi|45185490|ref|NP_983206.1| (45185490); ACL198Wp (*Ashbya gossypii* ATCC 10895) gi|44981208|gb|AAS51030.1|(44981208); acetohydroxyacid isomeroreductase; Ilv5x (*Saccharomyces cerevisiae*) gi|957238|gb|AAB33579.1||bbm|369068|bbs|165406 (957238); acetohydroxy-acid isomeroreductase; Ilv5g (*Saccharomyces cerevisiae*) gi|957236|gb|AAB33578.1|bbm|369064|bbs|165405 (957236); and ketol-acid reductoisomerase (*Schizosaccharomyces pombe*) gi|2696654|dbj|BAA24000.1|(2696654), each sequence associated with the accession number is incorporated herein by reference.

Dihydroxy-acid dehydratases catalyzes the fourth step in the biosynthesis of isoleucine and valine, the dehydratation of 2,3-dihydroxy-isovaleic acid into alpha-ketoisovaleric acid. IlvD and ilv3 encode a dihydroxy-acid dehydratase. Homologs and variants of dihydroxy-acid dehydratases are known and include, for example, IlvD (*Mycobacterium leprae*) gi|2104594|emb|CAB08798.1|(2104594); dihydroxyacid dehydratase (*Tropheryma whipplei* TW08/27) gi|28410848|emb|CAD67234.1|(28410848); dihydroxyacid dehydratase (*Mycobacterium leprae*) gi|3093837|emb|CAC32140.1|(13093837); dihydroxy-acid dehydratase (*Rhodopirellula baltica* SH 1) gi|32447871|emb|CAD77389.1|(32447871); and putative dihydroxy-acid dehydratase (*Staphylococcus aureus* subsp. *aureus* MRSA252) gi|49242408|emb|CAG41121.1| (49242408), each sequence associated with the accession numbers are incorporated herein by reference.

2-ketoacid decarboxylases catalyze the conversion of a 2-ketoacid to the respective aldehyde. For example, 2-ketoisovalerate decarboxylase catalyzes the conversion of 2-ketoisovalerate to isobutyraldehyde. A number of 2-ketoacid decarboxylases are known and are exemplified by the pdc, pdc1, pdc5, pdc6, aro10, thI3, kdcA and kivd genes. Exemplary homologs and variants useful for the conversion of a 2-ketoacid to the respective aldehyde comprise sequences designated by the following accession numbers and identified enzymatic activity: gi|44921617|gb|AAS49166.1| branched-chain alpha-keto acid decarboxylase (*Lactococcus lactis*); gi|5004729|ref|NP_149189.1| Pyruvate decarboxylase (*Clostridium acetobutylicum* ATCC 824); gi|82749898|ref|YP_415639.1| probable pyruvate decarboxylase (*Staphylococcus aureus* RF122);

gi|77961217|ref|ZP_00825060.1| COG3961: Pyruvate decarboxylase and related thiamine pyrophosphate-requiring enzymes (*Yersinia mollaretii* ATCC 43969); gi|71065418|ref|YP_264145.1| putative pyruvate decarboxylase (*Psychrobacter arcticus* 273-4); gi|16761331|ref|NP_456948.1| putative decarboxylase (*Salmonella enterica* subsp. *enterica* serovar *Typhi* str. CT18); gi|93005792|ref|YP_580229.1| Pyruvate decarboxylase (*Psychrobacter cryohalolentis* K5); gi|23129016|ref|ZP_00110850.1| COG3961: Pyruvate decarboxylase and related thiamine pyrophosphate-requiring enzymes (*Nostoc punctiforme* PCC 73102); gi|16417060|gb|AAL18557.1|AF354297_1 pyruvate decarboxylase (*Sarcina ventriculi*); gi|15607993|ref|NP_215368.1|PROBABLE PYRUVATE OR INDOLE-3-PYRUVATE DECARBOXYLASE PDC (*Mycobacterium tuberculosis* H37Rv); gi|41406881|ref|NP_959717.1| Pdc (*Mycobacterium avium* subsp. *paratuberculosis* K-10); gi|91779968|ref|YP_555176.1| putative pyruvate decarboxylase (*Burkholderia xenovorans* LB400); gi|15828161|ref|NP_302424.1| pyruvate (or indolepyruvate) decarboxylase (*Mycobacterium leprae* TN); gi|118616174|ref|YP_904506.1| pyruvate or indole-3-pyruvate decarboxylase Pdc (*Mycobacterium ulcerans* Agy99); gi|67989660|ref|NP_001018185.1| hypothetical protein SPAC3H8.01 (*Schizosaccharomyces pombe* 972h-); gi|21666011|gb|AAM73540.1|AF282847_1 pyruvate decarboxylase PdcB (*Rhizopus oryzae*); gi|69291130|ref|ZP_00619161.1| Pyruvate decarboxylase: Pyruvate decarboxylase (*Kineococcus radiotolerans* SRS30216); gi|66363022|ref|XP_628477.1| pyruvate decarboxylase (*Cryptosporidium parvum* Iowa II); gi|70981398|ref|XP_731481.1| pyruvate decarboxylase (*Aspergillus fumigatus* Af293); gi|121704274|ref|XP_001270401.1| pyruvate decarboxylase, putative (*Aspergillus clavatus* NRRL 1); gi|119467089|ref|XP_001257351.1| pyruvate decarboxylase, putative (*Neosartorya fischeri* NRRL 181); gi|26554143|ref|NP_758077.1| pyruvate decarboxylase (*Mycoplasma penetrans* HF-2); gi|21666009|gb|AAM73539.1|AF282846_1 pyruvate decarboxylase PdcA (*Rhizopus oryzae*).

Alcohol dehydrogenases (adh) catalyze the final step of amino acid catabolism, conversion of an aldehyde to a long chain or complex alcohol. Various adh genes are known in the art. As indicated herein adh1 homologs and variants include, for example, adh2, adh3, adh4, adh5, adh 6 and sfa1 (see, e.g., SFA (*Saccharomyces cerevisiae*) gi|288591|emb|CAA48161.1| (288591); the sequence associated with the accession number is incorporated herein by reference).

Citramalate synthase catalyzes the condensation of pyruvate and acetate. CimA encodes a citramalate synthase. Homologs and variants are known and include, for example, citramalate synthase (*Leptospira biflexa* serovar Patoc) gi|116664687|gb|ABK13757.1|(116664687); citramalate synthase (*Leptospira biflexa* serovar Monteralerio) gi|116664685|gb|ABK13756.1|(116664685); citramalate synthase (*Leptospira interrogans* serovar Hebdomadis) gi|116664683|gb|ABK13755.1|(116664683); citramalate synthase (*Leptospira interrogans* serovar Pomona) gi|116664681|gb|ABK13754.1|(116664681); citramalate synthase (*Leptospira interrogans* serovar *Australis*) gi|116664679|gb|ABK13753.1|(116664679); citramalate synthase (*Leptospira interrogans* serovar *Autumnalis*) gi|116664677|gb|ABK13752.1|(116664677); citramalate synthase (*Leptospira interrogans* serovar Pyrogenes) gi|116664675|gb|ABK13751.1|(116664675); citramalate synthase (*Leptospira interrogans* serovar *Canicola*) gi|116664673|gb|ABK13750.1|(116664673); citramalate synthase (*Leptospira interrogans* serovar Lai) gi|116664671|gb|ABK13749.1|(116664671); CimA (*Leptospira meyeri* serovar Semaranga) gi|119720987|gb|ABL98031.1|(119720987); (R)-citramalate synthase gi|2492795|sp|Q58787.1|CIMA_METJA (2492795); (R)-citramalate synthase gi|22095547|sp|P58966.1|CIMA_METMA (22095547); (R)-citramalate synthase gi|22001554|sp|Q8TJJ1.1|CIMA_METAC (22001554); (R)-citramalate synthase gi|22001553|sp|O26819.1|CIMA_METTH (22001553); (R)-citramalate synthase gi|22001555|sp|Q8TYB1.1|CIMA_METKA (22001555); (R)-citramalate synthase (*Methanococcus maripaludis* S2) gi|45358581|ref|NP_988138.1|(45358581); (R)-citramalate synthase (*Methanococcus maripaludis* S2) gi|44921339|emb|CAF30574.1|(44921339); and similar to (R)-citramalate synthase (*Candidatus Kuenenia* stuttgartiensis) gi|91203541|emb|CAJ71194.1|(91203541), each sequence associated with the foregoing accession numbers is incorporated herein by reference.

In one embodiment a microorganism of the disclosure can be characterized as an *E. coli* comprising rrnBT14DlacZWJ16 hsdR514 DaraBADAH33 DrhaBADLD78 (with F' transduced from XL-1 blue to supply lacIq), ΔadhE, ΔldhA, ΔfrdBC, Δfnr, Δpta and ΔpflB and containing pSA55 and pSA69, wherein pSA55 is a ColE1 origin derived plasmid with kivd (*Lactococcus lactis*) and adh2 (*Saccharomyces cerevisiae*) genes under the control of the PLlacO1 and an ampicillin resistance gene and pSA69 is a p15A origin derived plasmid with alsS (*Bacillus subtilis*), ilvC (*E. coli*) and ilvD (*E. coli*) genes under the control of the PLlacO1 and a kanamycin resistance gene.

In another embodiment a microorganism of the disclosure can be characterized as an *E. coli* comprising rrnBT14DlacZWJ16 hsdR514 DaraBADAH33 DrhaBADLD78 (with F' transduced from XL-1 blue to supply lacIq), ΔmetA, Δtdh, ΔilvB, ΔilvI and ΔadhE with pCS49, pSA62 and pSA55I, wherein pSA55I comprises a ColE1 origin derived plasmid with kivd (*Lactococcus lactis*) and adh2 (*Saccharomyces cerevisiae*) genes under the control of the PLlacO1 and an ampicillin resistance gene with lacI after the ampicillin resistance gene, pSA62 is a p15A origin derived plasmid with ilvA (*E. coli*) and leuABCD (*E. coli*) genes under the control of the PLlacO1 and a kanamycin resistance gene, and pCS49 is a pSC101* origin derived plasmid with thrA(fbr)BC (*E. coli*) genes under the control of the PLlacO1 and a spectinomycin resistance gene.

The disclosure also provides deposited microorganisms. The deposited microorganisms are exemplary only and, based upon the disclosure, one of ordinary skill in the art can modify additional parental organisms of different species or genotypes to arrive at a microorganism of the disclosure that produces isobutanol and n-butanol.

The disclosure provides a recombinant microorganism designated SA237 and having ATCC accession no. PTA-8945 as deposited with the ATCC on Feb. 7, 2008. The disclosure includes cultures of microorganisms comprising a population of a microorganism of ATCC accession no. PTA-8945, including mixed cultures. Also provided are polynucleotide fragments derived from ATCC accession no. PTA-8945, which are useful in the preparation of a microorganism that produces isobutanol at a yield of 0.12 to about 0.41 grams of isobutanol per gram of glucose. For examples such fragments can comprise a polynucleotide of about 1000 base pairs to several million base pairs. Also included are bioreactors comprising a population of the microorganism having ATCC accession no. PTA-8945 in the production of isobutanol or phenylethanol. One of ordinary skill in the art, using the deposited microorganism, can readily determine the sequence of the deposited organism or fragments thereof encoding any of the genes and polynucleotides described herein, including locations of knockouts or gene disruptions.

The disclosure also provides a recombinant microorganism designated CRS-BuOH23 and having ATCC accession no. PTA-8944 as deposited with the ATCC on Feb. 7, 2008. The disclosure includes cultures of microorganisms comprising a population of a microorganism of ATCC accession no. PTA-8944, including mixed cultures. Also provided are polynucleotide fragments derived from ATCC accession no. PTA-8944, which are useful in the preparation of a microorganism that produces n-butanol. For examples such fragments can comprise a polynucleotide of about 1000 base pairs to several million base pairs. Also included are bioreactors comprising a population of the microorganism having ATCC accession no. PTA-8944 in the production of n-butanol. One of ordinary skill in the art, using the deposited microorganism, can readily determine the sequence of the deposited organism or fragments thereof encoding any of the genes and polynucleotides described herein, including locations of knockouts or gene disruptions.

It is understood that a range of microorganisms can be modified to include a recombinant metabolic pathway suitable for the production of e.g., 1-propanol, isobutanol, 1-butanol, 2-methyl 1-butanol, 3-methyl 1-butanol or 2-phenylethanol. It is also understood that various microorganisms can act as "sources" for genetic material encoding target enzymes suitable for use in a recombinant microorganism provided herein. The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the procaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ((NaCl)); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or over-express endogenous polynucleotides, or to express non-endogenous sequences, such as those included in a vector, or which have a reduction in expression of an endogenous gene. The polynucleotide generally encodes a target enzyme involved in a metabolic pathway for producing a desired metabolite as described above. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

A "parental microorganism" refers to a cell used to generate a recombinant microorganism. The term "parental microorganism" describes a cell that occurs in nature, i.e. a "wild-type" cell that has not been genetically modified. The term "parental microorganism" also describes a cell that has been genetically modified but which does not express or over-express a target enzyme e.g., an enzyme involved in the biosynthetic pathway for the production of a desired metabolite such as 1-propanol, isobutanol, 1-butanol, 2-methyl 1-butanol, 3-methyl 1-butanol or 2-phenylethanol. For example, a wild-type microorganism can be genetically modified to express or over express a first target enzyme such as thiolase. This microorganism can act as a parental microorganism in the generation of a microorganism modified to express or over-express a second target enzyme e.g., hydroxybutyryl CoA dehydrogenase. In turn, the microorganism modified to express or over express e.g., thiolase and hydroxybutyryl CoA dehydrogenase can be modified to express or over express a third target enzyme e.g., crotonase. Accordingly, a parental microorganism functions as a reference cell for successive genetic modification events. Each modification event can be accomplished by introducing a nucleic acid molecule in to the reference cell. The introduction facilitates the expression or over-expression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

In another embodiment a method of producing a recombinant microorganism that converts a suitable carbon substrate to e.g., 1-propanol, isobutanol, 1-butanol, 2-methyl 1-butanol, 3-methyl 1-butanol or 2-phenylethanol is provided. The method includes transforming a microorganism with one or more recombinant polynucleotides encoding polypeptides that include, for example, acetohydroxy acid synthase (e.g., ilvIH operon), acetohydroxy acid isomeroreductase (e.g., ilvC), dihydroxy-acid dehydratase (e.g., ilvD), 2-keto-acid decarboxylase (e.g., PDC6, ARO10, THI3, kivd, or pdc), 2-isopropylmalate synthase (e.g., leuA), beta-isopropylmalate dehydrogenase (e.g., leuB), isopropylmalate isomerase (e.g., leuCD operon), threonine dehydratase (e.g., ilvA), alpha-isopropylmalate synthase (e.g., cimA), beta-isopropylmalate dehydrogenase (e.g., leuB), isopropylmalate isomerase (e.g., leuCD operon), threonine dehydratase (e.g., ilvA), acetolactate synthase (e.g., ilvMG or ilvNB), acetohydroxy acid isomeroreductase (e.g., ilvC), dihydroxy-acid dehydratase (e.g., ilvD), beta-isopropylmalate dehydrogenase (e.g., leuB), chorismate mutase P/prephenate dehydratase (e.g., pheA), chorismate mutase T/prephenate dehydrogenase (e.g., tyrA), 2-keto-acid decarboxylase (e.g., kivd, PDC6, or THI3), and alcohol dehydrogenase activity. Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. It is understood that the addition of sequences which do not alter the encoded activity of a polynucleotide, such as the addition of a non-functional or non-coding sequence, is a conservative variation of the basic nucleic acid. The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

It is understood that the polynucleotides described above include "genes" and that the nucleic acid molecules described above include "vectors" or "plasmids." For example, a polynucleotide encoding a keto thiolase can be encoded by an atoB gene or homolog thereof, or a fadA gene or homolog thereof. Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence. The term "nucleic acid" or "recombinant nucleic acid" refers to polynucleotides such as deoxyribonucleic acid (DNA), and, where appropriate, ribonucleic acid (RNA). The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The term "operon" refers two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

Those of skill in the art will recognize that, due to the degenerate nature of the genetic code, a variety of DNA compounds differing in their nucleotide sequences can be used to encode a given amino acid sequence of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate embodiments of the disclosure.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

Provided herein are methods for the heterologous expression of one or more of the biosynthetic genes involved in 1-propanol, isobutanol, 1-butanol, 2-methyl 1-butanol, 3-methyl 1-butanol, and/or 2-phenylethanol biosynthesis and recombinant DNA expression vectors useful in the method. Thus, included within the scope of the disclosure are recombinant expression vectors that include such nucleic acids. The term expression vector refers to a nucleic acid that can be introduced into a host microorganism or cell-free transcription and translation system. An expression vector can be maintained permanently or transiently in a microorganism, whether as part of the chromosomal or other DNA in the microorganism or in any cellular compartment, such as a replicating vector in the cytoplasm. An expression vector also comprises a promoter that drives expression of an RNA, which typically is translated into a polypeptide in the microorganism or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host microorganisms containing the vector can be identified and/or selected, may also be present in an expression vector. Selectable markers, i.e., genes that confer antibiotic resistance or sensitivity, are used and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of PKS and/or other biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

A nucleic acid of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Figure 6:
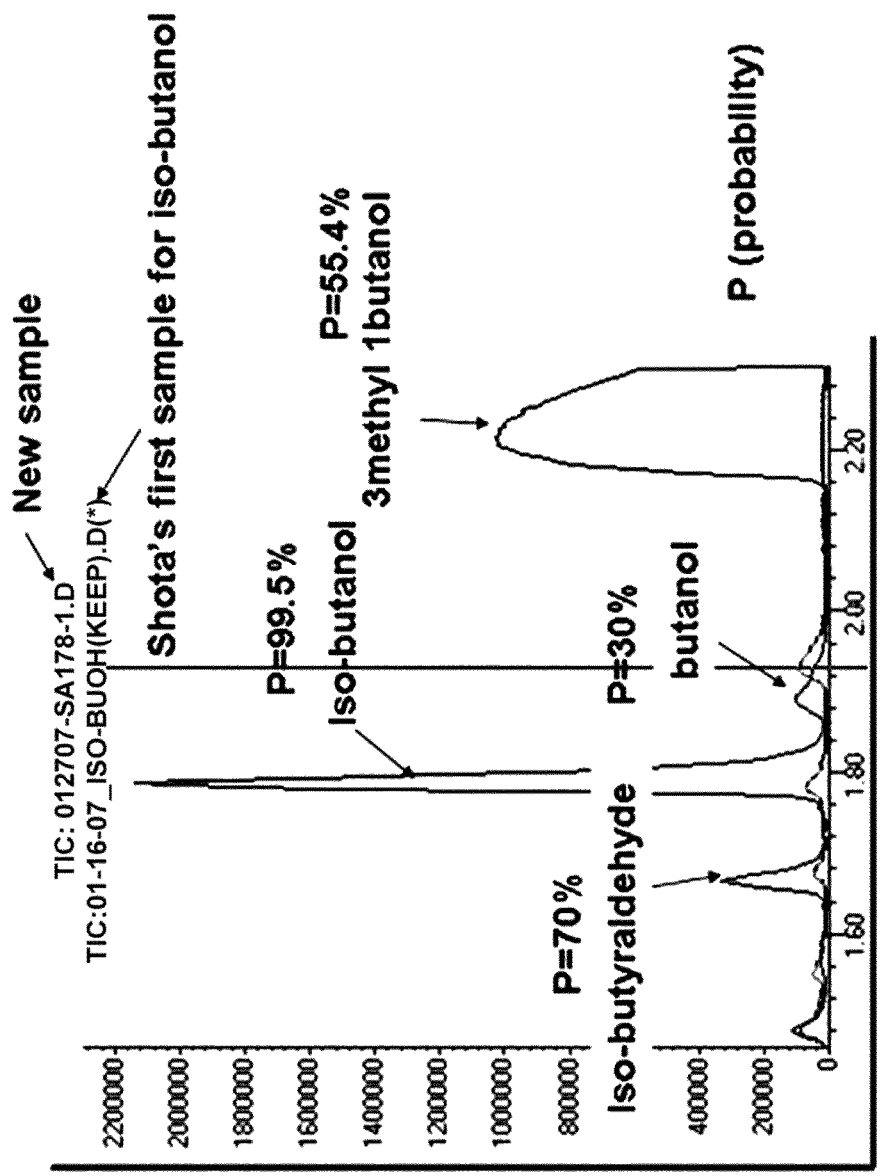
FIG. 6 depicts mass spectrometry data.
Figure 7:
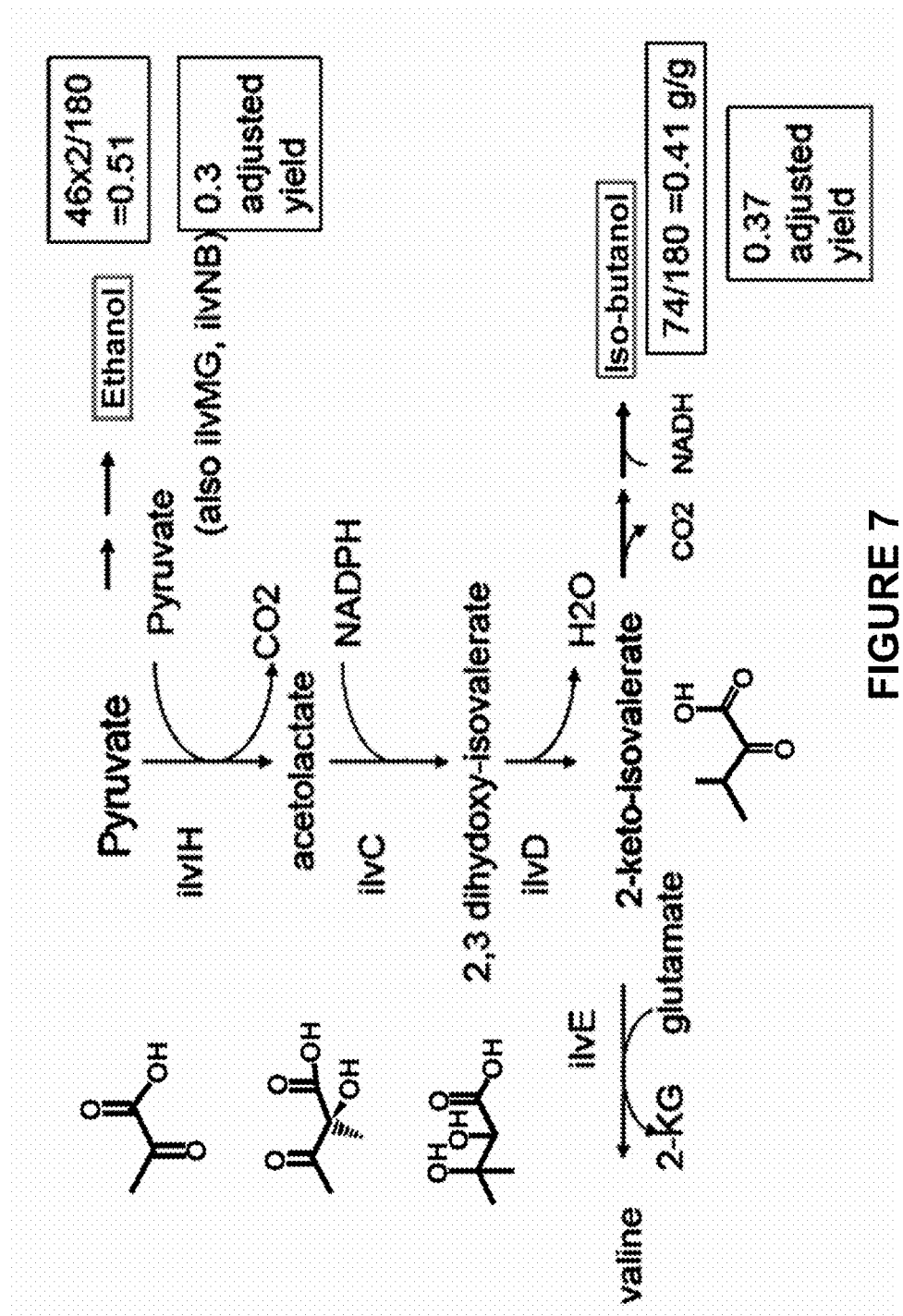
FIG. 7 depicts an exemplary pathway for the production of 2-keto-isovalerate from pyruvate.
Figure 8:
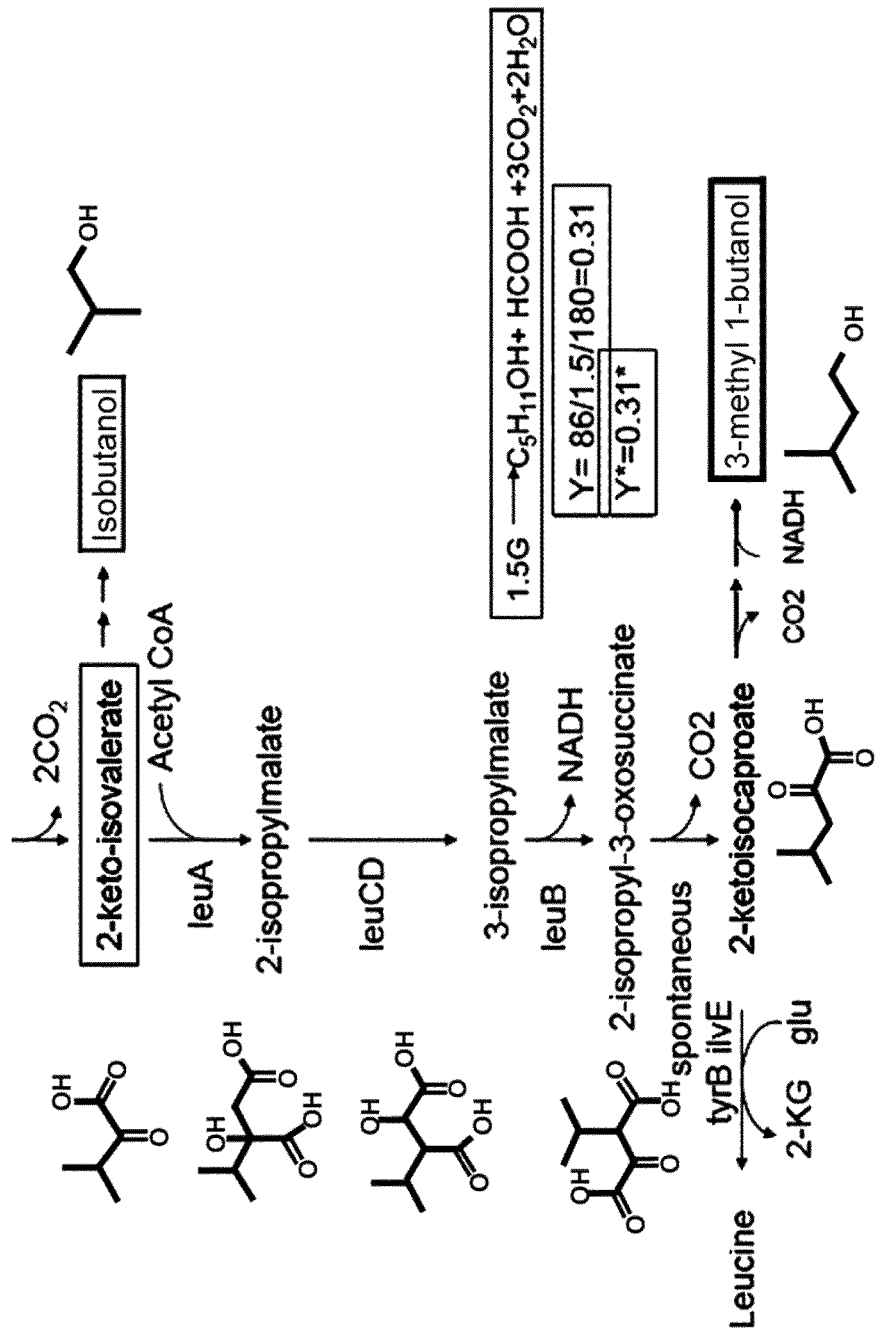
FIG. 8 depicts an exemplary pathway for leucine biosynthesis.
Figure 9:
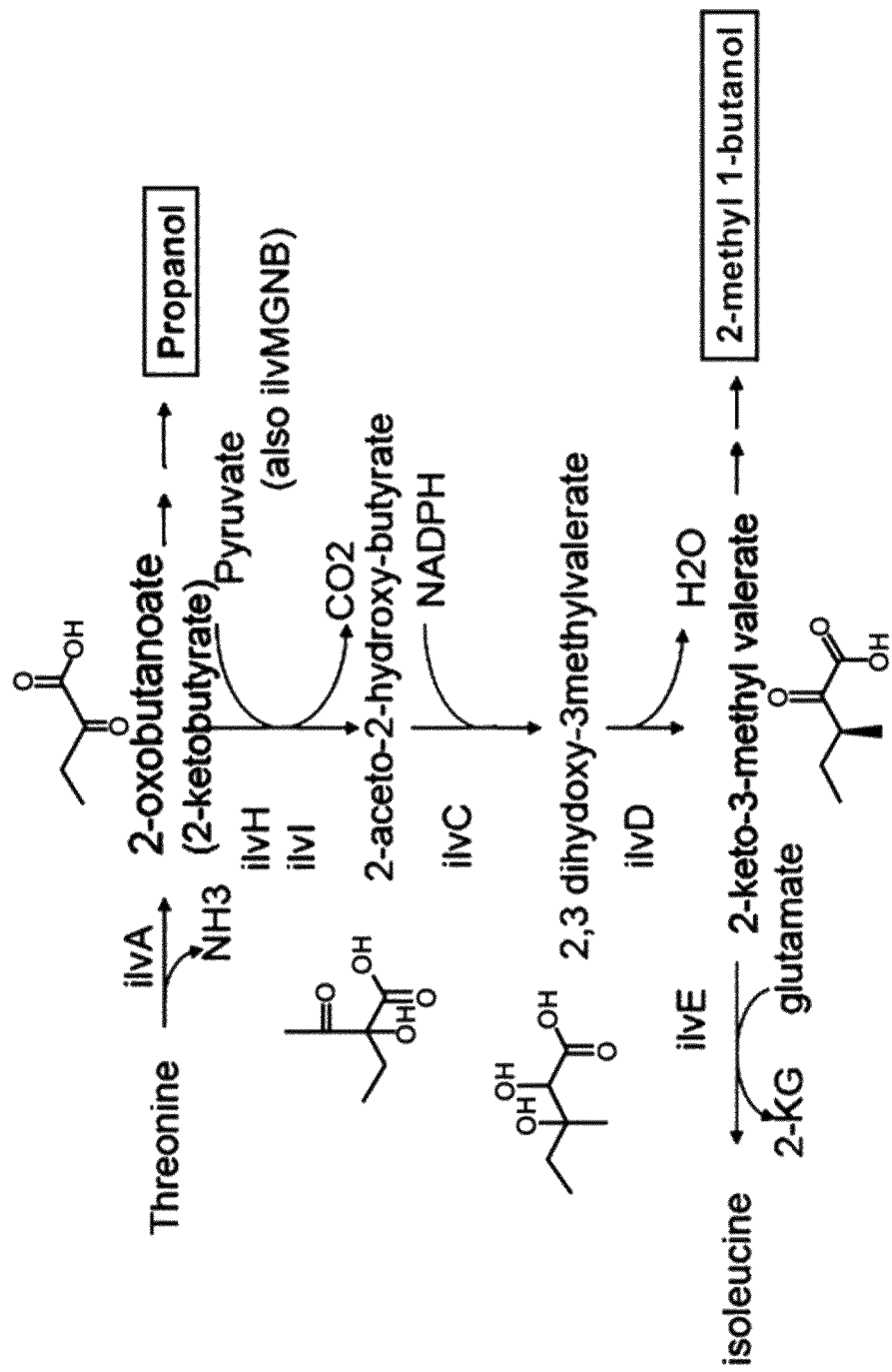
FIG. 9 depicts an exemplary pathway for isoleucine biosynthesis.
Figure 10:
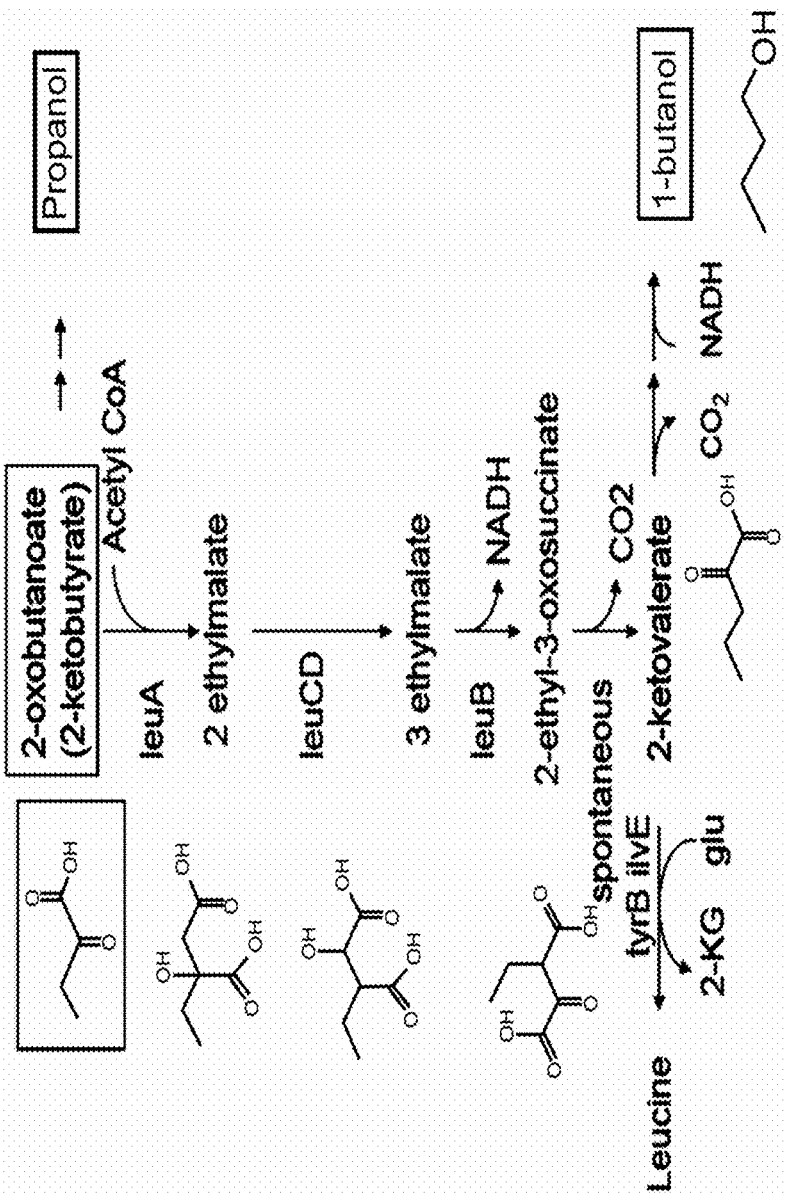
FIG. 10 depicts an exemplary pathway for butanol biosynthesis including 2-ketobutyrate as a biosynthetic intermediate.
Figure 11:
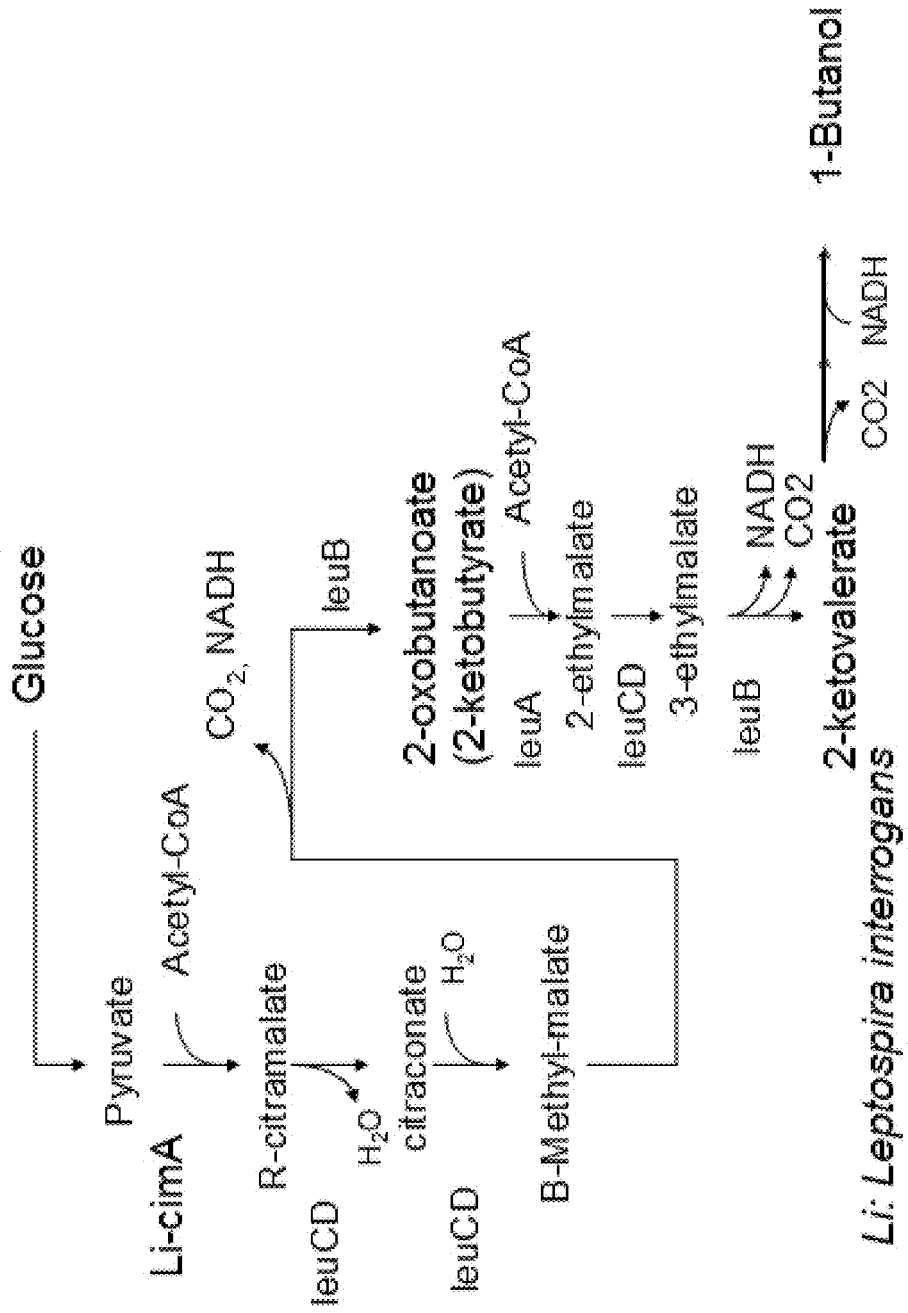
FIG. 11 depicts an exemplary pathway for butanol biosynthesis from pyruvate.
Figure 12:
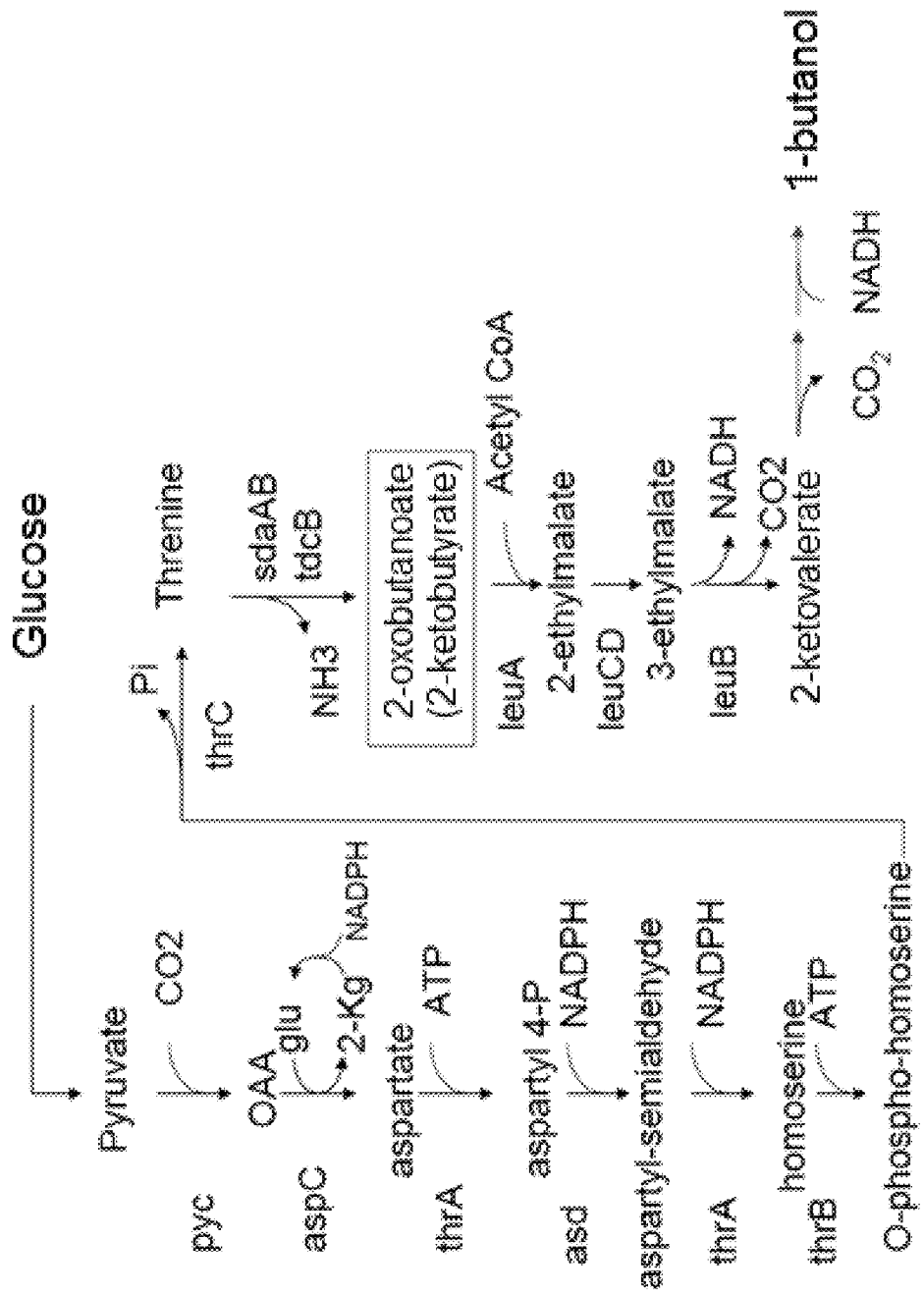
FIG. 12 depicts an exemplary pathway for butanol biosynthesis including threonine as a biosynthetic intermediate.
Figure 13:
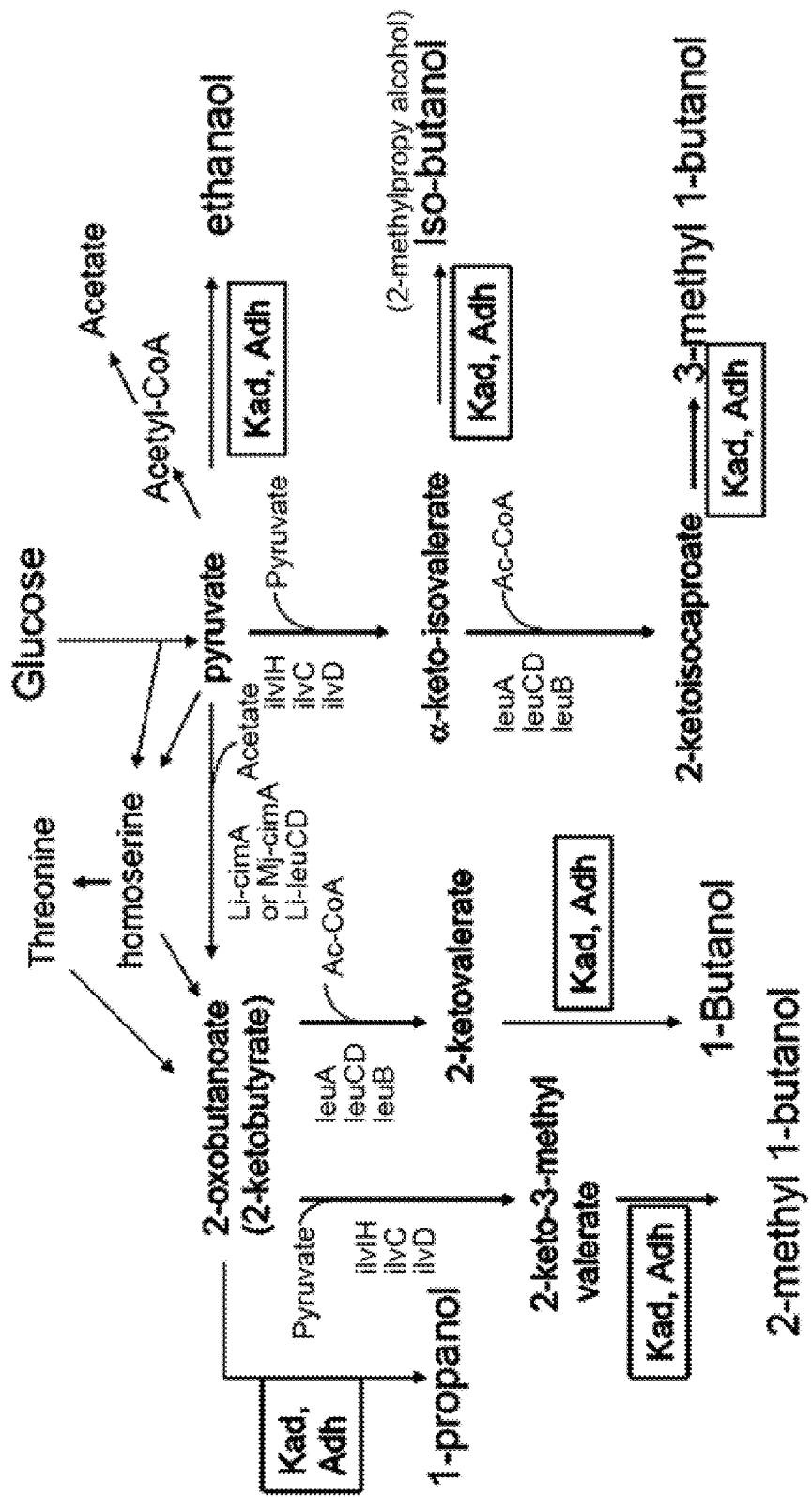
FIG. 13 depicts exemplary biosynthetic pathways for the production of isobutanol (e.g., 2-methylpropyl alcohol), 3-methyl 1-butanol, 1-butanol, ethanol, 2-methyl 1-butanol, and 1-propanol.
Figure 14:
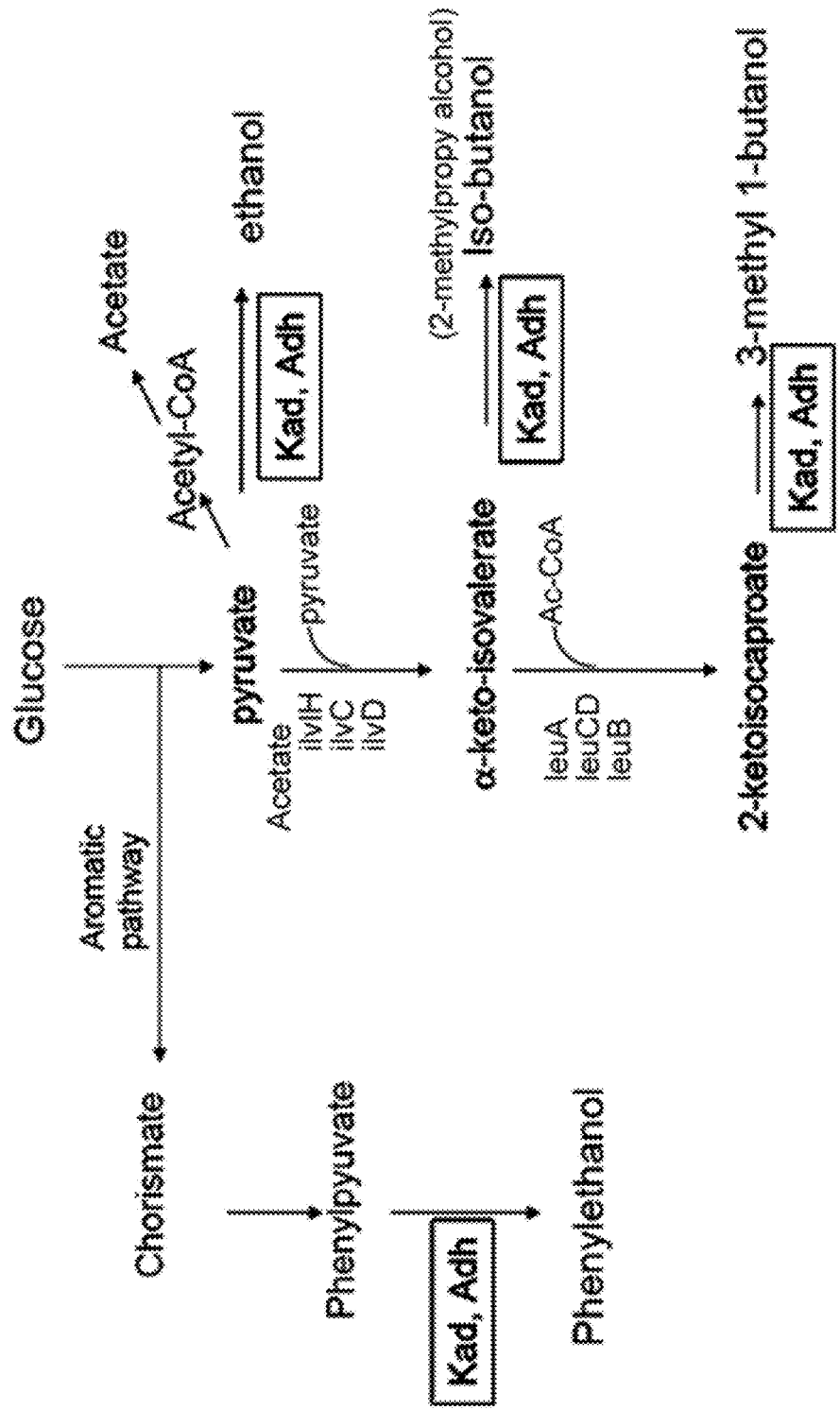
FIG. 14 depicts exemplary biosynthetic pathways for the production of phenylethanol, ethanol, 3-methyl 1-butanol, and isobutanol (e.g., 2-methylpropyl alcohol).

In another embodiment a method for producing e.g., 1-propanol, isobutanol, 1-butanol, 2-methyl 1-butanol, 3-methyl 1-butanol or 2-phenylethanol is provided. The method includes culturing a recombinant microorganism as provided herein in the presence of a suitable substrate and under conditions suitable for the conversion of the substrate to 1-propanol, isobutanol, 1-butanol, 2-methyl 1-butanol, 3-methyl 1-butanol or 2-phenylethanol. The alcohol produced by a microorganism provided herein can be detected by any method known to the skilled artisan. Such methods include mass spectrometry as described in more detail below and as shown in FIG. 6. Culture conditions suitable for the growth and maintenance of a recombinant microorganism provided herein are described in the Examples below. The skilled artisan will recognize that such conditions can be modified to accommodate the requirements of each microorganism.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Q-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Appropriate culture conditions are conditions of culture medium pH, ionic strength, nutritive content, etc.; temperature; oxygen/$CO_2$/nitrogen content; humidity; and other culture conditions that permit production of the compound by the host microorganism, i.e., by the metabolic action of the microorganism. Appropriate culture conditions are well known for microorganisms that can serve as host cells.

The disclosure is illustrated in the following examples, which are provided by way of illustration and are not intended to be limiting.

Exemplary microorganisms of the disclosure were deposited on Feb. 7, 2008 with the American Type Culture Collection, P.O. Box 1549 Manassas, Va. 20108, as ATCC Number PTA-8945 (designation SA237) and as ATCC Number PTA-8944 (designation CRS-BuOH23) under the Budapest Treaty. This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

EXAMPLES

DNA polymerase KOD for PCR reactions was purchased from EMD Chemicals (San Diego, Calif.). All restriction enzymes and Antarctic phosphatase were from New England Biolabs (Ipswich, Mass.). Rapid DNA ligation kit was obtained from Roche (Manheim, Germany). Oligonucleotides were ordered from Operon (Huntsville, Ala.). All antibiotics and reagents in media were purchased from either Sigma Aldrich (St. Louis, Mo.) or Fisher Scientifics (Houston, Tex.). A list of oligonucleotides used is given in Table 10.

TABLE 10

Strains, plasmids, and oligonucleotide used

| Strain | Genotype |
|---|---|
| BW25113 | rrnB$_{T14}$ ΔlacZ$_{WJ16}$ hsdR514 ΔaraBAD$_{AH33}$ ΔrhaBAD$_{LD78}$ |
| XL-1 Blue | recA1 endA1 gyrA96 thi-1 hsdR17 supE44 relA1 lac (F' proAB lacI$^q$ZΔM15 Tn10 (Tet$^R$)) |
| BW25113 F' | BW25113 (traD36, proAB+, lacI$^q$ ZΔM15 (Tet$^R$)) |
| CRS 21 | BW25113F' ΔmetA |
| CRS 22 | BW25113F' ΔmetA, tdh |
| CRS 23 | BW25113F' ΔmetA, tdh, ilvB |
| CRS 24 | BW25113F' ΔmetA, tdh, ilvB, ilvI |
| CRS 31 | BW25113F' ΔmetA, tdh, ilvB, ilvI, adhE |
| CRS-BuOH 2 | BW25113F' ΔmetA, tdh + pCS49/pSA62/pSA55I |
| CRS-BuOH 11 | BW25113F' ΔmetA, tdh, ilvB, ilvI + pCS49/pSA62/pSA55I |
| CRS-BuOH 12 | BW25113F' + pCS49/pSA62/pSA55I |
| CRS-BuOH 18 | BW25113F' ΔmetA, tdh, ilvB, ilvI + pCS49/pCS51/pSA55I |
| CRS-BuOH 19 | BW25113F' ΔmetA, tdh, ilvB, ilvI + pCS49/pCS20/pSA55I |

TABLE 10-continued

Strains, plasmids, and oligonucleotide used

| | |
|---|---|
| CRS-BuOH 20 | BW25113F' ΔmetA, tdh, ilvB, ilvI + pCS49/pCS50/pSA55I |
| CRS-BuOH 23 | BW25113F' ΔmetA, tdh, ilvB, ilvI, adhE +pCS49/pSA62/pSA55I |
| CRS-BuOH 31 | BW25113F' + pSA62/pSA55I |
| CRS-BuOH 32 | BW25113F' ΔmetA + pCS49/pSA62/pSA55I |

| Plasmid | Genotype |
|---|---|
| pZA31-luc | $P_L tetO_1$:: luc (VF); p15A ori; $Cm^R$ |
| pZS24-MCS1 | $P_L lac/ara_{-1}$:: MCS1; pSC101 ori; $Kan^R$ |
| pCS20 | $P_L lacO_1$:: tdcB(EC)-leuABCD(EC); p15A ori; $Kan^R$ |
| pCS27 | $P_L lacO_1$:: MCS1; p15A ori; $Kan^R$ |
| pCS49 | $P_L lacO_1$:: thrA*BC (EC ATCC 21277); pSC101 ori; $Spec^R$ |
| pCS50 | $P_L lacO_1$:: tdcB (EC)-leuA*BCD(EC G462D mut); p15A ori; $Kan^R$ |
| pCS51 | $P_L lacO_1$:: ilvA (EC)-leuA*BCD(EC G462D mut); p15A ori; $Kan^R$ |
| pSA55I | $P_L lacO_1$:: kivd (LL)-adh2 (SC), lacI; ColE1 ori; $Amp^R$ |
| pCS59 | $P_L lacO_1$:: thrABC (EC); pSC101 ori; $Spec^R$ |
| pSA62 | $P_L lacO_1$:: ilvA (EC)-leuABCD(EC); p15A ori; $Kan^R$ |

| Primer Name | Sequence 5'→3' |
|---|---|
| lacI SacI f | CTAGAGCTCGAAGGAGATATACCATGAAACCAGTAACGTTATACGATG (SEQ ID NO: 83) |
| lacI SacI r | CTAGAGCTCTCACTGCCCGCTTTCCAGTC (SEQ ID NO: 84) |
| tdcB f Acc65 | CGAGCGGTACCATGCATATTACATACGATCTGCCGG (SEQ ID NO: 85) |
| tdcB r SalI | ACGCAGTCGACTTAAGCGTCAACGAAACCGGTGATT (SEQ ID NO: 86) |
| thrA f Acc65 | TCAGGTACCATGCGAGTGTTGAAGTTCGGCGGTACAT (SEQ ID NO: 87) |
| thrC r HindIII | TCAAAGCTTTTACTGATGATTCATCATCAATTTACGCAA (SEQ ID NO: 88) |

Bacterial Strains.

*Escherichia coli* BW25113 (rrnB$_{T14}$ ΔlacZ$_{WJ16}$ hsdR514 ΔaraBAD$_{AH33}$ ΔrhaBAD$_{LD78}$) was designated as the wild-type (WT) (Datsenko and Wanner, Proc. Natl. Acad. Sci. USA 97, 6640-6645, 2000) for comparison. In some experiments for isobutanol, JCL16 (rrnB$_{T14}$ ΔlacZ$_{WJ16}$ hsdR514 ΔaraBAD$_{AH33}$ ΔrhaBAD$_{LD78}$/F' (traD36, proAB+, lacIq ZΔM15)) were used as wild-type (WT). Host gene deletions of metA, tdh, ilvB, ilvI, adhE, pta, ldhA, and pflB were achieved with P1 transduction using the Keio collection strains (Baba et al., Mol. Systems Biol. 2, 2006) as donor. The Kan® inserted into the target gene region was removed with pCP20 (Datsenko and Wanner, supra) in between each consecutive knock out. Then, removal of the gene segment was verified by colony PCR using the appropriate primers. XL-1 Blue (Stratagene, La Jolla, Calif.) was used to propogate all plasmids.

Plasmid Construction.

pSA40, pSA55, and pSA62 were designed and constructed as described elsewhere herein. The lacI gene was amplified with primers lacI SacI f and lacI SacI r from *E. coli* MG 1655 genomic DNA. The PCR product was then digested with SacI and ligated into the pSA55 open vector cut with the same enzyme behind the promoter of the ampicillin resistance gene, creating pSA55I.

The gene tdcB was amplified with PCR using primers tdcB f Acc65 and tdcB r SalI from the genomic DNA of *E. coli* BW25113 WT. The resulting PCR product was gel purified and digested with Acc65 and SalI. The digested fragment was then ligated into the pSA40 open vector cut with the same pair of enzymes, creating pCS14.

To replace the replication origin of pCS14 from colE1 to p15A, pZA31-luc was digested with SacI and AvrII. The shorter fragment was gel purified and cloned into plasmid pCS14 cut with the same enzymes, creating pCS16.

The operon leuABCD was amplified using primers A106 and A109 and *E. coli* BW25113 genomic DNA as the template. The PCR product was cut with SalI and BglII and ligated into pCS16 digested with SalI and BamHI, creating pCS20.

To create an expression plasmid identical to pSA40 but with p15A origin, the p15A fragment obtained from digesting pZA31-luc with SacI and AvrII was cloned into pSA40 open vector cut with the same restriction enzymes, creating pCS27.

The leuA* G462D mutant was constructed using SOE (Splice Overlap extension) with primers G462Df and G462Dr and the E. coli BW25113 WT genomic DNA as a template to obtain leuA*BCD. Then the SOE product was digested and cloned into the restriction sites Acc65 and XbaI to create PZE leuABCD. The resulting plasmid was next used as a template to PCR out the leuA*BCD using primers A106 and A109. The product was cut with SalI and BglII and ligated into pCS27 digested with SalI and BamHI, creating pCS48.

The gene ilvA was amplified from E. coli BW25113 WT genomic DNA with primers A110 and A112. Next, it was cut with Acc65 and XhoI and ligated into the pCS48 open vector digested with Acc65 and SalI, creating pCS51.

The gene tdcB from the genomic DNA of E. coli BW25113 WT was amplified with PCR using primers tdcB f Acc65 and tdcB r SalI. The resulting PCR product was gel purified, digested with Acc65 and SalI and then ligated into the pCS48 open vector cut with the same pair of enzymes, creating pCS50.

WT thrABC was amplified by PCR using primers thrA f Acc65 and thrC r HindIII. The resulting product was digested with Acc65 and HindIII and cloned into pSA40 cut with the same pair of enzymes, creating pCS41.

To replace the replication origin of pCS41 from colE1 to pSC101, pZS24-MCS1 was digested with SacI and AvrII. The shorter fragment was gel purified and cloned into plasmid pCS41 cut with the same enzymes, creating pCS59.

The feedback resistant mutant thrA* was amplified by PCR along with thrB and thrC from the genomic DNA isolated from the threonine over-producer ATCC 21277 using primers thrA f Acc65 and thrC r HindIII. The resulting product was digested with Acc65 and HindIII and cloned into pSA40 cut with the same pair of enzymes, creating pCS43.

To replace the replication origin of pCS43 from colE1 to pSC101, pZS24-MCS1 was digested with SacI and AvrII. The shorter fragment was gel purified and cloned into plasmid pCS43 cut with the same enzymes, creating pCS49.

Branched-chain amino-acid aminotransferase (encoded by ilvE) and tyrosine aminotransferase (encoded by tyrB) were deleted by P1 transduction from strains JWXXX and JWXXX (Baba et al.) respectively.

To clone the L-valine biosynthesis genes i) ilvIHCD (EC) and ii) als (BS) along with ilvCD (EC), the low copy origin of replication (ori) from pZS24-MCS1 was removed by digestion with SacI and AvrII, and ligated into the corresponding sites of i) pSA54 and ii) pSA69 to create plasmid pIAA1 and pIAA11, respectively.

To clone kivd from L. lactis and ADH2 from S. cerevisiae, the ColE1 ori of pSA55 was removed by digestion with SacI and AvrII and replaced with the p15A ori of pSA54 digested with the same restriction enzymes to create pIAA13. To better control the expression of these genes, lacI was amplified from E. coli MG1655 genomic DNA with KOD polymerase using primers lacISacIf and lacISacIr and ligated into the SacI site of pCS22 to be expressed along with the ampicillin resistance gene, bla, and create plasmid pIAA12.

In order to overexpress the leuABCD operon in BW25113/F' from the chromosome, the native promoter and leader sequence was replaced with the $P_{LlacO}$-1 promoter. The $P_{LlacO-1}$ promoter was amplified from pZE12-luc with KOD polymerase using primers lacO1KanSOEf and lacO1LeuAIr. The gene encoding resistance to kanamycin, aph, was amplified from pKD13 using primers KanLeuO1f and KanlacO1SOEr. 1 μL of product from each reaction was added as template along with primers KanLeuO2f and lacO1LeuA2r, and was amplified with KOD polymerase using SOE. The new construct was amplified from the genomic DNA of kanamycin resistant clones using primers leuKOv1 and leuKOv2 and sent out for sequence verification to confirm the accuracy of cloning. To overexpress the leuABCD operon from plasmid, the p15A ori from pSA54 was removed with SacI and AvrII and ligated into the corresponding sites of pCS22 (ColE1, Cm®, $P_{LlacO-1}$: leuABCD) to create plasmid pIAA2. In order for tighter expression, lacI was amplified and ligated as described previously for pIAA12 into pCS22 to be expressed along with the chloroamphenicol resistance gene, cat, and create plasmid pIAA15. Plasmid pIAA16 containing leuA(G1385A) encoding for IPMS (G462D) was created by ligating the 5.5 kb fragment of pIAA15 digested with XhoI and NdeI and ligating it with the 2.3 kb fragment of pZE12-leuABCD (ColE1, Amp®, $P_{LlacO-1}$: leuA(G1385A)BCD) cut with the same restriction enzymes. To control for expression level, the RBS was replaced in pIAA15 to match that of pIAA16. To do this, the 5.6 kb fragment of pIAA16 from digestion with HindIII and NdeI was ligated with the 2.2 kb fragment of pIAA15 digested with the same enzymes to create pIAA17.

Media and Cultivation.

For initial production experiments, strains were grown for in a modified M9 medium (6 g $Na_2HPO_4$, 3 g $KH_2PO_4$, 1 g $NH_4Cl$, 0.5 g NaCl, 1 mM $MgSO_4$, 1 mM $CaCl_2$, 10 mg Vitamin B1 per liter of water) containing 10 g/L of glucose, 5 g/L of yeast extract, and 1000× Trace Metals Mix A5 (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 49.4 mg $Co(NO_3)_2.6H_2O$ per liter water) inoculated 1% from 3 mL overnight cultures in LB into 10 mL of fresh media in 125 mL screw cap flasks and grown at 37° C. in a rotary shaker for 4 hours. The culture was then induced with 1 mM IPTG and grown at 30° C. for 18 hours. Antibiotics were added as needed (ampicillin 100 μg/mL, chloroamphenicol 35 μg/mL, kanamycin 50 μg/mL).

For some alcohol fermentation experiments, single colonies were picked from LB plates and inoculated into 3 ml of LB media with the appropriate antibiotics (ampicillin 100 pg/ml, kanamycin 50 μg/ml, and spectinomycin 50 μg/ml). The overnight culture grown in LB at 37° C. in a rotary shaker (250 rpm) was then inoculated (1% vol/vol) into 20 ml of M9 medium (6 g $Na_2HPO_4$, 3 g $KH_2PO_4$, 0.5 g NaCl, 1 g $NH_4Cl$, 1 mM $MgSO_4$, 10 mg vitamin B1 and 0.1 mM $CaCl_2$ per liter of water) containing 30 g/L glucose, 5 g/L yeast extract, appropriate antibiotics, and 1000× Trace Metal Mix A5 (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 49.4 mg $Co(NO_3)_2.6H_2O$ per liter water) in 250 ml conical flask. The culture was allowed to grow at 37° C. in a rotary shaker (250 rpm) to an $OD_{600}$ of 0.4~0.6, then 12 ml of the culture was transferred to a 250 ml screw capped conical flask and induced with 1 mM IPTG. The induced cultures were grown at 30° C. in a rotary shaker (240 rpm). Samples were taken throughout the next three to four days by opening the screwed caps of the flasks, and culture broths were either centrifuged or filtered to retrieve the supernatant. In some experiments as indicated, 8 g/L of threonine was added directly into the cell culture at the same time of induction.

All α-keto acid experiments were done under oxygen 'rich' conditions unless otherwise noted. For oxygen rich experiments, 10 mL cultures in 250 mL baffled shake flasks were inoculated 1% from 3 mL overnight cultures in LB. For oxygen poor experiments, 10 mL cultures were inoculated in 125 mL screw caps as previously described. All cultures were grown at 37° C. for 4 hours and induced with 1 mM IPTG and harvested after 18 hrs of growth at 30° C.

Final production experiments were conducted as previously described, except that 20 mL modified M9 media containing 5 g/L of glucose was used in a 250 mL screw cap flask.

Metabolite Detections.

The produced alcohol compounds were quantified by a gas chromatograph (GC) equipped with flame ionization detector. The system consisted of model 5890A GC (Hewlett-Packard, Avondale, Pa.) and a model 7673A automatic injector, sampler and controller (Hewlett-Packard).

Supernatant of culture broth (0.1 ml) was injected in split injection mode (1:15 split ratio) using methanol as the internal standard.

The separation of alcohol compounds was carried out by A DB-WAX capillary column (30 m, 0.32 mm-i.d., 0.50 μm-film thickness) purchased from Agilent Technologies (Santa Clara, Calif.). GC oven temperature was initially held at 40° C. for 5 min and raised with a gradient of 15° C./min until 120° C. It was then raised with a gradient 50° C./min until 230° C. and held for 4 min. Helium was used as the carrier gas with 9.3 psi inlet pressure. The injector and detector were maintained at 225° C. 0.5 ul supernatant of culture broth was injected in split injection mode with a 1:15 split ratio. Methanol was used as the internal standard.

For other secreted metabolites, filtered supernatant was applied (20 ul) to an Agilent 1100 HPLC equipped with an auto-sampler (Agilent Technologies) and a BioRad (Biorad Laboratories, Hercules, Calif.) Aminex HPX87 column (5 mM $H_2SO_4$, 0.6 ml/min, column temperature at 65° C.). Glucose was detected with a refractive index detector, while organic acids were detected using a photodiode array detector at 210 nm. Concentrations were determined by extrapolation from standard curves.

For other secreted metabolites, filtered supernatant was applied (0.02 ml) to an Agilent 1100 HPLC equipped with an auto-sampler (Agilent Technologies) and a BioRad (Biorad Laboratories, Hercules, Calif.) Aminex HPX87 column (0.5 mM H2SO4, 0.6 mL/min, column temperature at 65° C.). Glucose was detected with a refractive index detector while organic acids were detected using a photodiode array detector at 210 nm. Concentrations were determined by extrapolation from standard curves.

Expression of L-Valine and L-Leucine Biosynthesis Pathway Genes Leads to 3-Methyl-1-Butanol Production.

To produce 3-methyl-1-butanol in *E. coli*, the entire pathway from pyruvate to 3-methyl-1-butanol was overexpressed. ilvIHCD (*E. coli*), kivd (*L. lactis*), and ADH2 (*S. cerevisiae*) were all expressed from plasmid (pSA54 and pSA55) under control of the $P_{LlacO-1}$ promoter. The leuABCD operon was overexpressed by replacing the upstream non-coding region of leuA with the $P_{LlacO-1}$ promoter in JCL16. The strain was able to produce 56 mg/L of 3-methyl-1-butanol after 18 hr of induction with IPTG (FIG. 47A). In order to increase production of 3-methyl-1-butanol, ilvIH was replaced with alsS from *B. subtilils*. The replacement of ilvIH with alsS showed an increase in 3-methyl-1-butanol production (67 mg/L) (FIG. 47A). To increase the expression level of the leucine biosynthesis pathway, leuABCD was also cloned into a p15A derived plasmid and expressed under control of the $P_{LlacO-1}$ promoter. Plasmid based expression of leuABCD increased 3-methyl-1-butanol production for strains containing either ilvIH (177 mg/L) or alsS (124 mg/L) (FIG. 47B), although overexpression of alsS lead to a dramatic increase in isobutanol production.

Host pathways competing for carbon and reducing power were deleted. The deletion of adhE, frdBC, ldhA, pta, fnr, and pflB was shown to increase production of isobutanol in *E. coli* relative to a wild-type (WT) background. When the 3-methyl-1-butanol pathway was transformed into this strain, the final titer of 3-methyl-1-butanol was 76 mg/L for the strain expressing alsS (FIG. 47B). Although 3-methyl-1-butanol accumulation diminished, alcohol production was dominated by isobutanol, with a final concentration of greater than 1.3 g/L. With an isobutanol titer greater than 10 times that of the target product, the process and metabolic pathway was examined to explain this result.

Deregulation of Threonine Biosynthesis.

Figure 50:
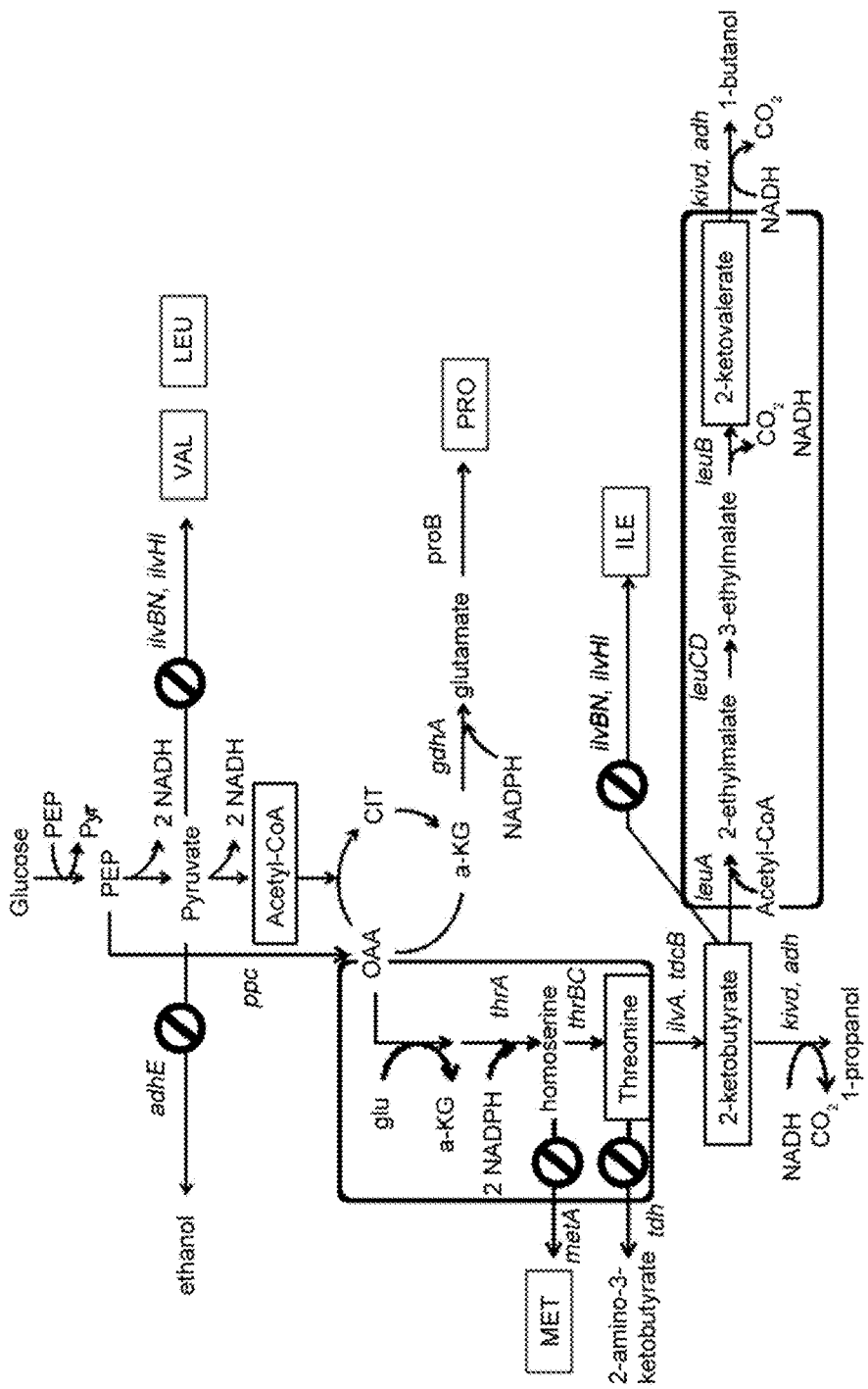
FIG. 50 is a schematic illustration of the propanol and butanol production via the threonine biosynthetic pathway in the genetically engineered *E. coli*. Depicted are disruption of the particular pathways; open rectangular boxes represent the precursors to the alcohol production. Also depicted is the unnatural norvaline pathway. Valine, leucine, isoleucine, proline, and methionine biosynthetic pathways are indicated by their corresponding abbreviations enclosed by gray boxes.

As shown in FIG. 50, 2-ketobutyrate and 2-ketovalerate are the precursor for 1-propanol and 1-butanol production, respectively. While 2-ketobutyrate is a common intermediate derived from threonine and a precursor for isoleucine biosynthesis, 2-ketovalerate is a rare metabolite used by the cell to synthesize the nonnative amino acid, norvaline. In order to increase the pool of 2-ketovalerate for 1-butanol, the gene ilvA and leuABCD from *E. coli* were over-expressed using plasmid pSA62 to i) direct higher metabolic flux towards 2-ketobutyrate and ii) utilize the norvaline synthetic chemistry as the major 2-ketovalerate production route (FIG. 50). Kivd and Adh2 were also over-expressed from pSA55I to convert the two keto acids into their corresponding alcohols.

Figure 51:
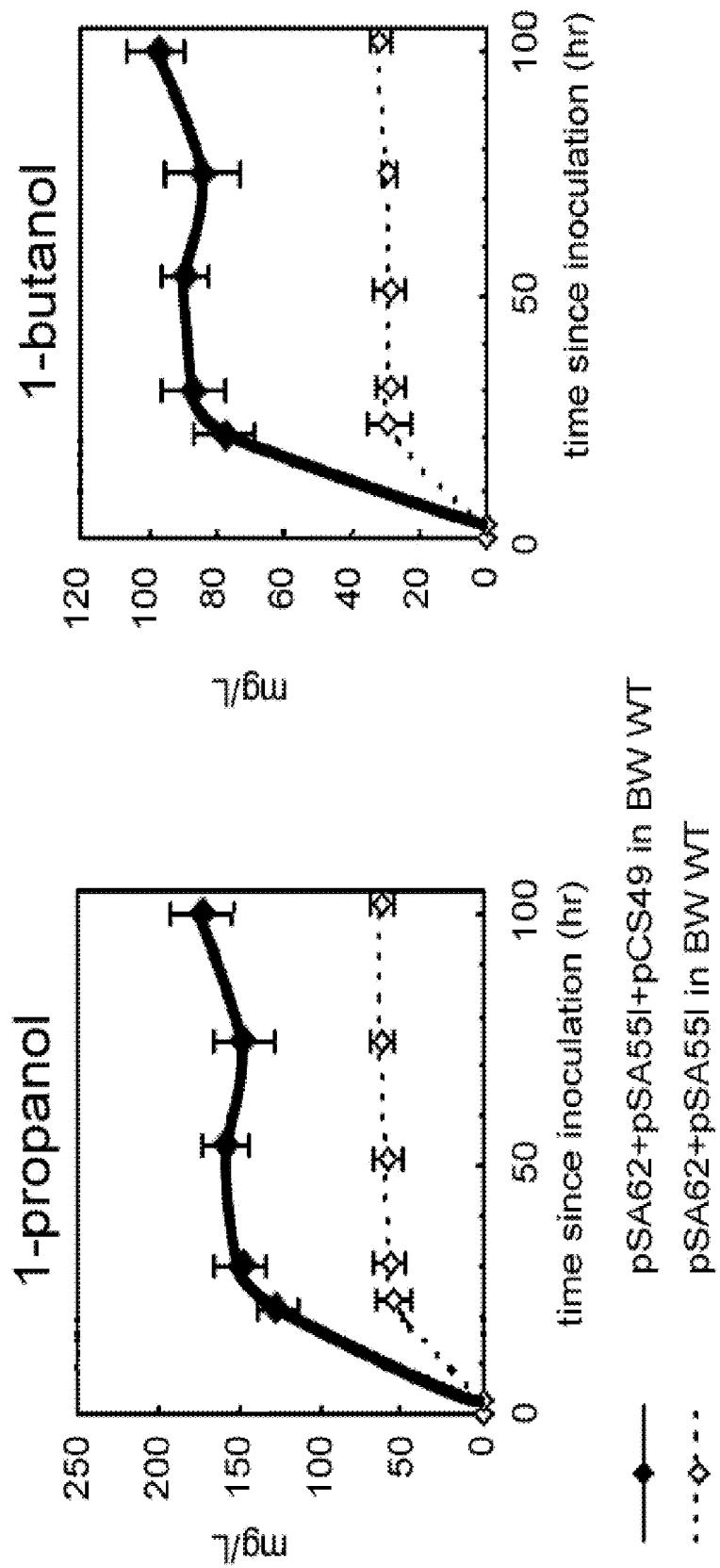
FIG. 51 shows the effect of thrA*BC over-expression on the alcohol and major metabolite productions in BW WT. Time course of propanol, butanol, major by-products, growth and glucose consumption in CRS-BuOH 12 (filled diamond) and CRS-BuOH 31 (open diamond) is shown. Both CRS-BuOH 12 and CRS-BuOH 31 were BW WT strains. CRS-BuOH 31 contained pSA62 and pSA55I while CRS-BuOH 12 contained an additional plasmid pCS49 which carried the thrA*BC behind PLlacO1. Cells were cultured as described in materials and methods.
Figure 51:
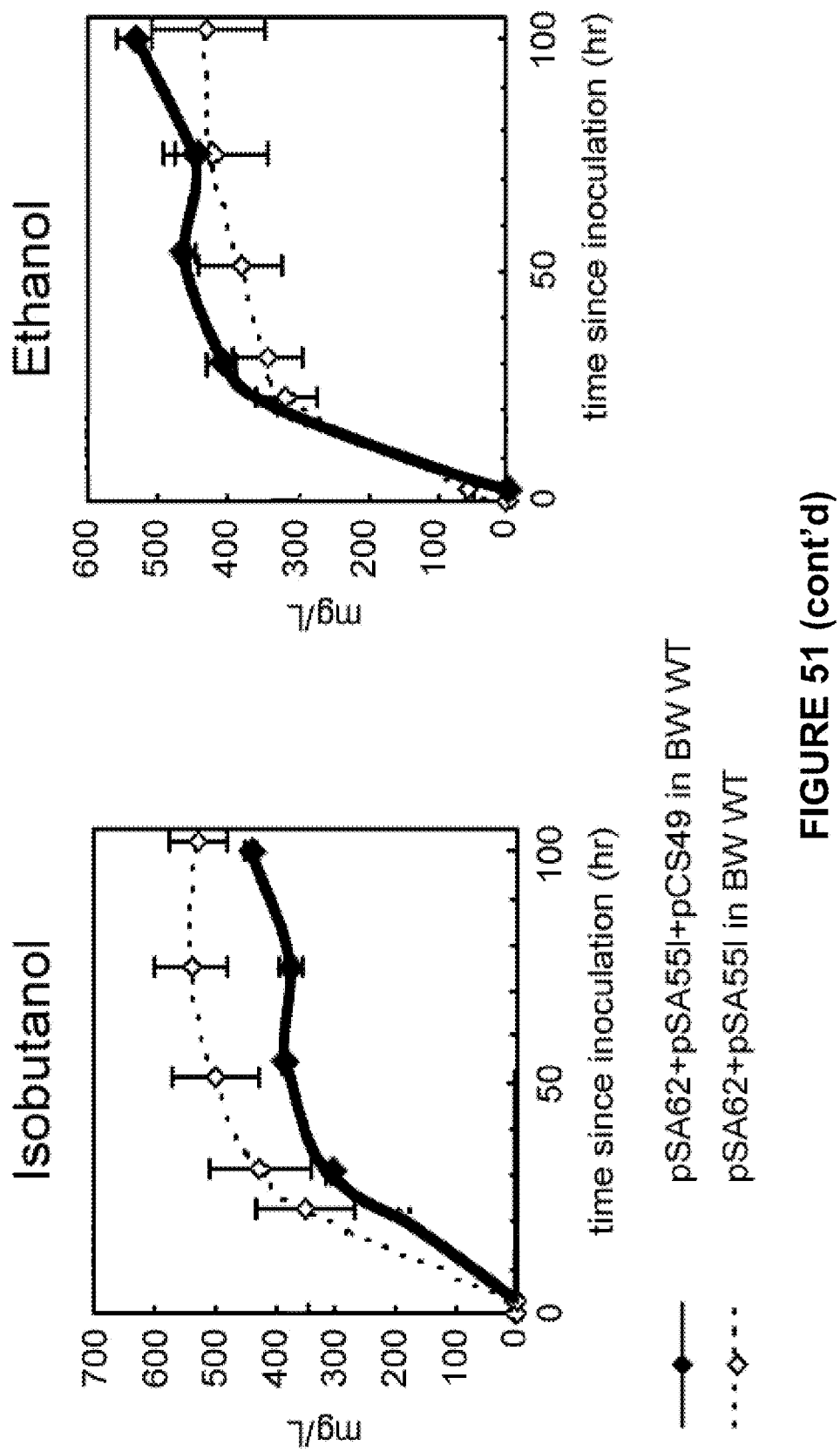
Figure 51:
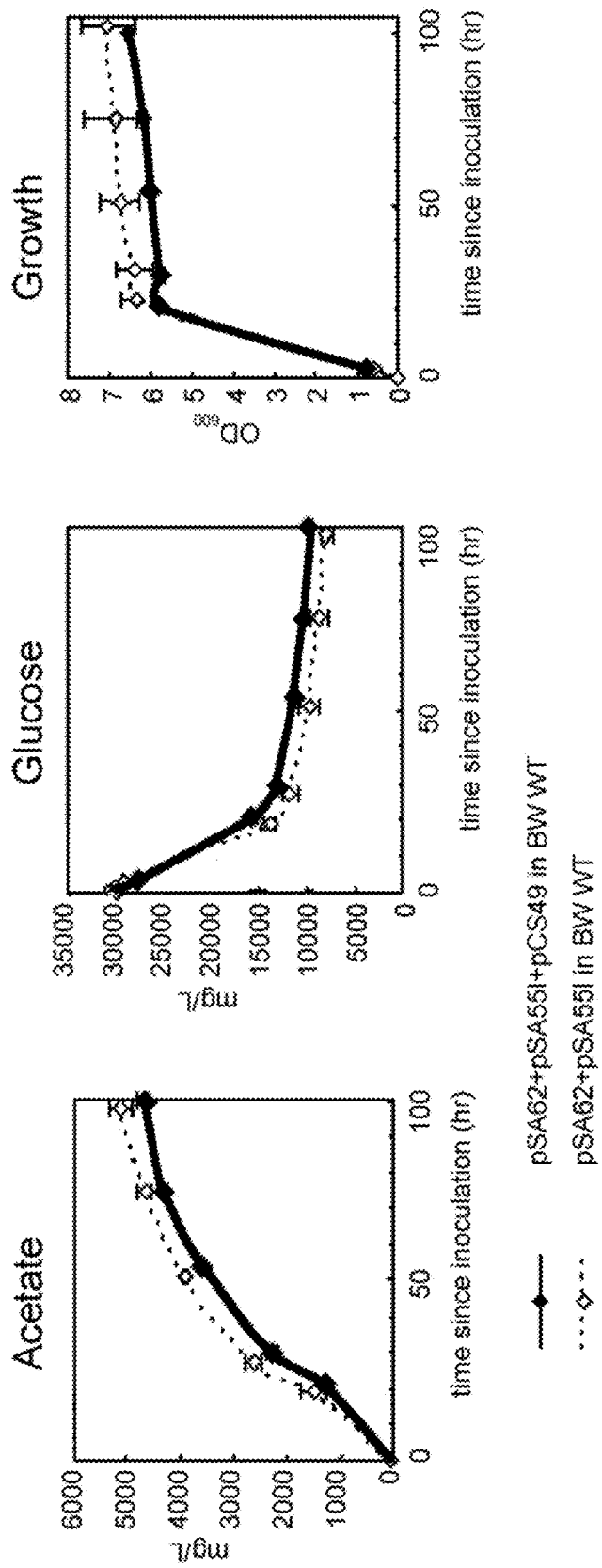

Over-expression of ilvA and leuABCD in addition to kivd and ADH2 raised both the 1-propanol and 1-butanol levels by nearly 5 fold in BW WT, from a virtually non-detectable amount to about 60 mg/L and 30 mg/L respectively (FIG. 51). Nevertheless, native feedback regulation of amino acid biosynthesis, both at the transcriptional and enzymatic level, continued to act on the threonine production, resulting in the plateau of 1-propanol and 1-butanol after 24 hours and the steady increase in isobutanol and ethanol formation to discard the excess NADH.

To identify if threonine limitation was the major bottleneck, 8 g/L threonine was added to the *E. coli* culture at induction. The result verified the hypothesis: the accumulated propanol and butanol in 72 hours was raised to 2 g/L, which was about a ten fold increase for both alcohols. Since transcription attenuation and allosteric feedback inhibition of ThrA by threonine are the major regulatory mechanisms, expressing a feedback-resistant mutant of ThrA behind a non-native promoter would help deregulate threonine synthesis and therefore improve production of the downstream alcohols. A feedback resistant ThrA (designated as ThrA* a threonine hyper-producer ATCC 21277). The thrA*BC operon of this strain was then cloned and expressed from plasmid pCS49 under the control of $P_L$lacO1 promoter. As a comparison, the WT thrABC operon was also cloned and expressed from pCS 59 under $P_L$lacO1. With the addition of ThrA*BC over-expression, the production levels of both 1-propanol and 1-butanol were boosted three to four fold higher relative to the case without ThrA*BC (FIG. 51). Strains with WT ThrABC over-expressed showed a 10~20% drop of the two target alcohols compare to the level produced by the same strains with ThrA*BC over-expressed (FIGS. 51 and 54), both in the BW WT background and in BW ΔmetA, Δtdh, ΔilvB, ΔilvI, ΔadhE. This demonstrated that the intracellular threonine accumulation was minor but still managed to affect the WT ThrA activity at a low level. As illustrated by the decrease of isobutanol production (FIG. 51), the presence of thrA*BC helped direct the metabolic flux more towards the threonine pathway, thus improved the overall 1-propanol and 1-butanol productivity.

Elimination of Competing Pathways.

Figure 52A:
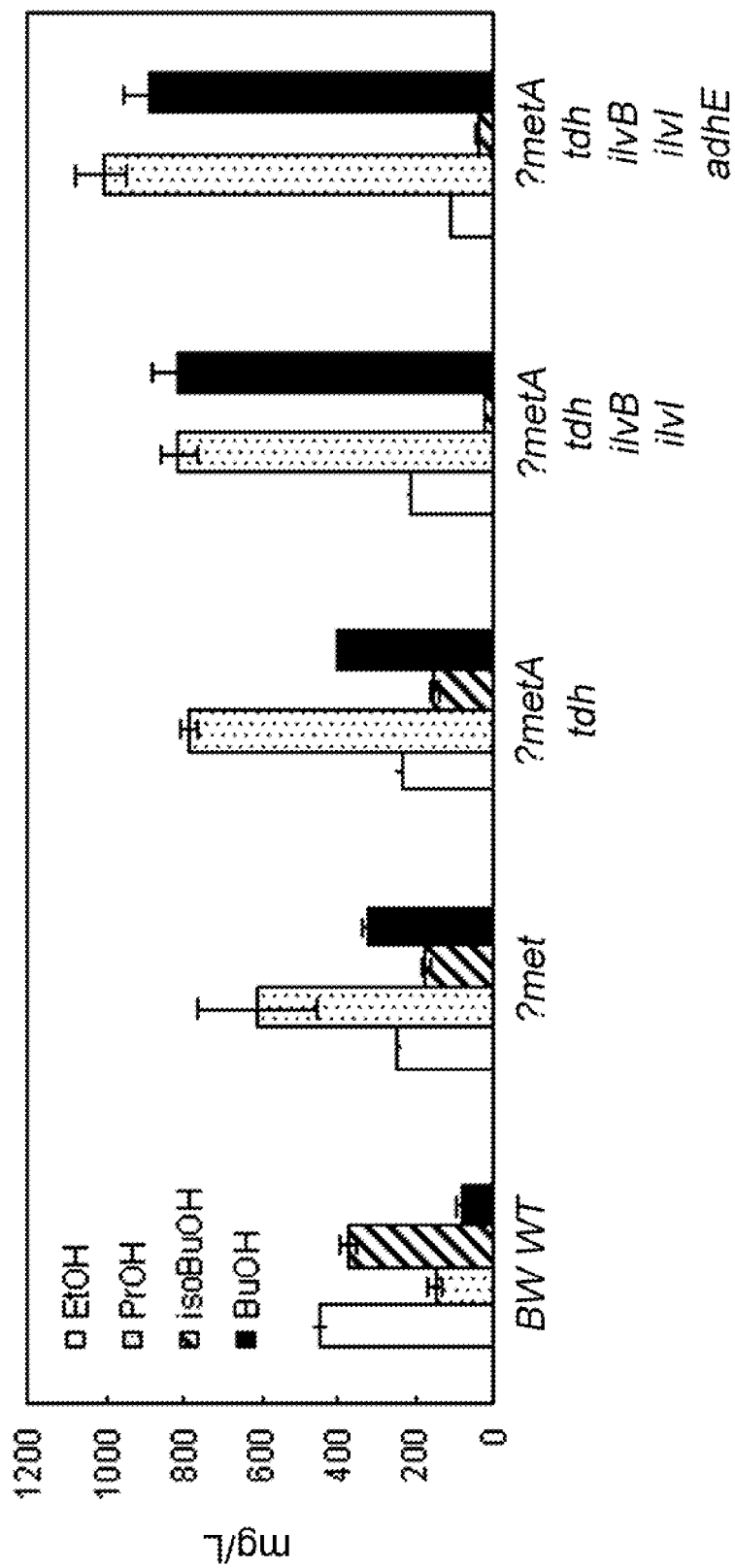
FIG. 52A-B shows a comparison of alcohol productions in various knock-out strains. A. Strains were numbered as CRS-BuOH 12, 32, 2, 11, 23 from left to right. All strains contained the same sets of plasmids pCS49, pSA62, and pSA55I. Cells were cultured for 72 hours as described herein. The data shown is the 72nd hour time point. B. Time course of growths for each of the strains shown in A.
Figure 52B:
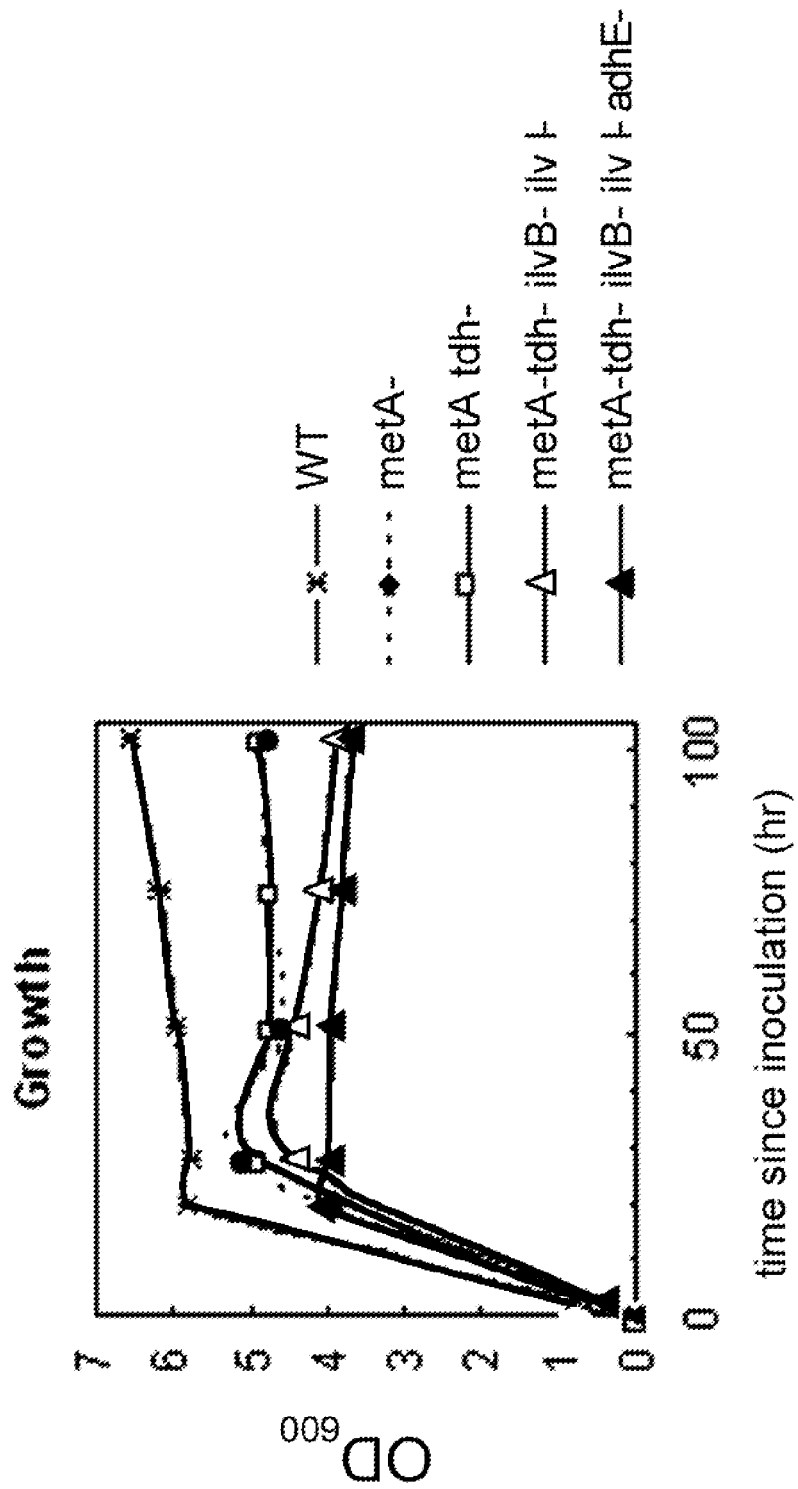

To further increase the propanol and butanol production titer, genes involved in the competing side reactions were removed to avoid the consumption or degradation of the desired intermediates. Since threonine production is the major check point in the synthesis of 2-ketobutyrate, homoserine O-succinyltransferase metA and threonine dehydrogenase tdh were first inactivated to minimize the loss of desired precursors to methionine biosynthesis and to block the catabolism of threonine into 2-amino-3-ketobutyrate. With metA and tdh disrupted, the combined production of 1-propanol and 1-butanol increased to about 1.2 g/L as seen from FIG. 52, with the major contribution primarily coming from 1-propanol. Less significant effect of these two gene deletions was seen in 1-butanol production, which may be attributed to the divergence of 2-ketobutyrate into the isoleucine pathway and/or the availability of acetyl-CoA. To further conserve acetyl-CoA and 2-ketobutyrate, the two key precursors for 1-butanol formation, the first enzymatic reaction in the biosynthesis of valine, leucine and isoleucine was disrupted. Elimination of the larger catalytic subunit (coded by ilvB) of the acetohydroxy acid synthase isozyme (AHAS I) and the catalytic subunit (coded by ilvI) of the AHAS III led to auxotroph of the above amino acids. These two additional deletions resulted in a two fold increase in the 1-butanol production (FIG. 52) while 1-propanol level stayed unchanged. It also nearly abolished the production of isobutanol and (2-, 3-) methyl-butanol by removal of their precursors. The minute accumulation of isobutanol might have resulted from the reverse reaction in the last step of valine synthesis catalyzed by IlvE, which took valine present in the media (supplemented with yeast extract) and converted it back into 2-keto-isovalerate.

To reduce ethanol production, the *E. coli* adhE gene was deleted. Although the adhE disruption did not improve the overall C3 and C4 alcohol production much, it did increase the specificity by lowering ethanol formation from 0.25 g/L down to approximately 0.1 g/L. With these genes eliminated from the genome, the final strain (ΔmetA, Δtdh, ΔilvB, ΔilvI, ΔadhE) showed a near 1:1 co-production of 1-propanol and 1-butanol with minor accumulation of ethanol and basal levels of isobutanol and (2-, 3-) methyl-butanol.

Assessment of Alternative Feedback Resistant Enzymes.

Because the 1-propanol and 1-butanol production presented here relied heavily on the host's amino acid biosynthetic machinery, it is important to verify that the essential alcohol precursors downstream of threonine were not limited by the various amino acid regulatory mechanisms present in the cell, particularly the inhibition of enzymatic activity of IlvA and LeuA by isoleucine and leucine respectively.

Figure 53:
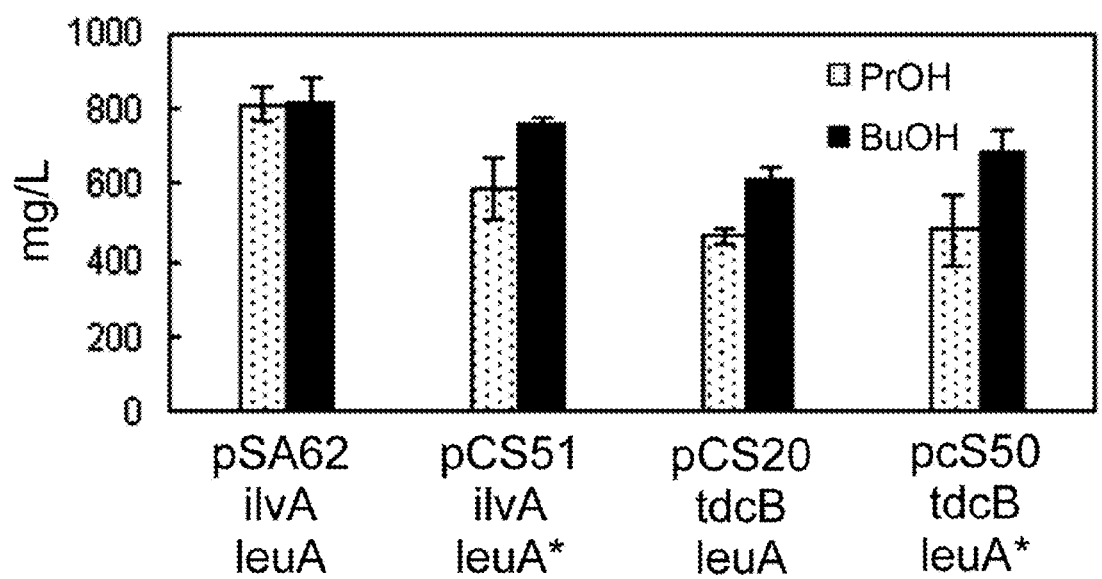
FIG. 53 shows a comparison of propanol and butanol production using alternative feedback resistant threonine dehydratase and 2-isopropylmalate synthase. BW ΔmetA, Δtdh, ΔilvB, ΔilvI was used as the background strain for the comparison. Strains were numbered as CRS-BuOH 11, 18, 19, 20 and all contained pSA62 and pSA55I in addition to the plasmids indicated below the figure. Gene names of the specific threonine dehydratase and 2-isopropylmalate synthase expressed are listed below the plasmid number. Cells were cultured for 72 hours as described herein. The data shown is the 72nd hour time point.

TdcB, *E. coli*'s catabolic threonine dehydratase, provided an alternative to IlvA for catalyzing the deamination of threonine into 2-ketobutyrate while being naturally insensitive to isoleucine feedback inhibition. To assess the benefit of this alternative enzyme towards the production, tdcB was overexpressed behind $P_L$lacO1 with leuABCD on pCS20. Results showed that TdcB led to a 70% lower production of both target alcohols compared to IlvA (FIG. 53). It is possible that the minute amount of isoleucine brought about by the addition of yeast extract was insignificant to inhibit IlvA enzymatic activity. As a result, the insensitivity towards feedback inhibition of TdcB became less important than the activity of the enzyme itself under the given experimental condition.

Similarly, feedback inhibition on LeuA by leucine present in the yeast extract led to the construction and testing of the leuA* feedback insensitive mutant G462D. The point mutation on leuA* was introduced by site-directed mutagenesis using SOE and the resulting operon leuA*BCD was over-expressed on plasmid pCS51. As shown in FIG. 53, the feedback insensitive LeuA* failed to increase the production of 1-propanol and 1-butanol. Again, this demonstrated that the amount of leucine present in the cells was probably below the inhibitory level to cause an adverse effect on the LeuA enzymatic activity.

Co-Production of 1-Propanol and 1-Butanol from CRS-BuOH 23 and its Major by-Products.

Figure 54E:
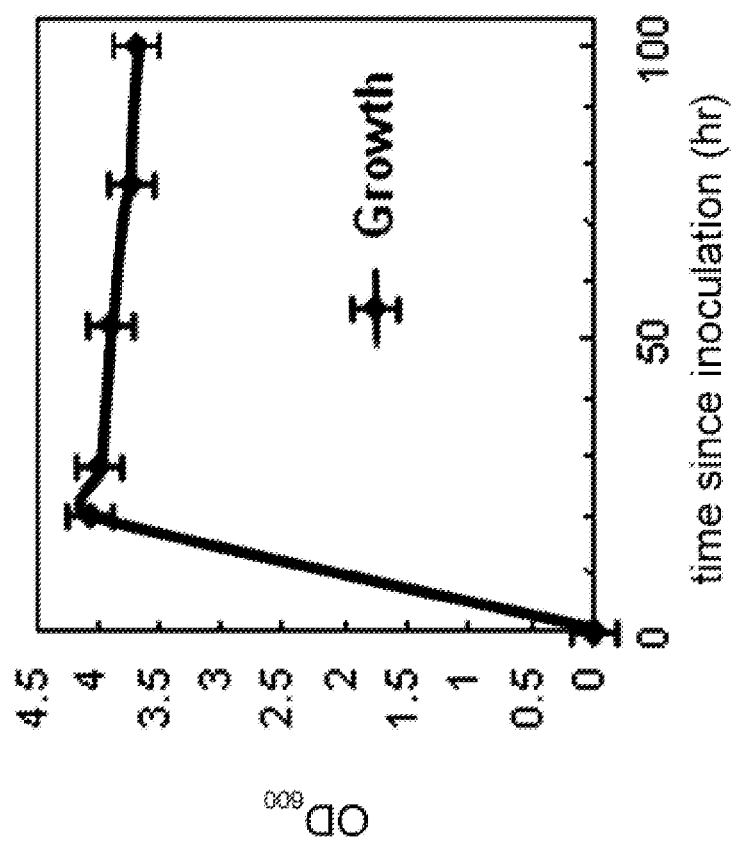

Time course of the alcohol and metabolite productions in the final strain BW ΔmetA, Δtdh, ΔilvB, ΔilvI, ΔadhE with plasmids pCS49, pSA62 and pSA55I (CRS-BuOH 23) is shown in FIG. 54. Both propanol and butanol production steadily climbed up in almost a linear fashion throughout the 72 hour period and appeared to plateau by the end of the third day. The same behavior was also observed in the ethanol production. Ethanol formation in the ΔadhE-background might be due to the slight affinity of Kivd towards pyruvate. On the other hand, extracellular levels of the major metabolites acetate and lactate continued to increase significantly after the alcohol production period, which might be a result of excess acetyl-CoA and NADH respectively. As seen in FIG. 54, major consumption of glucose occurred in the alcohol production period and appeared to be independent of growth alone. After the first 24 hours, cells stopped growing and remained somewhat stationary during the next few days of alcohol production.

Elimination of Fermentative Products and its Effect on the Biofuel Production.

The major mixed-acid fermentation genes adhE, ldhA, pta, pflB were deleted in various combinations to further characterize the present C3/C4 alcohol production system. As shown in Table 12, ethanol generation was the primary sink for excess NADH and disruption of adhE led to a more prominent accumulation of lactate. When ldhA was deleted, approximately 1 g/L of ethanol was secreted while acetate production also increased. Decrease in glucose consumption was observed in both the pta and ldhA knock-out strains. While the deletion of adhE, ldhA, pta, and combinations of them all resulted in lower propanol and butanol production, pflB knock-out had less prominent effect in that regard. This showed that the bulk acetyl-CoA pool came from the activity of pyruvate dehydrogenase complex (PDHc) instead of the PflB complex.

TABLE 11

Effect of fermentation gene knock outs on target alcohols and minor by-product levels

| Production level (mg/L) | Gene deleted in addition to ΔmetA, tdh, ilvB, ilvI in BW25113F' background | | | | | |
|---|---|---|---|---|---|---|
| | — | ΔadhE | Δpta | ΔldhA | ΔpflB | ΔadhE, pta |
| Propanol | 1017.0 | 1218.5 | 576.8 | 649.0 | 788.5 | 710.0 |
| Butanol | 1006.5 | 1094.5 | 770.5 | 581.5 | 932.5 | 853.5 |
| Ethanol | 278.0 | 127.4 | 358.5 | 923.0 | 285.5 | 122.0 |
| Pyruvate | 17.9 | 16.7 | 23.8 | 40.2 | 9.9 | 8.4 |
| Acetate | 2882.8 | 2726.7 | 2895.5 | 4230.0 | 3390.0 | 2346.1 |
| Lactate | 0.0 | 494.6 | 0.0 | 0.0 | 0.0 | 0.0 |
| Formate | 0.0 | 0.0 | 0.0 | 0.0 | 0.0 | 0.0 |
| Glucose consumed (g/L) | 25.3 | 26.1 | 23.7 | 18.7 | 23.4 | 25.4 |

Cells were cultured for 72 hours as described in materials and methods. The data shown is the $72^{nd}$ hour time point.

With over-expression of the heterologous kivd and adh2 and the *E. coli* ilvA, leuABCD, and thrA*BC, the disclosure demonstrates the production of 1-butanol and 1-propanol. The production of 1-butanol uses 2-ketovalerate, which inevitably involves the intermediate 2-ketobutyrate and the unnatural norvaline biosynthetic pathway. Since Kivd has similar affinity towards both 2-ketoacids and 2-ketobutyrate is a secondary substrate for LeuA, 1-propanol was co-produced with 1-butanol in similar amounts.

Deregulation of the threonine biosynthesis and removal of the diverging pathways catalyzed by metA and tdh successfully conserved the threonine pool and improved both 1-propanol and 1-butanol production titer. Lysine biosynthesis, on the other hand, although also branches off of the threonine pathway, was not eliminated for its essential intermediate diaminopimelate that participates in the synthesis of bacterial cell wall. Nevertheless, the significance of lysine auxotroph is contemplated. Threonine hyper-production using rational design has also hinted at the beneficial effect of lysA deletion. 1-butanol productivity was further optimized upon interruption of the valine, leucine, and isoleucine biosynthesis pathway by inactivating AHAS I and III, which led to a two-fold increase in 1-butanol but little effect on 1-propanol. This selective improvement was attributed to i) the increase in the availability of 2-ketobutyrate and acetyl-CoA and ii) the release of the essential enzymes LeuABCD from their natural substrates in the leucine pathway.

As seen from FIG. 54, an approximate 13~15 mg/L/hr production of each alcohol was observed under the experimental condition. Improvement of strain tolerance to 1-propanol and 1-butanol can lead towards higher productivity.

Transcriptional regulation and attenuation, which are two major mechanisms of amino acid regulation, had minimal effect on the key enzymes here since all essential genes were cloned and expressed behind a non-native promoter without the leader sequence. On the other hand, allosteric feedback inhibition of the enzymes by their own amino acid products could not be neglected, specifically IlvA and LeuA. TdcB is the biodegradative threonine dehydratase that provides metabolic energy for cells under anaerobic growth in the presence of excess amino acids and scarce glucose. Its expression is controlled transcriptionally through catabolite repression and is activated by its allosteric effector AMP by decreasing its $K_m$ for threonine. Since high concentrations of pyruvate and some 2-keto acids (including 2-ketobutyrate) were shown to inactivate TdcB enzymatically, build-up of these intermediates can have a detrimental impact on its enzymatic activity when there is not enough AMP to counter the negative effect. Also, the higher $K_m$ value for threonine associated with TdcB than IlvA in the absence of significant intracellular AMP level can result in a slower deamination rate, thus contribute to the poorer performance on the overall alcohol productivity as seen in FIG. 53 ($K_m$=8 mM for purified E. coli IlvA in the absence of isoleucine and 20 mM for E. coli TdcB in the absence of AMP). As for the LeuA* mutant, it is possible that the mutation G462D selected towards 2-keto-isovalerate in the leucine biosynthetic pathway has led to a further decrease in its affinity towards 2-ketobutyrate.

Attempts to minimize fermentation by-products in the semi-aerobic culture environment has brought attention to the NADH(P)H balance in the present production system. Threonine biosynthesis requires the expenditure of three moles of NADPH and two moles of ATP while 1-butanol and 1-propanol production starting from 2-ketobutyrate consume a net zero mole of NADH and a net one mole of NADH respectively. Phosphoenolpyruvate carboxylase encoded by the gene ppc worked constitutively to replenish the oxaloacetate (OAA) being taken away by the threonine pathway and kept the TCA cycle going. Partial activities of the TCA cycle under the semi-aerobic condition led to excess reducing power; as a result, fermentative products such as ethanol and lactate were used to discard the extra NADH. As seen in Table 11, ethanol was a more favorable NADH sink for its consumption of an additional mole of NADH than the production of lactate. When adhE was disrupted, lactate secretion was much more prominent; on the other hand, when ldhA was deleted, about 1 g/L of ethanol was accumulated in the culture broth. With low activity of the TCA cycle due to gradual loss of aerobicity and inefficiency of the downstream pathways relative to glycolysis, acetate production appeared to become the major source of ATP generation and sink for excess acetyl-CoA and/or pyruvate. These could explain the negative correlation between butanol production and acetate secretion as illustrated by comparing the WT strain and CRS-BuOH 23 in FIGS. 51 and 54. As expected, elimination of pta reduced glucose consumption and growth in the particular culture system. However, it failed to eliminate the acetate production for reasons under investigation. From the absence of formate in the culture broth and its insignificant effect on butanol productivity of the pflB knock-out, it appears that PDHc was the main acetyl-CoA provider during the alcohol production period.

Figure 48A:
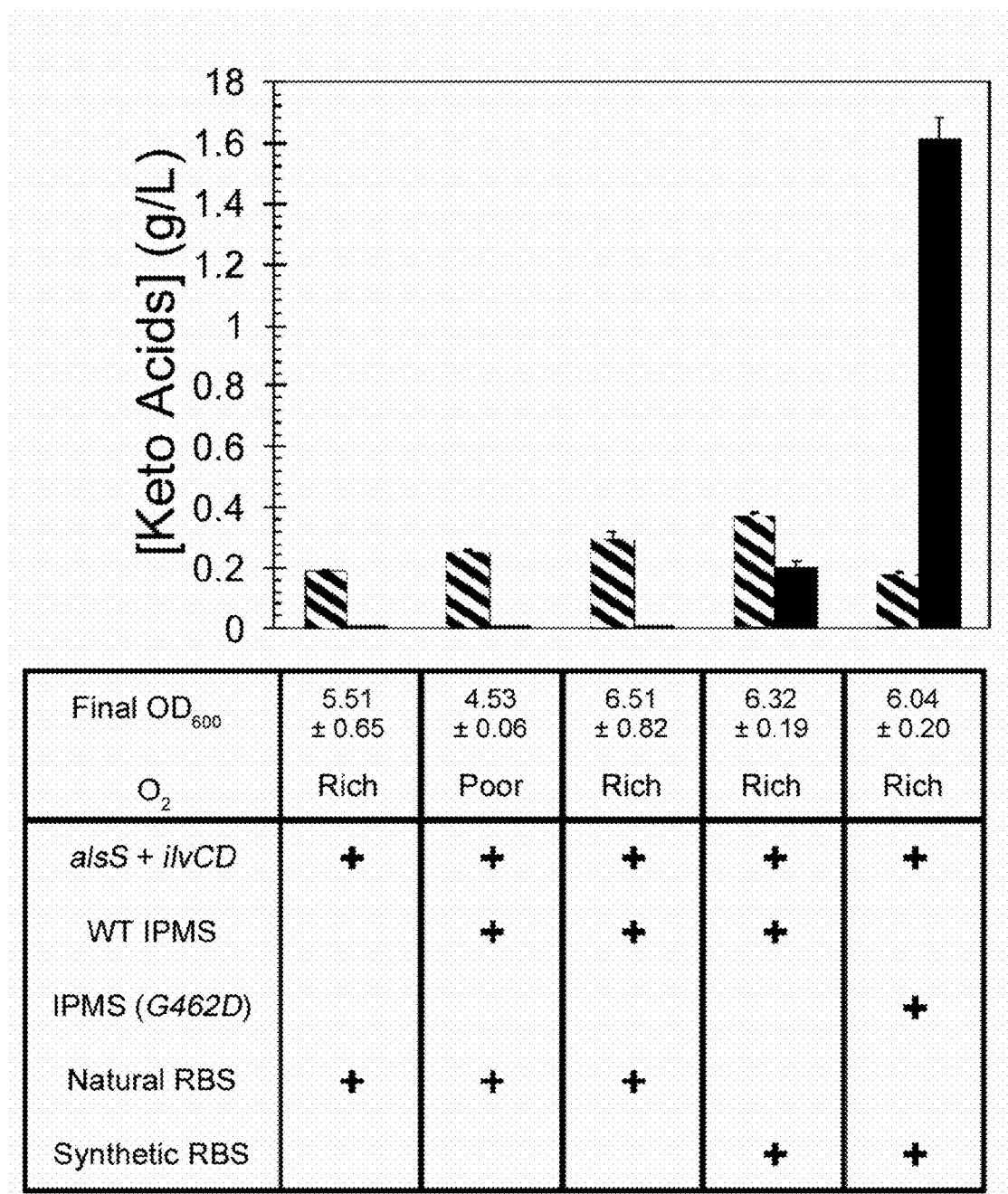
FIG. 48A-B is a graph and a table depicting α-keto acid production. Checkered columns indicate 2-ketoisovalerate; solid columns are for 2-ketoisocaproate. (A) Production of α-keto acids in JCL260 background. Strains were tested for production of 2-ketoisovalerate (isobutanol) and 2-ketoisocaproate (3-methyl-1-butanol). The RBS change is for the leuA gene product only (IPMS). (B) Production of α-keto acids in L-leucine synthesis knockout backgrounds. 'Δ' indicates deletion.

Initially the hypothesis was that isobutanol production was much higher than 3-methyl-1-butanol production due to competition of the substrate α-ketoisovalerate between the gene products of kivd and leuA. In order to investigate this hypothesis, the production of the α-keto acid precursors, the substrates for kivd, to isobutanol and 3-methyl-1-butanol were examined. To achieve this, leuABCD was expressed on a ColE1 derived plasmid along with alsS-ilvCD (pSC101 derived plasmid) under control of $P_{LlacO-1}$. Under oxygen poor and oxygen rich conditions, the isobutanol precursor and leuA substrate, α-ketoisovalerate (KIV), was the main product (FIG. 48A). KIV was produced to a final concentration of 0.25 and 0.29 g/L, respectively, while the 3-methyl-1-butanol precursor, α-ketoisocaproate (KIC), was not detected (<5 mg/L). In hopes of increasing the KIC pool, the expression level of leuA was increased by changing the RBS from its native sequence to a more consensus sequence. Elevated expression of the leuA gene product increased the KIC concentration to 0.20 g/L, although KIV was still the main product (0.37 g/L) (FIG. 48A). This result suggests that the decreased 3-methyl-1-butanol production was not due completely to competition for KIV but rather from the low activity of the leuA gene product (isopropylmalate synthase).

Isopropylmalate synthase (IPMS) catalyzes the condensation of KIV with acetyl-CoA. The accumulation of α-ketoisovalerate could be due to feedback inhibition of IPMS by free L-leucine synthesized from α-ketoisocaproate. To relieve the feedback inhibition of the leuA gene product, two strategies were employed. A feedback insensitive mutant of IPMS (IPMS (G462D)) was employed. Second, the final step in the L-leucine synthesis pathway was inactivated by deleting ilvE (branched-chain amino acid transferase) and tyrB (tyrosine aminotransferase), two isozymes responsible for converting α-ketoisocaproate into L-leucine.

Figure 48B:
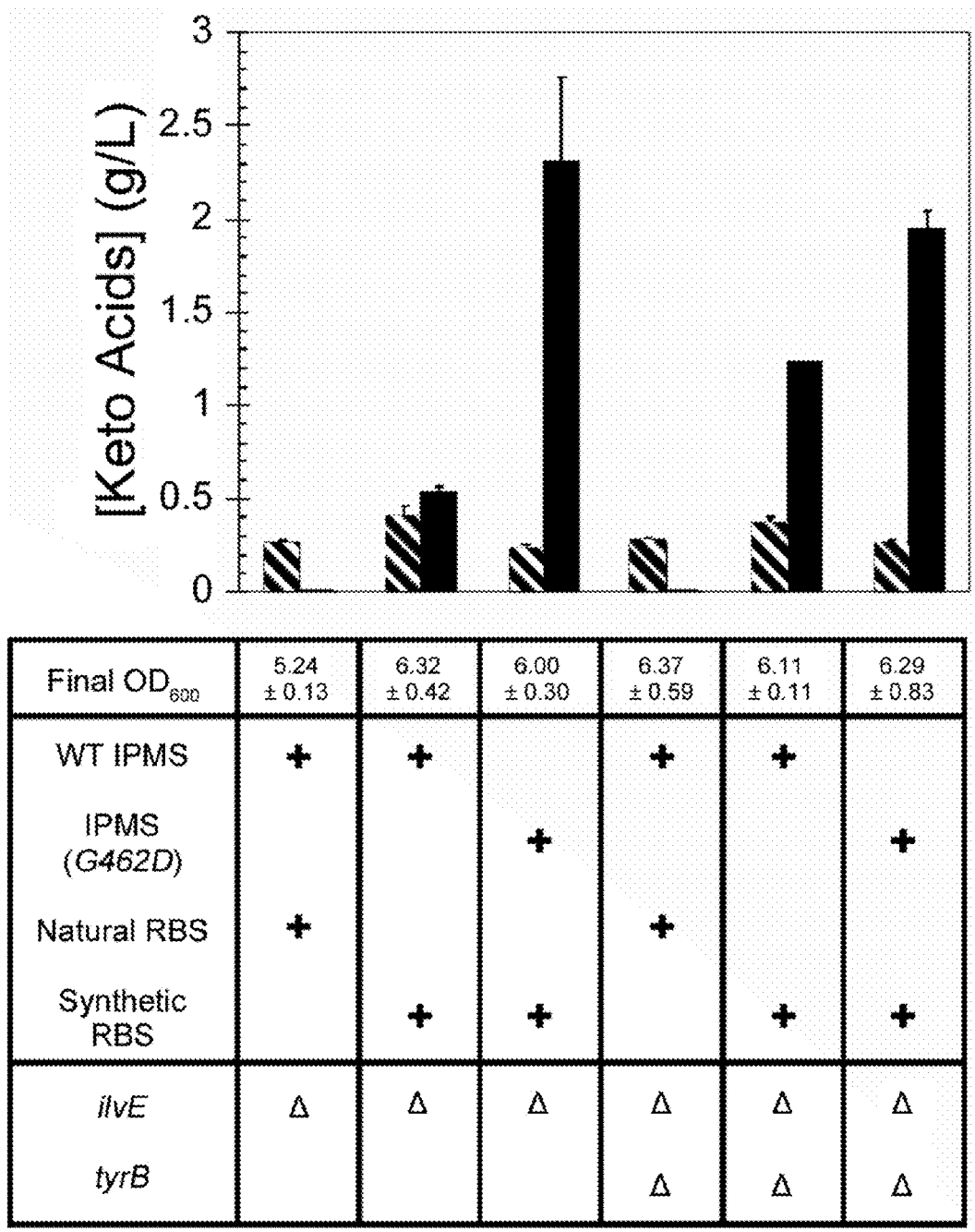

When IPMS (G462D) was expressed, the product distribution dramatically shifted toward KIC, with a final concentration of 1.61 g/L, while KIV accumulation decreased to 0.17 g/L (FIG. 48A). Inactivation of ilvE increased production of KIC to 0.53 g/L in the strain expressing WT IPMS, while deletion of ilvE and tyrB further increased accumulation of KIC to 1.23 g/L (FIG. 48B). The production of KIV in the ΔilvE and the ΔilvE ΔtyrB backgrounds remained similar to that of the ilvE⁺ tyrB⁺ strain, with final concentrations of 0.40 g/L and 0.37 g/L, respectively. By combining the ΔilvE and ΔilvE ΔtyrB host strains with the expression of IPMS (G462D), KIC increased to 2.31 g/L and 1.95 g/L, respectively (FIG. 48B).

Figure 49A:
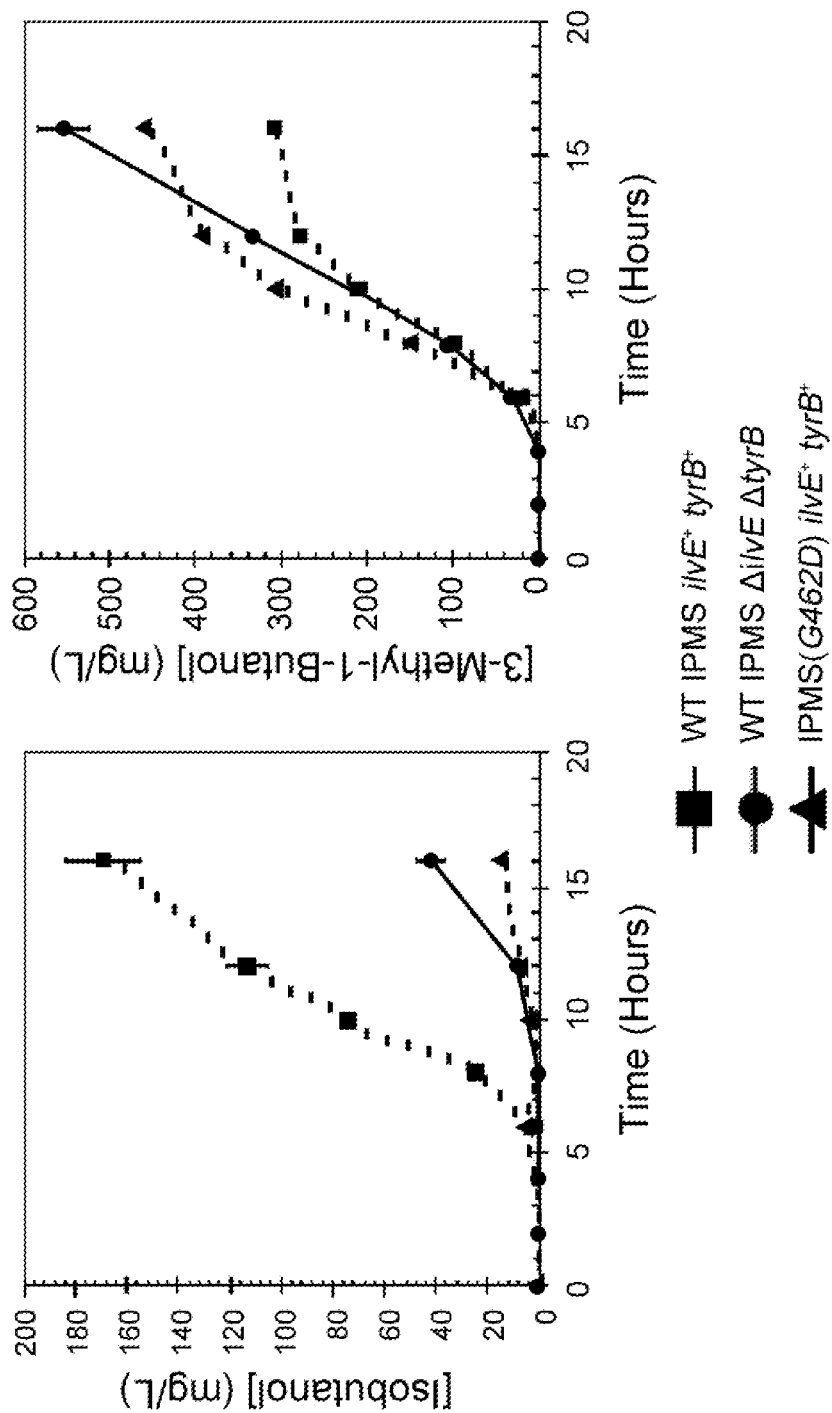
FIG. 49A-B show 3-methyl-1-butanol production with removal of feedback inhibition. (A) JCL260 hosts harboring WT IPMS (IAA88) and IPMS(G462D) (IAA89) were compared for growth and alcohol production. (B) Growth and alcohol production was quantified in the strain harboring WT IPMS (IAA90) in a JCL260 ΔilvE ΔtyrB (IAA69) background.
Figure 49B:
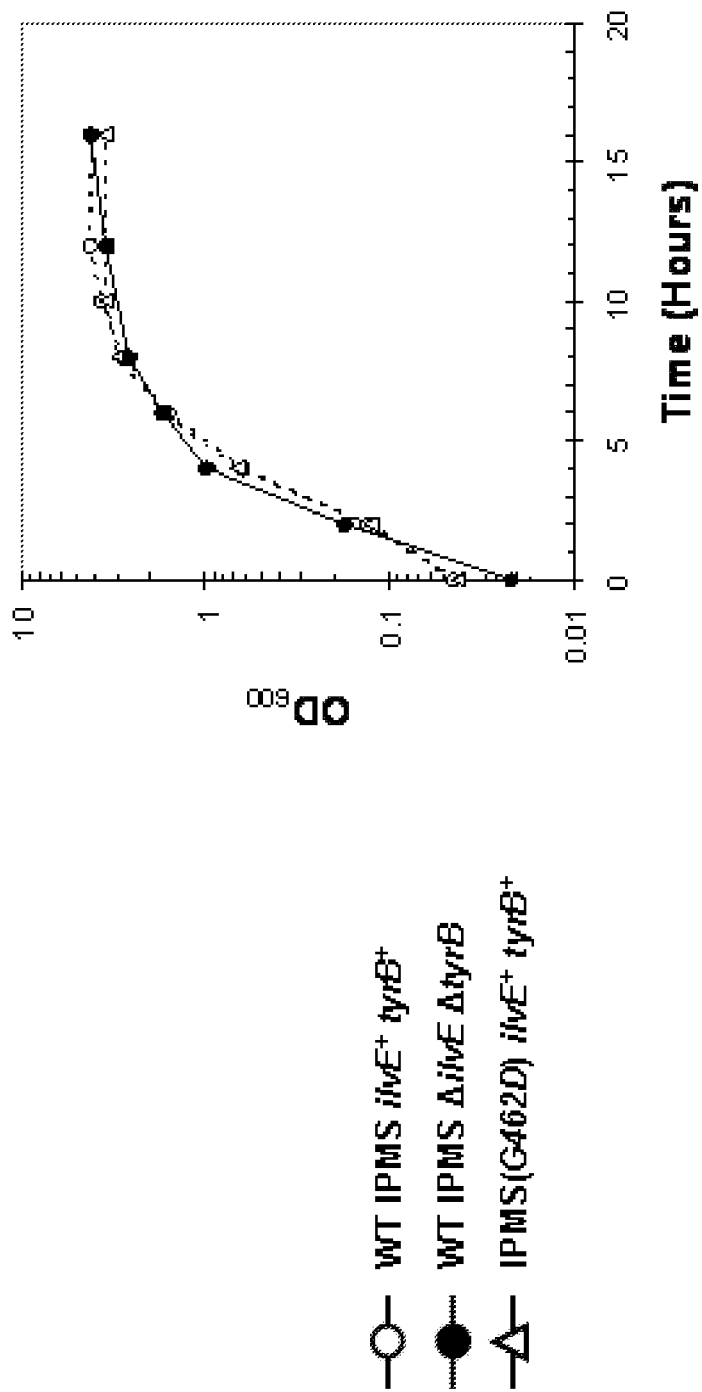

With an increased production of KIC, the entire pathway for 3-methyl-1-butanol production from pyruvate was transformed using either WT IPMS or IPMS (G462D). Similar to the results seen for keto-acid production, the strain with WT IPMS still produced a significant amount of isobutanol (169 mg/L) in an ilvE$^+$ tyrB$^+$ background, although 3-methyl-1-butanol was the main product (308 mg/L) (FIG. 49A). As expected, when IPMS (G462D) was expressed in the ilvE$^+$ tyrB$^+$ background, 3-methyl-1-butanol was the main product, with a final titer of 459 mg/L, with isobutanol accumulating to only 15 mg/L (FIG. 49). The removal of feedback inhibition of IPMS by mutation changed the product distribution from 1.8:1 (3-methyl-1-butanol:isobutanol) using WT IPMS to greater than 30:1. Accumulation of other common metabolic byproducts including pyruvate, fumarate, and acetate was minimal (Table 12).

TABLE 12

Metabolic byproducts of 3-methyl-1-butanol producing strains

| Strain | | Metabolite Concentration (g/L) | | | |
|---|---|---|---|---|---|
| | | Glucose | Pyruvate | Fumarate | Acetate |
| IAA88 | Initial (0 hr) | 4.7 | ND | ND | ND |
| IPMS (WT) | Final (16 hr) | ND$^a$ | ND | ND | 0.03 |
| ilvE$^+$ tyrB$^+$ | Maximum (hr) | 4.7 (0 hr) | 0.53 (4 hr) | 0.02 (6 hr) | 0.03 (16 hr) |
| IAA90 | Initial (0 hr) | 4.7 | ND | ND | ND |
| IPMS (WT) | Final (16 hr) | ND | ND | ND | 0.06 |
| ilvE$^-$ tyrB$^-$ | Maximum (hr) | 4.7 (0 hr) | 0.66 (4 hr) | 0.02 (6 hr) | 0.07 (6 hr) |
| IAA89 | Initial (0 hr) | 4.7 | ND | ND | ND |
| IPMS (G462D) | Final (16 hr) | ND | ND | ND | 0.02 |
| ilvE$^+$ tyrB$^+$ | Maximum (hr) | 4.7 (0 hr) | 0.54 (4 hr) | 0.02 (6 hr) | 0.02 (16 hr) |

$^a$ND = Not Detected
Other metabolites such as lactate and succinate were not detected When the ΔilvE ΔtyrB strain expressing the WT leuA gene product was examined for 3-methyl-1-butanol production, the results mimicked that of the strain containing the mutant IPMS. 3-methyl-1-butanol accumulated to a final concentration of 553 mg/L, while isobutanol was present at only 42 mg/L (FIG. 49). This corresponds to a product distribution of 3-methyl-1-butanol to isobutanol of greater than 13:1.

The disclosure provide synthetic approaches for the production of high-order alcohols as next-generation biofuels. The examples provided herein utilize *E. coli* as a host cell metabolically-modified to include recombinant biosynthetic pathways. However, it is understood that other microorganisms, such as *Saccharamyces cerevisiae*, provide suitable host cells for including recombinant biosynthetic pathways therein. These host organisms have fast growth rates and are facultative anaerobes, allowing for a flexible and economical process design for large-scale production. However, importing non-native pathways from other organisms has disadvantages. The expression of the heterologous pathways may lead to a metabolic imbalance, while the accumulation of the heterologous metabolites may cause cytotoxicity. For example, the 1-butanol production pathway of *C. acetobutylicum* has three intermediate metabolites carrying coenzyme A (CoA). An excess expression of this pathway may cause the depletion of the free CoA pool and perturb the metabolism in *E. coli*. To achieve the high productivity of the target foreign products, it is desirable to seek pathways that are compatible to the host. Instead of direct transfer of the common pathway for 1-butanol production into the non-native host, *E. coli*, the modified microorganisms provided herein take advantage of the existing metabolic capability in *E. coli* and the broad substrate range of the last two steps in the Ehrlich pathway for 2-keto acid degradation.

2-Keto acids are intermediates in amino acid biosynthesis pathways. These metabolites can be converted to aldehydes by broad-substrate range 2-keto-acid decarboxylases (KDCs) and then to alcohols by alcohol dehydrogenases (ADHs) Using this strategy, two non-native steps are needed to produce biofuels by shunting intermediates from amino acid biosynthesis pathways to alcohol production (FIG. 1A). Amino acid biosynthesis pathways produce various 2-keto acids (FIG. 1B). In the present studies, six different 2-keto acids were used for alcohol production. The isoleucine biosynthesis pathway generates 2-ketobutyrate and 2-keto-3-methyl-valerate which can be converted to 1-propanol and 2-methyl-1-butanol, respectively. The valine biosynthesis pathway produces 2-keto-isovalerate which is the precursor for isobutanol. The leucine biosynthesis pathway generates 2-keto-4-methyl-pentanoate which is the substrate for 3-methyl-1-butanol. The phenylalanine biosynthesis pathway produces phenylpyruvate which can lead to 2-phenylethanol. The norvaline biosynthesis pathway, which is a side-reaction of the leucine biosynthesis, produces a substrate for 1-butanol, 2-ketovalerate.

The 2-keto acid decarboxylase activity can be provided by one of the following genes: PDC6 from *Saccharomyces cerevisiae*, kivd from *Lactococcus lactis*, and THI3 *Saccharomyces cerevisiae* (α-ketoisocaproate decarboxylase) and pdc *Clostridium acetobutylicum*. The alcohol dehydrogenase (Adh) activity can be provided by ADH2 from *Saccharomyces cerevisiae*.

Valine is synthesized from two molecules of pyruvate in a pathway involving four reactions which are catalyzed by AHAS (the ilvBN gene product), isomeroreductase (the ilvC gene product), dihydroxyacid dehydratase (the ilvD gene product), and transaminase B (the ilvE gene product). As in other organisms, the same enzymes also catalyze the synthesis of L-isoleucine from pyruvate and 2-ketobutyrate. The latter is formed from L-threonine by threonine dehydratase (the ilvA gene product). AHAS is the key enzyme of branched-chain amino acid synthesis. Valine causes feedback inhibition of AHAS I, encoded by ilvBN, and AHAS III, encoded by the acetohydroxy acid synthase operon ilvIH, and their small regulatory subunits, IlvN and IlvH, were shown to be necessary for valine sensitivity.

A enzyme in this alcohol production strategy is KDC, which is common in plants, yeasts and fungi but less so in bacteria. The aldehydes produced can then be converted to alcohols by an Adh, which is commonly found in many organisms. Some of the KDCs have broad-substrate ranges, while others are more specific. To test the capability of the endogenous 2-keto acids as a substrate for KDC in *E. coli*, five KDCs including Pdc6, Aro10, Thi3, from *S. cerevisiae*, Kivd from *Lactococcus lactis*, and Pdc from *C. acetobutylycum* were over-produced with alcohol dehydrogenase 2 (Adh2) of *S. cerevisiae*. *E. coli* cultures expressing these foreign genes were grown in a minimal media with 0.2 M glucose. GC-MS analysis (see Table 13) revealed that the strains expressing either kivd or ARO10 produced all of the expected alcohols. *S. cerevisiae* PDC6 and *C. acetobutylum* pdc were not as versatile, whereas *S. cerevisiae* THI3 did not display the expected activity.

Table 13 shows alcohol productions with KDC and ADH in *E. coli* as follows:

| KDC plasmid | Kivd pSA55 | ARO10 pSA56 | PDC6 pSA49 | THI3 pSA57 | Pdc(C.A.) pSA59 |
|---|---|---|---|---|---|
| | Product (µM) | | | | |
| 1-propanol | 520 | 290 | 125 | ND | ND |
| isobutanol | 5242 | 2094 | 260 | ND | 75 |
| 1-butanol | 220 | 95 | ND | ND | ND |
| 2-methyl-1-butanol | 766 | 652 | 56 | ND | ND |
| 3-methyl-1-butanol | 1495 | 1099 | 92 | ND | ND |
| 2-phenylethanol | 324 | 469 | ND | ND | 175 |

Aldehydes were detected in trace amounts, indicating sufficient activity of Adh2. These results demonstrate that Kivd is an active and versatile decarboxylase and, therefore, suited for these objectives.

The addition of various 2-keto acids (see Table 12) to the *E. coli* culture expressing kivd confirmed the specific production of the corresponding alcohols by 2- to 23-fold. The supply of 2-keto acids also decreased the production of the other alcohols dramatically. These results indicate that increasing the flux to the 2-keto acids could improve both the productivity and specificity of the alcohols production.

Table 13 shows alcohol productions with the supply of 2-keto acids as follows:

| Product (µM) | 2-ketobutyrate | 2-keto-isovalerate | 2-ketovalerate | 2-keto-3-methyl-valerate | 2-keto-4-methyl-pentanoate | phenylpyruvate |
|---|---|---|---|---|---|---|
| 1-propanol | 2138 | ND | ND | ND | ND | 8 |
| isobutanol | 98 | 10016 | ND | ND | ND | 64 |
| 1-butanol | 492 | ND | 3926 | ND | ND | 23 |
| 2-methyl-1-butanol | 1315 | ND | ND | 5284 | ND | ND |
| 3-methyl-1-butanol | ND | ND | 52 | ND | 3756 | 105 |
| 2-phenylethanol | 26 | 109 | 66 | ND | ND | 7269 |

Existing *E. coli* metabolic pathways were genetically modified to increase the production of the specific 2-keto acid so that the desired alcohol is produced. To produce isobutanol, the ilvIHCD genes were amplified to enhance 2-ketoisovalerate biosynthesis (FIG. 1B). The ilvIH operon of *Escherichia coli* encodes acetohydroxy acid synthase, the first enzyme in the isoleucine, valine and leucine biosynthetic pathway. The acetohydroxy acid synthase III isozyme, which catalyzes the first common step in the biosynthesis of isoleucine, leucine, and valine in *Escherichia coli* K-12, is composed of two subunits, the ilvI (acetolactate synthase III large subunit) and ilvH (acetolactate synthase small subunit) gene products. The ilvIH operon of *Escherichia coli* encodes acetohydroxy acid synthase, the first enzyme in the isoleucine, valine and leucine biosynthetic pathway. The ilvC gene of *Escherichia coli* encodes acetohydroxy acid isomeroreductase, the second enzyme in the parallel isoleucine-valine biosynthetic pathway. The ilvD gene of *Escherichia coli* encodes dihydroxy-acid dehydratase, the third enzyme in the isoleucine-valine biosynthetic pathway.

An operon encoding the ilvI, ilvH, ilvC and ilvD genes under the control of $P_L$lacO1 was constructed on a plasmid. The amplified Ilv pathway is then combined with the synthetic alcohol producing pathway (Kivd and Adh2) to achieve isobutanol production. As a result of the ilvIHCD pathway expression, this strain produced 23 mM isobutanol, which is a ~5-fold increase over the strain without the ilvIHCD pathway overexpression (see Table 14 below and FIG. 2A).

Table 14 shows alcohol productions with the ilvIRD pathway and overexpression as follows:

| | KDC | | | | | |
|---|---|---|---|---|---|---|
| | kivd | kivd | kivd | kivd | kivd | kivd |
| | | | Strain | | | |
| | JCL16 | JCL16 | JCL16 | JCL16 | JCL88 | JCL88 |
| | | | plasmid | | | |
| | pSA55 | pSA55 | pSA54 pSA55 | pSA54 pSA55 | pSA54 pSA55 | pSA54 pSA55 |
| | | | Time (hr) | | | |
| Product (µM) | 16 | 24 | 16 | 24 | 16 | 24 |
| ethanol | 1277 | 1744 | 2047 | 2228 | 850 | 1430 |
| 1-propanol | 321 | 420 | 612 | 808 | 210 | 493 |
| isobutanol | 2069 | 2172 | 12979 | 20813 | 13794 | 30910 |
| 1-butanol | 67 | 112 | 146 | 198 | 89 | 127 |
| 2-methyl-1-butanol | 223 | 629 | 262 | 345 | 195 | 239 |
| 3-methyl-1-butanol | 1096 | 1696 | 1103 | 1577 | 727 | 1333 |
| 2-phenylethanol | 545 | 1220 | 282 | 425 | 454 | 820 |

These results demonstrate that the synthetic pathway was functional and capable of supplying the 2-ketoisovalerate required for the efficient production of isobutanol. To further increase the isobutanol production, one or more genes that contribute to byproduct formation, including adh, Idh, frd, fnr, pflB and/or pta, were deleted. These deletions could increase the level of pyruvate available for the ilvIHCD pathway. Indeed, this strain produced 30 mM isobutanol, indicating that these deletions were beneficial for isobutanol production. In addition, this strain converted glucose to isobutanol with a yield of 0.21 g of isobutanol per gram of glucose between 16 hr and 24 hr (FIG. 2A, right panel). Additional data illustrated in FIG. 42 further show that these deletions would also increase the level of pyruvate available for the acetolactate synthase pathway, affecting the isobutanol production with an increase from 4.5 g/L (61 mM) isobutanol for JCL16 to 13.2 g/L (356 mM) isobutanol for JCL260 after 64 h. This result demonstrates the potential of this strategy, since the yield has already reached 50% of the theoretical maximum without detailed optimization of the pathways and production conditions. This high yield is attributed to the full compatibility of the synthetic pathway with the host cell's physiology. Additional Yield Data is provided in the Table immediately below for strain SA237:

| Time (hr-hr) | Yield (g/g) | Time (hr) | (g/L) |
|---|---|---|---|
| 0-16 | ~0.32 | 0 | 0.00 |
| 16-40 | ~0.4 | 16 | ~7.172 |
| 40-64 | ~0.36 | 40 | ~12.01 |
| 64-88 | ~0.32 | 64 | ~17.11 |
| 88-112 | ~0.33 | 88 | ~19.41 |
| 0-40 | ~0.34 | 112 | ~21.89 |
| 0-64 | ~0.35 | | |
| 0-88 | ~0.34 | | |
| 0-112 | ~0.34 | | |

30 C.
M9 + 0.5% YE
0.1 mM IPTG

Ethanol production for 0-112 hrs was~0.0037 g/g (240 mg/L)

| | Isobutanol (mM) | | | | | IsoBuOH |
|---|---|---|---|---|---|---|
| Time | #1 | #2 | #3 | AVE | STDEV | (g/L) |
| 0 | | | | | | |
| 16 | 98.45 | 108.29 | 83.56 | 96.77 | 12.45 | 7.172345 |
| 40 | 158.21 | 173.42 | 154.3 | 161.98 | 10.10 | 12.00571 |
| 64 | 225.54 | 253.33 | 213.67 | 230.85 | 20.36 | 17.11035 |
| 88 | 256.23 | 281.21 | 248.11 | 261.85 | 17.25 | 19.40832 |
| 112 | 296.43 | 312.56 | 277.12 | 295.37 | 17.74 | 21.89282 |

| Time | | Glucose (g/L) | | | |
|---|---|---|---|---|---|
| 0 | 36 | 36 | 36 | 6.00 | |
| 16 | 13.2 | 12.5 | 14.1 | 13.27 | 0.80 |
| 40 | 1.2 | 0.9 | 1.5 | 1.20 | 0.30 |
| 40.1 | 31.2 | 30.9 | 31.5 | 31.20 | |
| 64 | 17.4 | 15.6 | 18.9 | 17.30 | 1.65 |
| 88 | 10.3 | 7.8 | 12.5 | 10.20 | 2.35 |
| 112 | 2.8 | 1.4 | 4.1 | 2.77 | 1.35 |

Initially 36 g/L glucose was present at T=0. At 40.1 hrs and additional 30 g of glucose was added to the culture. Glucose values at the different hours represent g/L at the specific time point (e.g., at 16 hrs. ~22.8 g of glucose was metabolized).

A similar strategy was applied to generating a microorganism that produces 1-butanol. The 1-butanol producing pathway in its native producers is used during fermentative growth, and many of the enzymes in this pathway are oxygen-sensitive and CoA-dependent. The data indicates that by overexpressing kivd or ARO10 in E. coli, which does not have the 1-butanol fermentative pathway, the cell already produced a small amount of 1-butanol (Table 13) from glucose in a non-fermentative growth, suggesting the existence of corresponding 2-keto acid precursor, 2-ketovalerate. However, 2-ketovalerate is not a common metabolite in E. coli. To increase the amount of synthesized 2-ketovalerate, the broad-substrate specificity of the leuABCD pathway whose natural substrate is 2-ketoisovalerate (FIG. 1B) was utilized. By using a smaller substrate, 2-ketobutyrate, which has one less methyl group than 2-ketoisovalerate (FIG. 1A), 2-ketovalerate was synthesized in a manner similar to the transformations in leucine biosynthesis. 2-ketobutyrate can be generated from L-threonine by the threonine dehydratase, encoded by the ilvA gene, or from an alternative pathway starting from acetate and pyruvate identified in *Leptospira interrogans* serovar and *Methanocaldococcus jannaschii*. In the latter pathway, 2-ketobutyrate is generated from citramalate by the enzymes isopropylmalate isomerase (LeuCD) and beta-isopropylmalate dehydrogenase (LeuB).

To produce 1-butanol, an operon encoding the ilvA-leuABCD pathway under the control of PLlacO1 was constructed. Strain with ilvA-leuABCD pathway produced 0.6 mM 1-butanol, which was a ~3-fold increase compared with the strain without the ilvA-leuABCD pathway overexpression (see Table 15 below and FIG. 2B).

Table 15 shows alcohol productions with threonine pathway overexpression as follows:

| KDC | kivd | kivd | kivd | kivd |
|---|---|---|---|---|
| plasmid | pSA55 | pSA55 | pSA55 | pSA54 |
| | | pSA62 | pSA62 | pSA62 |
| strain | JCL16 | JCL16 | JCL16 | SA203 |
| 0.8% L-threonine | − | − | + | + |
| | | Product (µM) | | |
| ethanol | 2450 | 2343 | 3243 | 1493 |
| 1-propanol | 520 | 1356 | 7592 | 9849 |
| isobutanol | 2242 | 4322 | 1061 | ND |
| 1-butanol | 220 | 583 | 3157 | 9232 |
| 2-methyl-1-butanol | 766 | 1444 | 2002 | ND |
| 3-methyl-1-butanol | 1495 | 4074 | 1349 | ND |
| 2-phenylethanol | 324 | 358 | 269 | 524 |

In addition, when the media was supplemented with 0.8% L-threonine, a dramatic increase of 1-butanol production to 3.2 mM was observed, indicating that 2-ketovalerate can be produced from L-threonine via an IlvA-mediated reaction (see FIG. 2C).

To further improve 1-butanol production, the ilvD gene was deleted. This gene encodes dihydroxy-acid dehydratase, an enzyme that produces both 2-ketoisovalerate (a precursor for leucine and valine) and 2-keto-3-methyl-valerate (a precursor for isoleucine). This deletion could be beneficial for two reasons. First, the deletion of ilvD eliminates the native substrate, 2-ketoisovalerate, for the leuABCD pathway, thus reducing the competitive substrate inhibition. Second, the deletion of ilvD eliminates of competing substrates for Kivd, 2-keto-3-methyl-valerate and 2-keto-4-methyl-pentanoate. As expected, deletion of ilvD improved 1-butanol production (FIG. 2C).

Since L-threonine hyperproduction in E. coli strains has been developed for commercial production, a threonine producing strain can be modified using the above strategy in order to manufacture an organism that produces 1-butanol. For further improvement, it would be necessary to increase the activity of the leuABCD pathway towards to the non-native substrate, 2-ketobutyrate, and to raise the specificity of Kivd for 2-ketovalerate. Since 2-ketobutyrate is also the substrate for 1-propanol (FIG. 1B), increasing 2-ketobutyrate availability also enhances the production of 1-propanol (FIG. 2B and FIG. 2C, right panel). Therefore, increasing the leuABCD activity and the specificity of KDC would be crucial for high-efficiency 1-butanol production.

Alcohol profiles and yield for 1-butanol and 1-propanol producing strain, CRS-BuOH23 is provided below:

| time period | PrOH | BuOH | total | EtOH |
|---|---|---|---|---|
| 0-20 | 0.037 | 0.015 | 0.053 | 0.004 |
| 20-28 | 0.054 | 0.046 | 0.1 | 0.004 |
| 28-52 | 0.033 | 0.042 | 0.075 | 0.003 |
| 52-76 | 0.061 | 0.066 | 0.127 | 0.009 |
| 76-100 | −0.016 | −0.014 | −0.03 | 0.003 |
| 0-76 | 0.043 | 0.038 | 0.081 | 0.005 |

-continued

| time period | PrOH | BuOH | total | EtOH |
|---|---|---|---|---|
| 0-28 | 0.042 | 0.024 | 0.066 | 0.004 |
| 20-76 | 0.046 | 0.05 | 0.097 | 0.005 |
| 28-76 | 0.044 | 0.052 | 0.096 | 0.005 | total = 1-propanol + 1-butanol;
Final EtOH: 116.2 mg/L

Alcohol profiles and yield for a 3-methyl-1-butanol producing strain is provided below:

3-methyl-1-butanol strain

| Time (hr-hr) | 3MB Yield (g/g) | Total Alcohol Yield (g/g) |
|---|---|---|
| 0-4 | 0.000 | 0.000 |
| 4-6 | 0.040 | 0.040 |
| 6-8 | 0.180 | 0.180 |
| 8-12 | 0.160 | 0.170 |
| 12-20 | 0.120 | 0.160 |
| 20-28 | −0.050 | −0.010 |
| 0-28 | 0.100 | 0.120 |

Alcohol profiles and yield for 2 different 2-methy-1-butanol strains are presented below:

2-methyl-1-butanol strain 1 (AFC-2MB-01BW25113: pAFC46: kivd(*L. lactis*) AHD2(*S. cerevisiae*) ilvA(*C. glutamicum*) pAFC3: ilvGM(*S. typhimurium*) ilvCD(*E. coli*) PCS49: thrA$^{FBR}$BC (*E. coli*))

| Time (hr-hr) | 2MB Yield (g/g) | Total Alcohol Yield (g/g) | EtOH Yield | EtOH mg/L |
|---|---|---|---|---|
| 0-9 | 0.026 | 0.081 | 0.063 | 230.6 |
| 9-15 | 0.050 | 0.171 | 0.019 | 156.1 |
| 15-18 | 0.043 | 0.164 | 0.016 | 196.0 |
| 18-21 | 0.038 | 0.163 | 0.016 | 226.2 |
| 21-24 | 0.037 | 0.157 | 0.017 | 271.6 |
| 24-27 | 0.034 | 0.144 | 0.017 | 288.7 |
| 27-33 | 0.046 | 0.146 | 0.022 | 376.4 |
| 33-39 | 0.031 | 0.123 | 0.018 | 329.5 |

2-methyl-1-butanol strain 2 (AFC-2MB-02: CRS22: BW25113 ΔmetA Δtdh pAFC46: kivd(*L. lactis*) AHD2(*S. cerevisiae*) ilvA(*C. glutamicum*) pAFC3: ilvGM(*S. typhimurium*) ilvCD(*E. coli*) PCS49: thrAFBRBC (*E. coli*))

Figure 3:
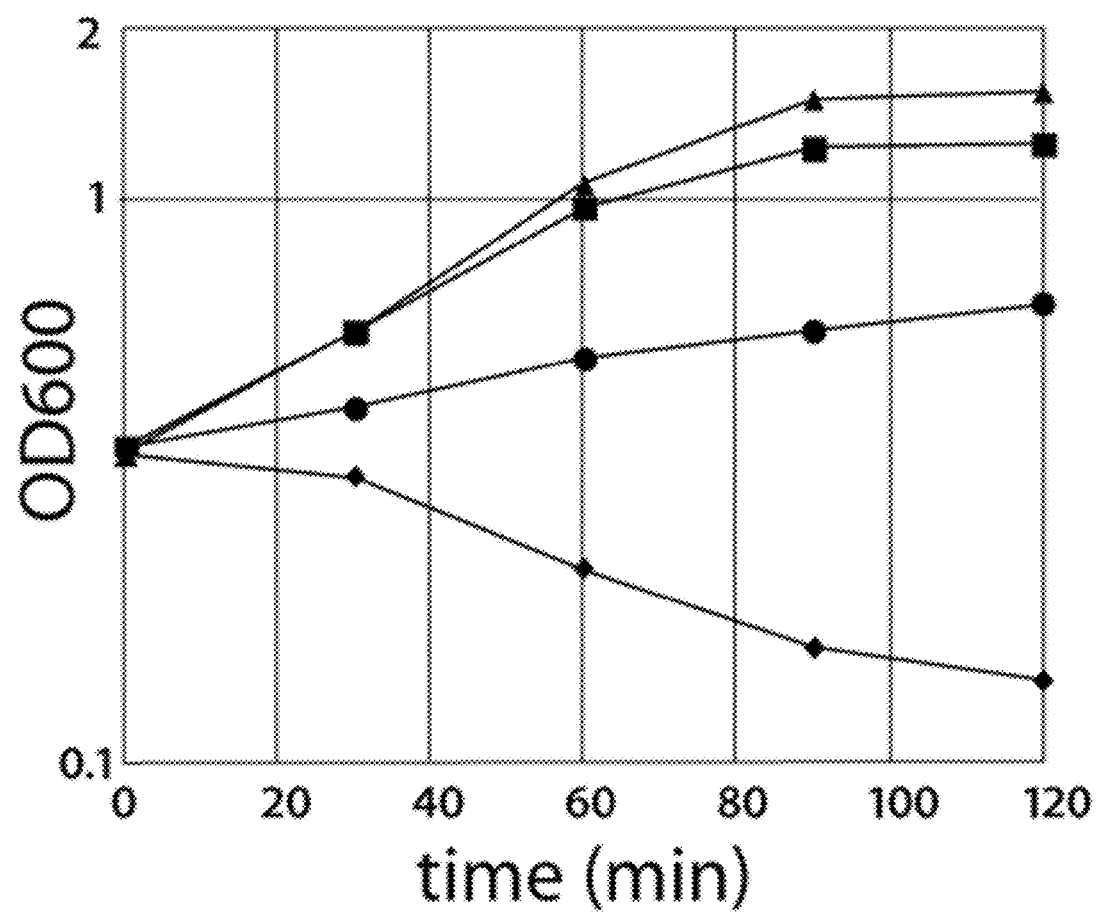
FIG. 3 depicts the effect of isobutanol on cell growth. A time course for cell growth of the wild type and the high tolerant mutant, with or without 2% isobutanol is shown. Both strains were grown in LB to exponential phase. At $OD_{600}$~3.5, 2% isobutanol was added to the medium. Triangles: wild type without isobutanol; diamonds: wild type with isobutanol; squares: the high tolerant mutant without isobutanol; circles: high tolerant mutant with isobutanol.
Figure 4:
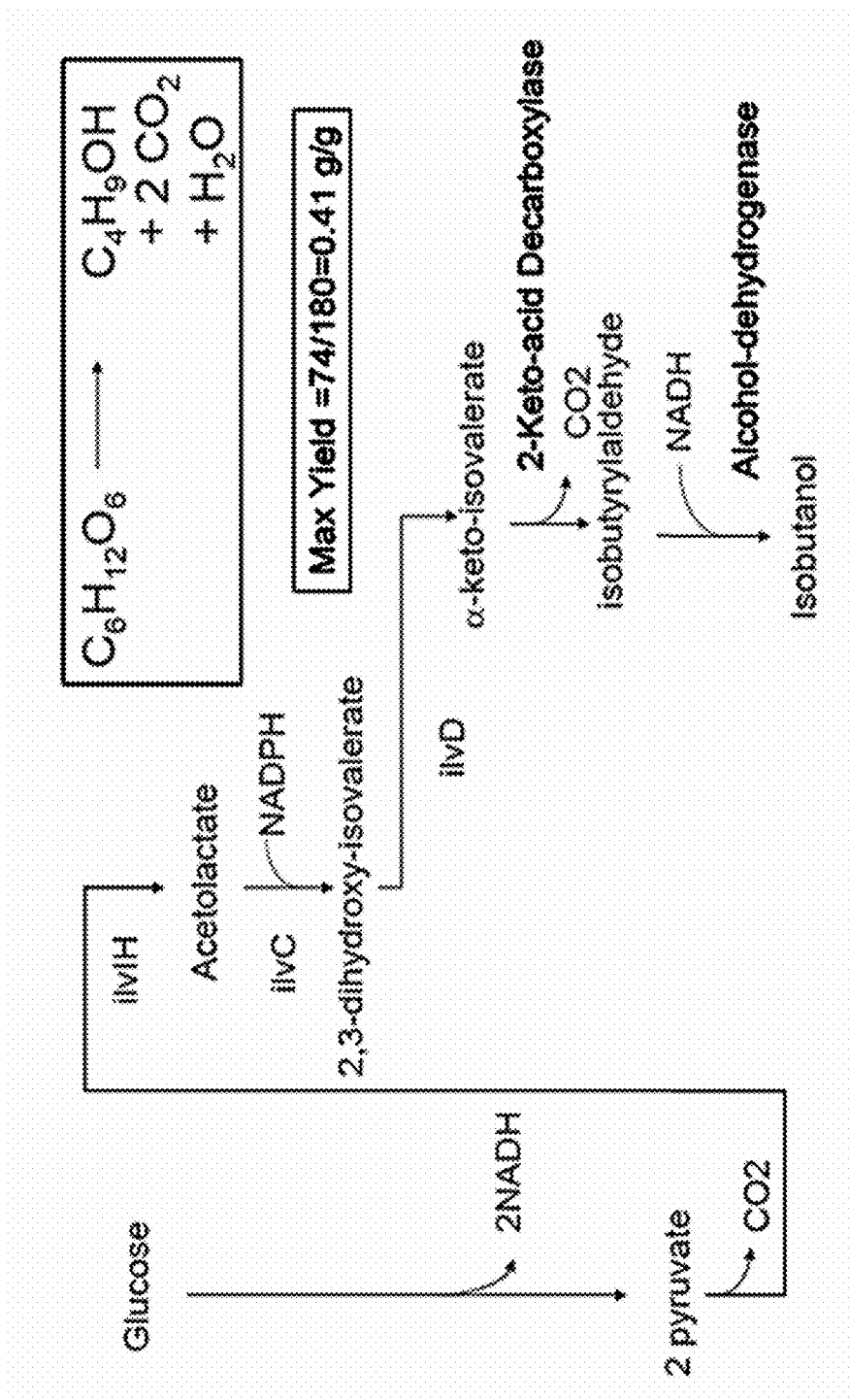
FIG. 4 depicts an exemplary pathway for the production of isobutanol in *E. coli*.
Figure 5:
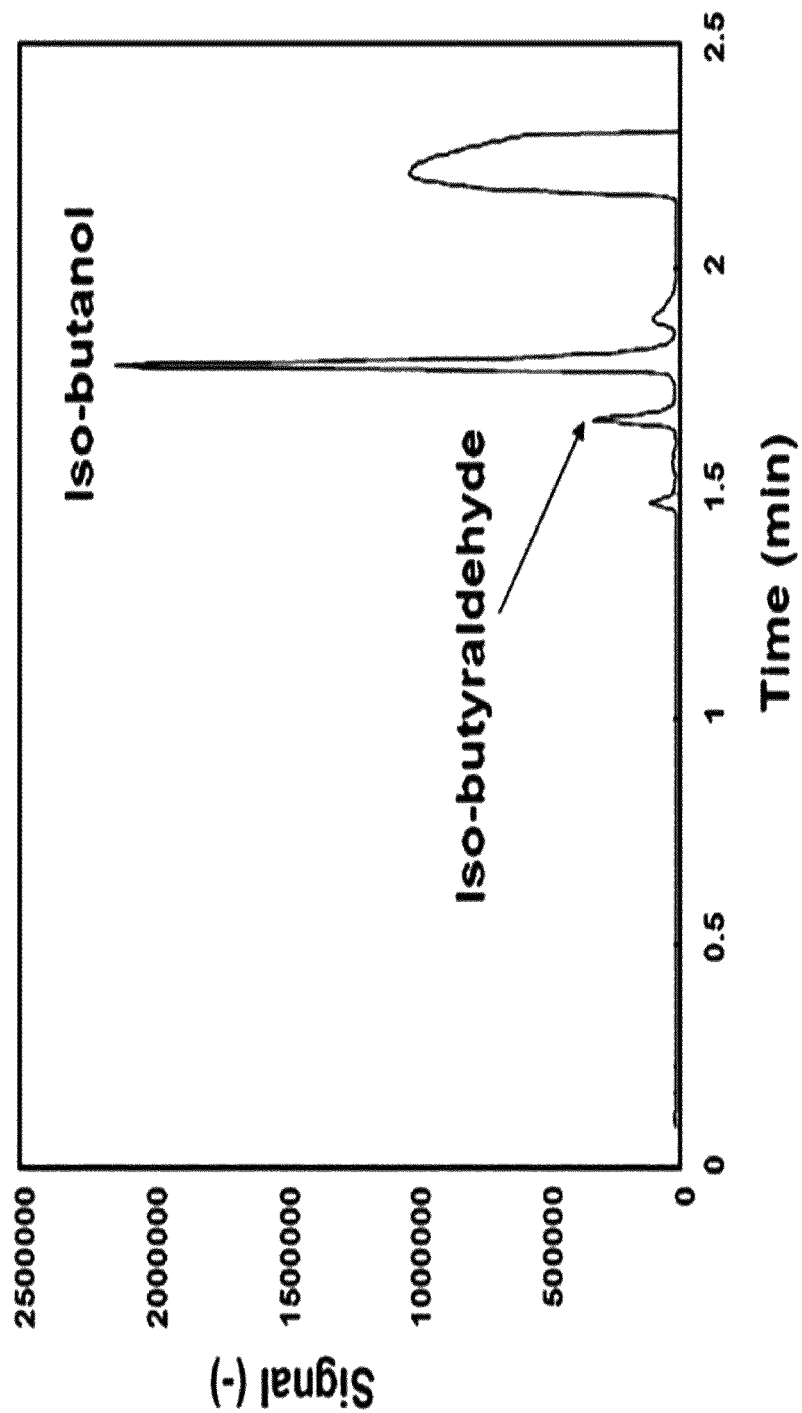
FIG. 5 depicts detection of isobutanol production by mass spectrometry.

| Time (hr-hr) | 2MB Yield | Total Alcohol Yield | EtOH Yield | EtOH mg/L |
|---|---|---|---|---|
| 0-9 | 0.183 | 0.305 | 0.243 | 301.7 |
| 9-15 | 0.089 | 0.161 | 0.014 | 133.4 |
| 15-18 | 0.083 | 0.164 | 0.014 | 166.5 |
| 18-21 | 0.080 | 0.169 | 0.016 | 214.8 |
| 21-24 | 0.073 | 0.161 | 0.016 | 256.7 |
| 24-27 | 0.065 | 0.149 | 0.017 | 315.1 |
| 27-33 | 0.058 | 0.138 | 0.017 | 326.5 |
| 33-39 | 0.064 | 0.151 | 0.018 | 344.8 | total alcohol yield = 2-methyl-1-butanol, 3-methyl-1-butanol, isobutanol, 1-butanol and 1-propanol Non-native hosts such as *E. coli* lack tolerance to high alcohols. Isobutanol is as toxic as 1-butanol to microorganisms, and the native 1-butanol producers can tolerate 1-butanol concentration up to about 2%. To show the potential for improving tolerance, in vitro evolution by the sequential transfer of cultures was used to enrich for strains with mutations which increase isobutanol tolerance. The data indicates that wild-type *E. coli* strain (JCL16) was inhibited by 1.5% isobutanol. However, after only 5 rounds of culture transfers with increasing isobutanol concentrations, mutants were found to grow in the presence of 2% isobutanol (FIG. 3). This level of solvent tolerance is comparable or better than the native producer of 1-butanol, suggesting that *E. coli* can adapt to high concentration of long chain alcohols. Other strategies such as gTME can be used for further improvement of tolerance.

The strategy described herein provides for biofuels production, both in *E. coli* and in other microorganisms. This strategy takes advantage of amino acid production technology and channels the amino acid intermediates to the 2-keto acid degradation pathway for alcohol production. The strategy avoids the CoA-mediated chemistry which is used in 1-butanol production in the native producer, and enables the synthesis of other higher and complex alcohols in an industrial scale. Specific strategies for producing other alcohols can be readily devised based on the synthetic pathways provided herein. For example, the production of 2-phenylethanol can be achieved by shunting the phenylalanine pathway, which has been efficiently amplified in *E. coli*. These strategies can also be readily implemented in yeast or other industrial microorganisms. In the case of isobutanol production, the complete pathway is CoA-independent and requires only pyruvate as a precursor. This feature avoids the mitochondria compartmentalization issue of acetyl-CoA when implementing the strategy in yeast. This strategy for production of isobutanol and 1-butanol offers the same theoretical yields (0.41 g/g glucose) as that from the native producer of 1-butanol.

Gene deletion was accomplished using methods known to the skilled artisan. Briefly, BW25113 (rrnB$_{T14}$ ΔlacZ$_{WJ16}$ hsdR514 ΔaraBAD$_{AH33}$ ΔrhaBAD$_{LD78}$) was used as the parent (e.g., wild-type) microorganism. The adhE, ldhA, frdBC, fnr, pflB and ilvD sequences were deleted as described (Datsenko and Wanner, Proc Natl Acad Sci U.S.A 97:6640 (2000)). The pta sequence deletion was made by P1 transduction with JW2294 (Baba et al., Mol Syst Biol 2:E1-E11 (2006)) as the donor. F' was transferred from XL-1 blue to supply lacIq. A list of the strains used in the present studies is provided in Table 16. In particular for the deletion of pta nucleotides 2,412,772-2,414,893 were removed. For the frdBC deletion nucleotides 4,377,400-4,378,540 were removed. For the deletion of adhE nucleotides 1,294,669-1,297,344 were removed. For the ldhA deletion nucleotides 1,439,878-1,440,867 were removed. For the fnr deletion nucleotides 1,396,798-1,397,550 were removed. For the pflB deletion nucleotides 950,508-952,784 were removed.

TABLE 16

| Strain | Relevant genotype |
|---|---|
| BW25113 | rrnB$_{T14}$ ΔlacZWJ16 hsdR514 ΔaraBAD$_{AH33}$ ΔrhaBAD$_{LD78}$ |
| JCL16 | BW25113, F' (traD36, proAB+, lacI$^q$ ZDM15) |
| JCL88 | JCL16, ΔadhE, ΔldhA-fnr, ΔfrdBC, Δpta |
| JCL93 | JCL16, ΔadhE, ΔldhA, ΔfrdBC |
| SA203 | JCL16 ΔilvD |
| JCL260 | JCL16, ΔadhE, ΔldhA-fnr, ΔfrdBC, ΔpflB, Δpta |
| JCL167 | JCL16, ΔadhE, ΔldhA-fnr, ΔfrdBC |
| JCL274 | JCL16, ΔadhE, ΔldhA, ΔfrdBC, Δpta |
| JCL168 | JCL16, ΔadhE, ΔldhA-fnr, ΔfrdBC, ΔpflB |
| JCL171 | JCL16, ΔadhE, ΔldhA, ΔfrdBC, ΔpflB, Δpta | pSA46 includes an PDC6 sequence. Genomic DNA of *Saccharomyces cerevisiae* (ATCC) was used as PCR template with a pair of primers A65 and A66 (see Table 17). PCR products were digested with Acc65I and SphI and cloned into pZE12-luc (3) cut with the same enzyme.

pSA49 includes an ADH2 sequence. To clone ADH2, genomic DNA of *Saccharomyces cerevisiae* (ATCC) was used as PCR template with a pair of primers A67 and A68 (see Table 17). PCR products were digested with SphI and XbaI and cloned into pSA46 cut with the same enzyme.

pSA53 was created by replacing the replication origin of pSA49 with p15A, pZA31-luc was digested with SacI and AvrII. Shorter fragment was purified and cloned into plasmid pSA49 cut with the same enzymes.

pSA55 includes a kivd sequence obtained by using the genomic DNA of *Lactococcus lactis* as a PCR template with a pair of primers A96 and A97 (see Table 17). PCR products were digested with Acc65I and SphI and cloned into pSA49 cut with the same enzyme.

pSA56 includes an ARO10 sequence. Genomic DNA of *Saccharomyces cerevisiae* (ATCC) was used as a PCR template with a pair of primers A98 and A99 (see Table 17). PCR products were digested with Acc65I and SphI and cloned into pSA49 cut with the same enzyme.

pSA57 includes a THI3 sequence. Genomic DNA of *Saccharomyces cerevisiae* (ATCC) was used as a PCR template with a pair of primers A100 and A101 (see Table 17). PCR products were digested with Acc65I. pSA49 was digested with SphI and blunted with Klenow Fragment, followed by digestion with Acc65I. This backbone was ligated with PCR products.

pSA58 includes a pdc sequence obtained from *Clostridium acetobutylicum*. Genomic DNA was used as a PCR template with a pair of primers A102 and A103 (see Table 17). PCR products were digested with Acc65I and SphI and cloned into pSA49 cut with the same enzyme.

To create pSA40, the P$_L$tetO1 sequence of pZE21-MCS1 was replaced with P$_L$lacO1. pZE12-luc was digested with AatII and Acc65I and the shorter fragment was purified and cloned into plasmid pZE21-MCS1 cut with the same enzymes.

pSA45 includes an ilvC sequence. The ilvC sequence was obtained using the genomic DNA of *E. coli* MG1655 as a PCR template with a pair of primers A71 and A72 (see Table 17). PCR products were digested with SalI and XmaI and cloned into pSA40 cut with the same enzyme.

pSA47 includes an ilvD sequence. The ilvD sequence was obtained using the genomic DNA of *E. coli* MG1655 as a PCR template with a pair of primers A74 and A84 (see Table 17). PCR products were digested with BspEI and MluI and cloned into pSA45 cut with SalI and MluI.

pSA51 includes ilvI and ilvH sequences. Genomic DNA of *Escherichia coli* MG1655 was used as PCR template with a pair of primers A70 and A83 (see Table 17). PCR products were digested with BsaI and SalI and cloned into pSA40 cut with Acc65I and SalI.

pSA52 includes ilvC and ilvD sequences downstream of ilvH. pSA47 was digested with SalI and MluI. The shorter fragment was purified and cloned into plasmid pSA51 cut with the same enzymes.

pSA54 was created by transferring the p15A replication origin from pZA31-luc, digested with SacI and AvrII, to plasmid pSA52.

pSA59 includes leuABCD sequence. The genomic DNA of *E. coli* MG1655 was used as PCR template with a pair of primers A106 and A109 (see Table 17). PCR products were digested with SalI and BglII and cloned into pSA40 cut with SalI and BamHI.

pSA60 includes ilvA sequence. The genomic DNA of *E. coli* MG1655 was used as PCR template with a pair of primers A104 and A105 (see Table 17). PCR products were digested with Acc65I and XhoI and cloned into pSA59 cut with Acc65I and SalI.

pSA62 was created by cloning the replication origin p15A from pZA31-luc into plasmid pSA60. A partial description of exemplary plasmids provided herein are listed in Table 18.

pSA66 includes 3' fragment of an alsS sequence. The alsS sequence was obtained using the genomic DNA of *Bacillus subtilis* as a PCR template with a pair of primers A123 and A124 (see Table 17). PCR products were digested with Acc65I and SalI and cloned into pSA40 cut with the same enzyme.

pSA67 includes alsS sequence. The 5' fragment of the alsS sequence was obtained using the genomic DNA of *Bacillus subtilis* as a PCR template with a pair of primers A125 and A126 (see Table 17). PCR products were digested with BsrGI and XbaI and cloned into pSA66 cut with Acc65I and XbaI.

pSA68 includes ilvC and ilvD sequence downstream of alsS. pSA47 was digested with SalI and MluI. The shorter fragment was purified and cloned into plasmid pSA67 cut with the same enzymes.

pSA69 was created by transferring the p15A replication origin from pZA31-luc, digested with SacI and AvrII, to plasmid pSA68.

TABLE 18

| Plasmid | Relevant genotype |
|---------|-------------------|
| pSA54 | Origin of p15A; P$_L$lacO1::ilvIHCD; kan$^r$ |
| pSA55 | Origin of ColE1; P$_L$lacO1::kivd-ADH2; amp$^r$ |
| pSA69 | Origin of p15A; P$_L$lacO1::alsS-ilvCD; kan$^r$ |

An exemplary list of oligonucleotides useful for PCR and cloning procedures is provided in Table 17. It is understood that the exemplary oligonucleotides can be modified according to the particular sequence targeted for PCR and/or cloning procedures.

TABLE 17

| name | sequence | (SEQ ID NO:) |
|------|----------|--------------|
| A65 | CGAGCGGTACCATGTCTGAAATTACTCTTGGAAAAT | (1) |
| A66 | GCCTGCGCATGCTTATTGTTTGGCATTTGTAGCGGCA | (2) |
| A67 | GCCTGCGCATGCAGGAGATATACCATGTCT ATTCCAGAAACTCAAAAAG | (3) |
| A68 | GCTCTAGATTATTTAGAAGTGTCAACAACGTAT | (4) |
| A70 | ACGCAGTCGACTCAACGCATTATTTTATCGCCGCGC | (5) |
| A71 | ACGCAGTCGACGAGGAATCACCATGGCTAACTACTT | (6) |
| A72 | AATAACCCGGGTTAACCCGCAACAGCAATACGTTTC | (7) |
| A74 | CGAGCACGCGTTTAACCCCCCAGTTTCGATTTATCG | (8) |
| A83 | GCCACCGGTCTCCGTACCATGGAGATGTTGTCTGGA GCCGAGA | (9) |
| A84 | GGCTCCGGAAGGAGATATACCATGCCTAAGTACCGT TCCGCCACCA | (10) |
| A96 | CGAGCGGTACCATGTATACAGTAGGAGATTACCTAT | (11) |
| A97 | GCCTGCGCATGCTTATGATTTATTTTGTTCAGCAAAT | (12) |
| A98 | CGAGCGGTACCATGGCACCTGTTACAATTGAAAAGT | (13) |

TABLE 17-continued

| name | sequence | (SEQ ID NO:) |
|---|---|---|
| A99 | GCCTGCGCATGCCTATTTTTATTTCTTTTAAGTGCCGC | (14) |
| A100 | CGAGCGGTACCATGAATTCTAGCTATACACAGAGAT | (15) |
| A101 | GGTCAGTATCCAACTTGATTTTTTTTAGAAG | (16) |
| A102 | CGAGCGGTACCATGAAGAGTGAATACACAATTGGAAG | (17) |
| A103 | GCCTGCGCATGCCTAATTATTTTGATTTGCAAAACGT | (18) |
| A104 | CGAGCGGTACCATGGCTGACTCGCAACCCCTGTCCG | (19) |
| A105 | CCGCTCGAGCTAACCCGCCAAAAAGAACCTGAAC | (20) |
| A106 | ACGCAGTCGACAAGAGACAAGGACCCAAACCATGAGCCAG | (21) |
| A109 | GGAAGATCTTTAATTCATAAACGCAGGTTGTTTTGC | (22) |
| A123 | GCCACCCGTCTCCGTACCATGTTGACAAAAGCAACAAAAGAAC | (23) |
| A124 | ACGCAGTCGACCTAGAGAGCTTTCGTTTTCATGAGT | (24) |
| A125 | CGAGCTGTACAATGTTGACAAAAGCAACAAAAGAAC | (25) |
| A126 | TCTCTAGAAAGGGTACCGGCAGCTTG | (26) |

In an exemplary procedure for the production of isobutanol, the host strain JCL260 was transformed with the plasmids pSA69 and pSA55. The transformation was plated on LB+0.5% glucose+50 mg/L kanamycin+200 mg/L ampicillin. Fresh transformants were used to inoculate 2 mL cultures in LB+0.5% glucose+50 mg/L kanamycin+200 mg/L ampicillin. The cultures were incubated at 37° C. and 290 rpm overnight.

200 L from the overnight culture were used to inoculate 20 mL of M9+1× Trace Metal Mix A5+7.2% glucose+3% tryptone+30 mg/L kanamycin+100 mg/L ampicillin in 250 mL screw cap flasks. The cultures were incubated at 37° C./260 rpm. At OD600 of between 1 and 2 (~5 h) the cultures were induced with 0.1 mM IPTG and incubated at 30° C./260 rpm for 24 hours.

The above solutions should be sterilized separately by filtration (thiamine) or autoclaving. The medium is sterilized by filtration.

Figure 43:
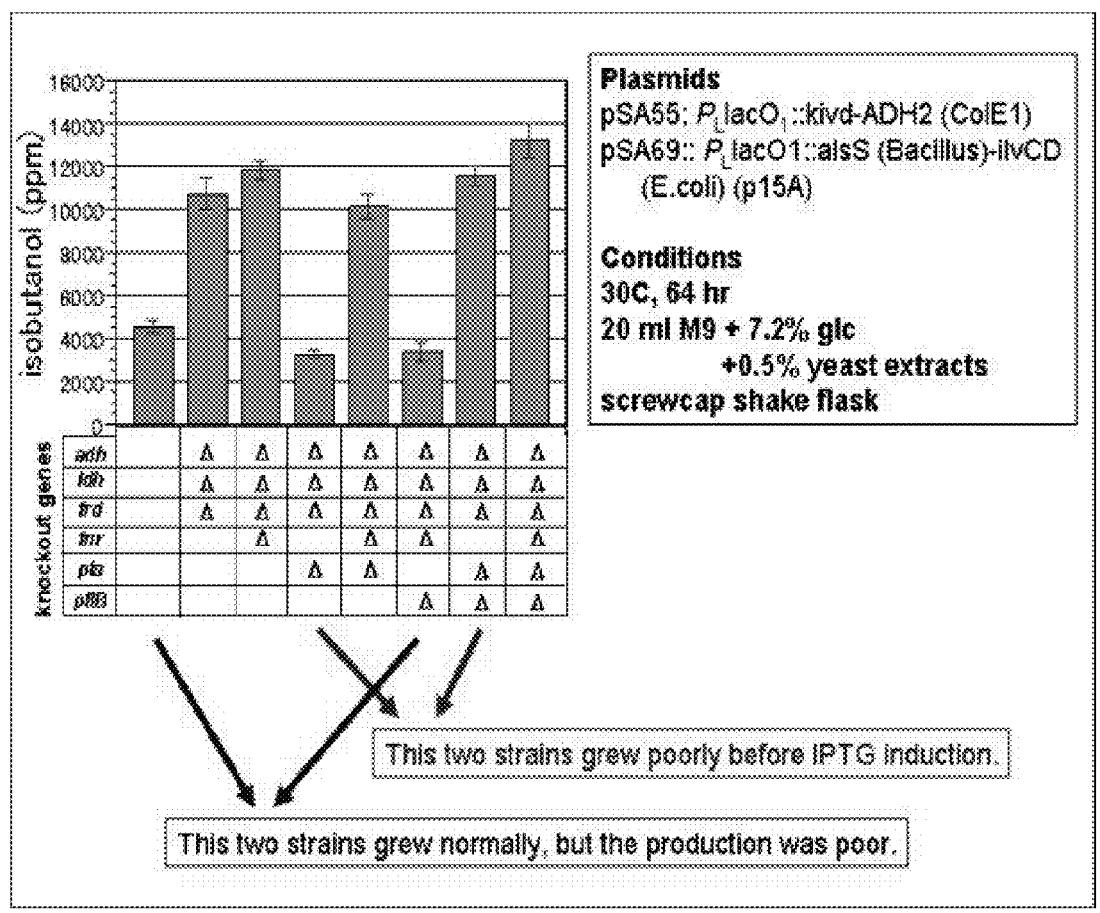
FIG. 43 depicts the correlation between knockout mutations and the production of isobutanol for various organisms.
Figure 45:
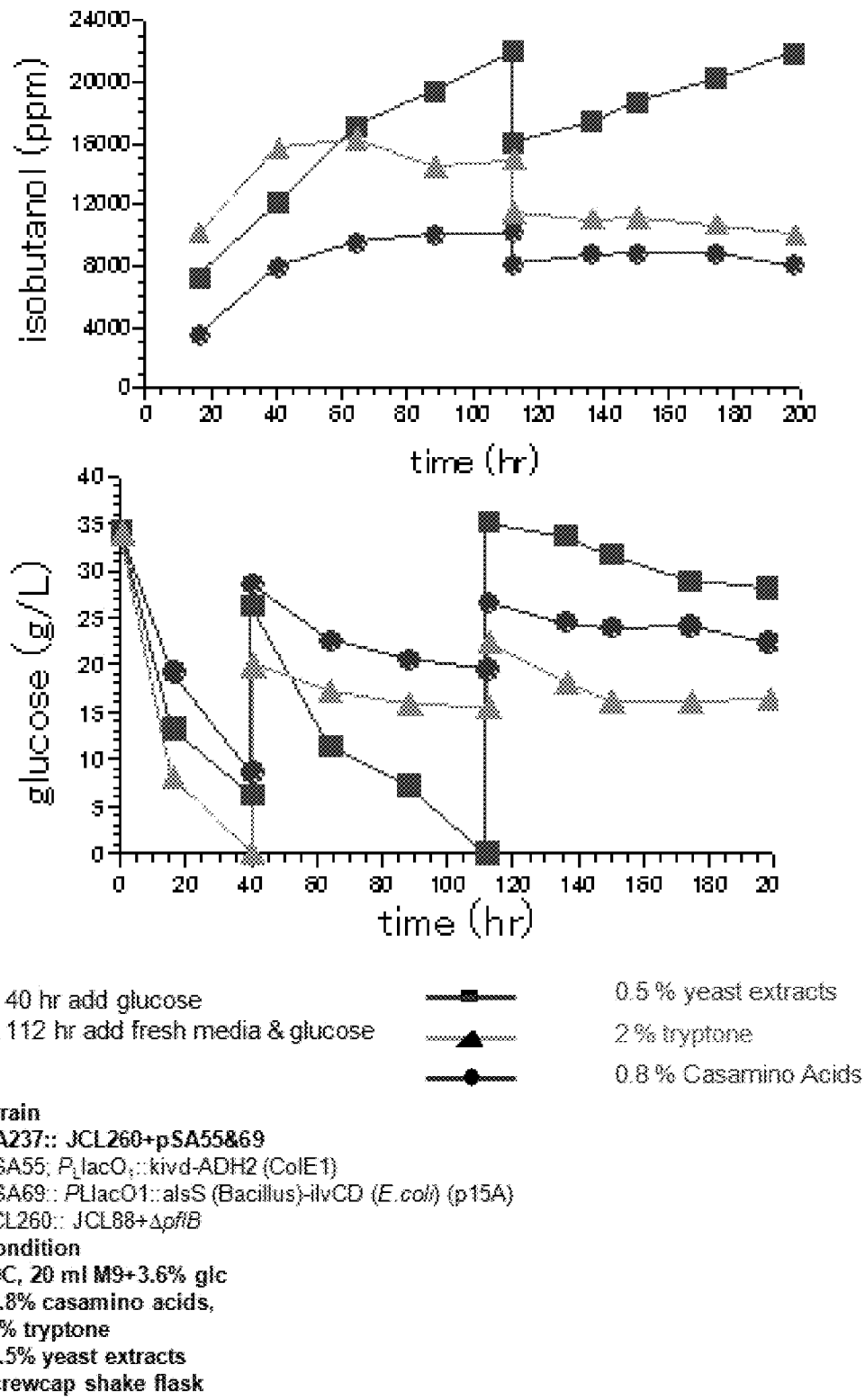
FIG. 45 depicts the influence of the addition of different complex media components on isobutanol production in a fed batch over 200 hrs.
Figure 45:
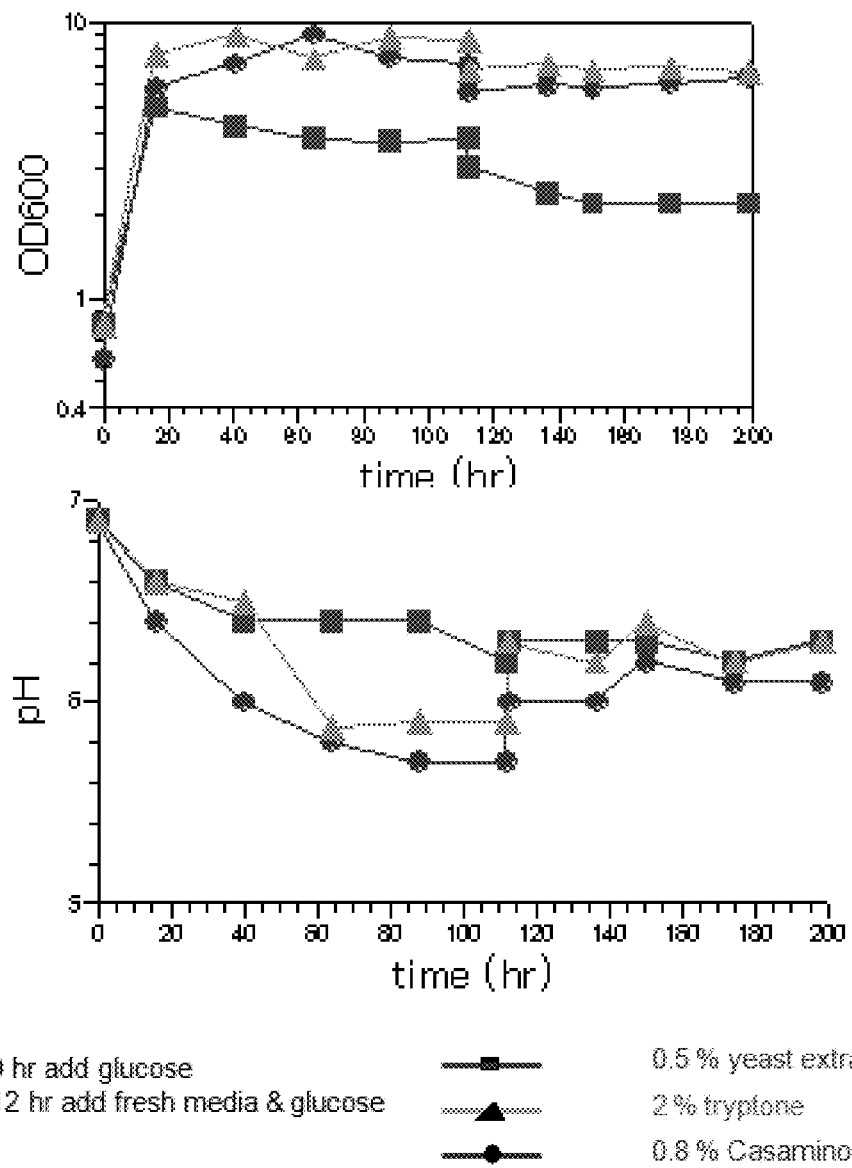
Figure 46:
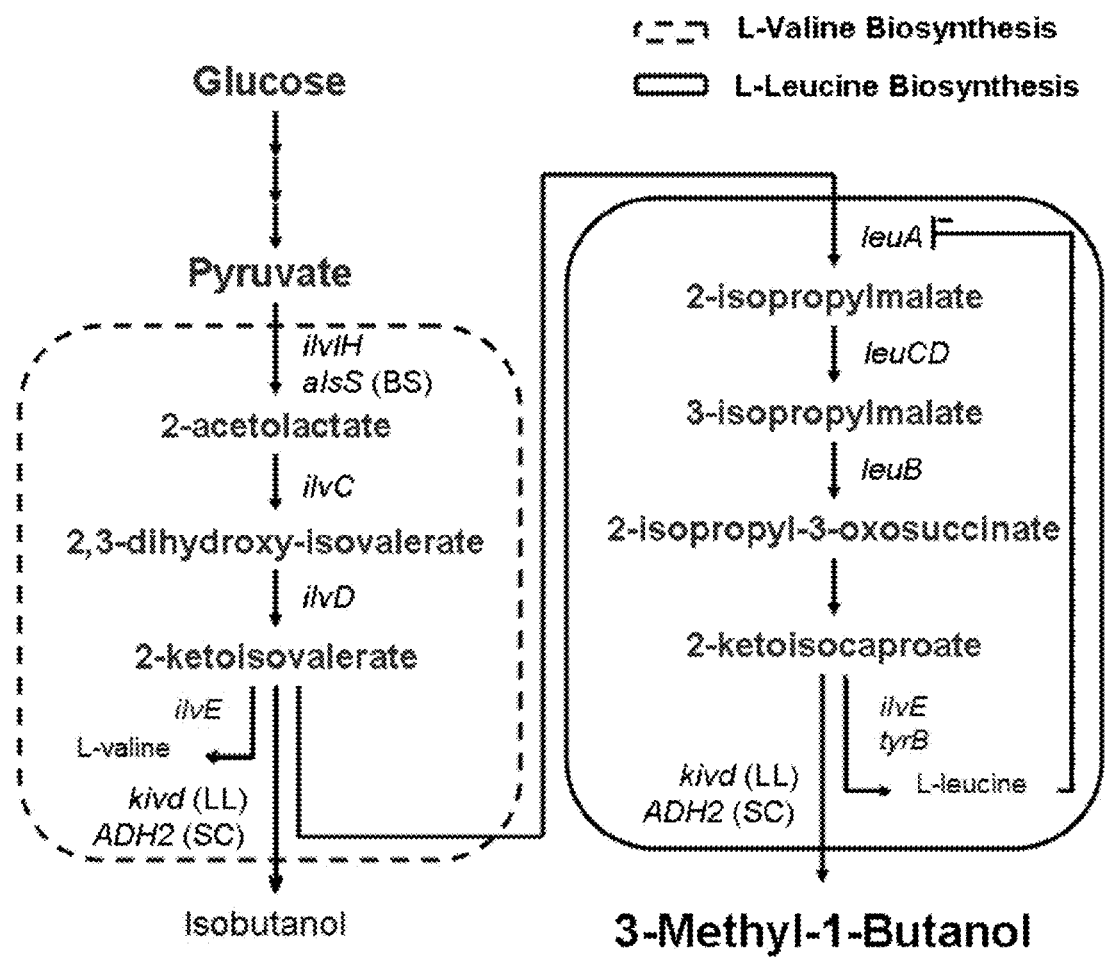
FIG. 46 shows a metabolic pathway from glucose to 3-methyl-1-butanol. All genes are from *E. coli* unless otherwise noted. BS=*Bacillus subtilis*; LL=*Lactococcus lactis*; SC=*Saccharomyces cerevisiae*.

Production of isobutanol was measured by gas chromatography and the results are illustrated in FIGS. 42-44. In FIG. 42, cultivation was performed as follows: M9 medium containing 7.2% glucose, 0.5% yeast extract, 100 μg/ml ampicillin, 30 μg/ml kanamycin and 1000× Trace Metal Mix A5 was prepared. Preculture of various knockout strains containing pSA55 and pSA69 in test tubes containing 3 ml of LB medium were performed at 37° C. overnight on a rotary shaker (250 rpm). Overnight cultures were diluted 1:100 into 20 ml of fresh medium in a 250 ml screw cap conical flask. Cells were grown to an $OD_{600}$ of ~2.0 at 37° C., followed by adding 0.1 mM IPTG. After IPTG addition, cells were cultured at 30° C. for 64 hr on a rotary shaker (250 rpm). Screw cap was opened at 16 hr, 40 hr and 64 hr for sampling. The cultivation samples were analyzed by GC/FID. In FIG. 43, cultivation was performed as follows: M9 medium containing 3.6% glucose, 100 μg/ml ampicillin, 30 μg/ml kanamycin and 1000× Trace Metal Mix A5 was prepared. Precultures of SA237 (JCL260 containing pSA55 and pSA69) in test tubes containing 3 ml of LB medium were performed at 37° C. overnight on a rotary shaker (250 rpm). Overnight cultures were diluted 1:100 into 20 ml of fresh medium in a 250 ml screw cap conical flask (red) or a 250 ml conical flask (blue). Cells were grown to an $OD_{600}$ of ~0.3 at 37° C., followed by adding 0.1 mM IPTG. After IPTG addition, the cultures were incubated in 30° C. for 72 hr on a rotary shaker (250 rpm). Isobutanol concentration, $OD_{600}$ and pH of the cultivation samples were measured at 24 hr, 48 hr and 72 hr. In FIG. 45, cultivation was performed as follows: For the cultivation, M9 medium containing 3.6% glucose, 100 μg/ml ampicillin, 30 μg/ml kanamycin and 1000× Trace Metal Mix A5 was prepared. To this cultivation medium, 0.8% casamino acids (red), 2% tryptone (green) or 0.5% yeast extract (blue) was added. Preculture of SA237 (JCL260 containing pSA55 and pSA69) in test tubes containing 3 ml of LB medium were performed at 37° C. overnight on a rotary shaker (250 rpm). Overnight culture was diluted 1:100 into 20 ml of fresh medium in a 250 ml screw cap conical flask. Cells were grown to an OD600 of ~0.8 at 37° C., followed by adding 0.1 mM IPTG. After IPTG addition, the cultures were incubated in 30° C. for 198 hr on a rotary shaker (250 rpm). Isobutanol concentration, glucose concentration, $OD_{600}$ and pH of the cultures were measured at each time points. At 40 hr, 1 ml of 36% glucose was added to all cultures. At 112 hr, 5 ml of fresh medium was added to the casamino acids-containing culture (red) and the tryptone-containing culture (green). At 112 hr, 5 ml of fresh medium and 2 ml of 36% glucose were added to the yeast extract-containing culture (blue).

The examples set forth above are provided to give those of ordinary skill in the art a complete disclosure and description of how to make and use the embodiments of the devices, systems and methods of the disclosure, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. A recombinant prokaryote comprising:
    (a) an α-isopropylmalate synthase polypeptide having at least 90% identity to SEQ ID NO:50 and having α-isopropylmalate synthase activity;
    (b) a β-isopropylmalate dehydrogenase polypeptide having at least 90% identity to SEQ ID NO:52 and having β-isopropylmalate dehydrogenase activity;
    (c) an α-isopropylmalate isomerase polypeptide having at least 90% identity to SEQ ID NO:54;
    (d) an α-isopropylmalate isomerase polypeptide having at least 90% identity to SEQ ID NO:56 and having α-isopropylmalate isomerase activity in combination with the α-isopropylmalate isomerase polypeptide of (c);
    (e) a 2-keto-acid decarboxylase polypeptide having at least 90% identity to SEQ ID NO:28 and having 2-keto acid decarboxylase activity;
    (f) a NADH-dependent alcohol dehydrogenase having at least 90% identity to SEQ ID NO:38;
    (g) an acetohydroxy acid synthase polypeptide having at least 90% identity to SEQ ID NO:42;
    (h) an acetohydroxy acid synthase polypeptide having at least 90% identity to SEQ ID NO:40 and having acetohydroxy acid synthase activity in combination with the acetohydroxy acid synthase polypeptide of (g);
    (i) an acetohydroxy acid isomeroreductase polypeptide having at least 90% identity to SEQ ID NO:44 and having acetohydroxy acid isomeroreductase activity; and
    (j) a dihydroxy-acid dehydratase polypeptide having at least 90% identity to SEQ ID NO:46 and having dihydroxy-acid dehydratase activity;
    and wherein the recombinant prokaryote produces 3-methyl-1-butanol.

2. The recombinant prokaryote of claim 1, wherein the recombinant prokaryote is *E. coli*.

3. The recombinant prokaryote of claim 2, wherein the recombinant prokaryote has a disruption of an endogenous adhE gene, or the endogenous adhE gene and an endogenous ldhA gene.

4. The recombinant prokaryote of claim 3, wherein the recombinant prokaryote produces less than about 240 mg/L of ethanol at about 112 h of culture.

5. The recombinant prokaryote of claim 1, wherein said 2-keto-acid decarboxylase polypeptide is KivD of *Lactococcus lactis* or a homolog, or variant of KivD having at least 98% identity to SEQ ID NO:28 and having 2-keto-acid decarboxylase activity.

6. The recombinant prokaryote of claim 1, wherein said NADH-dependent alcohol dehydrogenase has at least 98% identity to SEQ ID NO:38 and converts 3 methylbutyraldehyde to 3-methyl-1-butanol.

* * * * *